(12) United States Patent
Ullrich et al.

(10) Patent No.: US 9,206,130 B2
(45) Date of Patent: Dec. 8, 2015

(54) QUINOLINE DERIVATIVES AS AXL KINASE INHIBITORS

(75) Inventors: Axel Ullrich, München (DE); Pjotr Knyazev, Stockdorf (DE); Yixiang Zhang, Boston, MA (US); Kéri György, Budapest (HU); László Örfi, Budapest (HU); István Szabadkai, Budapest (HU)

(73) Assignee: Max-Planck-Gesellschaft zur Förderung der Wissenschaften E.V., Müchen (DE)

(*) Notice: Subject to any disclaimer, the term of this patent is extended or adjusted under 35 U.S.C. 154(b) by 659 days.

(21) Appl. No.: 12/933,070

(22) PCT Filed: Apr. 16, 2009

(86) PCT No.: PCT/EP2009/002798
§ 371 (c)(1),
(2), (4) Date: Dec. 13, 2010

(87) PCT Pub. No.: WO2009/127417
PCT Pub. Date: Oct. 22, 2009

(65) Prior Publication Data
US 2011/0092503 A1 Apr. 21, 2011

Related U.S. Application Data

(60) Provisional application No. 61/045,398, filed on Apr. 16, 2008.

(51) Int. Cl.
| | |
|---|---|
| *C07D 413/12* | (2006.01) |
| *C07D 409/12* | (2006.01) |
| *C07D 405/12* | (2006.01) |
| *C07D 401/12* | (2006.01) |
| *C07D 215/20* | (2006.01) |

(52) U.S. Cl.
CPC ............ *C07D 215/20* (2013.01); *C07D 401/12* (2013.01); *C07D 405/12* (2013.01); *C07D 409/12* (2013.01); *C07D 413/12* (2013.01)

(58) Field of Classification Search
CPC .. C07D 413/12; C07D 405/12; C07D 401/12; C07D 409/12; C07D 215/20
USPC .......................................... 514/312; 546/135
See application file for complete search history.

(56) References Cited

U.S. PATENT DOCUMENTS

| | | | |
|---|---|---|---|
| 6,797,823 B1 | 9/2004 | Kubo et al. | |
| 7,041,691 B1 * | 5/2006 | McGee et al. | 514/367 |
| 2008/0166359 A1 | 7/2008 | Lamb | |

FOREIGN PATENT DOCUMENTS

| | | | |
|---|---|---|---|
| WO | WO 2005/030140 | * | 4/2005 |
| WO | WO 2006/117552 | * | 11/2006 |

OTHER PUBLICATIONS

Voskoglou-Nomikos et al., Clinical Cancer Research, vol. 9, 4227-4239.*
ptcl.chem.ox.ac.uk/MSDS structure activity relationship; Jaworska, 1-8, 2004.*
Cancer and Metastasis Reviews (1998), 17(1), 91-106.*
Science (1999), vol. 286, 531-537.*
International Search Report for PCT Application No. PCT/EP2009/002798 issued Sep. 9, 2009.
Written Opinion for PCT Application No. PCT/EP2009/002798 issued Sep. 9, 2009.
International Preliminary Report on Patentability for PCT Application No. PCT/EP2009/002798 issued Oct. 19, 2010.
Weigelt et al. "Breast Cancer Metastasis: Markers and Models" Nature Reviews: Cancer, 2005 (5), 591-602.
Shawver et al. "Smart drugs:Tyrosine kinase inhibitors in cancer therapy" Cancer Cell, 2002(1), 117-123.
Sebolt-Leopold et al. "Mechanisms of drug inhibition of signalling molecules" Nature 2006, 441, 457-462.
Blume-Jensen "Oncogenic kinase signalling" Nature 2001, 411, 355-365.
Varnum et al. "Axl receptor tyrosine kinase stimulated by the vitamin K-dependent protein encoded by growth-arrest-specific gene 6" Nature, 1995, 373, 623-626.
Slamon et al. "Human Breast Cancer: Correlation of Relapse and Survival with Amplification of the HER-2lneu Oncogene" Science, 1987, 235, 177-182.
Hanahan et al. "Hallmarks of Cancer: The Next Generation" Cell, 2011, 144, 646-674.
Nagata et al. "Identification of the Product of Growth Arrest-specific Gene 6 as a Common Ligand for Axl, Sky, and Mer Receptor Tyrosine Kinases." The Journal of Biological Chemistry, 1996, 271(47), 30022-30027.
Slamon et al. "Use of Chemotherapy Plus a Monoclonal Antibody Against HER2 for Metastatic Breast Cancer That Overexpresses HER2" 2001, 344(11), 783-792.
Stitt et al. "The Anticoagulation Factor Protein S and Its Relative, Gas6, Are Ligands for the Tyro 3/Axl Family of Receptor Tyrosine Kinases" Cell, 1995, 80, 661-670.
Cobleigh et al. "Multinational Study of the Efficacy and Safety of Humanized Anti-HER2 Monoclonal Antibody in Women Who Have HER2-Overexpressing Metastatic Breast Cancer That Has Progressed After Chemotherapy for Metastatic Disease" Journal of Clinical Oncology, 1999, 17(9), 2639-2648.

(Continued)

*Primary Examiner* — Rebecca Anderson
(74) *Attorney, Agent, or Firm* — Meyertons, Hood, Kivlin, Kowert & Goetzel, P.C.; Eric B. Meyertons

(57) ABSTRACT

Novel compounds which are inhibitors of receptor tyrosine kinases of the AXL receptor family are described herein. These compounds are suitable for the treatment or prevention of disorders associated with, accompanied by or caused by hyperfunction of a receptor of the AXL family. The compounds are suitable for the treatment of hyperproliferative disorders, such as cancer, particularly cancer metastases.

9 Claims, No Drawings

(56) References Cited

OTHER PUBLICATIONS

Hafizi et al. "Signalling and functional diversity within the Axl subfamily of receptor tyrosine kinases" Cytokine & Growth Factor Reviews, 2006, 17, 295-304.
Janssen "A novel putative tyrosine kinase receptor with oncogenic potential" Oncogene, 1991, 6, 2113-2120.
O'Bryan et al. "axl, a Transforming Gene Isolated from Primary Human Myeloid Leukemia Cells, Encodes a Novel Receptor Tyrosine Kinase" Molecular and Cellular Biology, 1991, 5016-5031.
Berclaz et al. "Estrogen dependent expression of the receptor tyrosine kinase axl in normal and malignant human breast" Annals of Oncology 2001, 12, 819-824.
Craven et al. "Receptor Tyrosine Kinases Expressed in Metastatic Colon Cancer" Int. J. Cancer, 1995, 60, 791-797.
Shieh et al. "Expression of Axl in Lung Adenocarcinoma and Correlation with Tumor Progression" Neoplasia, 2005, 7(12) 2005, pp. 1058-1064.
Sun et al. "Coexpression of Gas6/Axl in Human Ovarian Cancers" Oncology, 2004, 66, 450-457.
Green et al. "Overexpression of the Axl tyrosine kinase receptor in cutaneous SCC-derived cell lines and tumours" British Journal of Cancer, 2006, 94, 1446-1451.
Ito et al. "Expression of the Axl Receptor Tyrosine Kinase in Human Thyroid Carcinoma" Thyroid, 1999, 9(6), 563-567.
Holland et al. "Multiple Roles for the Receptor Tyrosine Kinase Axl in Tumor Formation" Cancer Res, 2005, 65 (20), 9294-9303.
Vajkoczy et al. "Dominant-negative inhibition of the Axl receptor tyrosine kinase suppresses brain tumor cell growth and invasion and prolongs survival" PNAS, 2006, 103(15), 5799-5804.
Price et al., Organic Syntheses, Coll., 1955, 3, 272; Organic Syntheses, Coll., 1948, 28, 38.
Zhang et al. "AXL Is a Potential Target for Therapeutic Intervention in Breast Cancer Progression" Cancer Res 2008;68, 1905-1915.
Robinson et al. "The Protein Kinase Family of the Human Genome" Oncogene (2000) 19, 5548-5557.
Zhang et al. "AXL Is a Potential Target for Therapeutic Intervention in Breast Cancer Progression" Cancer Res (2008) 68, 1905-1915.

* cited by examiner

QUINOLINE DERIVATIVES AS AXL KINASE INHIBITORS

PRIORITY CLAIM

This application is a 371 of PCT Application No. PCT/EP2009/002798, filed Apr. 16, 2009, which claims priority to U.S. Provisional Application Ser. No. 61/045,398, filed Apr. 16, 2008.

BACKGROUND OF THE INVENTION

1. Field of the Invention

The present invention relates to novel compounds which are inhibitors of receptor tyrosine kinases of the AXL receptor family. These compounds are suitable for the treatment or prevention of disorders associated with, accompanied by or caused by hyperfunction of a receptor of the AXL family. The compounds are suitable for the treatment of hyperproliferative disorders, such as cancer, particularly cancer metastases.

2. Description of the Relevant Art

Breast cancer is the most common malignant disease in western women. In these patients, it is not the primary tumour, but its metastases at distant sites that are the main cause of death (1). Despite surgical removal of the primary tumour, relapse at local or distant sites may occur because of incomplete removal of primary tumour tissue or the presence of micrometastases undetectable at the time of diagnosis. The development of chemotherapy as well as endocrine- and radiation therapy, administered as adjuvant treatment after surgery, has led to a reduction in the risk of relapse to 20-40%. However, adjuvant treatment has a wide range of acute and long-term side effects. Over the past twenty years, with the advances in understanding the molecular basis of signalling pathway dysregulation in various cancers, a new era of cancer therapy has begun, which is characterized by the identification of critical regulators of malignant properties of cancer cells as molecular targets (2, 3).

Deregulated expression of protein kinases by gene deletion, -mutation or -amplification has been found to be important for tumour initiation and -progression, involving cancer cell proliferation, -survival, -motility and -invasivity as well as tumour angiogenesis and chemotherapy resistance (4, 5). Because of the advanced understanding of their critical functions in oncogenesis, protein kinases have been at the forefront of targeted cancer therapy development since the 1980s. Most of the novel targeted cancer therapeutics currently approved by the FDA in clinical use is interfering with the signalling action of protein kinases. More than 100 additional protein kinase inhibitors and antibodies are in clinical trials, making kinases after G protein-coupled receptors the second most popular drug target class in the pharmaceutical and biotech industries (3).

In breast cancer, the receptor tyrosine kinase HER2/neu is overexpressed due to gene amplification in tumours of about 25% of breast cancer patients, and enhanced expression correlates with lack of response to adjuvant therapy and poor prognosis (6). Based on this discovery, Herceptin, a monoclonal antibody against HER2/neu oncoprotein, has been developed and is in clinical use since 1998 both as a single agent and in combination with chemotherapies for HER2/neu overexpressing metastatic breast cancer, which has helped to significantly prolong survival of patients (7, 8). However, metastatic breast cancer patients showing no overexpression of HER2/neu do not benefit from this therapy. Therefore, novel therapeutic targets are still urgently needed for intervention in breast cancer metastatic progression.

To identify the genes that mediate progression of breast cancer, we have focused on key elements of the phosphoprotein-mediated signalling system because of its established role in human cancer. After systematically analyzing expression profiles of kinases of thirteen weakly invasive and eight highly invasive breast cancer cell lines and normal mammary epithelia cell lines by cDNA array hybridization analysis, we identified a cluster of genes characteristic for highly invasive cell types. The RTK AXL was part of the gene cluster predictive of the aggressiveness of breast cancer cells.

The mammalian AXL RTK subfamily includes three closely related members: AXL, SKY, and MER. The subfamily is characterised by an extracellular domain, consisting of two immunoglobulin-like domains followed by two fibronectin type 3-like domains. GAS6, originally isolated as a growth arrest-specific gene, is the common ligand for AXL subfamily receptors (9-11). GAS6 has the highest affinity for AXL, followed by SKY, and finally MER (11). GAS6-AXL signalling has been implicated in a host of discrete cellular responses including cell survival, proliferation, migration and adhesion (12).

AXL was originally isolated from patients with chronic myelogenous leukaemia and was shown to have transforming potential when overexpressed (13, 14). Subsequently, AXL expression has been reported in a wide variety of human cancers (15-20). Especially, in breast cancer patients a significant correlation was found between AXL and tumour stage (15). Moreover, some reports indicated that AXL might be involved in cancer progression (21, 22).

SUMMARY OF THE INVENTION

Compounds represented by formula (I) or pharmaceutically acceptable salts or solvates thereof are provided:

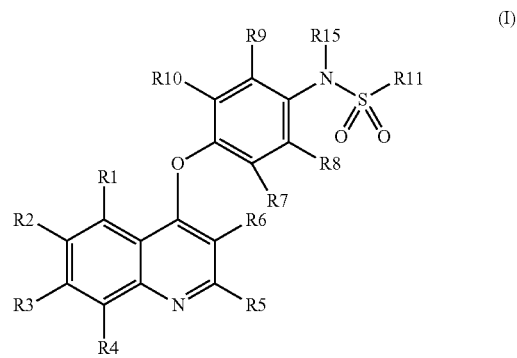

wherein
$R^1$, $R^2$, $R^3$ and $R^4$, which may be the same or different, represent hydrogen, hydroxyl, nitro, halogen, cyano, $NR^{12}R^{13}$, $C_{1-6}$ alkyl, $C_{2-6}$ alkenyl, $C_{2-6}$ alkynyl, or $C_{1-6}$ alkoxy, wherein the $C_{1-6}$ alkyl, $C_{2-6}$ alkenyl, $C_{2-6}$ alkynyl, and $C_{1-6}$ alkoxy groups are optionally mono- or polysubstituted by hydroxyl; halogen, $C_{1-6}$ alkoxy; $C_{1-6}$ alkylcarbonyl; carboxyl; $C_{1-6}$ alkoxycarbonyl; —(C=O)—$NR^{12}R^{13}$, and/or —$NR^{12}R^{13}$ wherein $R^{12}$ and $R^{13}$, which may be the same or different, represent a hydrogen atom or $C_{1-4}$ alkyl optionally substituted by hydroxyl, or alternatively $R^{12}$ and $R^{13}$ may combine with the nitrogen atom attached thereto to form a saturated or unsaturated five- or six-membered heterocyclic group; which is optionally mono- or polysubstituted by hydroxyl, an oxygen atom, $C_{1-6}$ alkyl, $C_{2-6}$ alkenyl, $C_{2-6}$ alkynyl, $C_{1-6}$ alkoxy, $C_{1-6}$ alkoxycarbonyl, or a saturated or unsaturated three- to twelve-membered carbocyclic or heterocyclic ring system; wherein the $C_{1-6}$ alkyl, $C_{2-6}$ alkenyl, and $C_{2-6}$ alkynyl groups are optionally substituted by hydroxyl, $C_{1-6}$ alkoxy, or a saturated or unsaturated three- to twelve-membered carbocyclic or heterocyclic ring system; wherein $R^2$ and/or $R^3$ also may be $-O-(CH_2)_n-R^{14}$ wherein n is an integer of 0 to 6, $-(CH_2)_n-$ is optionally substituted by $C_{1-6}$ alkyl, hydroxyl, or a halogen atom, and $R^{14}$ represents a hydrogen atom; hydroxyl; a halogen atom; $C_{1-6}$ alkoxy; $C_{1-6}$ alkylcarbonyl; carboxyl; $C_{1-6}$ alkoxycarbonyl; $-(C=O)-NR^{12}R^{13}$, $-NR^{12}R^{13}$ wherein $R^{12}$ or $R^{13}$ which may be the same or different, represent a hydrogen atom or $C_{1-4}$ alkyl optionally substituted by hydroxyl, or alternatively $R^{12}$ and $R^{13}$ may combine with the nitrogen atom attached thereto to form a saturated or unsaturated five- or six-membered heterocyclic group; in which the heterocyclic group is optionally substituted by hydroxyl, an oxygen atom, $C_{1-6}$ alkyl, $C_{2-6}$ alkenyl, $C_{2-6}$ alkynyl, $C_{1-6}$ alkoxy, $C_{1-6}$ alkoxycarbonyl, or a saturated or unsaturated three- to twelve-membered carbocyclic or heterocyclic ring system; wherein the $C_{1-6}$ alkyl, $C_{2-6}$ alkenyl, and $C_{2-6}$ alkynyl groups are optionally substituted by hydroxyl, $C_{1-6}$ alkoxy, or a saturated or unsaturated three- to twelve-membered carbocyclic or heterocyclic ring system; amino in which one or two hydrogen atoms on the amino group are optionally substituted by $C_{1-6}$ alkyl or a saturated or unsaturated three- to twelve-membered carbocyclic or heterocyclic ring system, and the $C_{1-6}$ alkyl group is optionally substituted by hydroxyl, $C_{1-6}$ alkoxy, or a saturated or unsaturated three- to twelve-membered carbocyclic or heterocyclic ring system; or a saturated or unsaturated three- to twelve-membered carbocyclic or heterocyclic ring system optionally substituted by hydroxyl, an oxygen atom, $C_{1-6}$ alkyl, $C_{2-6}$ alkenyl, $C_{2-6}$ alkynyl, $C_{1-6}$ alkoxy, $C_{1-6}$ alkoxycarbonyl, or a saturated or unsaturated three- to twelve-membered carbocyclic or heterocyclic ring system wherein the $C_{1-6}$ alkyl, $C_{2-6}$ alkenyl, and $C_{2-6}$ alkynyl groups are optionally substituted by hydroxyl, $C_{1-6}$ alkoxy, or a saturated or unsaturated three- to twelve-membered carbocyclic or heterocyclic ring system; when the carbocyclic or heterocyclic group is substituted by two $C_{1-6}$ alkyl groups, the two alkyl groups may combine together to form an alkylene chain; and the carbocyclic or heterocyclic group may be condensed with another saturated or unsaturated five- to seven-membered carbocyclic or heterocyclic group to form a bicyclic group. When n=0, $-(CH_2)_n-$ represents a bond, $R^5$ and $R^6$, which may be the same or different, represent a hydrogen atom, $C_{1-6}$ alkyl, $C_{2-6}$ alkenyl, $C_{2-6}$ alkynyl, $C_{1-6}$ alkoxy, halogen, cyano or nitro, wherein the $C_{1-6}$ alkyl, $C_{2-6}$ alkenyl, $C_{2-6}$ alkynyl, and $C_{1-6}$ alkoxy groups are optionally mono- or polysubstituted by hydroxyl; halogen, $C_{1-6}$ alkoxy; $C_{1-6}$ alkylcarbonyl; carboxyl; $C_{1-6}$ alkoxycarbonyl; $-(C=O)-NR^{12}R^{13}$, and/or $-NR^{12}R^{13}$; wherein $R^{12}$ and $R^{13}$, which may be the same or different, represent a hydrogen atom or $C_{1-4}$ alkyl optionally substituted by hydroxyl, or alternatively $R^{12}$ and $R^{13}$ may combine with the nitrogen atom attached thereto to form a saturated or unsaturated five- or six-membered heterocyclic group; in which the heterocyclic group is optionally substituted by hydroxyl, an oxygen atom, $C_{1-6}$ alkyl, $C_{2-6}$ alkenyl, $C_{2-6}$ alkynyl, $C_{1-6}$ alkoxy, $C_{1-6}$ alkoxycarbonyl, or a saturated or unsaturated three- to twelve-membered carbocyclic or heterocyclic ring system; wherein the $C_{1-6}$ alkyl, $C_{2-6}$ alkenyl, and $C_{2-6}$ alkynyl groups are optionally substituted by hydroxyl, $C_{1-6}$ alkoxy, or a saturated or unsaturated three- to twelve-membered carbocyclic or heterocyclic ring system, $R^7$, $R^8$, $R^9$ and $R^{10}$, which may be the same or different, represent a hydrogen atom, halogen, nitro, $C_{1-6}$ alkyl, $C_{1-6}$ alkoxy, wherein the $C_{1-6}$ alkyl or $C_{1-6}$ alkoxy groups are optionally mono- or polysubstituted by hydroxyl and/or halogen, $C_{1-4}$ alkyl and/or $C_{1-4}$ alkoxy, wherein the $C_{1-6}$ alkyl, $C_{1-6}$ alkoxy, wherein the $C_{1-6}$ alkyl or $C_{1-6}$ alkoxy groups are optionally mono- or polysubstituted by hydroxyl and/or halogen, $R^{11}$ represents (i) a saturated or unsaturated three- to twelve-membered carbocyclic or heterocyclic ring system which is optionally mono- or polysubstituted by an oxygen atom, $C_{1-6}$ alkyl, $C_{2-6}$ alkenyl, $C_{2-6}$ alkynyl, $C_{1-6}$ alkoxy, a halogen atom, or a saturated or unsaturated three- to eight-membered carbocyclic or heterocyclic group, and the $C_{1-6}$ alkyl, $C_{2-6}$ alkenyl, $C_{2-6}$ alkynyl, and $C_{1-6}$ alkoxy groups are optionally substituted by a halogen atom or a saturated or unsaturated three- to eight-membered carbocyclic or heterocyclic group, (ii) $C_{1-6}$ alkyl or $C_{1-6}$ alkoxy which is unsubstituted or substituted by a saturated or unsaturated three- to twelve-membered carbocyclic or heterocyclic ring system which is optionally mono- or polysubstituted by an oxygen atom, $C_{1-6}$ alkyl, $C_{2-6}$ alkenyl, $C_{2-6}$ alkynyl, $C_{1-6}$ alkoxy, a halogen atom, or a saturated or unsaturated three- to eight-membered carbocyclic or heterocyclic group, and the $C_{1-6}$ alkyl, $C_{2-6}$ alkenyl, $C_{2-6}$ alkynyl, and $C_{1-6}$ alkoxy groups are optionally substituted by a halogen atom or a saturated or unsaturated three- to eight-membered carbocyclic or heterocyclic group, or (iii) a nitrogen atom substituted with a saturated or unsaturated three- to twelve-membered carbocyclic or heterocyclic ring system which is optionally mono- or polysubstituted by an oxygen atom, $C_{1-6}$ alkyl, $C_{2-6}$ alkenyl, $C_{2-6}$ alkynyl, $C_{1-6}$ alkoxy, a halogen atom, or a saturated or unsaturated three- to eight-membered carbocyclic or heterocyclic group, and the $C_{1-6}$ alkyl, $C_{2-6}$ alkenyl, $C_{2-6}$ alkynyl, and $C_{1-6}$ alkoxy groups are optionally substituted by a halogen atom or a saturated or unsaturated three- to eight-membered carbocyclic or heterocyclic group, and $R^{15}$ represents a hydrogen atom or $C_{1-6}$ alkyl.

In one embodiment, embodiments relate to compounds as described above, preferably with the proviso that the compound is not N-[4-[(6,7-dimethoxy-4-quinolinyl)oxy]-3-fluorophenyl]-benzenemethanesulfonamide, N44-[(6,7-dimethoxy-4-quinolinyl)oxy]-3-fluorophenyl]-benzeneethanesulfonamide, or N44-[(6,7-dimethoxy-4-quinolinyl)oxy]-3-fluorophenyl]-benzenepropanesulfonamide. Further embodiments refer to compounds as described above, preferably with the proviso that compounds wherein R' is F and $R^{10}$ is H are excluded.

The compounds described herein are efficient inhibitors of AXL receptor tyrosine kinase autophosphorylation and, thus, are suitable for the treatment of hyperproliferative disorders associated with, accompanied by and/or caused by AXL hyperfunction, particularly AXL receptor tyrosine kinase induced hyperproliferative disorders.

DETAILED DESCRIPTION OF THE INVENTION

The compounds described herein are quinoline-substituted sulfonamide derivatives which are inhibitors of autophosphorylation of receptors of the AXL family, particularly of the human AXL receptor. The compounds are capable of inhibiting cell proliferation and, thus, are suitable for the treatment and/or prevention of AXL receptor tyrosine kinase induced hyperproliferative disorders, particularly selected from the group consisting of cancer and primary tumor metastases. In a preferred embodiment, the AXL receptor tyrosine kinase induced disorders are associated with AXL receptor tyrosine kinase receptor overexpression and/or hyperactivity, e.g. an increased degree of autophosphorylation compared to normal tissues. The disorders may be selected from breast, colon, prostate, lung, gastric, ovarian, endometrial, renal, hepatocellular, thyroid, uterine, esophagus, squamous cell cancer, leukemia, osteosarcoma, melanoma, glioblastoma and neuroblastoma. In an especially preferred embodiment, the disorders are selected from breast cancer, glioblastoma, renal cancer, non-small cell lung cancer (NSCLC), and melanoma. Most preferably, the disorder is breast cancer. It should be noted, however, that the compounds are also suitable for the prevention and/or treatment for other hyperproliferative disorders, particularly benign hyperproliferative disorders such as benign prostate hyperplasia.

In a further especially preferred embodiment, the compounds as described above are used for the treatment of cancer metastases, particularly primary metastases, optionally in combination with surgery, irradiation and/or administration of further antitumor agents, such as chemotherapeutic agents and/or antitumor antibodies.

The compounds are characterized by their ability to inhibit AXL receptor tyrosine kinase autophosphorylation in a cellular system, e.g. in NIH3T3 cells. In a preferred embodiment, the compounds have an $IC_{50}$ value of 10 µM or less, more preferably of 5 µM or less, even more preferably of 2.5 µM or less, and most preferably of 1 µM or less.

In the compounds of formula (I), the terms "alkyl," "alkoxy," "alkenyl," and "alkynyl" as used herein as a group or a part of a group respectively mean straight chain or branched chain alkyl, alkoxy, alkenyl, and alkynyl.

$C_{1-6}$ alkyl is preferably $C_{1-4}$ alkyl.
$C_{1-6}$ alkoxy is preferably $C_{1-4}$ alkoxy.
$C_{2-6}$ alkenyl is preferably $C_{2-4}$ alkenyl.
$C_{2-6}$ alkynyl is preferably $C_{2-4}$ alkynyl.

Examples of $C_{1-6}$ alkyl include methyl, ethyl, n-propyl, isopropyl, n-butyl, i-butyl, s-butyl, t-butyl, n-pentyl, and n-hexyl.

Examples of $C_{1-6}$ alkoxy include methoxy, ethoxy, n-propoxy, i-propoxy, n-butoxy, i-butoxy, s-butoxy, and t-butoxy.

Examples of $C_{2-6}$ alkenyl include allyl, butenyl, pentenyl, and hexenyl.

Examples of $C_{2-6}$ alkynyl include 2-propynyl, butynyl, pentynyl, and hexynyl.

The expression "alkyl optionally substituted by" as used herein refers to alkyl, in which one or more hydrogen atoms on the alkyl group have been substituted by one or more substituents which may be the same or different, and unsubstituted alkyl. It will be apparent to a person having ordinary skill in the art that the maximum number of substituents may be determined depending upon the number of substitutable hydrogen atoms on the alkyl group. This is true of a group having a substituent other than the alkyl group.

The term "halogen" means a fluorine, chlorine, bromine, or iodine atom.

Preferably, the term halogen means a fluorine or chlorine atom.

The three- to twelve-membered ring system may include a saturated or unsaturated three- to eight-membered carbocyclic ring, preferably a four- to seven-membered, more preferably five- or six-membered, saturated or unsaturated carbocyclic ring. Examples of saturated or unsaturated three- to ten-membered carbocyclic rings include phenyl, cyclopropyl, cyclobutyl, cyclopentyl, cyclohexyl, and cycloheptyl.

Further, the three- to twelve-membered ring system may include a saturated or unsaturated three- to eight-membered heterocyclic group containing at least one hetero-atom selected from oxygen, nitrogen, and sulfur atoms. The heterocyclic group preferably contains one, two or three heteroatoms with the remaining ring-constituting atoms being carbon atoms. The heterocyclic group preferably includes a saturated or unsaturated four- to seven-membered heterocyclic ring, more preferably a saturated or unsaturated five- or six-membered heterocyclic ring. Examples of saturated or unsaturated three- to eight-membered heterocyclic groups include thienyl, pyridyl, 1,2,3-triazolyl, thiazolyl, imidazolyl, isoxazolyl, pyrazolyl, piperazinyl, quinolinyl, piperidyl, morpholinyl, homopiperazinyl, thiomorpholinyl, tetrahydropyrrolyl, and azepanyl.

Further, the saturated or unsaturated carboxylic and heterocyclic ring systems include condensed ring systems wherein a cyclic group is condensed with another saturated or unsaturated five- to seven-membered carbocyclic or heterocyclic ring to form a bicyclic group, preferably a saturated or unsaturated nine- to twelve-membered bicyclic carbocyclic or heterocyclic group. Such bicyclic groups include naphthyl, quinolyl, 1,2,3,4-tetrahydroquinolyl, 1,4-benzoxanyl, indanyl, indolyl, 1,2,3,4-tetrahydronaphthyl, and phthalimidyl.

$R^1$ preferably represents a hydrogen atom or $C_{1-4}$ alkyl, e.g. methyl. More preferably, $R^1$ represents a hydrogen atom.

$R^2$ and $R^3$ may be the same or different. Preferably, one of $R^2$ and $R^3$ represents a group other than a hydrogen atom. More preferably, $R^2$ and/or $R^3$ represent hydroxyl, optionally substituted $C_{1-6}$ alkoxy, halogen, or cyano. In a preferred embodiment, $C_{1-6}$ alkoxy is not substituted by amino. In an especially preferred embodiment, $R^2$ represents unsubstituted $C_{1-6}$ alkoxy, still more preferably methoxy or fluorine. In a further preferred embodiment, $R^2$ represents unsubstituted $C_{1-6}$ alkoxy, still more preferably, methoxy, and $R^3$ represents hydroxyl or optionally substituted $C_{1-6}$ alkoxy, or alternatively $R^2$ represents hydroxyl or optionally substituted $C_{1-6}$ alkoxy and $R^3$ represents unsubstituted $C_{1-6}$ alkoxy, still more preferably unsubstituted methoxy. For example, $R^2$ and $R^3$ both represent methoxy. In a further preferred embodiment, $R^2$ is halogen, e.g. fluorine and $R^3$ is hydrogen. According to another preferred embodiment, $R^3$ is preferably selected from the group consisting of benzyloxy, 3-aminopropoxy, 2-morpholin-4-yl-ethoxy, 3-(4-methyl-piperidin-1-yl), 3-(3-methyl-piperidin-1-yl), 3-morpholin-4-yl-propoxy). In a particular preferred embodiment, $R^2$ is methoxy and $R^3$ is selected from said group.

In a still further preferred embodiment, $R^2$ and/or $R^3$ may represent —O—$(CH_2)_n$—$R^{14}$ wherein n is an integer of 0 to 6, —$(CH_2)_n$— is optionally substituted by $C_{1-6}$ alkyl, hydroxyl, or a halogen atom, and $R^{14}$ represents a hydrogen atom; hydroxyl; a halogen atom; $C_{1-6}$ alkoxy; $C_{1-6}$ alkylcarbonyl; carboxyl; $C_{1-6}$ alkoxycarbonyl; —(C=O)—$NR^{12}R^{13}$, —$NR^{12}R^{13}$ wherein $R^{12}$ or $R^{13}$ which may be the same or different, represent a hydrogen atom or $C_{1-4}$ alkyl optionally substituted by hydroxyl, or alternatively $R^{12}$ and $R^{13}$ may combine with the nitrogen atom attached thereto to form a saturated or unsaturated five- or six-membered heterocyclic group, in which the heterocyclic group is optionally substituted by hydroxyl, an oxygen atom, $C_{1-6}$ alkyl, $C_{2-6}$ alkenyl, $C_{2-6}$ alkynyl, $C_{1-6}$ alkoxy, $C_{1-6}$ alkoxycarbonyl, or a saturated or unsaturated three- to twelve-membered carbocyclic or heterocyclic ring system; wherein the $C_{1-6}$ alkyl, $C_{2-6}$ alkenyl, and $C_{2-6}$ alkynyl groups are optionally substituted by hydroxyl, $C_{1-6}$ alkoxy, or a saturated or unsaturated three- to twelve-membered carbocyclic or heterocyclic ring system, amino in which one or two hydrogen atoms on the amino group are optionally substituted by $C_{1-6}$ alkyl or a saturated or unsaturated three- to twelve-membered carbocyclic or heterocyclic ring system, and the $C_{1-6}$ alkyl group is optionally substituted by hydroxyl, $C_{1-6}$ alkoxy, or a saturated or unsaturated three- to twelve-membered carbocyclic or heterocyclic ring system; or a saturated or unsaturated three- to twelve-membered carbocyclic or heterocyclic ring system optionally substituted by hydroxyl, an oxygen atom, $C_{1-6}$ alkyl, $C_{2-6}$ alkenyl, $C_{2-6}$ alkynyl, $C_{1-6}$ alkoxy, $C_{1-6}$ alkoxycarbonyl, or a saturated or unsaturated three- to twelve-membered carbocyclic or heterocyclic ring system wherein the $C_{1-6}$ alkyl, $C_{2-6}$ alkenyl, and $C_{2-6}$ alkynyl groups are optionally substituted by hydroxyl, $C_{1-6}$ alkoxy, or a saturated or unsaturated three- to twelve-membered carbocyclic or heterocyclic ring system; when the carbocyclic or heterocyclic group is substituted by two $C_{1-6}$ alkyl groups, the two alkyl groups may combine together to form an alkylene chain; and the carbocyclic or heterocyclic group may be condensed with another saturated or unsaturated five- to seven-membered carbocyclic or heterocyclic group to form a bicyclic group. When n=0, —$(CH_2)_n$— represents a bond.

More preferably, $R^{14}$ may represent a saturated heterocyclic ring attached through its nitrogen atom, wherein $R^{14}$ is selected from the following:

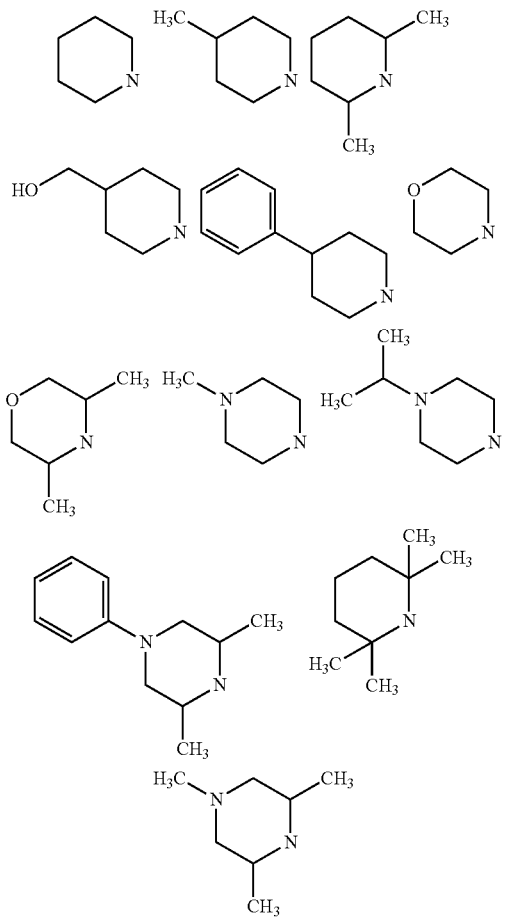

More preferably, $R^{14}$ may represent an unsaturated heterocyclic ring attached through its $CH_2$ group, wherein $R^{14}$ is selected from the following:

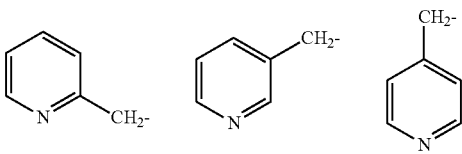

$R^4$ is preferably hydrogen, $C_{1-6}$ alkyl or $C_{1-6}$ alkoxy, wherein the $C_{1-6}$ alkyl or $C_{1-6}$ alkoxy group is optionally substituted with one or more halogen atoms. More preferably, $R^4$ is hydrogen or trifluoromethyl.

In an especially preferred embodiment, $R^1$ and $R^4$ are hydrogen and $R^2$ and $R^3$ are $C_{1-6}$ alkoxy, particularly methoxy. In a further especially preferred embodiment, $R^1$, $R^2$ and $R^3$ are hydrogen and $R^4$ is $C_{1-6}$ alkyl optionally substituted, particularly trifluoromethyl. In a still further especially preferred embodiment, $R^1$, $R^3$ and $R^4$ are hydrogen and $R^2$ is halogen, e.g. fluorine.

$R^5$ and $R^6$ are preferably selected from hydrogen, $C_{1-6}$ alkyl or $C_{1-6}$ alkoxy, optionally substituted, e.g. by halogen and/or $NR^{12}R^{13}$ as described above. More preferably, $R^5$ and $R^6$ are hydrogen.

$R^7$, $R^8$, $R^9$ and $R^{10}$, which may be the same or different, preferably represent a hydrogen atom, a halogen atom, nitro or $C_{1-4}$ alkyl, or $C_{1-4}$ alkoxy, each optionally halogenated such as methoxy or trifluoromethyl. More preferably, $R^7$ and $R^{10}$ are hydrogen and at least one of $R^8$ and $R^9$ is different from hydrogen, e.g. halogen, such as fluorine.

More preferably, the carboxylic ring substituted by $R^7$, $R^8$, $R^9$ and $R^{10}$ is selected from the following:

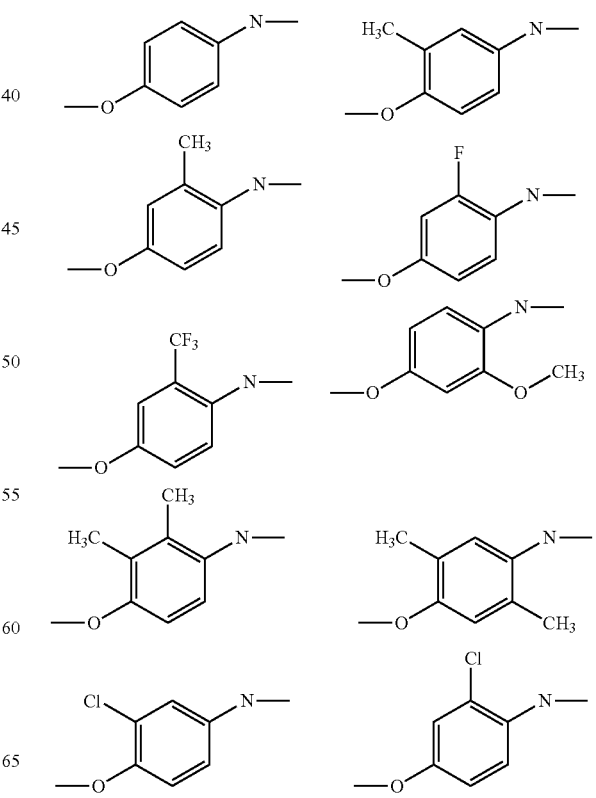

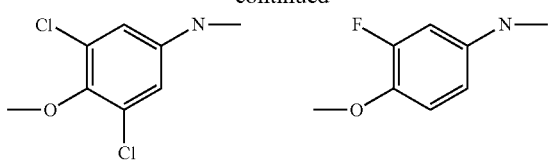

In one embodiment, it is preferred that in case $R^{11}$ is $C_{1-6}$ alkyl substituted by a phenyl ring, the phenyl ring is mono- or polysubstituted. $R^{11}$ preferably represents a saturated or unsaturated three- to twelve-membered carbocyclic or heterocyclic ring system which is optionally substituted, e.g. mono-, di- or trisubstituted by an oxygen atom, $C_{1-6}$ alkyl, $C_{2-6}$ alkenyl, $C_{2-6}$ alkynyl, $C_{1-6}$ alkoxy, a halogen atom, or a saturated or unsaturated three- to eight-membered carbocyclic or heterocyclic group, and the $C_{1-6}$ alkyl, $C_{2-6}$ alkenyl, $C_{2-6}$ alkynyl, and $C_{1-6}$ alkoxy groups are optionally substituted by a halogen atom or a saturated or unsaturated three- to eight-membered carbocyclic or heterocyclic group. Examples of preferred substituents on the carbocyclic or heterocyclic group are halogen, e.g. F, Cl or Br, $C_{1-4}$ alkyl optionally halogenated, such as methyl, ethyl, or trifluoromethyl, $C_{1-4}$ alkoxy, optionally halogenated such as methoxy, difluoromethoxy or trifluoromethoxy, hydroxyl, cyano, and optionally substituted amino. Still more preferably the carbocyclic or heterocyclic group in $R^{11}$ includes at least one halogen, e.g. fluorine or chlorine, trifluoromethyl or trifluoromethoxy substituent.

More preferably, $R^{11}$ represents an optionally substituted carbocyclic ring selected from the following (connecting atom attached to the sulfonyl group):

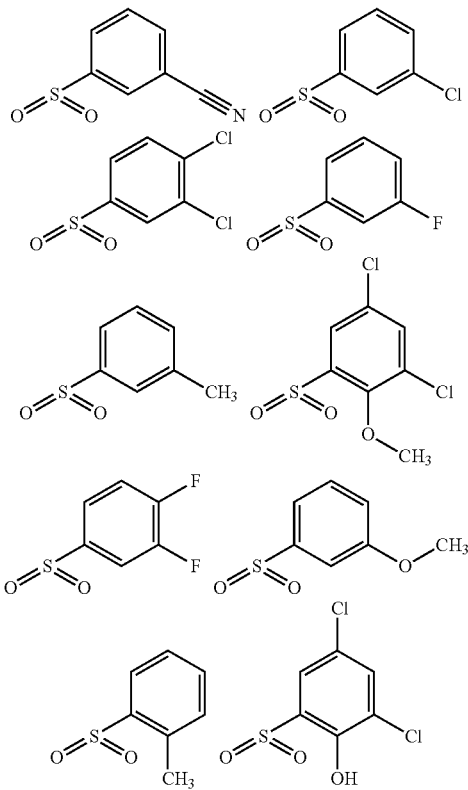
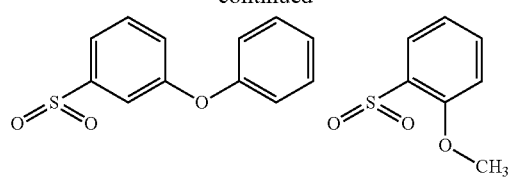
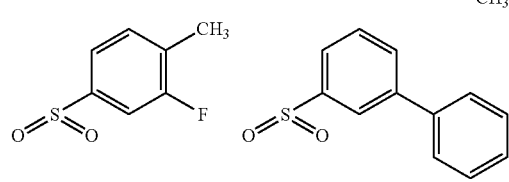
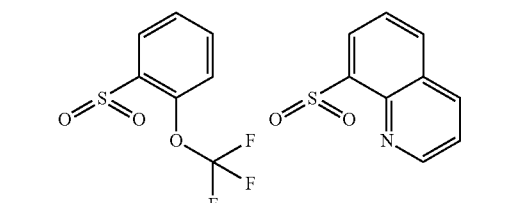
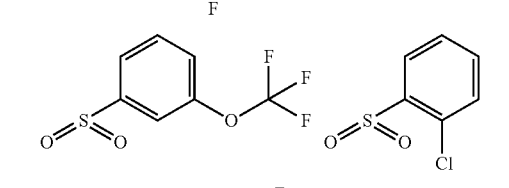
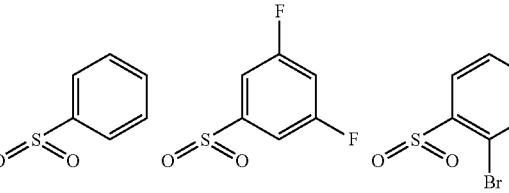
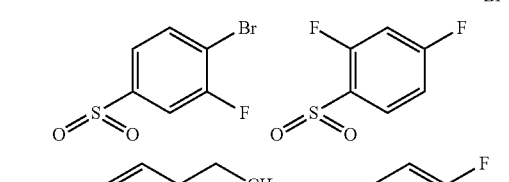
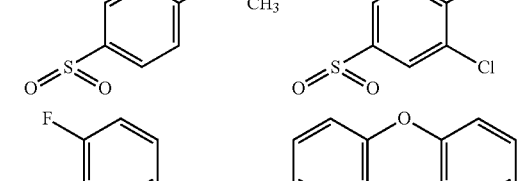
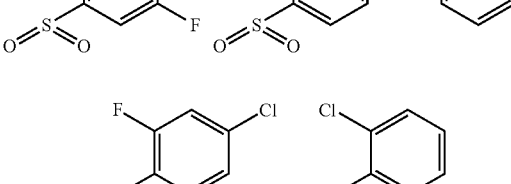
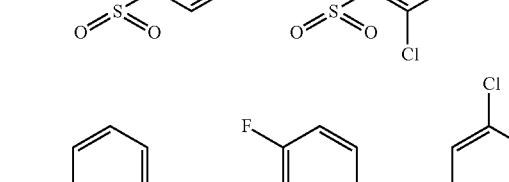
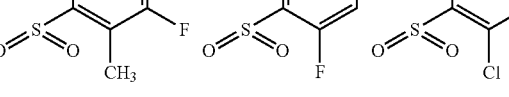

-continued
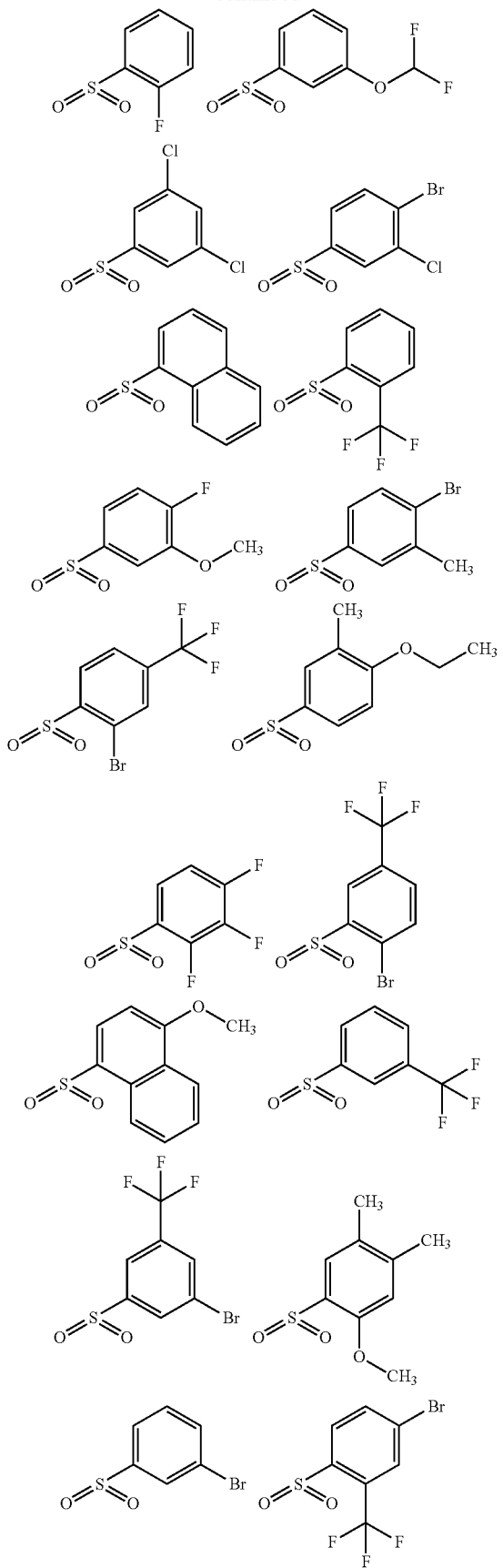
-continued
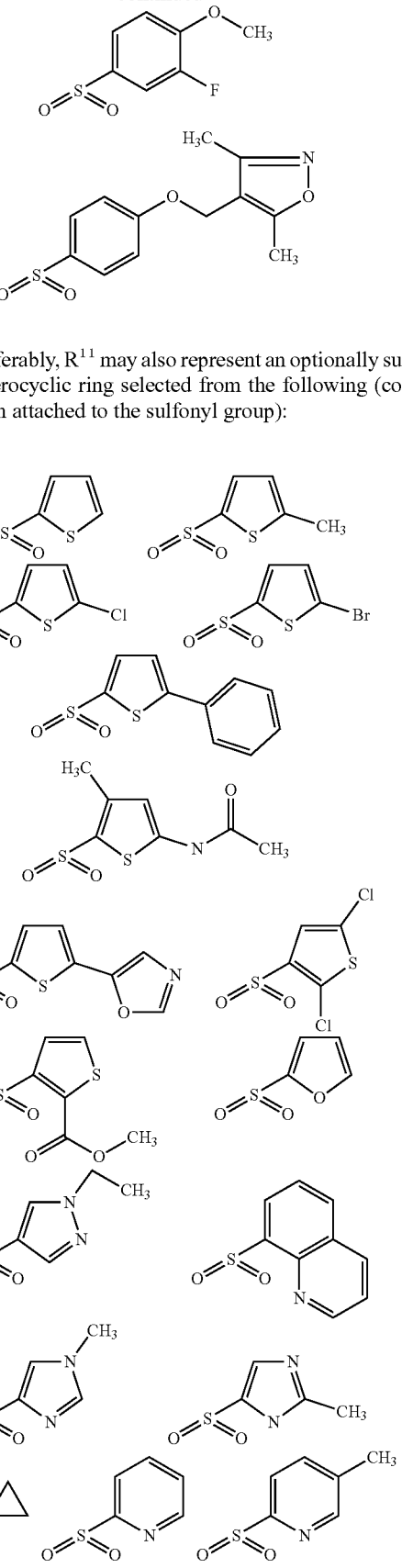
More preferably, $R^{11}$ may also represent an optionally substituted heterocyclic ring selected from the following (connecting atom attached to the sulfonyl group):

More preferably, $R^{11}$ represents an optionally substituted nitrogen atom selected from the following (connecting atom labeled by sulfonyl group):

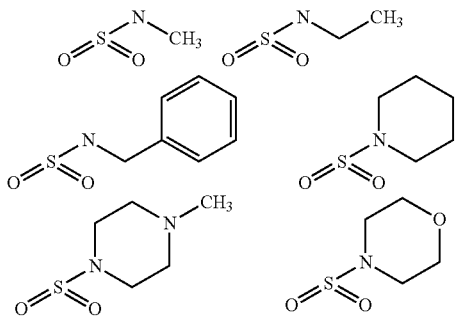

$R^{11}$ represents (iii) a nitrogen atom substituted with a saturated or unsaturated three- to twelve-membered carbocyclic or heterocyclic ring system which is optionally mono- or polysubstituted by an oxygen atom, $C_{1-6}$ alkyl, $C_{2-6}$ alkenyl, $C_{2-6}$ alkynyl, $C_{1-6}$ alkoxy, a halogen atom, or a saturated or unsaturated three- to eight-membered carbocyclic or heterocyclic group, and the $C_{1-6}$ alkyl, $C_{2-6}$ alkenyl, $C_{2-6}$ alkynyl, and $C_{1-6}$ alkoxy groups are optionally substituted by a halogen atom or a saturated or unsaturated three- to eight-membered carbocyclic or heterocyclic group, Examples of more preferred compounds include compounds represented by formula:

| | Reference |
|---|---|
| A1 | 3-Cyano-N-[4-(6,7-dimethoxy-quinolin-4-yloxy)-2-fluoro-phenyl]-benzenesulfonamide |
| A2 | N-[4-(6,7-Dimethoxy-quinolin-4-yloxy)-2-fluoro-phenyl]-3-fluoro-benzenesulfonamide |
| A3 | N-[4-(6,7-Dimethoxy-quinolin-4-yloxy)-2-fluoro-phenyl]-3,4-difluoro-benzenesulfonamide |
| A4 | Thiophene-2-sulfonic acid 4-(6,7-dimethoxy-quinolin-4-yloxy)-2-fluoro-phenyl]-amide |
| A5 | 3,5-Dichloro-N-[4-(6,7-dimethoxy-quinolin-4-yloxy)-2-fluoro-phenyl]-2-hydroxy-benzenesulfonamide |
| A6 | N-[4-(6,7-Dimethoxy-quinolin-4-yloxy)-2-fluoro-phenyl]-3-fluoro-4-methyl-benzenesulfonamide |
| A7 | N-{5-[4-(6,7-Dimethoxy-quinolin-4-yloxy)-2-fluoro-phenylsulfamoyl]-4-methyl-thiophen-2-yl}-acetamide |
| A8 | Quinoline-8-sulfonic acid [4-(6,7-dimethoxy-quinolin-4-yloxy)-2-fluoro-phenyl]-amide |
| A9 | 3-[4-(6,7-Dimethoxy-quinolin-4-yloxy)-2-fluoro-phenylsulfamoyl]-thiophene-2-carboxylic acid methyl ester |
| A10 | N-[4-(6,7-Dimethoxy-quinolin-4-yloxy)-2-fluoro-phenyl]-benzenesulfonamide |
| A11 | 4-Bromo-N-[4-(6,7-dimethoxy-quinolin-4-yloxy)-2-fluoro-phenyl]-3-fluoro-benzenesulfonamide |
| A12 | 3-Chloro-N-[4-(6,7-dimethoxy-quinolin-4-yloxy)-2-fluoro-phenyl]-4-fluoro-benzenesulfonamide |
| A13 | 4-Chloro-N-[4-(6,7-dimethoxy-quinolin-4-yloxy)-2-fluoro-phenyl]-2-fluoro-benzenesulfonamide |
| A14 | N-[4-(6,7-Dimethoxy-quinolin-4-yloxy)-2-fluoro-phenyl]-2,6-difluoro-benzenesulfonamide |
| A15 | 3-Difluoromethoxy-N-[4-(6,7-dimethoxy-quinolin-4-yloxy)-2-fluoro-phenyl]-benzenesulfonamide |
| A16 | 2-Phenyl-ethenesulfonic acid] 4-(6,7-dimethoxy-quinolin-4-yloxy)-2-fluoro-phenyl]-amide |
| A17 | Naphthalene-1-sulfonic acid] 4-(6,7-dimethoxy-quinolin-4-yloxy)-2-fluoro-phenyl]-amide |
| A18 | 2'5-Dichloro-thiophene-3-sulfonic acid [4-(6,7-dimethoxy-quinolin-4-yloxy)-2-fluoro-phenyl]-amide |
| A19 | 4-Bromo-N-[4-(6,7-dimethoxy-quinolin-4-yloxy)-2-fluoro-phenyl]-3-methyl-benzenesulfonamide |
| A20 | N-[4-(6,7-Dimethoxy-quinolin-4-yloxy)-2-fluoro-phenyl]-2,3,4-trifluoro-benzenesulfonamide |
| A21 | 5-Methyl-thiophene-2-sulfonic acid [4-(6,7-dimethoxy-quinolin-4-yloxy)-2-fluoro-phenyl]-amide |
| A22 | Furan-2-sulfonic acid [4-(6,7-dimethoxy-quinolin-4-yloxy)-2-fluoro-phenyl]-amide |
| A23 | N-[4-(6,7-Dimethoxy-quinolin-4-yloxy)-2-fluoro-phenyl]-3-trifluoromethyl-benzenesulfonamide |
| A24 | 3-Bromo-N-[4-(6,7-dimethoxy-quinolin-4-yloxy)-2-fluoro-phenyl]-benzenesulfonamide |
| A25 | 3-Chloro-N-[4-(6,7-dimethoxy-quinolin-4-yloxy)-2-fluoro-phenyl]-benzenesulfonamide |
| A26 | N-[4-(6,7-Dimethoxy-quinolin-4-yloxy)-2-fluoro-phenyl]-3-methyl-benzenesulfonamide |
| A27 | N-[4-(6,7-Dimethoxy-quinolin-4-yloxy)-2-fluoro-phenyl]-3-methoxy-benzenesulfonamide |
| A28 | 5-Chloro-thiophene-2-sulfonic acid [4-(6,7-dimethoxy-quinolin-4-yloxy)-2-fluoro-phenyl]-amide |
| A29 | 5-Bromo-thiophene-2-sulfonic acid [4-(6,7-dimethoxy-quinolin-4-yloxy)-2-fluoro-phenyl]-amide |
| A30 | N-[4-(6,7-Dimethoxy-quinolin-4-yloxy)-2-fluoro-phenyl]-3-phenoxy-benzenesulfonamide |
| A31 | 1-Ethyl-1H-pyrazole-4-sulfonic acid [4-(6,7-dimethoxy-quinolin-4-yloxy)-2-fluoro-phenyl]-amide |
| A32 | 1-Methyl-1H-imidazole-4-sulfonic acid [4-(6,7-dimethoxy-quinolin-4-yloxy)-2-fluoro-phenyl]-amide |
| A33 | Cyclopropanesulfonic acid [4-(6,7-dimethoxy-quinolin-4-yloxy)-2-fluoro-phenyl]-amide |
| A34 | Biphenyl-3-sulfonic acid [4-(6,7-dimethoxy-quinolin-4-yloxy)-2-fluoro-phenyl]-amide |
| A35 | N-[4-(6,7-Dimethoxy-quinolin-4-yloxy)-2-fluoro-phenyl]-3-trifluoromethoxy-benzenesulfonamide |
| A36 | 5-Phenyl-thiophene-2-sulfonic acid [4-(6,7-dimethoxy-quinolin-4-yloxy)-2-fluoro-phenyl]-amide |
| A37 | 5-Oxazol-5-yl-thiophene-2-sulfonic acid [4-(6,7-dimethoxy-quinolin-4-yloxy)-2-fluoro-phenyl]-amide |
| A38 | N-[4-(6,7-Dimethoxy-quinolin-4-yloxy)-2-fluoro-phenyl]-3,5-difluoro-benzenesulfonamide |
| A39 | N-[4-(6,7-Dimethoxy-quinolin-4-yloxy)-2-fluoro-phenyl]-2,4-difluoro-benzenesulfonamide |
| A40 | N-[4-(6,7-Dimethoxy-quinolin-4-yloxy)-2-fluoro-phenyl]-2,5-difluoro-benzenesulfonamide |
| A41 | 2,6-Dichloro-N-[4-(6,7-dimethoxy-quinolin-4-yloxy)-2-fluoro-phenyl]-benzenesulfonamide |
| A42 | 2,5-Dichloro-N-[4-(6,7-dimethoxy-quinolin-4-yloxy)-2-fluoro-phenyl]-benzenesulfonamide |
| A43 | 3,5-Dichloro-N-[4-(6,7-dimethoxy-quinolin-4-yloxy)-2-fluoro-phenyl]-benzenesulfonamide |
| A44 | N-[4-(6,7-Dimethoxy-quinolin-4-yloxy)-2-fluoro-phenyl]-2-trifluoromethyl-benzenesulfonamide |
| A45 | 2-Bromo-N-[4-(6,7-dimethoxy-quinolin-4-yloxy)-2-fluoro-phenyl]-4-trifluoromethyl-benzenesulfonamide |
| A46 | 2-Bromo-N-[4-(6,7-dimethoxy-quinolin-4-yloxy)-2-fluoro-phenyl]-5-trifluoromethyl-benzenesulfonamide |
| A47 | 3-Bromo-N-[4-(6,7-dimethoxy-quinolin-4-yloxy)-2-fluoro-phenyl]-5-trifluoromethyl-benzenesulfonamide |
| A48 | 4-Bromo-N-[4-(6,7-dimethoxy-quinolin-4-yloxy)-2-fluoro-phenyl]-2-trifluoromethyl-benzenesulfonamide |
| A49 | 3,4-Dichloro-N-[4-(6,7-dimethoxy-quinolin-4-yloxy)-2-fluoro-phenyl]-benzenesulfonamide |
| A50 | 3,5-Dichloro-N-[4-(6,7-dimethoxy-quinolin-4-yloxy)-2-fluoro-phenyl]-2-methoxy-benzenesulfonamide |
| A51 | N-[4-(6,7-Dimethoxy-quinolin-4-yloxy)-2-fluoro-phenyl]-2-methyl-benzenesulfonamide |
| A52 | N-[4-(6,7-Dimethoxy-quinolin-4-yloxy)-2-fluoro-phenyl]-2-methoxy-benzenesulfonamide |
| A53 | N-[4-(6,7-Dimethoxy-quinolin-4-yloxy)-2-fluoro-phenyl]-2-trifluoromethoxy-benzenesulfonamide |
| A54 | 2-Chloro-N-[4-(6,7-dimethoxy-quinolin-4-yloxy)-2-fluoro-phenyl]-benzenesulfonamide |
| A55 | 2-Bromo-N-[4-(6,7-dimethoxy-quinolin-4-yloxy)-2-fluoro-phenyl]-benzenesulfonamide |
| A56 | N-[4-(6,7-Dimethoxy-quinolin-4-yloxy)-2-fluoro-phenyl]-4-ethyl-benzenesulfonamide |
| A57 | N-[4-(6,7-Dimethoxy-quinolin-4-yloxy)-2-fluoro-phenyl]-4-phenoxy-benzenesulfonamide |

-continued

| | Reference |
|---|---|
| A58 | N-[4-(6,7-Dimethoxy-quinolin-4-yloxy)-2-fluoro-phenyl]-3-fluoro-2-methyl-benzenesulfonamide |
| A59 | N-[4-(6,7-Dimethoxy-quinolin-4-yloxy)-2-fluoro-phenyl]-2-fluoro-benzenesulfonamide |
| A60 | 4-Bromo-3-chloro-N-[4-(6,7-dimethoxy-quinolin-4-yloxy)-2-fluoro-phenyl]-benzenesulfonamide |
| A61 | N-[4-(6,7-Dimethoxy-quinolin-4-yloxy)-2-fluoro-phenyl]-4-fluoro-3-methoxy-benzenesulfonamide |
| A62 | N-[4-(6,7-Dimethoxy-quinolin-4-yloxy)-2-fluoro-phenyl]-4-ethoxy-3-methyl-benzenesulfonamide |
| A63 | 4-Methoxy-naphthalene-1-sulfonic acid [4-(6,7-dimethoxy-quinolin-4-yloxy)-2-fluoro-phenyl]-amide |
| A64 | N-[4-(6,7-Dimethoxy-quinolin-4-yloxy)-2-fluoro-phenyl]-2-methoxy-4,5-dimethyl-benzenesulfonamide |
| A65 | N-{2-[4-(6,7-Dimethoxy-quinolin-4-yloxy)-phenylsulfamoyl]-4-methyl-phenyl}-acetamide |
| A66 | N-{4-[4-(6,7-Dimethoxy-quinolin-4-yloxy)-phenylsulfamoyl]-2,6-dimethyl-phenyl}-acetamide |
| A67 | 3-Chloro-N-[4-(6,7-dimethoxy-quinolin-4-yloxy)-phenyl]-4-methoxy-benzenesulfonamide |
| A68 | 5-Chloro-N-[4-(6,7-dimethoxy-quinolin-4-yloxy)-phenyl]-2-methoxy-benzenesulfonamide |
| A69 | 5-Chloro-N-[4-(6,7-dimethoxy-quinolin-4-yloxy)-phenyl]-2-methoxy-4-methyl-benzenesulfonamide |
| A70 | 3-tert-Butyl-N-[4-(6,7-dimethoxy-quinolin-4-yloxy)-phenyl]-4-methoxy-benzenesulfonamide |
| A71 | Butane-1-sulfonic acid [4-(6,7-dimethoxy-quinolin-4-yloxy)-2-fluoro-phenyl]-amide |
| A72 | 2-Methyl-propane-1-sulfonic acid [4-(6,7-dimethoxy-quinolin-4-yloxy)-2-fluoro-phenyl]-amide |
| A73 | N-[4-(6,7-Dimethoxy-quinolin-4-yloxy)-2-fluoro-phenyl]-phenyl-methanesulfonamide |
| A74 | 3-Bromo-N-[4-(6,7-dimethoxy-quinolin-4-yloxy)-phenyl]-4-methoxy-benzenesulfonamide |
| A75 | Biphenyl-3-sulfonic acid [4-(6,7-dimethoxy-quinolin-4-yloxy)-3-methyl-phenyl]-amide |
| A76 | N-[4-(6,7-Dimethoxy-quinolin-4-yloxy)-3-methyl-phenyl]-3-phenoxy-benzenesulfonamide |
| A77 | Naphthalene-1-sulfonic acid [4-(6,7-dimethoxy-quinolin-4-yloxy)-3-methyl-phenyl]-amide |
| A78 | Isoquinoline-5-sulfonic acid [4-(6,7-dimethoxy-quinolin-4-yloxy)-phenyl]-amide |
| A79 | 3,5-Dichloro-N-[4-(6,7-dimethoxy-quinolin-4-yloxy)-3-methyl-phenyl]-2-hydroxy-benzenesulfonamide |
| A80 | 2-Methyl-3H-imidazole-4-sulfonic acid [4-(6,7-dimethoxy-quinolin-4-yloxy)-phenyl]-amide |
| A81 | Biphenyl-4-sulfonic acid [4-(6,7-dimethoxy-quinolin-4-yloxy)-phenyl]-amide |
| A82 | N-[4-(6,7-Dimethoxy-quinolin-4-yloxy)-phenyl]-3-pyrimidin-2-yl-benzenesulfonamide |
| A83 | Benzo[b]thiophene-2-sulfonic acid [4-(6,7-dimethoxy-quinolin-4-yloxy)-phenyl]-amide |
| A84 | Benzo[b]thiophene-3-sulfonic acid [4-(6,7-dimethoxy-quinolin-4-yloxy)-phenyl]-amide |
| A85 | 1-Methyl-2-oxo-2,3-dihydro-1H-indole-5-sulfonic acid [4-(6,7-dimethoxy-quinolin-4-yloxy)-phenyl]-amide |
| A86 | Biphenyl-3-sulfonic acid [4-(6,7-dimethoxy-quinolin-4-yloxy)-phenyl]-amide |
| A87 | N-[4-(6,7-Dimethoxy-quinolin-4-yloxy)-phenyl]-4-(3,5-dimethyl-isoxazol-4-ylmethoxy)-benzenesulfonamide |
| A88 | N-[4-(6,7-Dimethoxy-quinolin-4-yloxy)-phenyl]-3-fluoro-4-methoxy-benzenesulfonamide |
| A89 | Biphenyl-3-sulfonic acid [4-(6,7-dimethoxy-quinolin-4-yloxy)-2-methyl-phenyl]-amide |
| A90 | N-[4-(6,7-Dimethoxy-quinolin-4-yloxy)-2-methyl-phenyl]-3-phenoxy-benzenesulfonamide |
| A91 | Naphthalene-1-sulfonic acid [4-(6,7-dimethoxy-quinolin-4-yloxy)-2-methyl-phenyl]-amide |
| A92 | Biphenyl-4-sulfonic acid [4-(6,7-dimethoxy-quinolin-4-yloxy)-2-methyl-phenyl]-amide |
| A93 | N-[4-(6,7-Dimethoxy-quinolin-4-yloxy)-2-methyl-phenyl]-3-pyrimidin-2-yl-benzenesulfonamide |
| A94 | Benzo[b]thiophene-2-sulfonic acid [4-(6,7-dimethoxy-quinolin-4-yloxy)-2-methyl-phenyl]-amide |
| A95 | 1-Methyl-2-oxo-2,3-dihydro-1H-indole-5-sulfonic acid [4-(6,7-dimethoxy-quinolin-4-yloxy)-2-methyl-phenyl]-amide |
| A96 | N-[4-(6,7-Dimethoxy-quinolin-4-yloxy)-3-fluoro-phenyl]-2-trifluoromethyl-benzenesulfonamide |
| A97 | Biphenyl-3-sulfonic acid [4-(6,7-dimethoxy-quinolin-4-yloxy)-3-fluoro-phenyl]-amide |
| A98 | N-[4-(6,7-Dimethoxy-quinolin-4-yloxy)-3-fluoro-phenyl]-3-phenoxy-benzenesulfonamide |
| A99 | N-[4-(6,7-Dimethoxy-quinolin-4-yloxy)-3-fluoro-phenyl]-2,5-difluoro-benzenesulfonamide |
| A100 | Naphthalene-1-sulfonic acid [4-(6,7-dimethoxy-quinolin-4-yloxy)-3-fluoro-phenyl]-amide |
| A101 | N-[4-(6,7-Dimethoxy-quinolin-4-yloxy)-3-fluoro-phenyl]-3-pyrimidin-2-yl-benzenesulfonamide |
| A102 | N-[4-(6,7-Dimethoxy-quinolin-4-yloxy)-2-fluoro-phenyl]-3-pyrimidin-2-yl-benzenesulfonamide |
| A103 | N-[4-(6,7-Dimethoxy-quinolin-4-yloxy)-phenyl]-2-trifluoromethyl-benzenesulfonamide |
| A104 | Naphthalene-1-sulfonic acid [4-(6,7-dimethoxy-quinolin-4-yloxy)-phenyl]-amide |
| A105 | 3,5-Dichloro-N-[4-(6,7-dimethoxy-quinolin-4-yloxy)-2-methyl-phenyl]-4-hydroxy-benzenesulfonamide |
| A106 | 3,5-Dichloro-N-[4-(6,7-dimethoxy-quinolin-4-yloxy)-3-fluoro-phenyl]-2-methoxy-benzenesulfonamide |
| A107 | Biphenyl-4-sulfonic acid [4-(6,7-dimethoxy-quinolin-4-yloxy)-3-fluoro-phenyl]-amide |
| A108 | Benzo[b]thiophene-3-sulfonic acid [4-(6,7-dimethoxy-quinolin-4-yloxy)-3-fluoro-phenyl]-amide |
| A109 | N-[4-(6,7-Dimethoxy-quinolin-4-yloxy)-3-fluoro-phenyl]-4-fluoro-3-methoxy-benzenesulfonamide |
| A110 | 4-Chloro-N-[4-(6,7-dimethoxy-quinolin-4-yloxy)-3-fluoro-phenyl]-2-fluoro-benzenesulfonamide |
| A111 | 3,5-Dichloro-N-[4-(6,7-dimethoxy-quinolin-4-yloxy)-2-methyl-phenyl]-2-methoxy-benzenesulfonamide |
| A112 | N-[4-(6,7-Dimethoxy-quinolin-4-yloxy)-2-methyl-phenyl]-2-trifluoromethoxy-benzenesulfonamide |
| A113 | N-[4-(6,7-Dimethoxy-quinolin-4-yloxy)-2-methyl-phenyl]-2-trifluoromethyl-benzenesulfonamide |
| A114 | N-[4-(6,7-Dimethoxy-quinolin-4-yloxy)-phenyl]-2-trifluoromethoxy-benzenesulfonamide |
| A115 | N-[4-(6,7-Dimethoxy-quinolin-4-yloxy)-phenyl]-3-phenoxy-benzenesulfonamide |
| A116 | N-[4-(6,7-Dimethoxy-quinolin-4-yloxy)-phenyl]-4-fluoro-3-methoxy-benzenesulfonamide |
| A117 | 4-Bromo-3-chloro-N-[4-(6,7-dimethoxy-quinolin-4-yloxy)-phenyl]-benzenesulfonamide |
| A118 | N-[4-(6,7-Dimethoxy-quinolin-4-yloxy)-phenyl]-2,5-difluoro-benzenesulfonamide |
| A119 | N-[4-(6,7-Dimethoxy-quinolin-4-yloxy)-3-methoxy-phenyl]-2-trifluoromethoxy-benzenesulfonamide |
| A120 | N-[4-(6,7-Dimethoxy-quinolin-4-yloxy)-3-methoxy-phenyl]-3-phenoxy-benzenesulfonamide |
| A121 | N-[4-(6,7-Dimethoxy-quinolin-4-yloxy)-3-methoxy-phenyl]-4-fluoro-3-methoxy-benzenesulfonamide |
| A122 | 4-Bromo-3-chloro-N-[4-(6,7-dimethoxy-quinolin-4-yloxy)-3-methoxy-phenyl]-benzenesulfonamide |
| A123 | N-[4-(6,7-Dimethoxy-quinolin-4-yloxy)-3-methoxy-phenyl]-2-trifluoromethyl-benzenesulfonamide |
| A124 | 04-Bromo-3-chloro-N-[4-(6,7-dimethoxy-quinolin-4-yloxy)-3-fluoro-phenyl]-benzenesulfonamide |
| A125 | 1-Methyl-2-oxo-2,3-dihydro-1H-indole-5-sulfonic acid [4-(6,7-dimethoxy-quinolin-4-yloxy)-3-fluoro-phenyl]-amide |
| A126 | N-[4-(6,7-Dimethoxy-quinolin-4-yloxy)-3-fluoro-phenyl]-2-trifluoromethoxy-benzenesulfonamide |
| A127 | 3,5-Dichloro-N-[4-(6,7-dimethoxy-quinolin-4-yloxy)-3-methyl-phenyl]-2-methoxy-benzenesulfonamide |
| A128 | N-[4-(6,7-Dimethoxy-quinolin-4-yloxy)-3-methyl-phenyl]-2-trifluoromethyl-benzenesulfonamide |
| A129 | N-[4-(6,7-Dimethoxy-quinolin-4-yloxy)-3-methyl-phenyl]-2-trifluoromethyl-benzenesulfonamide |
| A130 | 4-Methoxy-naphthalene-1-sulfonic acid [4-(6,7-dimethoxy-quinolin-4-yloxy)-3-methyl-phenyl]-amide |
| A131 | N-[4-(6,7-Dimethoxy-quinolin-4-yloxy)-3-methyl-phenyl]-2,5-difluoro-benzenesulfonamide |
| A132 | N-[4-(6,7-Dimethoxy-quinolin-4-yloxy)-3-methyl-phenyl]-3-pyrimidin-2-yl-benzenesulfonamide |
| A133 | 4-Methoxy-naphthalene-1-sulfonic acid [4-(6,7-dimethoxy-quinolin-4-yloxy)-phenyl]-amide |

| Reference | |
|---|---|
| A134 | 4-Chloro-N-[4-(6,7-dimethoxy-quinolin-4-yloxy)-phenyl]-2-fluoro-benzenesulfonamide |
| A135 | 4-Methoxy-naphthalene-1-sulfonic acid [4-(6,7-dimethoxy-quinolin-4-yloxy)-3-fluoro-phenyl]-amide |
| A136 | Biphenyl-4-sulfonic acid [4-(6,7-dimethoxy-quinolin-4-yloxy)-2-fluoro-phenyl]-amide |
| A137 | 1-Methyl-2-oxo-2,3-dihydro-1H-indole-5-sulfonic acid [4-(6,7-dimethoxy-quinolin-4-yloxy)-2-fluoro-phenyl]-amide |
| A138 | Biphenyl-3-sulfonic acid [4-(6,7-dimethoxy-quinolin-4-yloxy)-3-methoxy-phenyl]-amide |
| A139 | N-[4-(6,7-Dimethoxy-quinolin-4-yloxy)-3-methoxy-phenyl]-2,5-difluoro-benzenesulfonamide |
| A140 | Naphthalene-1-sulfonic acid [4-(6,7-dimethoxy-quinolin-4-yloxy)-3-methoxy-phenyl]-amide |
| A141 | 4-Chloro-N-[4-(6,7-dimethoxy-quinolin-4-yloxy)-3-methoxy-phenyl]-2-fluoro-benzenesulfonamide |
| A142 | Biphenyl-4-sulfonic acid [4-(6,7-dimethoxy-quinolin-4-yloxy)-3-methoxy-phenyl]-amide |
| A143 | N-[4-(6,7-Dimethoxy-quinolin-4-yloxy)-3-methoxy-phenyl]-3-pyrimidin-2-yl-benzenesulfonamide |
| A144 | Benzo[b]thiophene-3-sulfonic acid [4-(6,7-dimethoxy-quinolin-4-yloxy)-3-methoxy-phenyl]-amide |
| A145 | 1-Methyl-2-oxo-2,3-dihydro-1H-indole-5-sulfonic acid [4-(6,7-dimethoxy-quinolin-4-yloxy)-3-methoxy-phenyl]-amide |
| A146 | 4-Bromo-N-[4-(6,7-dimethoxy-quinolin-4-yloxy)-3-fluoro-phenyl]-2-trifluoromethoxy-benzenesulfonamide |
| A147 | 4-Bromo-N-[4-(6,7-dimethoxy-quinolin-4-yloxy)-2-fluoro-phenyl]-2-trifluoromethoxy-benzenesulfonamide |
| A148 | 4-Bromo-N-[4-(6,7-dimethoxy-quinolin-4-yloxy)-3-methoxy-phenyl]-2-trifluoromethoxy-benzenesulfonamide |
| A149 | 4-Bromo-N-[4-(6,7-dimethoxy-quinolin-4-yloxy)-phenyl]-2-trifluoromethoxy-benzenesulfonamide |
| A150 | 4-Methoxy-naphthalene-1-sulfonic acid [4-(6,7-dimethoxy-quinolin-4-yloxy)-2-methyl-phenyl]-amide |
| A151 | N-[4-(6,7-Dimethoxy-quinolin-4-yloxy)-2-methyl-phenyl]-2,5-difluoro-benzenesulfonamide |
| A152 | 4-Bromo-3-chloro-N-[4-(6,7-dimethoxy-quinolin-4-yloxy)-2-methyl-phenyl]-benzenesulfonamide |
| A153 | 4-Chloro-N-[4-(6,7-dimethoxy-quinolin-4-yloxy)-2-methyl-phenyl]-2-fluoro-benzenesulfonamide |
| A154 | N-[4-(6,7-Dimethoxy-quinolin-4-yloxy)-2-methyl-phenyl]-4-fluoro-3-methoxy-benzenesulfonamide |
| A155 | 3,5-Dichloro-N-[4-(6,7-dimethoxy-quinolin-4-yloxy)-phenyl]-4-hydroxy-benzenesulfonamide |
| A156 | 3,5-Dichloro-N-[4-(6,7-dimethoxy-quinolin-4-yloxy)-3-methoxy-phenyl]-2-hydroxy-benzenesulfonamide |
| B1 | Thiophene-2-sulfonic acid [2-fluoro-4-(6-fluoro-2-methyl-quinolin-4-yloxy)-phenyl]-amide |
| B2 | 3-Cyano-N-[2-fluoro-4-(6-fluoro-2-methyl-quinolin-4-yloxy)-phenyl]-benzenesulfonamide |
| B3 | N-[2-Fluoro-4-(6-fluoro-2-methyl-quinolin-4-yloxy)-phenyl]-3-methoxy-benzenesulfonamide |
| B4 | Cyclopropanesulfonic acid [2-fluoro-4-(6-fluoro-2-methyl-quinolin-4-yloxy)-phenyl]-amide |
| B5 | 3-Chloro-4-fluoro-N-[2-fluoro-4-(6-fluoro-2-methyl-quinolin-4-yloxy)-phenyl]-benzenesulfonamide |
| B6 | 2,6-Difluoro-N-[2-fluoro-4-(6-fluoro-2-methyl-quinolin-4-yloxy)-phenyl]-benzenesulfonamide |
| B7 | 5-Methyl-thiophene-2-sulfonic acid [2-fluoro-4-(6-fluoro-2-methyl-quinolin-4-yloxy)-phenyl]-amide |
| B8 | N-[2-Fluoro-4-(6-fluoro-2-methyl-quinolin-4-yloxy)-phenyl]-3-trifluoromethyl-benzenesulfonamide |
| B9 | N-[4-(6-Fluoro-2-methyl-quinolin-4-yloxy)-phenyl]-benzenesulfonamide |
| B10 | 3,5-Dichloro-N-[4-(6-fluoro-2-methyl-quinolin-4-yloxy)-phenyl]-benzenesulfonamide |
| B11 | 3,5-Dichloro-N-[4-(6-fluoro-2-methyl-quinolin-4-yloxy)-phenyl]-2-methoxy-benzenesulfonamide |
| B12 | 2,4-Difluoro-N-[4-(6-fluoro-2-methyl-quinolin-4-yloxy)-phenyl]-benzenesulfonamide |
| B13 | 3,5-Difluoro-N-[4-(6-fluoro-2-methyl-quinolin-4-yloxy)-phenyl]-benzenesulfonamide |
| B14 | 3-Bromo-N-[4-(6-fluoro-2-methyl-quinolin-4-yloxy)-phenyl]-benzenesulfonamide |
| B15 | 4-Bromo-N-[4-(6-fluoro-2-methyl-quinolin-4-yloxy)-phenyl]-2-trifluoromethyl-benzenesulfonamide |
| B16 | Thiophene-3-sulfonic acid [4-(6-fluoro-2-methyl-quinolin-4-yloxy)-phenyl]-amide |
| B17 | 3-[4-(6-Fluoro-2-methyl-quinolin-4-yloxy)-phenylsulfamoyl]-thiophene-2-carboxylic acid methyl ester |
| B18 | 5-Chloro-thiophene-2-sulfonic acid [4-(6-fluoro-2-methyl-quinolin-4-yloxy)-phenyl]-amide |
| B19 | 5-Oxazol-5-yl-thiophene-2-sulfonic acid [4-(6-fluoro-2-methyl-quinolin-4-yloxy)-phenyl]-amide |
| B20 | Naphthalene-1-sulfonic acid [4-(6-fluoro-2-methyl-quinolin-4-yloxy)-phenyl]-amide |
| B21 | 1-Ethyl-1H-pyrazole-4-sulfonic acid [4-(6-fluoro-2-methyl-quinolin-4-yloxy)-phenyl]-amide |
| B22 | 3,5-Dichloro-N-[4-(6-fluoro-2-methyl-quinolin-4-yloxy)-phenyl]-2-hydroxy-benzenesulfonamide |
| C1 | 3,5-Dichloro-N-[2-fluoro-4-(2-methyl-8-trifluoromethyl-quinolin-4-yloxy)-phenyl]-benzenesulfonamide |
| C2 | Biphenyl-3-sulfonic acid [2-fluoro-4-(2-methyl-8-trifluoromethyl-quinolin-4-yloxy)-phenyl]-amide |
| C3 | N-[2-Fluoro-4-(2-methyl-8-trifluoromethyl-quinolin-4-yloxy)-phenyl]-3-phenoxy-benzenesulfonamide |
| C4 | Naphthalene-1-sulfonic acid [2-fluoro-4-(2-methyl-8-trifluoromethyl-quinolin-4-yloxy)-phenyl]-amide |
| C5 | 2,5-Dichloro-N-[2-fluoro-4-(2-methyl-8-trifluoromethyl-quinolin-4-yloxy)-phenyl]-benzenesulfonamide |
| C6 | 2,6-Dichloro-N-[2-fluoro-4-(2-methyl-8-trifluoromethyl-quinolin-4-yloxy)-phenyl]-benzenesulfonamide |
| C7 | N-[2-Fluoro-4-(2-methyl-8-trifluoromethyl-quinolin-4-yloxy)-phenyl]-2-trifluoromethyl-benzenesulfonamide |
| C8 | 4-Methoxy-naphthalene-1-sulfonic acid [3-fluoro-4-(2-methyl-8-trifluoromethyl-quinolin-4-yloxy)-phenyl]-amide |
| C9 | 3-Fluoro-N-[3-fluoro-4-(2-methyl-8-trifluoromethyl-quinolin-4-yloxy)-phenyl]-4-methoxy-benzenesulfonamide |
| C10 | N-[3-Fluoro-4-(2-methyl-8-trifluoromethyl-quinolin-4-yloxy)-phenyl]-2-methoxy-4,5-dimethyl-benzenesulfonamide |
| C11 | 2,5-Difluoro-N-[2-fluoro-4-(2-methyl-8-trifluoromethyl-quinolin-4-yloxy)-phenyl]-benzenesulfonamide |
| C12 | 3-Chloro-4-fluoro-N-[2-fluoro-4-(2-methyl-8-trifluoromethyl-quinolin-4-yloxy)-phenyl]-benzenesulfonamide |
| C13 | 2-Methyl-3H-imidazole-4-sulfonic acid [3-fluoro-4-(2-methyl-8-trifluoromethyl-quinolin-4-yloxy)-phenyl]-amide |
| C14 | 4-(3,5-Dimethyl-isoxazol-4-ylmethoxy)-N-[3-fluoro-4-(2-methyl-8-trifluoromethyl-quinolin-4-yloxy)-phenyl]-benzenesulfonamide |
| C15 | Biphenyl-4-sulfonic acid [2-fluoro-4-(2-methyl-8-trifluoromethyl-quinolin-4-yloxy)-phenyl-amide |
| C16 | N-[2-Fluoro-4-(2-methyl-8-trifluoromethyl-quinolin-4-yloxy)-phenyl]-3-pyrimidin-2-yl-benzenesulfonamide |
| C17 | Benzo[b]thiophene-2-sulfonic acid [2-fluoro-4-(2-methyl-8-trifluoromethyl-quinolin-4-yloxy)-phenyl]-amide |
| C18 | Benzo[b]thiophene-3-sulfonic acid [2-fluoro-4-(2-methyl-8-trifluoromethyl-quinolin-4-yloxy)-phenyl]-amide |
| C19 | 1-Methyl-2-oxo-2,3-dihydro-1H-indole-5-sulfonic acid [2-fluoro-4-(2-methyl-8-trifluoromethyl-quinolin-4-yloxy)-phenyl]-amide |
| D1 | Biphenyl-3-sulfonic acid [4-(7-benzyloxy-6-methoxy-quinolin-4-yloxy)-2-fluoro-phenyl]-amide |
| D2 | Naphthalene-1-sulfonic acid {4-[7-(3-amino-propoxy)-6-methoxy-quinolin-4-yloxy)-3-fluoro-phenyl}-amide |
| D3 | Biphenyl-3-sulfonic acid {4-[7-(3-amino-propoxy)-6-methoxy-quinolin-4-yloxy)-3-fluoro-phenyl}-amide |
| D4 | Biphenyl-3-sulfonic acid {3-fluoro-4-[6-methoxy-7-(2-morpholin-4-yl-ethoxy)-quinolin-4-yloxy]-phenyl}-amide |
| D5 | N-{3-Fluoro-4-[6-methoxy-7-(2-morpholin-4-yl-ethoxy)-quinolin-4-yloxy]-phenyl}-2-trifluoromethyl-benzenesulfonamide |
| D6 | N-{3-Fluoro-4-[6-methoxy-7-(2-morpholin-4-yl-ethoxy)-quinolin-4-yloxy]-phenyl}-2-trifluoromethoxy-benzenesulfonamide |
| D7 | Biphenyl-3-sulfonic acid {4-[6-methoxy-7-(2-morpholin-4-yl-ethoxy)-quinolin-4-yloxy]-2-methyl-phenyl}-amide |
| D8 | N-{4-[6-Methoxy-7-(2-morpholin-4-yl-ethoxy)-quinolin-4-yloxy]-2-methyl-phenyl}-2-trifluoromethoxy-benzenesulfonamide |
| D9 | 2,5-Difluoro-N-{4-[6-methoxy-7-(2-morpholin-4-yl-ethoxy)-quinqlin-4-yloxy]-2-methyl-phenyl}-benzenesulfonamide |
| D10 | 2,5-Difluoro-N-{3-fluoro-4-[6-methoxy-7-(2-morpholin-4-yl-ethoxy)-quinolin-4-yloxy]-phenyl}-benzenesulfonamide |

-continued

| Reference | |
|---|---|
| D11 | N-{4-[6-Methoxy-7-(2-morpholin-4-yl-ethoxy)-quinolin-4-yloxy]-2-methyl-phenyl}-2-trifluoromethyl-benzenesulfonamide |
| D12 | 4-Chloro-2-fluoro-N-{3-fluoro-4-[6-methoxy-7-(2-morpholin-4-yl-ethoxy)-quinolin-4-yloxy]-phenyl}-benzenesulfonamide |
| D13 | 4-Methoxy-naphthalene-1-sulfonic acid {3-fluoro-4-[6-methoxy-7-(2-morpholin-4-yl-ethoxy)-quinolin-4-yloxy]-phenyl}-amide |
| D14 | N-{4-[7-(3-Amino-propoxy)-6-methoxy-quinolin-4-yloxy]-3-fluoro-phenyl}-2-trifluoromethyl-benzenesulfonamide |
| D15 | N-{4-[7-(3-Amino-propoxy)-6-methoxy-quinolin-4-yloxy]-3-fluoro-phenyl}-2-trifluoromethoxy-benzenesulfonamide |
| D16 | (3-{4-[2-Fluoro-4-(2-trifluoromethoxy-benzenesulfonylamino)-phenoxy]-6-methoxy-quinolin-7-yloxy}-propyl)-carbamic acid tert-butyl ester |
| D17 | N-(3-Fluoro-4-{6-methoxy-7-[3-(4-methyl-piperidin-1-yl)-propoxy]-quinolin-4-yloxy}-phenyl)-2-trifluoromethyl-benzenesulfonamide |
| D18 | 2-Bromo-N-(3-fluoro-4-{6-methoxy-7-[3-(4-methyl-piperidin-1-yl)-propoxy]-quinolin-4-yloxy}-phenyl)-benzenesulfonamide |
| D19 | 2,4-Difluoro-N-(3-fluoro-4-{6-methoxy-7-[3-(4-methyl-piperidin-1-yl)-propoxy]-quinolin-4-yloxy}-phenyl)-benzenesulfonamide |
| D20 | 2,6-Difluoro-N-(3-fluoro-4-{6-methoxy-7-[3-(4-methyl-piperidin-1-yl)-propoxy]-quinolin-4-yloxy}-phenyl)-benzenesulfonamide |
| D21 | Naphthalene-1-sulfonic acid (3-fluoro-4-{6-methoxy-7-[3-(4-methyl-piperidin-1-yl)-propoxy]-quinolin-4-yloxy}-phenyl)-amide |
| D22 | Propane-1-sulfonic acid (3-fluoro-4-{6-methoxy-7-[3-(4-methyl-piperidin-1-yl)-propoxy]-quinolin-4-yloxy}-phenyl)-amide |
| D23 | 2-Cyano-N-(3-fluoro-4-{6-methoxy-7-[3-(4-methyl-piperidin-1-yl)-propoxy]-quinolin-4-yloxy}-phenyl)-benzenesulfonamide |
| D24 | 4-Chloro-2-fluoro-N-(3-fluoro-4-{6-methoxy-7-[3-(3-methyl-piperidin-1-yl)-propoxy]-quinolin-4-yloxy}-phenyl)-benzenesulfonamide |
| D25 | Butane-1-sulfonic acid (3-fluoro-4-{6-methoxy-7-[3-(3-methyl-piperidin-1-yl)-propoxy]-quinolin-4-yloxy}-phenyl)-amide |
| D26 | 2-Bromo-N-{3-fluoro-4-[6-methoxy-7-(2-morpholin-4-yl-ethoxy)-quinolin-4-yloxy]-phenyl}-benzenesulfonamide |
| D27 | 2-Cyano-N-{3-fluoro-4-[6-methoxy-7-(2-morpholin-4-yl-ethoxy)-quinolin-4-yloxy]-phenyl}-benzenesulfonamide |
| D28 | 2,4-Difluoro-N-{3-fluoro-4-[6-methoxy-7-(2-morpholin-4-yl-ethoxy)-quinolin-4-yloxy]-phenyl}-benzenesulfonamide |
| D29 | Biphenyl-3-sulfonic acid (3-fluoro-4-{6-methoxy-7-[3-(4-methyl-piperidin-1-yl)-propoxy]-quinolin-4-yloxy}-phenyl)-amide |
| D30 | 2-Fluoro-N-(3-fluoro-4-{6-methoxy-7-[3-(3-methyl-piperidin-1-yl)-propoxy]-quinolin-4-yloxy}-phenyl)-benzenesulfonamide |
| D31 | 2-Cyano-N-(3-fluoro-4-{6-methoxy-7-[3-(3-methyl-piperidin-1-yl)-propoxy]-quinolin-4-yloxy}-phenyl)-benzenesulfonamide |
| D32 | 2,6-Difluoro-N-(3-fluoro-4-{6-methoxy-7-[3-(3-methyl-piperidin-1-yl)-propoxy]-quinolin-4-yloxy}-phenyl)-benzenesulfonamide |
| D33 | N-(3-Fluoro-4-{6-methoxy-7-[3-(4-methyl-piperidin-1-yl)-propoxy]-quinolin-4-yloxy}-phenyl)-2-trifluoromethoxy-benzenesulfonamide |
| D34 | 2,5-Difluoro-N-(3-fluoro-4-{6-methoxy-7-[3-(4-methyl-piperidin-1-yl)-propoxy]-quinolin-4-yloxy}-phenyl)-benzenesulfonamide |
| D35 | N-(3-Fluoro-4-{6-methoxy-7-[3-(3-methyl-piperidin-1-yl)-propoxy]-quinolin-4-yloxy}phenyl)-2-trifluoromethyl-benzenesulfonamide |
| D36 | 2,5-Difluoro-N-(3-fluoro-4-{6-methoxy-7-[3-(3-methyl-piperidin-1-yl)-propoxy]-quinolin-4-yloxy}-phenyl)-benzenesulfonamide |
| D37 | Biphenyl-3-sulfonic acid (3-fluoro-4-{6-methoxy-7-[3-(3-methyl-piperidin-1-yl)-propoxy]-quinolin-4-yloxy}-phenyl)-amide |
| D38 | 4-Fluoro-N-(3-fluoro-4-{6-methoxy-7-[3-(3-methyl-piperidin-1-yl)-propoxy]-quinolin-4-yloxy}-phenyl)-3-methoxy-benzenesulfonamide |
| D39 | N-{3-Fluoro-4-[6-methoxy-7-(3-morpholin-4-yl-propoxy)-quinolin-4-yloxy]-phenyl}-2-trifluoromethyl-benzenesulfonamide |
| D40 | N-{3-Fluoro-4-[6-methoxy-7-(3-morpholin-4-yl-propoxy)-quinolin-4-yloxy]-phenyl}-2-trifluoromethoxy-benzenesulfonamide |
| D41 | 2,5-Difluoro-N-{3-fluoro-4-[6-methoxy-7-(3-morpholin-4-yl-propoxy)-quinolin-4-yloxy]-phenyl}-benzenesulfonamide |
| D42 | Biphenyl-3-sulfonic acid {3-fluoro-4-[6-methoxy-7-(3-morpholin-4-yl-propoxy)-quinolin-4-yloxy]-phenyl}-amide |
| D43 | 4-Chloro-2-fluoro-N-{3-fluoro-4-[6-methoxy-7-(3-morpholin-4-yl-propoxy)-quinolin-4-yloxy]-phenyl}-benzenesulfonamide |
| D44 | 4-Fluoro-N-{3-fluoro-4-[6-methoxy-7-(3-morpholin-4-yl-propoxy)-quinolin-4-yloxy]-phenyl}-3-methoxy-benzenesulfonamide |
| D45 | 2-Fluoro-N-{3-fluoro-4-[6-methoxy-7-(3-morpholin-4-yl-propoxy)-quinolin-4-yloxy]-phenyl}-benzenesulfonamide |
| D46 | N-{3-Fluoro-4-[6-methoxy-7-(3-morpholin-4-yl-propoxy)-quinolin-4-yloxy]-phenyl}-2-nitro-benzenesulfonamide |
| D47 | 2,6-Dichloro-N-{3-fluoro-4-[6-methoxy-7-(3-morpholin-4-yl-propoxy)-quinolin-4-yloxy]-phenyl}-benzenesulfonamide |
| D48 | Naphthalene-1-sulfonic acid {3-fluoro-4-[6-methoxy-7-(3-morpholin-4-yl-propoxy)-quinolin-4-yloxy]-phenyl}-amide |
| D49 | 2-Bromo-N-{3-fluoro-4-[6-methoxy-7-(3-morpholin-4-yl-propoxy)-quinolin-4-yloxy]-phenyl}-benzenesulfonamide |

Preparation of Starting Materials

The compounds are suitable for use in medicine, particularly in human medicine, but also in veterinary medicine. The compounds may be administered in a pharmaceutically effective amount by any suitable route to subjects in need thereof, e.g. parenterally, topically, rectally, nasally, bucally, vaginally, transdermally, by inhalation, by injection or infusion, by spray or via implanted reservoirs. Preferably, the compounds are administered orally or by injection or infusion, e.g. intravenously. For medical purposes, the compounds are preferably formulated as a pharmaceutical composition, which includes at least one compound as described above, and pharmaceutically acceptable carriers, diluents and/or adjuvants. The pharmaceutical composition may e.g. be a solid dosage form, e.g. a tablet, a capsule etc., or a liquid dosage form, e.g. an injectable or infundible solution.

The dosage of the compounds may be determined by a skilled practitioner according to the type and severity of the disorder to be treated. In general, the dosage of the compound may vary from 0.0001 to 1000 or even more mg/day.

The compounds may be administered as a monotherapy or together with further active agents, particularly chemotherapeutic agents or antitumor antibodies.

The compounds may be produced, for example, according to synthesis routes as depicted in schemes 1 to 3. Starting compounds necessary for the synthesis of the compounds are commercially available or alternatively can be easily produced by conventional methods. In the schemes, $R^1$ to $R^{10}$ are as defined in formula (I).

The 4-chloroquinoline derivatives can be synthesized from substituted anilines by methods described in Org. Synth. Col. Vol. 3, 272 (1955) or from substituted acetophenones by methods described in EP 1153920 (Scheme 1).

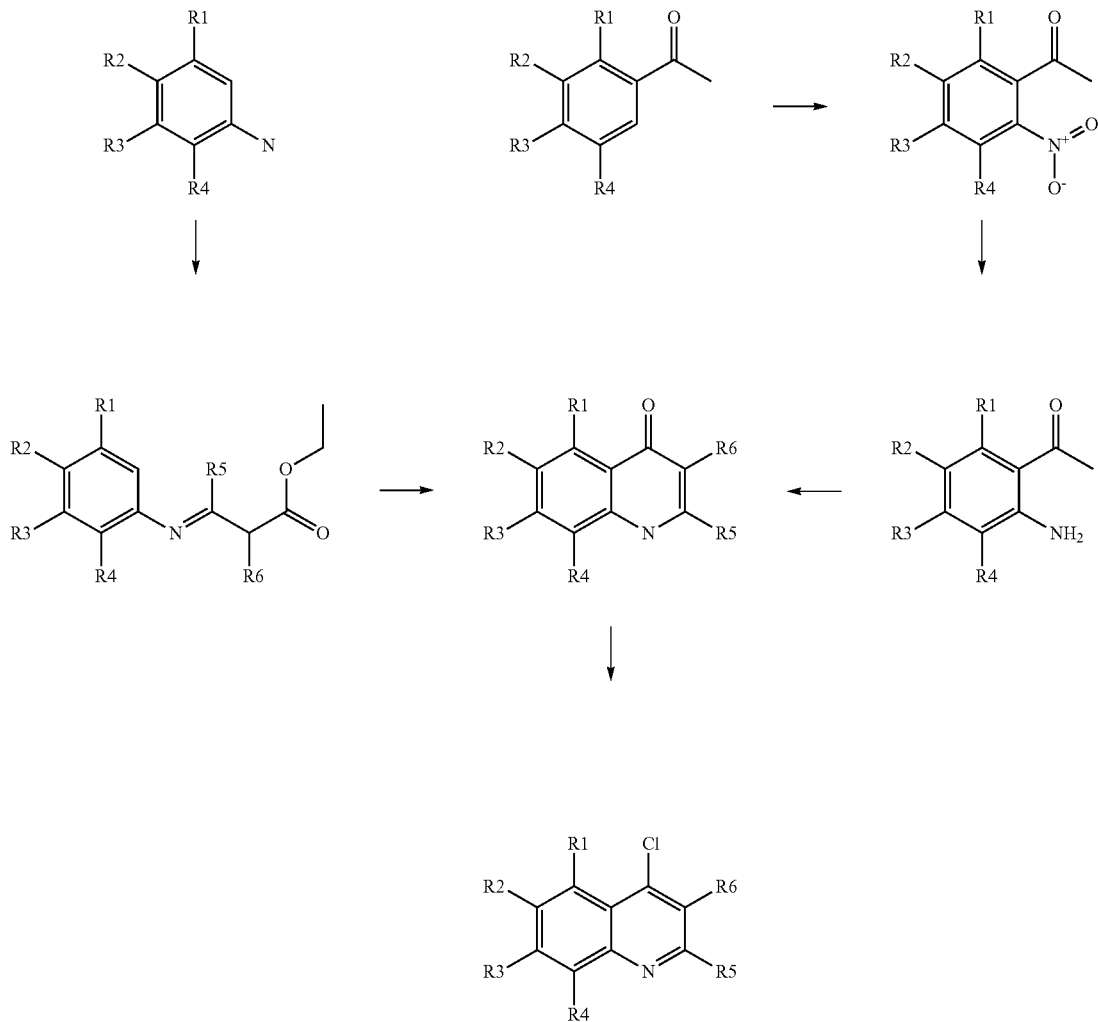

Scheme 1.

A 4-(aminophenoxy)quinoline derivative may be produced by reacting a nitrophenol derivative with the 4-chloroquinoline derivative in a suitable solvent, for example, chlorobenzene, to synthesize a 4-(nitrophenoxy)quinoline derivative or a corresponding quinazoline derivative and then reacting the 4-(nitrophenoxy)quinoline derivative in a suitable solvent, for example, N,N-dimethyl formamide, in the presence of a catalyst, for example, palladium hydroxide-carbon or palladium-carbon, under a hydrogen atmosphere. The nitro group can also be reduced with zinc, iron or the like (Scheme 2).

Alternatively, the 4-(aminophenoxy)quinoline derivative can be produced by reacting an aminophenol derivative with the 4-chloroquinoline derivative in a suitable solvent, for example, dimethyl sulfoxide, in the presence of a base, for example, sodium hydride. Alternatively, the 4-(aminophenoxy)quinazoline derivative can also be produced by dissolving an aminophenol derivative in an aqueous sodium hydroxide solution and subjecting the solution to a two-phase reaction with a solution of the 4-chloroquinazoline derivative in a suitable organic solvent, for example, ethyl methyl ketone, in the presence of a phase transfer catalyst, for example, tetra-n-butylammonium chloride, or in the absence of a catalyst (Scheme 2).

Scheme 2.

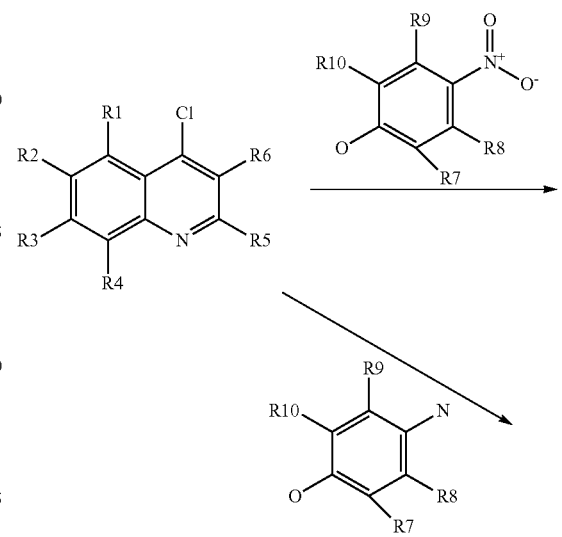

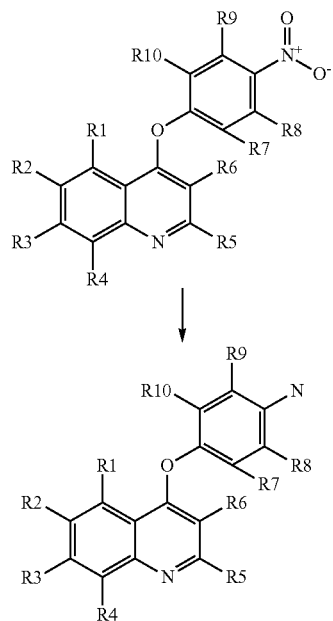

A 4-(sulfamoylphenoxy)quinoline derivative may be produced by reacting a 4-(aminophenoxy)quinoline derivative with sulfonyl chloride derivative in a suitable solvent, for example, pyridine (Scheme 3). The reaction may be carried out in room temperature. The solvent can be diluted with hydrochloric acid, when the product precipitated. The crystals can be collected by filtration and the obtained solid material can be dissolved in e.g. 10% sodium acetate solution and extracted e.g. with ethyl acetate. The organic layer can be washed e.g. with sodium chloride solution, dried and the solvent can be evaporated. The resulted solid can be treated with diisopropyl ether. The product can be purified with column chromatography (if necessary).

EXAMPLES

1) Analytical Methods (HPLC, NMR, TLC and Melting Point)

Analytical HPLC/MS was performed on an Waters HPLC/MS system using reverse phase Waters XTerra MS C18 (5 cm×4.6 mm, 5 um), gradient 0-95% B (0.00 min 5% B, 0.50 min 5% B, 5.50 min 95% B, 6.00 min 95% B, 6.50 min 5% B, 7.00 min 5% B), Solvent A: Water/0.05% HCOOH, Solvent B: AcCN/0.05% HCOOH over 7.00 min, flow=2.0 ml/min. Separation module was Waters Alliance 2795.

UV spectra were recorded using a Waters 996 DAD UV detector. Mass spectra were obtained using Waters SQD MS detector (Ionization: ES$^+$/ES$^-$, Source block temp: 120 C, Desolvation temp: 350° C., Desolvation Gas: 400 L/h, Cone Gas: 100 L/h, Capillary: 3000 V, Cone: 25 V, Extractor: 3 V, Rf Lens: 0.2 V, Scan: 120 to 1000 m/z in 1 sec., Inter-scan delay: 0.1 s).

$^1$H NMR spectra were recorded on a Bruker Avanve 300 MHz AV spectrometer in deuterated solvents (DMSO-d$_6$). Chemical shifts are in parts per million (ppm).

Thin-layer chromatography (TLC) analysis was performed with Kieselgel 60 F254 (Merck) plates and visualized using UV light.

Melting point measurement was Büchi melting Point B-54 instrument.

2) Manufacture of Compounds

The following Examples illustrate the preparation of specific compounds, and the AXL Kinase inhibitory properties thereof:

General Procedure for Sulfonamide Compounds (Type A-C):

0.31 mmol appropriately substituted sulfonylchloride and 0.3 mmol 4-(4-amino-phenoxy)quinoine derivative was dissolved 3 ml abs. pyridine and stirred at room temperature while the starting amine disappears (2-3 days). The reaction mixture was poured on ice cold 1M hydrochloric acid, stirred for 1 hour and the precipitated crystals were filtered out. The obtained solid material was dissolved in 10% sodium acetate solution and extracted with ethyl acetate. The organic layer was washed with sodium chloride solution, dried and the solvent was evaporated. The resulted solid was treated with diisopropyl ether. The product was purified with column chromatography (if it was necessary).

General Procedure for Sulfonamide Compounds (Type D):

0.31 mmol appropriately substituted sulfonylchloride and 0.3 mmol 4-(4-amino-phenoxy)quinoine derivative was dissolved 3 ml abs. pyridine and stirred at room temperature while the starting amine disappears (2-3 days). The reaction mixture was poured into 50 ml of water, extracted with 30 ml of chloroform, and separated the two layers. The organic phase was dried over anhydrous sodium sulfate, evaporated and the residue was purified on TLC plate (eluent chloroform-methanol 95:5, 9:1). The pure product was solidified over diisopropyl ether.

Example A1

3-Cyano-N-[4-(6,7-dimethoxy-quinolin-4-yloxy)-2-fluoro-phenyl]-enzenesulfonamide

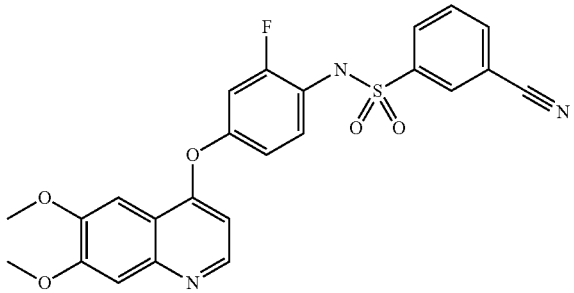 [SMILES: COc1cc2nccc(Oc3ccc(NS(=O)(=O)c4cccc(C#N)c4)c(F)c3)c2cc1OC]

$C_{24}H_{18}FN_3O_5S$ Mw. 479.49

LC/MS purity: 92%, m/z 480 [M+H]$^+$ Rt. 2.71 min.

$^1$H NMR (300 MHz, DMSO-d6): 10.46 (s, 1H), 8.51 (d, 1H), 8.15 (m, 2H), 8.04 (d, 2H), 7.82 (t, 1H), 7.41 (s, 1H), 7.40 (s, 1H), 7.28 (m, 2H), 7.07 (d, 1H), 6.56 (d, 1H), 3.94 (s, 3H), 3.90 (s, 3H)

Melting point: 223-224° C. Yield: 45%

Example A2

N-[4-(6,7-Dimethoxy-quinolin-4-yloxy)-2-fluoro-phenyl]-3-fluoro-benzenesulfonamide

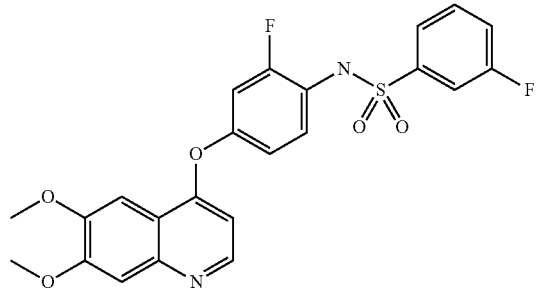 [SMILES: COc1cc2nccc(Oc3ccc(NS(=O)(=O)c4cccc(F)c4)c(F)c3)c2cc1OC]

$C_{23}H_{18}F_2N_2O_5S$ Mw. 472.47

LC/MS purity: 97%, m/z 471 [M−H]$^-$ Rt. 2.80 min.

$^1$H NMR (300 MHz, DMSO-d6): 10.37 (s, 1H), 8.51 (d, 1H), 7.76-7.23 (m, 8H), 7.07 (d, 1H), 6.56 (d, 1H), 3.94 (s, 3H), 3.90 (s, 3H)

Melting point: 233-235° C. Yield: 49%

Example A3

N-[4-(6,7-Dimethoxy-quinolin-4-yloxy)-2-fluoro-phenyl]-3,4-difluoro-benzenesulfonamide

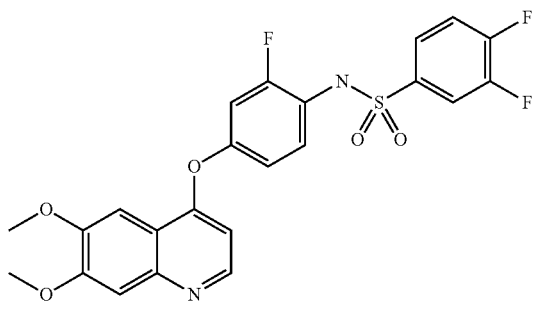 [SMILES: COc1cc2nccc(Oc3ccc(NS(=O)(=O)c4ccc(F)c(F)c4)c(F)c3)c2cc1OC]

$C_{23}H_{17}F_3N_2O_5S$ Mw. 490.46

LC/MS purity: 94%, m/z 489 [M−H]$^-$ Rt. 2.89 min.

$^1$H NMR (300 MHz, DMSO-d6): 10.38 (s, 1H), 8.50 (d, 1H), 7.81-7.61 (m, 3H), 7.41 (s, 1H), 7.40 (s, 1H), 7.29 (m, 2H), 7.07 (d, 1H), 6.57 (d, 1H), 3.94 (s, 3H), 3.90 (s, 3H)

Melting point: 217-219° C. Yield: 38%

Example A4

Thiophene-2-sulfonic acid 4-(6,7-dimethoxy-quinolin-4-yloxy)-2-fluoro-phenyl]-amide

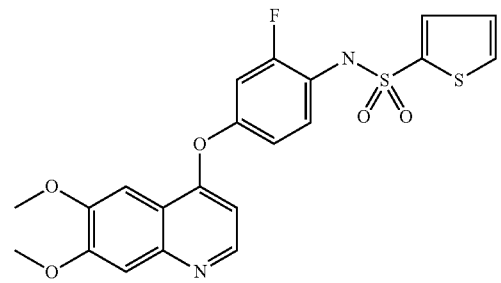

$C_{21}H_{17}FN_2O_5S_2$ Mw. 460.51

LC/MS purity: 96%, m/z 459 [M−H]$^-$ Rt. 2.66 min.

$^1$H NMR (300 MHz, DMSO-d6): 10.35 (s, 1H), 8.52 (d, 1H), 7.96 (d, 1H), 7.52 (d, 1H), 7.43 (s, 1H), 7.41 (s, 1H), 7.32 (m, 1H), 7.17 (t, 1H), 7.09 (d, 1H), 6.67 (d, 1H), 3.94 (s, 3H), 3.90 (s, 3H)

Melting point: 214-216° C. Yield: 37%

Example A5

3,5-Dichloro-N-[4-(6,7-dimethoxy-quinolin-4-yloxy)-2-fluoro-phenyl]-2-hydroxy-benzenesulfonamide

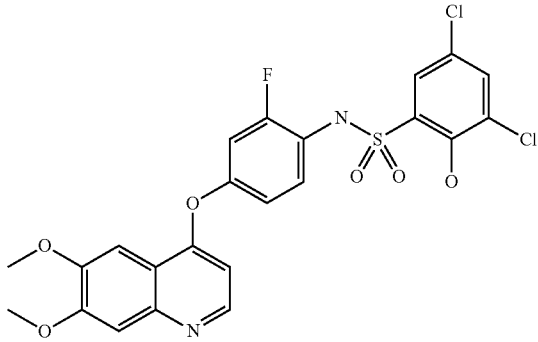

$C_{23}H_{17}Cl_2FN_2O_6S$ Mw. 539.37

LC/MS purity: 96%, m/z 537 [M−H]⁻ Rt. 3.01 min.

¹H NMR (300 MHz, DMSO-d6): 8.52 (d, 1H), 7.76 (d, 1H), 7.48 (d, 1H), 7.44 (s, 1H), 7.41 (s, 1H), 7.35 (m, 1H), 7.25 (dd, 1H), 7.04 (d, 1H), 6.57 (d, 1H), 3.95 (s, 3H), 3.91 (s, 3H), 3.6 (bs, 2H)

Melting point: 232-234° C. Yield: 35%

Example A6

N-[4-(6,7-Dimethoxy-quinolin-4-yloxy)-2-fluoro-phenyl]-3-fluoro-4-methyl-benzenesulfonamide

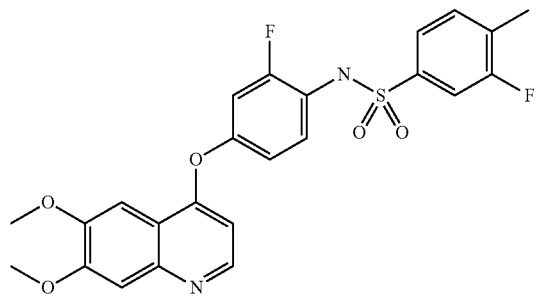 [SMILES: COc1cc2nccc(Oc3ccc(NS(=O)(=O)c4ccc(C)c(F)c4)c(F)c3)c2cc1OC]

$C_{24}H_{20}F_2N_2O_5S$ Mw. 486.50

LC/MS purity: 95%, m/z 485 [M−H]⁻ Rt. 2.93 min.

¹H NMR (300 MHz, DMSO-d6): 10.28 (s, 1H), 8.51 (d, 1H), 7.55-7.23 (m, 7H), 7.07 (dd, 1H), 6.56 (d, 1H), 3.94 (s, 3H), 3.90 (s, 3H), 2.31 (s, 3H)

Melting point: 211-212° C. Yield: 54%

Example A7

N-{5-[4-(6,7-Dimethoxy-quinolin-4-yloxy)-2-fluoro-phenylsulfamoyl]-4-methyl-thiophen-2-yl}-acetamide

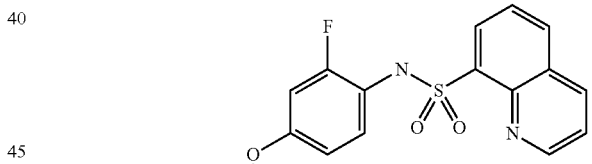

$C_{24}H_{22}FN_3O_6S_2$ Mw. 531.59

LC/MS purity: 98%, m/z 533 [M+H]⁺ Rt. 2.53 min.

¹H NMR (300 MHz, DMSO-d6): 12.52 (s, 1H), 10.33 (s, 1H), 8.50 (d, 1H), 7.36 (m, 4H), 7.11 (d, 1H), 6.51 (d, 1H), 3.94 (s, 3H), 3.90 (s, 3H), 2.30 (s, 3H), 2.16 (s, 3H)

Melting point: 133-135° C. Yield: 48%

Example A8

Quinoline-8-sulfonic acid [4-(6,7-dimethoxy-quinolin-4-yloxy)-2-fluoro-phenyl]-amide $C_{26}H_{20}FN_3O_5S$ Mw. 505.53

LC/MS purity: 97%, m/z 506 [M+H]⁺ Rt. 2.81 min.

¹H NMR (300 MHz, DMSO-d6): 9.75 (s, 1H), 9.11 (d, 1H), 8.58 (d, 1H), 8.48 (d, 1H), 8.30 (m, 2H), 7.74 (m, 2H), 7.19 (m, 3H), 7.03 (d, 1H), 6.96 (d, 1H), 6.48 (s, 1H), 3.92 (s, 3H), 3.86 (s, 3H)

Melting point: 255-257° C. Yield: 36%

Example A9

3-[4-(6,7-Dimethoxy-quinolin-4-yloxy)-2-fluoro-phenylsulfamoyl]-thiophene-2-carboxylic acid methyl ester

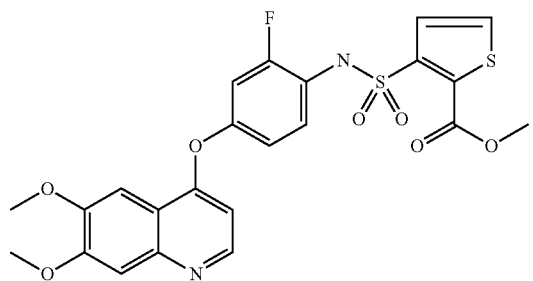

$C_{23}H_{19}FN_2O_7S_2$ Mw. 518.54

LC/MS purity: 96%, m/z 519 [M+H]⁺ Rt. 2.84 min.

$^1$H NMR (300 MHz, DMSO-d6): 9.80 (s, 1H), 8.51 (d, 1H), 7.97 (d, 1H), 7.39 (m, 4H), 7.26 (d, 1H), 7.05 (d, 1H), 6.55 (d, 1H), 3.94 (s, 3H), 3.89 (s, 3H), 3.88 (s, 3H).

Melting point: 189-190° C. Yield: 45%

Example A10

N-[4-(6,7-Dimethoxy-quinolin-4-yloxy)-2-fluoro-phenyl]-benzenesulfonamide

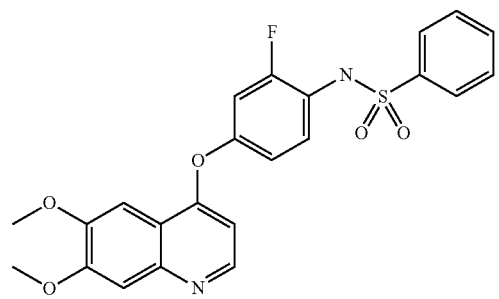 [SMILES: COc1cc2nccc(Oc3ccc(NS(=O)(=O)c4ccccc4)c(F)c3)c2cc1OC]

$C_{23}H_{19}FN_2O_5S$ Mw. 454.48

LC/MS purity: 98%, m/z 453 [M−H]⁻ Rt. 2.70 min.

$^1$H NMR (300 MHz, DMSO-d6): 10.22 (s, 1H), 8.50 (d, 1H), 7.75-7.56 (m, 5H), 7.41 (s, 1H), 7.40 (s, 1H), 7.32 (t, 1H), 7.23 (dd, 1H), 7.06 (d, 1H), 6.53 (d, 1H), 3.94 (s, 3H), 3.90 (s, 3H)

Melting point: 234-235° C. Yield: 59%

Example A11

4-Bromo-N-[4-(6,7-dimethoxy-quinolin-4-yloxy)-2-fluoro-phenyl]-3-fluoro-benzenesulfonamide

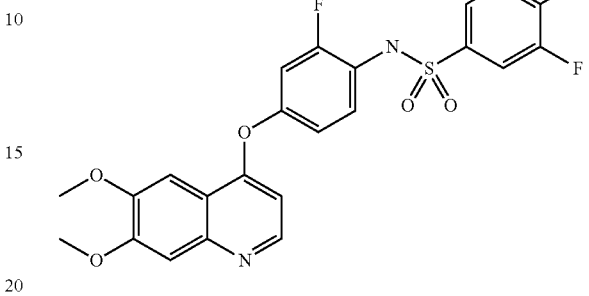

$C_{23}H_{17}BrF_2N_2O_5S$ Mw. 551.37

LC/MS purity: 97%, m/z 551 [M+H]⁺ Rt. 3.06 min.

$^1$H NMR (300 MHz, DMSO-d6): 10.46 (s, 1H), 8.51 (d, 1H), 7.99 (t, 1H), 7.67 (dd, 1H), 7.50 (dd, 1H), 7.41 (s, 1H), 7.40 (s, 1H), 7.30 (m, 2H), 7.07 (d, 1H), 6.58 (d, 1H), 3.94 (s, 3H), 3.90 (s, 3H).

Melting point: 209-211° C. Yield: 62%

Example A12

3-Chloro-N-[4-(6,7-dimethoxy-quinolin-4-yloxy)-2-fluoro-phenyl]-4-fluoro-benzenesulfonamide

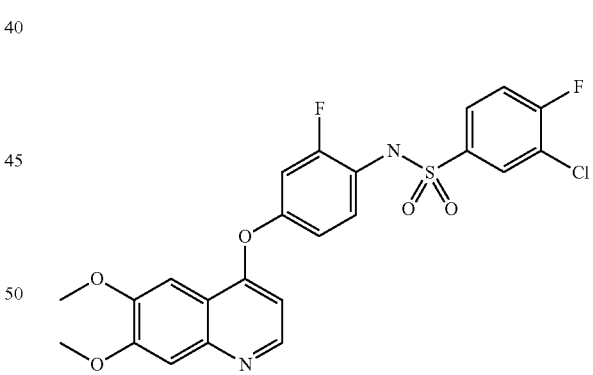

$C_{23}H_{17}ClF_2N_2O_5S$ Mw. 506.92

LC/MS purity: 95%, m/z 505 [M−H]⁻ Rt. 3.00 min.

$^1$H NMR (300 MHz, DMSO-d6): 10.39 (s, 1H), 8.51 (d, 1H), 7.89 (dd, 1H), 7.72 (m, 2H), 7.41 (s, 1H), 7.40 (s, 1H), 7.30 (m, 2H), 7.08 (dd, 1H), 6.56 (d, 1H), 3.94 (s, 3H), 3.90 (s, 3H)

Melting point: 208-210° C. Yield: 65%

Example A13

4-Chloro-N-[4-(6,7-dimethoxy-quinolin-4-yloxy)-2-fluoro-phenyl]-2-fluoro-benzenesulfonamide

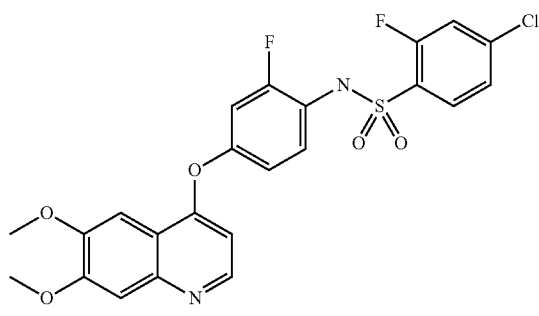

$C_{23}H_{17}ClF_2N_2O_5S$ Mw. 506.92

LC/MS purity: 95%, m/z 505 [M−H]⁻ Rt. 2.97 min.

¹H NMR (300 MHz, DMSO-d6): 10.63 (s, 1H), 8.52 (d, 1H), 7.76 (dd, 1H), 7.70 (t, 1H), 7.48-7.25 (m, 5H), 7.07 (d, 1H), 6.55 (d, 1H), 3.94 (s, 3H), 3.90 (s, 3H).

Melting point: 218-219° C. Yield: 53%

Example A14

N-[4-(6,7-Dimethoxy-quinolin-4-yloxy)-2-fluoro-phenyl]-2,6-difluoro-benzenesulfonamide

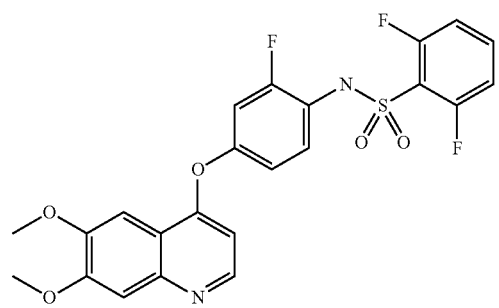 [SMILES: COc1cc2nccc(Oc3ccc(NS(=O)(=O)c4c(F)cccc4F)c(F)c3)c2cc1OC]

$C_{23}H_{17}F_3N_2O_5S$ Mw. 490.46

LC/MS purity: 96%, m/z 489 [M−H]⁻ Rt. 2.73 min.

¹H NMR (300 MHz, DMSO-d6): 10.82 (s, 1H), 8.52 (d, 1H), 7.73 (m, 1H), 7.41 (s, 1H), 7.40 (s, 1H), 7.32 (m, 4H), 7.09 (d, 1H), 6.54 (d, 1H), 3.94 (s, 3H), 3.90 (s, 3H)

Melting point: 223-225° C. Yield: 45%

Example A15

3-Difluoromethoxy-N-[4-(6,7-dimethoxy-quinolin-4-yloxy)-2-fluoro-phenyl]-benzenesulfonamide

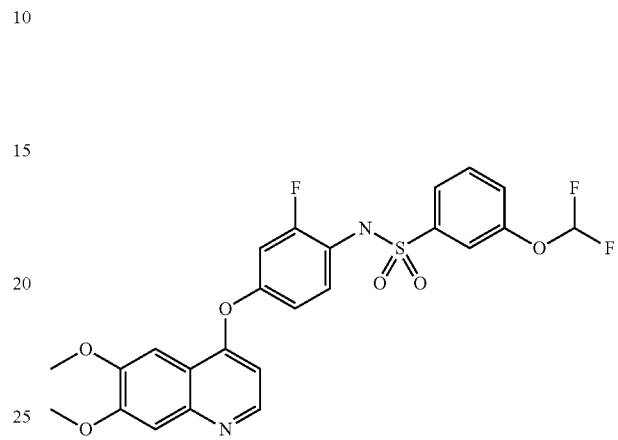

$C_{24}H_{19}F_3N_2O_6S$ Mw. 520.49

LC/MS purity: 98%, m/z 519 [M−H]⁻ Rt. 2.93 min.

¹H NMR (300 MHz, DMSO-d6): 10.36 (s, 1H), 8.50 (d, 1H), 7.62 (m, 2H), 7.49 (m, 2H), 7.41 (s, 1H), 7.40 (s, 1H), 7.35-7.23 (m, 2H), 7.07 (d, 1H), 6.64 (d, 1H), 3.94 (s, 3H), 3.90 (s, 3H)

Melting point: 238-239° C. Yield: 61%

Example A16

2-Phenyl-ethenesulfonic acid [4-(6,7-dimethoxy-quinolin-4-yloxy)-2-fluoro-phenyl]-amide

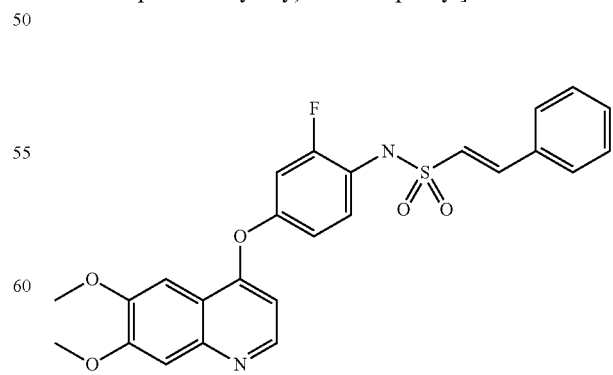

$C_{25}H_{21}FN_2O_5S$ Mw. 480.52

LC/MS purity: 98%, m/z 479 [M−H]⁻ Rt. 2.91 min.

¹H NMR (300 MHz, DMSO-d6): 9.94 (s, 1H), 8.48 (d, 1H), 7.71 (m, 2H), 7.52-7.29 (m, 9H), 7.09 (d, 1H), 6.55 (d, 1H), 3.94 (s, 3H), 3.90 (s, 3H) Melting point: 224-225° C. Yield: 26%

Example A17

Naphthalene-1-sulfonic acid [4-(6,7-dimethoxy-quinolin-4-yloxy)-2-fluoro-phenyl]-amide

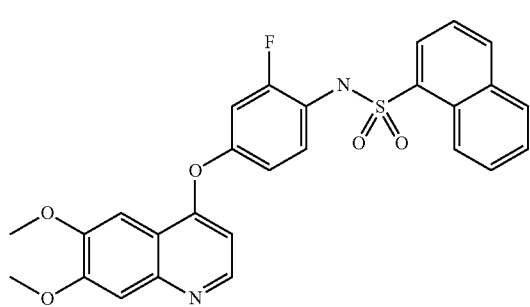 [SMILES: COc1cc2nccc(Oc3ccc(NS(=O)(=O)c4cccc5ccccc45)c(F)c3)c2cc1OC]

$C_{27}H_{21}FN_2O_5S$ Mw. 504.54

LC/MS purity: 98%, m/z 503 [M−H]⁻ Rt. 3.01 min.

¹H NMR (300 MHz, DMSO-d6): 10.51 (s, 1H), 8.71 (d, 1H), 8.49 (d, 1H), 8.25 (d, 1H), 8.10 (d, 2H), 7.71 (m, 2H), 7.62 (t, 1H), 7.38 (s, 2H), 7.28 (t, 1H), 7.12 (dd, 1H), 6.99 (d, 1H), 6.44 (d, 1H), 3.93 (s, 3H), 3.87 (s, 3H)

Melting point: 243-245° C. Yield: 41%

Example A18

2,5-Dichloro-thiophene-3-sulfonic acid [4-(6,7-dimethoxy-quinolin-4-yloxy)-2-fluoro-phenyl]-amide

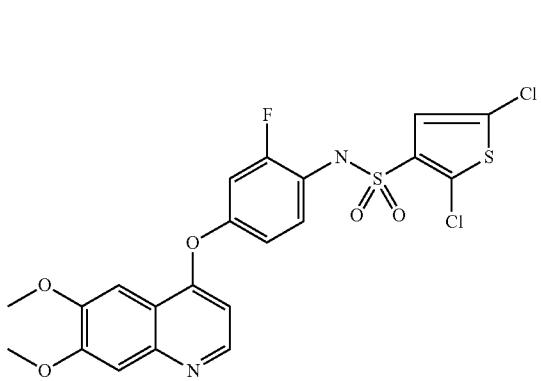 [SMILES: COc1cc2nccc(Oc3ccc(NS(=O)(=O)c4cc(Cl)sc4Cl)c(F)c3)c2cc1OC]

$C_{21}H_{15}Cl_2FN_2O_5S_2$ Mw. 529.40

LC/MS purity: 93%, m/z 527 [M−H]⁻ Rt. 3.05 min.

¹H NMR (300 MHz, DMSO-d6): 10.60 (s, 1H), 8.52 (d, 1H), 7.43-7.26 (m, 5H), 7.09 (d, 1H), 6.57 (d, 1H), 3.94 (s, 3H), 3.90 (s, 3H)

Melting point: 223-225° C. Yield: 35%

Example A19

4-Bromo-N-[4-(6,7-dimethoxy-quinolin-4-yloxy)-2-fluoro-phenyl]-3-methyl-benzenesulfonamide

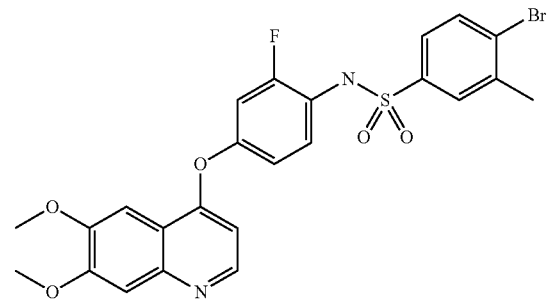 [SMILES: COc1cc2nccc(Oc3ccc(NS(=O)(=O)c4ccc(Br)c(C)c4)c(F)c3)c2cc1OC]

$C_{24}H_{20}BrFN_2O_5S$ Mw. 547.40

LC/MS purity: 95%, m/z 545 [M−H]⁻ Rt. 3.10 min.

¹H NMR (300 MHz, DMSO-d6): 10.28 (s, 1H), 8.51 (d, 1H), 7.82 (d, 1H), 7.71 (s, 1H), 7.46 (d, 1H), 7.41 (s, 1H), 7.40 (s, 1H), 7.30 (m, 1H), 7.06 (d, 1H), 6.55 (d, 1H), 3.94 (s, 3H), 3.90 (s, 3H), 2.41 (s, 3H)

Melting point: 199-201° C. Yield: 56%

Example A20

N-[4-(6,7-Dimethoxy-quinolin-4-yloxy)-2-fluoro-phenyl]-2,3,4-trifluoro-benzenesulfonamide $C_{23}H_{16}F_4N_2O_5S$ Mw. 508.45

LC/MS purity: 95%, m/z 507 [M−H]⁻ Rt. 2.92 min.

¹H NMR (300 MHz, DMSO-d6): 10.78 (s, 1H), 8.52 (d, 1H), 7.63-7.27 (m, 6H), 7.07 (d, 1H), 6.57 (d, 1H), 3.94 (s, 3H), 3.90 (s, 3H)

Melting point: 188-190° C. Yield: 38%

Example A21

5-Methyl-thiophene-2-sulfonic acid [4-(6,7-dimethoxy-quinolin-4-yloxy)-2-fluoro-phenyl]-amide

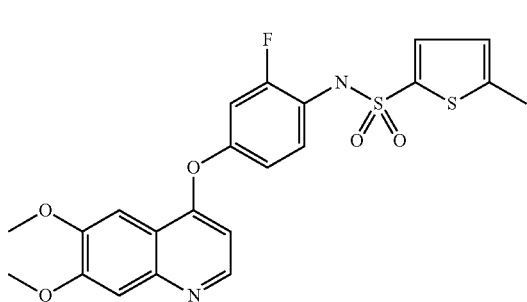

$C_{22}H_{19}FN_2O_5S_2$ Mw. 474.53

LC/MS purity: 97%, m/z 475 [M+H]$^+$ Rt. 2.60 min.

$^1$H NMR (300 MHz, DMSO-d6): 10.30 (s, 1H), 8.52 (d, 1H), 7.43-7.26 (m, 5H), 7.09 (d, 1H), 6.88 (d, 1H), 6.57 (d, 1H), 3.94 (s, 3H), 3.91 (s, 3H), 2.50 (s, 3H)

Melting point: 218-220° C. Yield: 68%

Example A22

Furan-2-sulfonic acid [4-(6,7-dimethoxy-quinolin-4-yloxy)-2-fluoro-phenyl]-amide

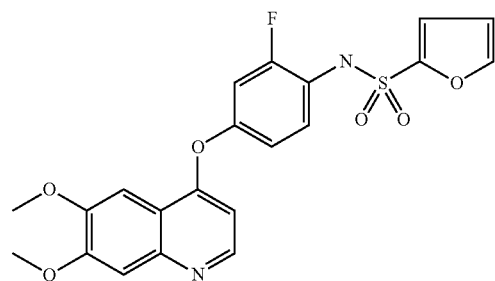 [SMILES: COc1cc2nccc(Oc3ccc(NS(=O)(=O)c4ccco4)c(F)c3)c2cc1OC]

$C_{21}H_{17}FN_2O_6S$ Mw. 444.44

LC/MS purity: 96%, m/z 443 [M−H]$^-$ Rt. 2.59 min.

$^1$H NMR (300 MHz, DMSO-d6): 10.53 (s, 1H), 8.52 (d, 1H), 8.02 (d, 1H), 7.42 (s, 1H), 7.41 (s, 1H), 7.30 (m, 2H), 7.08 (d, 1H), 7.06 (s, 1H), 6.67 (dd, 1H), 6.59 (d, 1H), 3.94 (s, 3H), 3.90 (s, 3H)

Melting point: 210-212° C. Yield: 59%

Example A23

N-[4-(6,7-Dimethoxy-quinolin-4-yloxy)-2-fluoro-phenyl]-3-trifluoromethyl-benzenesulfonamide

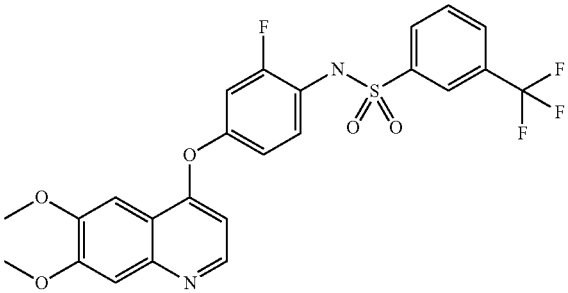 [SMILES: COc1cc2nccc(Oc3ccc(NS(=O)(=O)c4cccc(C(F)(F)F)c4)c(F)c3)c2cc1OC]

$C_{24}H_{18}F_4N_2O_5S$ Mw. 522.48

LC/MS purity: 94%, m/z 521 [M−H]$^-$ Rt. 3.03 min.

$^1$H NMR (300 MHz, DMSO-d6): 10.46 (s, 1H), 8.50 (d, 1H), 8.05 (m, 3H), 7.85 (t, 1H), 7.40 (s, 2H), 7.33 (t, 1H), 7.22 (dd, 1H), 7.08 (d, 1H), 6.53 (d, 1H, 3.94 (s, 3H), 3.89 (s, 3H)

Melting point: 230-231° C. Yield: 53%

Example A24

3-Bromo-N-[4-(6,7-dimethoxy-quinolin-4-yloxy)-2-fluoro-phenyl]-benzenesulfonamide

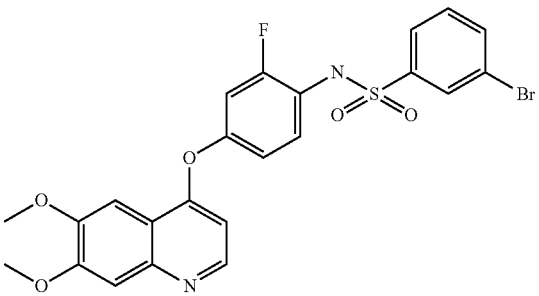 [SMILES: COc1cc2nccc(Oc3ccc(NS(=O)(=O)c4cccc(Br)c4)c(F)c3)c2cc1OC]

$C_{23}H_{18}BrFN_2O_5S$ Mw. 533.38

LC/MS purity: 96%, m/z 533 [M+H]$^+$ Rt. 2.96 min.

$^1$H NMR (300 MHz, DMSO-d6): 11.9 (bs, 1H), 8.45 (d, 1H), 7.81 (s, 1H), 7.70 (d, 1H), 7.64 (d, 1H), 7.42 (m, 3H), 7.23 (t, 1H), 6.98 (dd, 1H), 6.79 (d, 1H), 6.44 (d, 1H), 3.93 (s, 3H), 3.90 (s, 3H)

Melting point: 255-257° C. Yield: 37%

Example A25

3-Chloro-N-[4-(6,7-dimethoxy-quinolin-4-yloxy)-2-fluoro-phenyl]-benzenesulfonamide

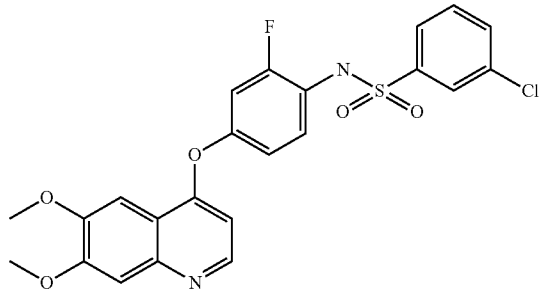 [SMILES: COc1cc2nccc(Oc3ccc(NS(=O)(=O)c4cccc(Cl)c4)c(F)c3)c2cc1OC]

$C_{23}H_{18}ClFN_2O_5S$ Mw. 488.93

LC/MS purity: 96%, m/z 487 [M−H]− Rt. 2.93 min.

$^1$H NMR (300 MHz, DMSO-d6): 10.38 (s, 1H), 8.49 (d, 1H), 7.65 (m, 4H), 7.42 (s, 1H), 7.39 (s, 1H), 7.30 (t, 1H), 7.18 (d, 1H), 7.00 (d, 1H), 6.52 (d, 1H), 3.93 (s, 3H), 3.90 (s, 3H)

Melting point: 250-251° C. Yield: 62%

Example A26

N-[4-(6,7-Dimethoxy-quinolin-4-yloxy)-2-fluoro-phenyl]-3-methyl-benzenesulfonamide

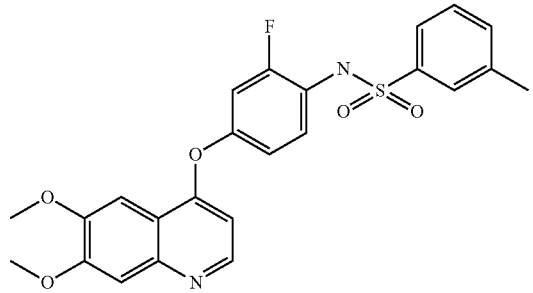

$C_{24}H_{21}FN_2O_5S$ Mw. 468.51

LC/MS purity: 98%, m/z 467 [M−H]− Rt. 2.85 min.

$^1$H NMR (300 MHz, DMSO-d6): 10.16 (s, 1H), 8.50 (d, 1H), 7.56-7.40 (m, 6H), 7.31 (t, 1H), 7.22 (dd, 1H), 7.04 (dd, 1H), 6.52 (d, 1H), 3.94 (s, 3H), 3.90 (s, 3H), 2.37 (s, 3H)

Melting point: 244-245° C. Yield: 49%

Example A27

N-[4-(6,7-Dimethoxy-quinolin-4-yloxy)-2-fluoro-phenyl]-3-methoxy-benzenesulfonamide

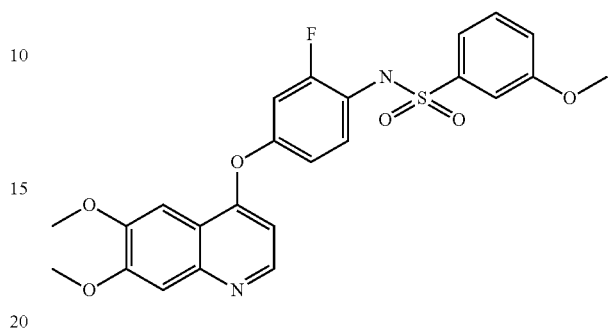

$C_{24}H_{21}FN_2O_6S$ Mw. 484.51

LC/MS purity: 95%, m/z 483 [M−H]− Rt. 2.78 min.

$^1$H NMR (300 MHz, DMSO-d6): 10.22 (s, 1H), 8.50 (d, 1H), 7.50 (t, 1H), 7.41 (s, 1H), 7.40 (s, 1H), 7.35-7.2 (m, 5H), 7.05 (dd, 1H), 6.53 (d, 1H), 3.94 (s, 3H), 3.90 (s, 3H), 3.80 (s, 3H)

Melting point: 224-225° C. Yield: 68%

Example A28

5-Chloro-thiophene-2-sulfonic acid [4-(6,7-dimethoxy-quinolin-4-yloxy)-2-fluoro-phenyl]-amide

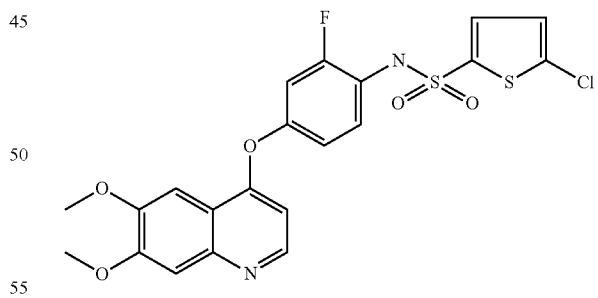

$C_{21}H_{16}ClFN_2O_5S_2$ Mw. 494.95

LC/MS purity: 94%, m/z 493 [M−H]− Rt. 2.94 min.

$^1$H NMR (300 MHz, DMSO-d6): 10.57 (s, 1H), 8.52 (d, 1H), 7.43-7.25 (m, 7H), 7.1 (d, 1H), 6.60 (d, 1H), 3.94 (s, 3H), 3.90 (s, 3H)

Melting point: 187-189° C. Yield: 54%

Example A29

5-Bromo-thiophene-2-sulfonic acid [4-(6,7-dimethoxy-quinolin-4-yloxy)-2-fluoro-phenyl]-amide

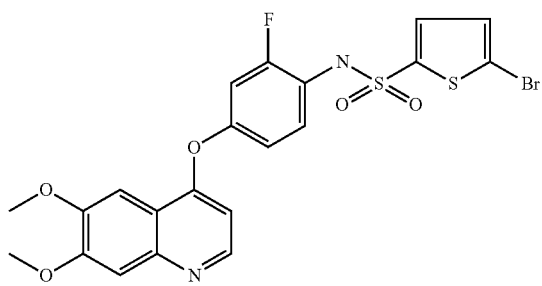 [SMILES: COc1cc2nccc(Oc3ccc(NS(=O)(=O)c4ccc(Br)s4)c(F)c3)c2cc1OC]

$C_{21}H_{16}BrFN_2O_5S_2$ Mw. 539.40

LC/MS purity: 95%, m/z 537 [M−H]⁻ Rt. 2.83 min.

¹H NMR (300 MHz, DMSO-d6): 10.55 (s, 1H), 8.52 (d, 1H), 7.40 (m, 6H), 7.1 (d, 1H), 6.59 (d, 1H), 3.95 (s, 3H), 3.91 (s, 3H)

Melting point: 207-209° C. Yield: 55%

Example A30

N-[4-(6,7-Dimethoxy-quinolin-4-yloxy)-2-fluoro-phenyl]-3-phenoxy-benzenesulfonamide

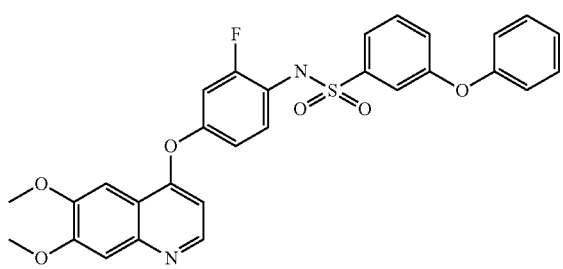 [SMILES: COc1cc2nccc(Oc3ccc(NS(=O)(=O)c4cccc(Oc5ccccc5)c4)c(F)c3)c2cc1OC]

$C_{29}H_{23}FN_2O_6S$ Mw. 546.58

LC/MS purity: 97%, m/z 545 [M−H]⁻ Rt. 3.23 min.

¹H NMR (300 MHz, DMSO-d6): 10.22 (bs, 1H), 8.49 (d, 1H), 7.61 (t, 1H), 7.44 (m, 5H), 7.27 (m, 5H), 7.04 (m, 3H), 6.54 (d, 1H), 3.95 (s, 3H), 3.90 (s, 3H)

Melting point: 179-180° C. Yield: 75%

Example A31

1-Ethyl-1H-pyrazole-4-sulfonic acid [4-(6,7-dimethoxy-quinolin-4-yloxy)-2-fluoro-phenyl]-amide

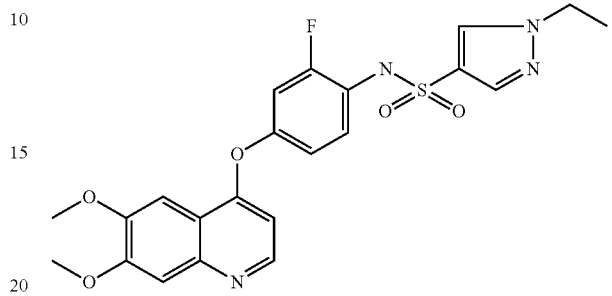

$C_{22}H_{21}FN_4O_5S$ Mw. 472.50

LC/MS purity: 98%, m/z 471 [M−H]⁻ Rt. 2.45 min.

¹H NMR (300 MHz, DMSO-d6): 9.94 (s, 1H), 8.51 (d, 1H), 8.23 (s, 1H), 7.68 (s, 1H), 7.43 (s, 1H), 7.41 (s, 1H), 7.28 (m, 2H), 7.07 (dd, 1H), 6.58 (d, 1H), 4.17 (q, 2H), 3.95 (s, 3H), 3.91 (s, 3H), 1.34 (t, 3H)

Melting point: 211-213° C. Yield: 49%

Example A32

1-Methyl-1H-imidazole-4-sulfonic acid [4-(6,7-dimethoxy-quinolin-4-yloxy)-2-fluoro-phenyl]-amide

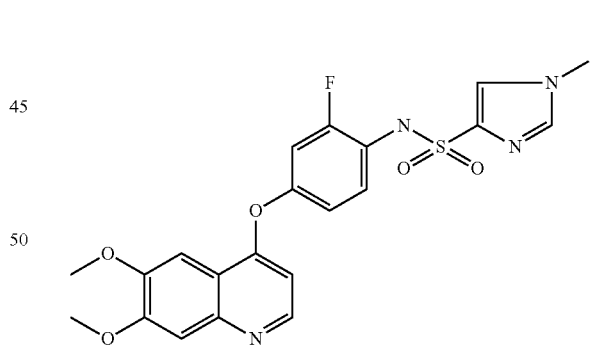

$C_{21}H_{19}FN_4O_5S$ Mw. 458.47

LC/MS purity: 98%, m/z 459 [M+H]⁺ Rt. 2.21 min.

¹H NMR (300 MHz, DMSO-d6): 9.97 (s, 1H), 8.51 (d, 2H), 7.78 (s, 1H), 7.73 (s, 1H), 7.41 (m, 3H), 7.23 (d, 1H), 7.03 (d, 1H); 6.55 (d, 1H), 3.94 (s, 3H), 3.91 (s, 3H), 3.68 (s, 3H)

Melting point: 215-217° C. Yield: 35%

Example A33

Cyclopropanesulfonic acid [4-(6,7-dimethoxy-quinolin-4-yloxy)-2-fluoro-phenyl]-amide

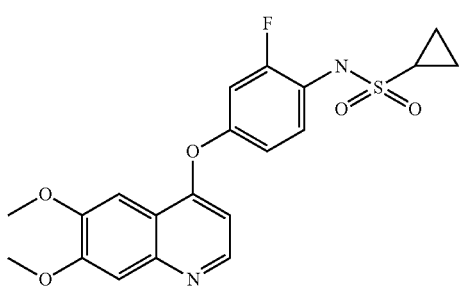 [SMILES: COc1cc2nccc(Oc3ccc(NS(=O)(=O)C4CC4)c(F)c3)c2cc1OC]

$C_{20}H_{19}FN_2O_5S$ Mw. 418.45

LC/MS purity: 98%, m/z 417 [M−H]⁻ Rt. 2.40 min.

¹H NMR (300 MHz, DMSO-d6): 9.64 (bs, 1H), 8.51 (bs, 1H), 7.44 (m, 4H), 7.11 (bs, 1H), 6.62 (bs, 1H), 3.94 (bs, 6H), 2.67 (bs, 1H), 0.97 (bs, 2H), 0.90 (bs, 2H)

Melting point: 179-180° C. Yield: 38%

Example A34

Biphenyl-3-sulfonic acid [4-(6,7-dimethoxy-quinolin-4-yloxy)-2-fluoro-phenyl]-amide

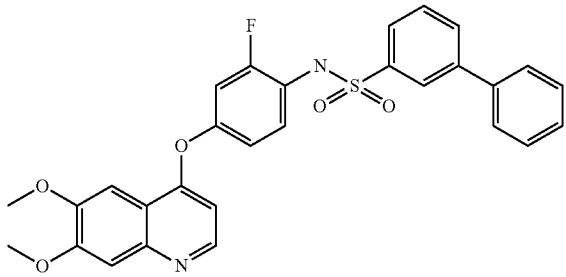 [SMILES: COc1cc2nccc(Oc3ccc(NS(=O)(=O)c4cccc(-c5ccccc5)c4)c(F)c3)c2cc1OC]

$C_{29}H_{23}FN_2O_5S$ Mw. 530.58

LC/MS purity: 98%, m/z 529 [M−H]⁻ Rt. 3.20 min.

¹H NMR (300 MHz, DMSO-d6): 10.25 (bs, 1H), 8.44 (d, 1H), 7.96 (m, 2H), 7.70 (m, 4H), 7.54-7.33 (m, 6H), 7.22 (bd, 1H), 7.06 (d, 1H), 6.48 (d, 1H), 3.94 (s, 3H), 3.89 (s, 3H)

Melting point: 193-195° C. Yield: 64%

Example A35

N-[4-(6,7-Dimethoxy-quinolin-4-yloxy)-2-fluoro-phenyl]-3-trifluoromethoxy-benzenesulfonamide

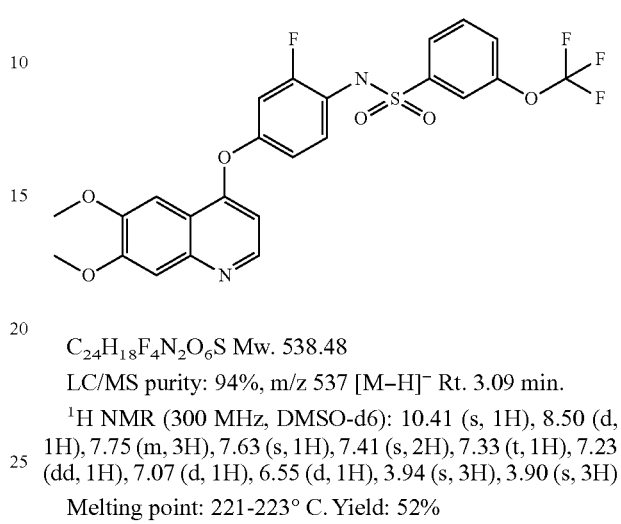

$C_{24}H_{18}F_4N_2O_6S$ Mw. 538.48

LC/MS purity: 94%, m/z 537 [M−H]⁻ Rt. 3.09 min.

¹H NMR (300 MHz, DMSO-d6): 10.41 (s, 1H), 8.50 (d, 1H), 7.75 (m, 3H), 7.63 (s, 1H), 7.41 (s, 2H), 7.33 (t, 1H), 7.23 (dd, 1H), 7.07 (d, 1H), 6.55 (d, 1H), 3.94 (s, 3H), 3.90 (s, 3H)

Melting point: 221-223° C. Yield: 52%

Example A36

5-Phenyl-thiophene-2-sulfonic acid [4-(6,7-dimethoxy-quinolin-4-yloxy)-2-fluoro-phenyl]-amide

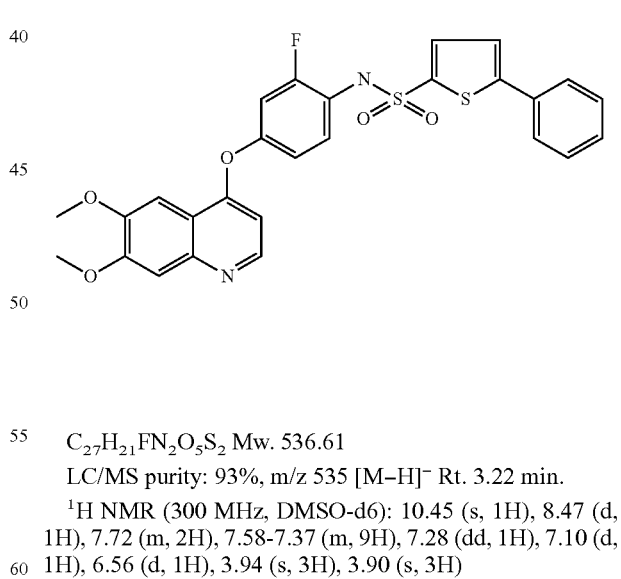

$C_{27}H_{21}FN_2O_5S_2$ Mw. 536.61

LC/MS purity: 93%, m/z 535 [M−H]⁻ Rt. 3.22 min.

¹H NMR (300 MHz, DMSO-d6): 10.45 (s, 1H), 8.47 (d, 1H), 7.72 (m, 2H), 7.58-7.37 (m, 9H), 7.28 (dd, 1H), 7.10 (d, 1H), 6.56 (d, 1H), 3.94 (s, 3H), 3.90 (s, 3H)

Melting point: 186-188° C. Yield: 52%

Example A37

5-Oxazol-5-yl-thiophene-2-sulfonic acid [4-(6,7-dimethoxy-quinolin-4-yloxy)-2-fluoro-phenyl]-amide

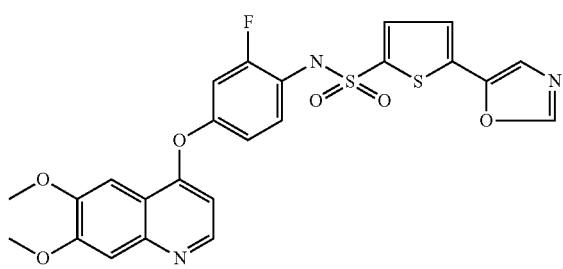 [SMILES: COc1cc2nccc(Oc3ccc(NS(=O)(=O)c4ccc(-c5cnco5)s4)c(F)c3)c2cc1OC]

C$_{24}$H$_{18}$FN$_3$O$_6$S$_2$ Mw. 527.55

LC/MS purity: 98%, m/z 528 [M+H]$^+$ Rt. 2.51 min.

$^1$H NMR (300 MHz, DMSO-d6): 10.56 (s, 1H), 8.52 (s, 1H), 8.51 (d, 1H), 7.77 (s, 1H), 7.53 (m, 2H), 7.39 (m, 3H), 7.29 (dd, 1H), 7.10 (d, 1H), 6.58 (d, 1H), 3.94 (s, 3H), 3.90 (s, 3H)

Melting point: 206-208° C. Yield: 36%

Example A38

N-[4-(6,7-Dimethoxy-quinolin-4-yloxy)-2-fluoro-phenyl]-3,5-difluoro-benzenesulfonamide

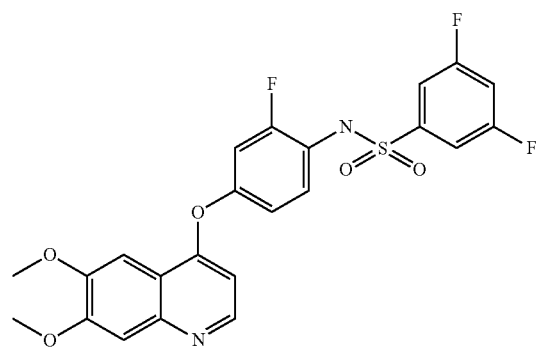 [SMILES: COc1cc2nccc(Oc3ccc(NS(=O)(=O)c4cc(F)cc(F)c4)c(F)c3)c2cc1OC]

C$_{23}$H$_{17}$F$_3$N$_2$O$_5$S Mw. 490.46

LC/MS purity: 96%, m/z 489 [M−H]$^-$ Rt. 2.91 min.

$^1$H NMR (300 MHz, DMSO-d6): 10.49 (s, 1H), 8.51 (d, 1H), 7.67 (m, 1H), 7.44-7.25 (m, 6H), 7.07 (dd, 1H), 6.59 (d, 1H), 3.94 (s, 3H), 3.90 (s, 3H)

Melting point: 243-245° C. Yield: 47%

Example A39

N-[4-(6,7-Dimethoxy-quinolin-4-yloxy)-2-fluoro-phenyl]-2,4-difluoro-benzenesulfonamide

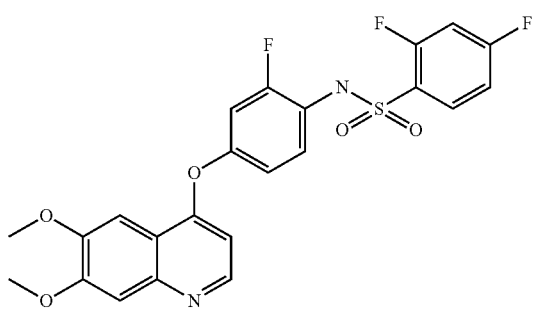 [SMILES: COc1cc2nccc(Oc3ccc(NS(=O)(=O)c4ccc(F)cc4F)c(F)c3)c2cc1OC]

C$_{23}$H$_{17}$F$_3$N$_2$O$_5$S Mw. 490.46

LC/MS purity: 95%, m/z 489 [M−H]$^-$ Rt. 2.81 min.

$^1$H NMR (300 MHz, DMSO-d6): 10.56 (s, 1H), 8.51 (d, 1H), 7.78 (dd, 1H), 7.56 (dd, 1H), 7.44-7.23 (m, 5H), 7.06 (dd, 1H), 6.55 (d, 1H), 3.94 (s, 3H), 3.89 (s, 3H)

Melting point: 212-214° C. Yield: 52%

Example A40

N-[4-(6,7-Dimethoxy-quinolin-4-yloxy)-2-fluoro-phenyl]-2,5-difluoro-benzenesulfonamide

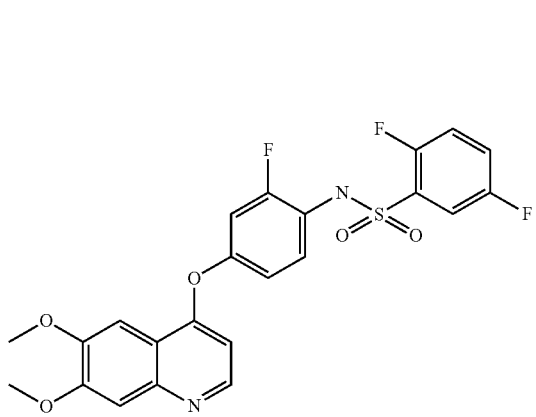 [SMILES: COc1cc2nccc(Oc3ccc(NS(=O)(=O)c4cc(F)ccc4F)c(F)c3)c2cc1OC]

C$_{23}$H$_{17}$F$_3$N$_2$O$_5$S Mw. 490.46

LC/MS purity: 99%, m/z 489 [M−H]$^-$ Rt. 2.82 min.

$^1$H NMR (300 MHz, DMSO-d6): 10.68 (s, 1H), 8.51 (d, 1H), 7.55 (m, 3H), 7.41 (s, 1H), 7.40 (s, 1H), 7.36 (t, 1H), 7.26 (dd, 1H), 7.06 (dd, 1H), 6.56 (d, 1H), 3.94 (s, 3H), 3.89 (s, 3H)

Melting point: 232-234° C. Yield: 45%

Example A41

2,6-Dichloro-N-[4-(6,7-dimethoxy-quinolin-4-yloxy)-2-fluoro-phenyl]-benzenesulfonamide

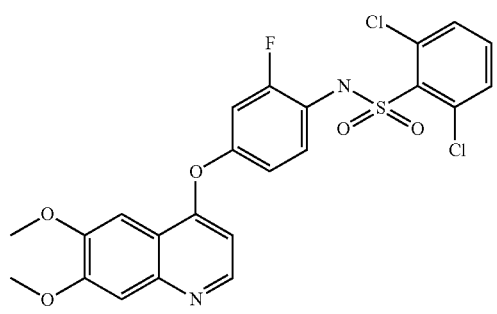 [SMILES: COc1cc2nccc(Oc3ccc(NS(=O)(=O)c4c(Cl)cccc4Cl)c(F)c3)c2cc1OC]

$C_{23}H_{17}Cl_2FN_2O_5S$ Mw. 523.37

LC/MS purity: 96%, m/z 523 [M+H]$^+$ Rt. 2.92 min.

$^1$H NMR (300 MHz, DMSO-d6): 10.61 (s, 1H), 8.51 (d, 1H), 7.57 (m, 3H), 7.41 (s, 2H), 7.34 (t, 1H), 7.25 (dd, 1H), 7.06 (d, 1H), 6.53 (d, 1H), 3.94 (s, 3H), 3.89 (s, 3H)

Melting point: 217-218° C. Yield: 58%

Example A42

2,5-Dichloro-N-[4-(6,7-dimethoxy-quinolin-4-yloxy)-2-fluoro-phenyl]-benzenesulfonamide

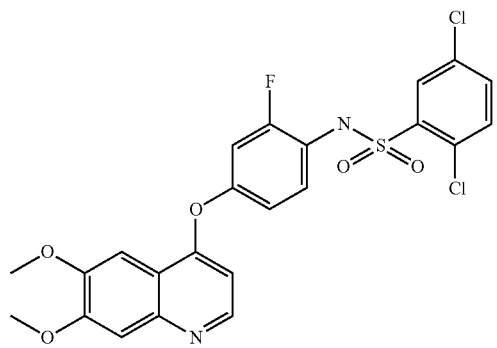 [SMILES: COc1cc2nccc(Oc3ccc(NS(=O)(=O)c4cc(Cl)ccc4Cl)c(F)c3)c2cc1OC]

$C_{23}H_{17}Cl_2FN_2O_5S$ Mw. 523.37

LC/MS purity: 95%, m/z 523 [M−H]$^-$ Rt. 3.05 min.

$^1$H NMR (300 MHz, DMSO-d6): 10.64 (s, 1H), 8.51 (d, 1H), 7.85 (s, 1H), 7.76 (s, 2H), 7.40 (s, 2H), 7.35 (t, 1H), 7.26 (dd, 1H), 7.06 (d, 1H), 6.56 (d, 1H), 3.94 (s, 3H), 3.89 (s, 3H)

Melting point: 228-230° C. Yield: 63%

Example A43

3,5-Dichloro-N-[4-(6,7-dimethoxy-quinolin-4-yloxy)-2-fluoro-phenyl]-benzenesulfonamide

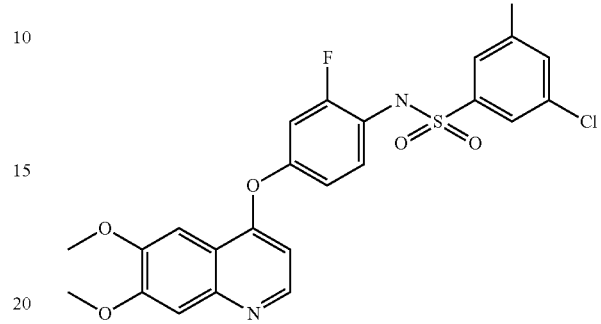

$C_{23}H_{17}Cl_2FN_2O_5S$ Mw. 523.37

LC/MS purity: 95%, m/z 521 [M−H]$^-$ Rt. 3.16 min.

$^1$H NMR (300 MHz, DMSO-d6): 10.51 (s, 1H), 8.52 (d, 1H), 8.00 (s, 1H), 7.69 (s, 2H), 7.42 (s, 1H), 7.41 (s, 1H), 7.33 (t, 1H), 7.28 (dd, 1H), 7.09 (d, 1H), 6.57 (d, 1H), 3.94 (s, 3H), 3.90 (s, 3H)

Melting point: 240-242° C.; Yield: 46%

Example A44

N-[4-(6,7-Dimethoxy-quinolin-4-yloxy)-2-fluoro-phenyl]-2-trifluoromethyl-benzenesulfonamide

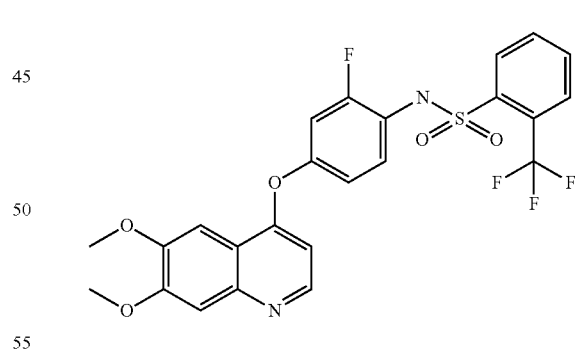

$C_{24}H_{18}F_4N_2O_5S$ Mw. 522.48

LC/MS purity: 96%, m/z 521 [M−H]$^-$ Rt. 2.95 min.

$^1$H NMR (300 MHz, DMSO-d6): 10.37 (s, 1H), 8.51 (d, 1H), 8.03 (m, 2H), 7.87 (m, 2H), 7.40 (s, 2H), 7.34 (t, 1H), 7.24 (dd, 1H), 7.06 (d, 1H), 6.53 (d, 1H), 3.94 (s, 3H), 3.89 (s, 3H)

Melting point: 237-239° C. Yield: 72%

Example A45

2-Bromo-N-[4-(6,7-dimethoxy-quinolin-4-yloxy)-2-fluoro-phenyl]-4-trifluoromethyl-benzenesulfonamide

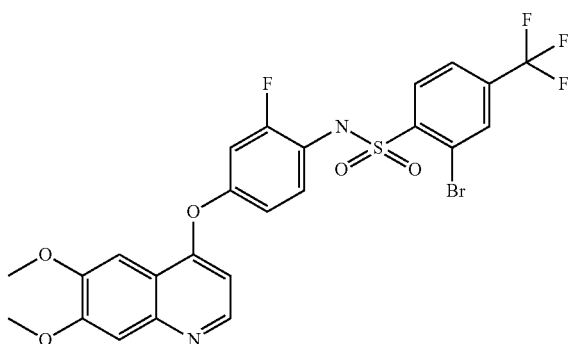 [SMILES: COc1cc2nccc(Oc3ccc(NS(=O)(=O)c4ccc(C(F)(F)F)cc4Br)c(F)c3)c2cc1OC]

$C_{24}H_{17}BrF_4N_2O_5S$ Mw. 601.38

LC/MS purity: 96%, m/z 599 [M−H]⁻ Rt. 3.13 min.

¹H NMR (300 MHz, DMSO-d6): 10.70 (s, 1H), 8.51 (d, 1H), 8.30 (s, 1H), 8.15 (d, 1H), 7.97 (d, 1H), 7.40 (s, 2H), 7.34 (t, 1H), 7.27 (dd, 1H), 7.05 (dd, 1H), 6.57 (d, 1H), 3.94 (s, 3H), 3.89 (s, 3H)

Melting point: 236-238° C. Yield: 65%

Example A46

2-Bromo-N-[4-(6,7-dimethoxy-quinolin-4-yloxy)-2-fluoro-phenyl]-5-trifluoromethyl-benzenesulfonamide

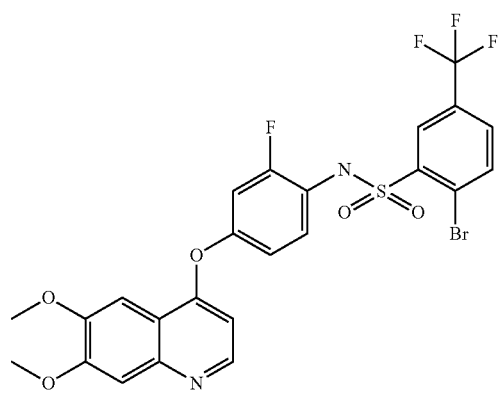 [SMILES: COc1cc2nccc(Oc3ccc(NS(=O)(=O)c4cc(C(F)(F)F)ccc4Br)c(F)c3)c2cc1OC]

$C_{24}H_{17}BrF_4N_2O_5S$ Mw. 601.38

LC/MS purity: 96%, m/z 599 [M−H]⁻ Rt. 3.17 min.

¹H NMR (300 MHz, DMSO-d6): 10.72 (s, 1H), 8.50 (d, 1H), 8.16 (d, 1H), 8.14 (s, 1H), 7.95 (dd, 1H), 7.40 (s, 2H), 7.36 (t, 1H), 7.26 (dd, 1H), 7.06 (dd, 1H), 6.53 (d, 1H), 3.94 (s, 3H), 3.89 (s, 3H)

Melting point: 227-230° C. Yield: 42%

Example A47

3-Bromo-N-[4-(6,7-dimethoxy-quinolin-4-yloxy)-2-fluoro-phenyl]-5-trifluoromethyl-benzenesulfonamide

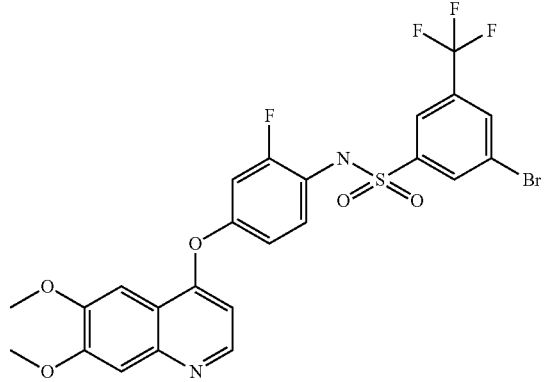 [SMILES: COc1cc2nccc(Oc3ccc(NS(=O)(=O)c4cc(Br)cc(C(F)(F)F)c4)c(F)c3)c2cc1OC]

$C_{24}H_{17}BrF_4N_2O_5S$ Mw. 601.38

LC/MS purity: 95%, m/z 599 [M−H]⁻ Rt. 3.27 min.

¹H NMR (300 MHz, DMSO-d6): 10.60 (s, 1H), 8.52 (d, 1H), 8.39 (s, 1H), 8.12 (s, 1H), 7.97 (s, 1H), 7.41 (s, 2H), 7.34 (t, 1H), 7.28 (dd, 1H), 7.09 (d, 1H), 6.55 (d, 1H), 3.94 (s, 3H), 3.90 (s, 3H)

Melting point: 214-216° C. Yield: 58%

Example A48

4-Bromo-N-[4-(6,7-dimethoxy-quinolin-4-yloxy)-2-fluoro-phenyl]-2-trifluoromethyl-benzenesulfonamide

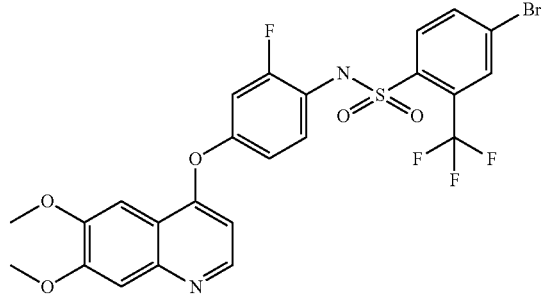 [SMILES: COc1cc2nccc(Oc3ccc(NS(=O)(=O)c4ccc(Br)cc4C(F)(F)F)c(F)c3)c2cc1OC]

$C_{24}H_{17}BrF_4N_2O_5S$ Mw. 601.38

LC/MS purity: 96%, m/z 599 [M−H]⁻ Rt. 3.14 min.

¹H NMR (300 MHz, DMSO-d6): 10.51 (s, 1H), 8.52 (d, 1H), 8.18 (s, 1H), 8.13 (dd, 1H), 7.94 (d, 1H), 7.41 (s, 2H), 7.34 (t, 1H), 7.27 (dd, 1H), 7.07 (dd, 1H), 6.56 (d, 1H), 3.95 (s, 3H), 3.90 (s, 3H)

Melting point: 242-244° C. Yield: 69%

Example A49

3,4-Dichloro-N-[4-(6,7-dimethoxy-quinolin-4-yloxy)-2-fluoro-phenyl]-benzenesulfonamide

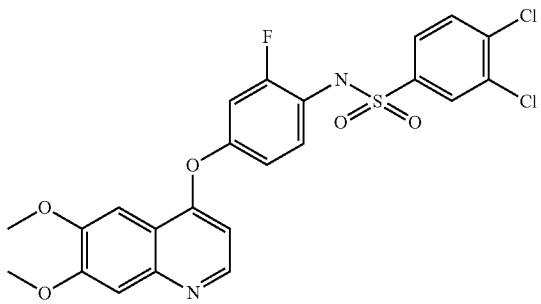 [SMILES: COc1cc2nccc(Oc3ccc(NS(=O)(=O)c4ccc(Cl)c(Cl)c4)c(F)c3)c2cc1OC]

$C_{23}H_{17}Cl_2FN_2O_5S$ Mw. 523.37

LC/MS purity: 97%, m/z 521 [M−H]⁻ Rt. 3.12 min.

¹H NMR (300 MHz, DMSO-d6): 10.45 (s, 1H), 8.50 (d, 1H), 8.31 (s, 1H), 7.86 (m, 2H), 7.68 (d, 2H), 7.42 (s, 1H), 7.40 (s, 1H), 7.31 (t, 1H), 7.23 (dd, 1H), 7.03 (d, 1H), 6.56 (d, 1H), 3.94 (s, 3H), 3.90 (s, 3H)

Melting point: 225-227° C. Yield: 38%

Example A50

3,5-Dichloro-N-[4-(6,7-dimethoxy-quinolin-4-yloxy)-2-fluoro-phenyl]-2-methoxy-benzenesulfonamide

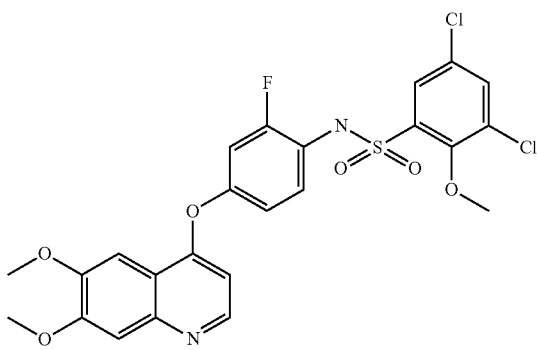 [SMILES: COc1cc2nccc(Oc3ccc(NS(=O)(=O)c4cc(Cl)cc(Cl)c4OC)c(F)c3)c2cc1OC]

$C_{24}H_{19}Cl_2FN_2O_6S$ Mw. 553.40

LC/MS purity: 99%, m/z 551 [M−H]⁻ Rt. 3.23 min.

¹H NMR (300 MHz, DMSO-d6): 10.37 (s, 1H), 8.51 (d, 1H), 8.03 (d, 1H), 7.63 (d, 1H), 7.42 (s, 1H), 7.40 (s, 1H), 7.33 (t, 1H), 7.25 (dd, 1H), 7.04 (dd, 1H), 6.55 (d, 1H), 3.94 (s, 3H), 3.91 (s, 3H), 3.90 (s, 3H)

Melting point: 193-195° C. Yield: 51%

Example A51

N-[4-(6,7-Dimethoxy-quinolin-4-yloxy)-2-fluoro-phenyl]-2-methyl-benzenesulfonamide

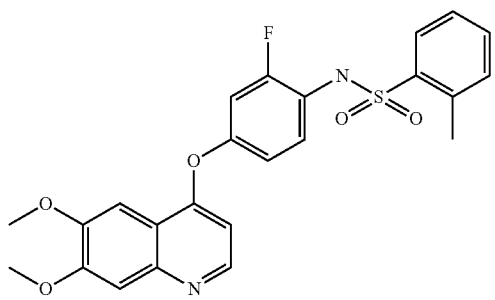 [SMILES: COc1cc2nccc(Oc3ccc(NS(=O)(=O)c4ccccc4C)c(F)c3)c2cc1OC]

$C_{24}H_{21}FN_2O_5S$ Mw. 468.51

LC/MS purity: 94%, m/z 467 [M−H]⁻ m/z 469 [M−H]⁺ Rt. 2.82 min.

¹H NMR (300 MHz, DMSO-d6): 10.47 (bs, 1H), 8.49 (d, 1H), 7.92 (d, 1H), 7.68-7.18 (m, 7H), 7.00 (dd, 1H), 6.51 (d, 1H), 3.93 (s, 3H), 3.89 (s, 3H), 2.58 (s, 3H)

Melting point: 218-220° C. Yield: 62%

Example A52

N-[4-(6,7-Dimethoxy-quinolin-4-yloxy)-2-fluoro-phenyl]-2-methoxy-benzenesulfonamide

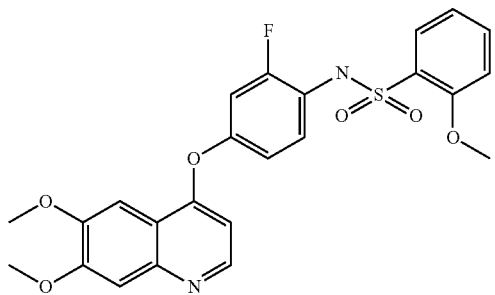

$C_{24}H_{21}FN_2O_6S$ Mw. 484.51

LC/MS purity: 98% m/z 483 [M−H]⁻ m/z 485 [M−H]⁺ Rt. 2.71 min.

¹H NMR (300 MHz, DMSO-d6): 9.82 (bs, 1H), 8.50 (d, 1H), 7.65 (m, 2H), 7.39-7.01 (m, 7H), 6.50 (d, 1H), 3.94 (s, 3H), 3.89 (s, 3H), 2.59 (s, 3H)

Melting point: 213-215° C. Yield: 55%

Example A53

N-[4-(6,7-Dimethoxy-quinolin-4-yloxy)-2-fluoro-phenyl]-2-trifluoromethoxy-benzenesulfonami

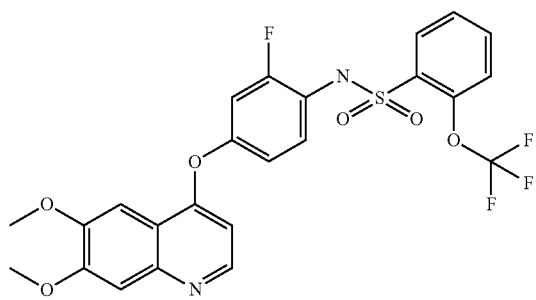 [SMILES: COc1cc2nccc(Oc3ccc(NS(=O)(=O)c4ccccc4OC(F)(F)F)c(F)c3)c2cc1OC]

$C_{24}H_{18}F_4N_2O_6S$ Mw. 538.48

LC/MS purity: 96% m/z 537 [M–H]⁻ m/z 539 [M–H]⁺ Rt. 3.00 min.

¹H NMR (300 MHz, DMSO-d6): 10.40 (bs, 1H), 8.52 (d, 1H), 7.90 (d, 1H), 7.80 (m, 1H), 7.70-7.05 (m, 7H), 6.54 (d, 1H), 3.94 (s, 3H), 3.90 (s, 3H)

Melting point: 204-206° C. Yield: 69%

Example A54

2-Chloro-N-[4-(6,7-dimethoxy-quinolin-4-yloxy)-2-fluoro-phenyl]-benzenesulfonamid

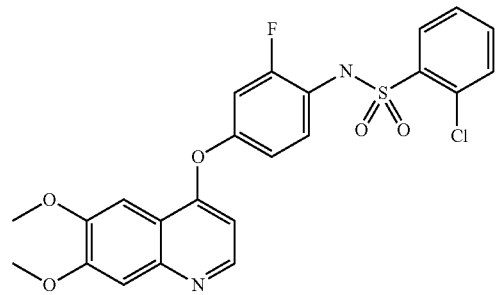

$C_{23}H_{18}ClFN_2O_5S$ Mw. 488.93

LC/MS purity: 98% m/z 487 [M–H]⁻, m/z 489 [M–H]⁺ Rt. 2.81 min.

¹H NMR (300 MHz, DMSO-d6): 10.43 (bs, 1H), 8.50 (d, 1H), 7.69 (d, 1H), 7.64 (m, 2H), 7.51-7.17 (m, 5H), 7.00 (d, 1H), 6.52 (d, 1H), 3.94 (s, 3H), 3.89 (s, 3H)

Melting point: 232-234° C. Yield: 76%

Example A55

2-Bromo-N-[4-(6,7-dimethoxy-quinolin-4-yloxy)-2-fluoro-phenyl]-benzenesulfonamide

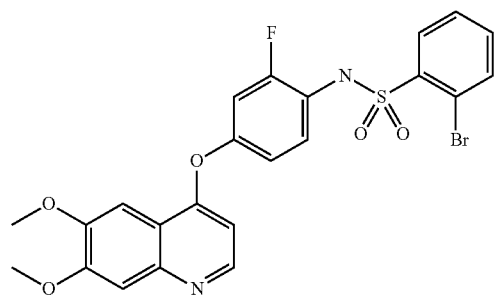 [SMILES: COc1cc2nccc(Oc3ccc(NS(=O)(=O)c4ccccc4Br)c(F)c3)c2cc1OC]

$C_{23}H_{18}BrFN_2O_5S$ Mw. 533.38

LC/MS purity: 98%, m/z 531 [M–H]⁻, m/z 533 [M–H]⁺ Rt. 2.85 min.

¹H NMR (300 MHz, DMSO-d6): 10.40 (bs, 1H), 8.50 (d, 1H), 7.95 (dd, 1H), 7.88 (dd, 1H), 7.55 (m, 2H), 7.40 (s, 2H), 7.26 (m, 2H), 7.04 (dd, 1H), 6.53 (d, 1H), 3.94 (s, 3H), 3.89 (s, 3H)

Melting point: 225-227° C. Yield: 47%

Example A56

N-[4-(6,7-Dimethoxy-quinolin-4-yloxy)-2-fluoro-phenyl]-4-ethyl-benzenesulfonamide

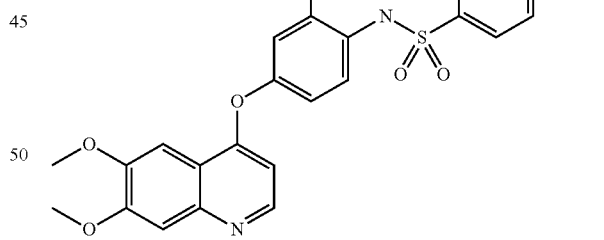

$C_{25}H_{23}FN_2O_5S$ Mw. 482.53

LC/MS purity: 94%, m/z 481 [M–H]⁻, m/z 483 [M–H]⁺ Rt. 3.01 min.

¹H NMR (300 MHz, DMSO-d6): 10.14 (bs, 1H), 8.50 (d, 1H), 7.66 (d, 2H), 7.41 (m, 3H), 7.32 (t, 1H), 7.22 (dd, 1H), 7.04 (dd, 1H), 6.54 (d, 1H), 3.94 (s, 3H), 3.90 (s, 3H), 2.68 (q, 2H), 1.20 (t, 3H)

Melting point: 193-195° C. Yield: 66%

Example A57

N-[4-(6,7-Dimethoxy-quinolin-4-yloxy)-2-fluoro-phenyl]-4-phenoxy-benzenesulfonamide

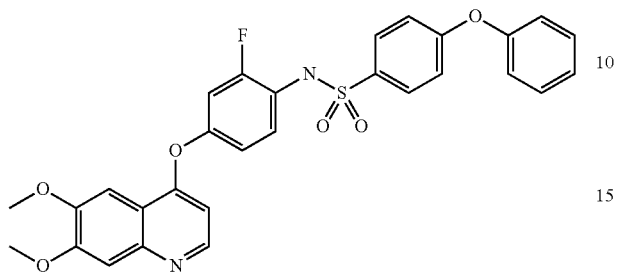

$C_{29}H_{23}FN_2O_6S$ Mw. 546.58

LC/MS purity: 95%, m/z 545 [M−H]⁻, m/z 547 [M−H]⁺ Rt. 3.23 min.

¹H NMR (300 MHz, DMSO-d6): 10.13 (bs, 1H), 8.49 (d, 1H), 7.73 (d, 2H), 7.43 (m, 4H), 7.32-7.22 (m, 4H), 7.10 (m, 4H), 6.55 (d, 1H), 3.94 (s, 3H), 3.90 (s, 3H)

Melting point: 202-204° C. Yield: 76%

Example A58

N-[4-(6,7-Dimethoxy-quinolin-4-yloxy)-2-fluoro-phenyl]-3-fluoro-2-methyl-benzenesulfonamide

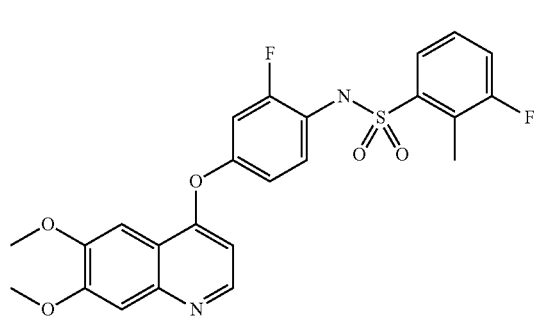 [SMILES: COc1cc2nccc(Oc3ccc(NS(=O)(=O)c4cccc(F)c4C)c(F)c3)c2cc1OC]

$C_{24}H_{20}F_2N_2O_5S$ Mw. 486.50

LC/MS purity: 94%, m/z 485 [M−H]⁻, m/z 487 [M−H]⁺ Rt. 2.92 min.

¹H NMR (300 MHz, DMSO-d6): 10.39 (bs, 1H), 8.57 (d, 1H), 7.60-7.31 (m, 6H), 7.23 (dd, 1H), 7.04 (d, 1H), 6.52 (d, 1H), 3.94 (s, 3H), 3.89 (s, 3H)

Melting point: 204-206° C. Yield: 78%

Example A59

N-[4-(6,7-Dimethoxy-quinolin-4-yloxy)-2-fluoro-phenyl]-2-fluoro-benzenesulfonamide $C_{23}H_{18}F_2N_2O_5S$ Mw. 472.47

LC/MS purity: 98%, m/z 471 [M−H]⁻, m/z 473 [M−H]⁺ Rt. 2.72 min.

¹H NMR (300 MHz, DMSO-d6): 10.47 (bs, 1H), 8.51 (d, 1H), 7.70 (m, 1H), 7.70 (m, 2H), 7.37 (m, 5H), 7.22 (dd, 1H), 7.03 (dd, 1H), 6.53 (d, 1H), 3.94 (s, 3H), 3.89 (s, 3H)

Melting point: 235-236° C. Yield: 51%

Example A60

4-Bromo-3-chloro-N-[4-(6,7-dimethoxy-quinolin-4-yloxy)-2-fluoro-phenyl]-benzenesulfonamide $C_{23}H_{17}BrClFN_2O_5S$ Mw. 567.82

LC/MS purity: 98%, m/z 565 [M−H]⁻, m/z 567 [M−H]⁺ Rt. 3.14 min.

¹H NMR (300 MHz, DMSO-d6): 10.45 (bs, 1H), 8.51 (d, 1H), 8.02 (d, 1H), 7.87 (s, 1H), 7.58 (dd, 1H), 7.42-7.24 (m, 4H), 7.07 (d, 1H), 6.57 (d, 1H), 3.94 (s, 3H), 3.90 (s, 3H)

Melting point: 231-232° C. Yield: 55%

Example A61

N-[4-(6,7-Dimethoxy-quinolin-4-yloxy)-2-fluoro-phenyl]-4-fluoro-3-methoxy-benzenesulfonamide

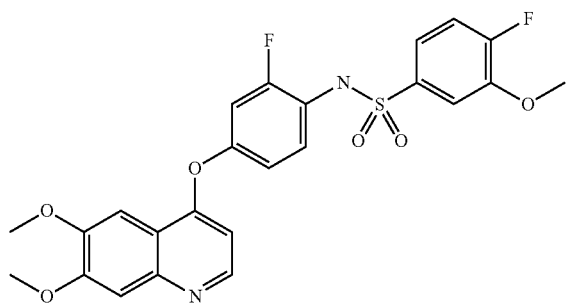

$C_{24}H_{20}F_2N_2O_6S$ Mw. 502.50

LC/MS purity: 100%, m/z 501 [M–H]$^-$, m/z 503 [M–H]$^+$ Rt. 2.69 min.

$^1$H NMR (300 MHz, DMSO-d6): 10.20 (bs, 1H), 8.50 (d, 1H), 7.49-7.22 (m, 7H), 7.05 (d, 1H), 6.55 (d, 1H), 3.94 (s, 3H), 3.90 (s, 3H), 3.87 (s, 3H)

Melting point: 214-216° C. Yield: 45%

Example A62

N-[4-(6,7-Dimethoxy-quinolin-4-yloxy)-2-fluoro-phenyl]-4-ethoxy-3-methyl-benzenesulfonamid

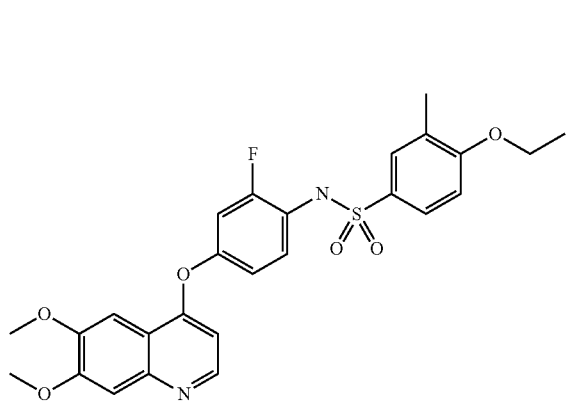 [SMILES: CCOc1ccc(S(=O)(=O)Nc2ccc(Oc3ccnc4cc(OC)c(OC)cc34)cc2F)cc1C]

$C_{26}H_{25}FN_2O_6S$ Mw. 512.56

LC/MS purity: 100%, m/z 521 [M–H]$^-$ Rt. 3.09 min.

$^1$H NMR (300 MHz, DMSO-d6): 9.96 (s, 1H), 8.50 (d, 1H), 7.52 (m, 2H), 7.42 (s, 1H), 7.40 (s, 1H), 7.30 (t, 1H), 7.20 (d, 1H), 7.04 (m, 2H), 6.52 (d, 1H), 4.10 (q, 2H), 3.94 (s, 3H), 3.90 (s, 3H), 1.36 (t, 3H)

Melting point: 158-160° C. Yield: 61%

Example A63

4-Methoxy-naphthalene-1-sulfonic acid [4-(6,7-dimethoxy-quinolin-4-yloxy)-2-fluoro-phenyl]-amid

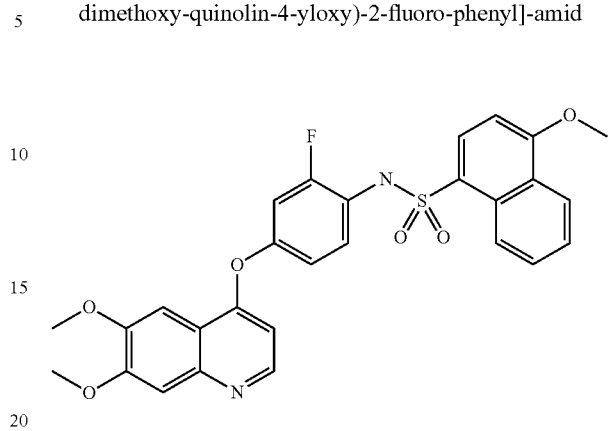

$C_{28}H_{23}FN_2O_6S$ Mw. 534.57

LC/MS purity: 97%, m/z 533 [M–H]$^-$ Rt. 3.07 min.

$^1$H NMR (300 MHz, DMSO-d6): 10.31 (s, 1H), 8.68 (d, 1H), 8.48 (d, 2H), 8.29 (d, 1H), 8.07 (d, 1H), 7.70 (m, 2H), 7.38 (s, 1H), 7.37 (s, 1H), 7.28 (t, 1H), 7.07 (m, 3H), 6.45 (d, 1H), 4.05 (s, 3H), 3.93 (s, 3H), 3.88 (s, 3H)

Melting point: 226-227° C. Yield: 62%

Example A64

N-[4-(6,7-Dimethoxy-quinolin-4-yloxy)-2-fluoro-phenyl]-2-methoxy-4,5-dimethyl-benzenesulfonamide

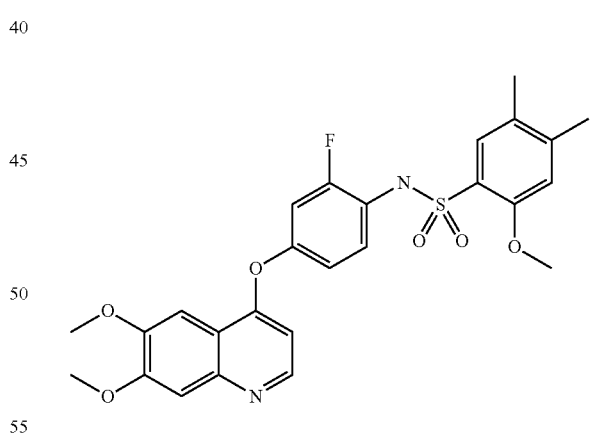

$C_{26}H_{25}FN_2O_6S$ Mw. 512.56

LC/MS purity: 97%, m/z 511 [M–H]$^-$ Rt. 2.97 min.

$^1$H NMR (300 MHz, DMSO-d6): 9.63 (s, 1H), 8.50 (d, 1H), 7.40 (s, 3H), 7.33 (t, 1H), 7.20 (dd, 1H), 7.02 (m, 2H), 6.51 (d, 1H), 3.94 (s, 3H), 3.88 (s, 3H), 3.84 (s, 3H), 2.27 (s, 3H), 2.15 (s, 3H)

Melting point: 238-240° C. Yield: 53%

Example A65

N-{2-[4-(6,7-Dimethoxy-quinolin-4-yloxy)-phenyl-sulfamoyl]-4-methyl-phenyl}-acetamide

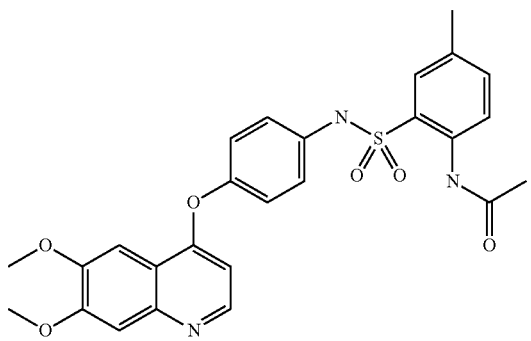 [SMILES: COc1cc2nccc(Oc3ccc(NS(=O)(=O)c4cc(C)ccc4NC(C)=O)cc3)c2cc1OC]

C$_{26}$H$_{25}$N$_3$O$_6$S Mw. 507.57

LC/MS purity: 99%, m/z 506 [M–H]$^-$, m/z 508 [M–H]$^+$ Rt. 2.51 min.

$^1$H NMR (300 MHz, DMSO-d6): 10.2 (bs, 1H), 10.13 (s, 1H), 8.43 (d, 1H), 8.15 (d, 1H), 7.72 (d, 1H), 7.44 (s, 1H), 7.37 (s, 1H), 7.29 (d, 1H), 7.13 (dd, 4H), 6.35 (d, 1H), 3.93 (s, 3H), 3.89 (s, 3H), 2.54 (s, 3H), 2.03 (s, 3H)

Melting point: 134-136° C. Yield: 49%

Example A66

N-{4-[4-(6,7-Dimethoxy-quinolin-4-yloxy)-phenyl-sulfamoyl]-2,6-dimethyl-phenyl}-acetamide

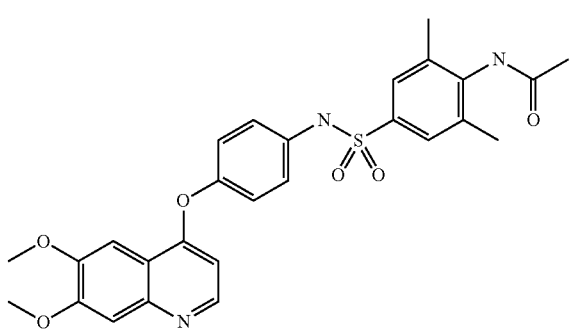 [SMILES: COc1cc2nccc(Oc3ccc(NS(=O)(=O)c4cc(C)c(NC(C)=O)c(C)c4)cc3)c2cc1OC]

C$_{27}$H$_{27}$N$_3$O$_6$S Mw. 521.60

LC/MS purity: 94%, m/z 520 [M–H]$^-$, m/z 522 [M–H]$^+$ Rt. 2.49 min.

$^1$H NMR (300 MHz, DMSO-d6): 13.5 (bs, 1H), 8.44 (d, 1H), 7.73 (d, 1H), 7.45 (s, 1H), 7.37 (s, 1H), 7.25 (d, 1H), 7.14 (m, 4H), 6.37 (d, 1H), 3.93 (s, 3H), 3.89 (s, 3H), 2.44 (s, 3H), 2.17 (s, 3H), 2.07 (s, 3H)

Melting point: 145-147° C. Yield: 67%

Example A67

3-Chloro-N-[4-(6,7-dimethoxy-quinolin-4-yloxy)-phenyl]-4-methoxy-benzenesulfonamide

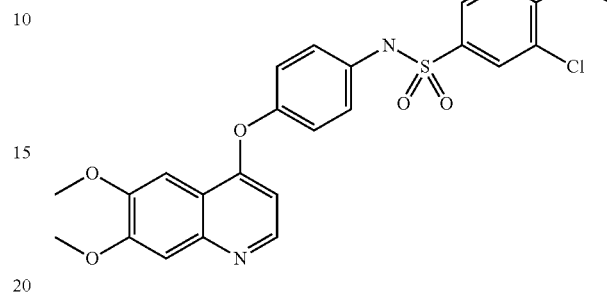

C$_{24}$H$_{21}$ClN$_2$O$_6$S Mw. 500.96

LC/MS purity: 99%, m/z 499 [M–H]$^-$ m/z 501 [M–H]$^+$ Rt. 2.89 min.

$^1$H NMR (300 MHz, DMSO-d6): 10.27 (bs, 1H), 8.45 (d, 1H), 7.70 (m, 2H), 7.36 (m, 3H), 7.18 (m, 4H), 6.37 (d, 1H), 3.93 (s, 3H), 3.90 (s, 3H)

Melting point: 226-227° C. Yield: 51%

Example A68

5-Chloro-N-[4-(6,7-dimethoxy-quinolin-4-yloxy)-phenyl]-2-methoxy-benzenesulfonamide

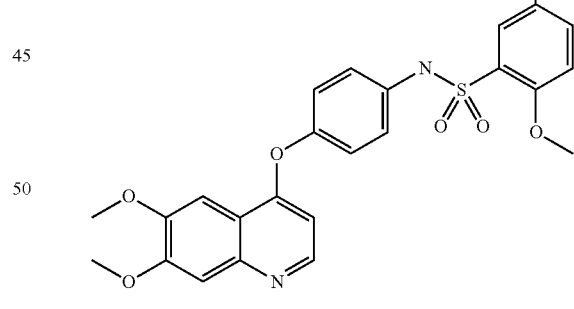

C$_{24}$H$_{21}$ClN$_2$O$_6$S Mw. 500.96

LC/MS purity: 98%, m/z 499 [M–H]$^-$ m/z 501 [M–H]$^+$ Rt. 2.90 min.

$^1$H NMR (300 MHz, DMSO-d6): 10.24 (s, 1H), 8.44 (d, 1H), 7.66 (m, 2H), 7.44 (s, 1H), 7.37 (s, 1H), 7.27-7.13 (m, 5H), 6.32 (d, 1H), 3.93 (s, 3H), 3.92 (s, 3H), 3.89 (s, 3H),

Melting point: 255-257° C. Yield: 63%

Example A69

5-Chloro-N-[4-(6,7-dimethoxy-quinolin-4-yloxy)-phenyl]-2-methoxy-4-methyl-benzenesulfonamide

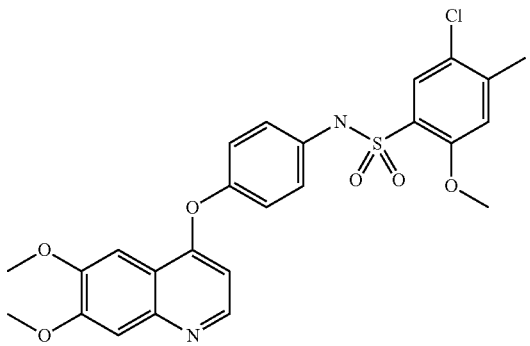

$C_{25}H_{23}ClN_2O_6S$ Mw. 514.99

LC/MS purity: 98%, m/z 513 [M−H]⁻ Rt. 3.04 min.

¹H NMR (300 MHz, DMSO-d6): 12.0 (bs, 1H), 10.17 (bs, 1H), 8.44 (d, 1H), 7.65 (s, 1H), 7.44 (s, 3H), 7.37 (s, 1H), 7.17 (m, 5H), 6.33 (d, 1H), 3.93 (s, 3H), 3.91 (s, 3H), 3.89 (s, 3H), 2.36 (s, 3H)

Melting point: 236-238° C. Yield: 70%

Example A70

3-tert-Butyl-N-[4-(6,7-dimethoxy-quinolin-4-yloxy)-phenyl]-4-methoxy-benzenesulfonamide

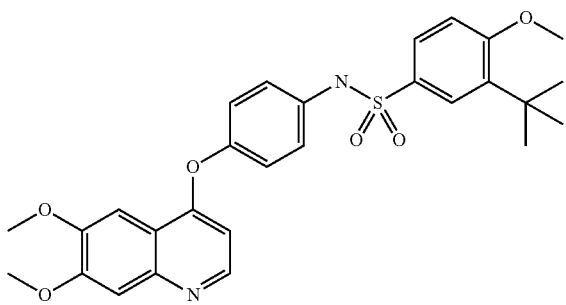 [SMILES: COc1cc2nccc(Oc3ccc(NS(=O)(=O)c4ccc(OC)c(C(C)(C)C)c4)cc3)c2cc1OC]

$C_{28}H_{30}N_2O_6S$ Mw. 522.63

LC/MS purity: 98%, m/z 521 [M−H]⁻ Rt. 3.24 min.

¹H NMR (300 MHz, DMSO-d6): 10.13 (bs, 1H), 8.43 (d, 1H), 7.62 (d, 1H), 7.56 (s, 1H), 7.44 (s, 1H), 7.38 (s, 5H), 7.16 (m, 5H), 6.33 (d, 1H), 3.94 (s, 3H), 3.90 (s, 3H), 3.87 (s, 3H), 1.29 (s, 9H).

Melting point: 229-231° C. Yield: 56%

Example A71

Butane-1-sulfonic acid [4-(6,7-dimethoxy-quinolin-4-yloxy)-2-fluoro-phenyl]-amide

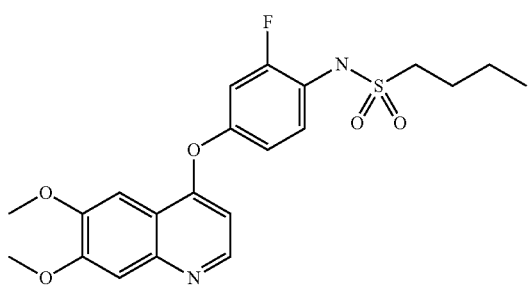 [SMILES: CCCCS(=O)(=O)Nc1ccc(Oc2ccnc3cc(OC)c(OC)cc23)cc1F]

$C_{21}H_{23}FN_2O_5S$ Mw. 434.49

LC/MS purity: 99%, m/z 433 [M−H]⁻, m/z 435 [M−H]⁺ Rt. 2.67 min.

¹H NMR (300 MHz, DMSO-d6): 9.66 (s, 1H), 8.52 (d, 1H), 7.45 (m, 4H), 7.09 (d, 1H), 6.63 (d, 1H), 3.95 (s, 3H), 3.92 (s, 3H), 3.11 (t, 2H), 1.70 (m, 2H), 1.40 (q, 2H), 0.89 (t, 3H)

Melting point: 164-166° C. Yield: 42%

Example A72

2-Methyl-propane-1-sulfonic acid [4-(6,7-dimethoxy-quinolin-4-yloxy)-2-fluoro-phenyl]-amide

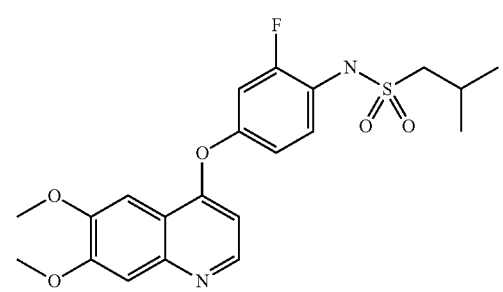 [SMILES: COc1cc2nccc(Oc3ccc(NS(=O)(=O)CC(C)C)c(F)c3)c2cc1OC]

$C_{21}H_{23}FN_2O_5S$ Mw. 434.49

LC/MS purity: 100%, m/z 433 [M−H]⁻, m/z 435 [M−H]⁺ Rt. 2.48 min.

¹H NMR (300 MHz, DMSO-d6): 9.68 (s, 1H), 8.52 (d, 1H), 7.52-7.41 (m, 3H), 7.43 (dd, 1H), 7.09 (dd, 1H), 3.95 (s, 3H), 3.92 (s, 3H), 3.02 (d, 2H), 2.20 (m, 1H), 1.04 (s, 6H)

Melting point: 175-176° C. Yield: 46%

Example A73

N-[4-(6,7-Dimethoxy-quinolin-4-yloxy)-2-fluoro-phenyl]-C-phenyl-methanesulfonamide

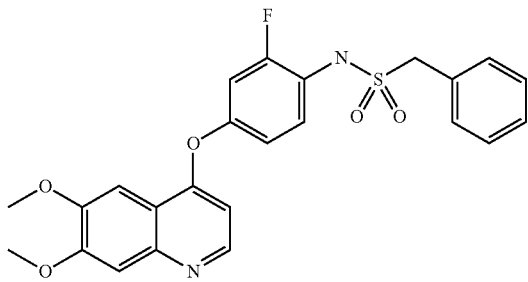 [SMILES: COc1cc2nccc(Oc3ccc(NS(=O)(=O)Cc4ccccc4)c(F)c3)c2cc1OC]

$C_{24}H_{21}FN_2O_5S$ Mw. 468.51

LC/MS purity: 99%, m/z 467 [M–H]⁻, m/z 469 [M–H]⁺ Rt. 2.57 min.

¹H NMR (300 MHz, DMSO-d6): 9.73 (s, 1H), 8.54 (d, 1H), 7.38 (m, 9H), 7.03 (d, 1H), 6.58 (d, 1H), 3.95 (s, 3H), 3.92 (s, 3H),

Melting point: 204-205° C. Yield: 47%

Example A74

3-Bromo-N-[4-(6,7-dimethoxy-quinolin-4-yloxy)-phenyl]-4-methoxy-benzenesulfonamide

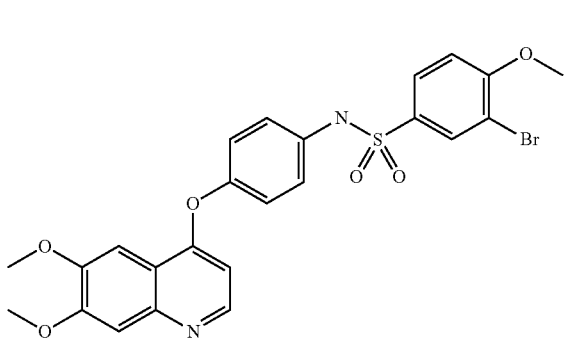

$C_{24}H_{21}BrN_2O_6S$ Mw. 545.41

LC/MS purity: 100%, m/z 543 [M–H]⁻, m/z 545 [M–H]⁺ Rt. 2.78 min.

¹H NMR (300 MHz, DMSO-d6): 10.25 (bs, 1H), 8.46 (d, 1H), 7.81 (s, 1H), 7.73 (dd, 1H), 7.45 (s, 1H), 7.38 (s, 1H), 7.27 (dd, 1H), 7.17 (m, 4H), 6.35 (s, 1H), 3.93 (s, 3H), 3.92 (s, 3H), 3.90 (s, 3H).

Melting point: 211-212° C. Yield: 74%

Example A75

Biphenyl-3-sulfonic acid [4-(6,7-dimethoxy-quinolin-4-yloxy)-3-methyl-phenyl]-amide

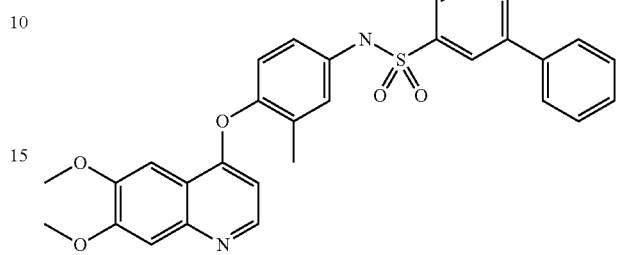

$C_{30}H_{26}N_2O_5S$ Mw. 526.62

LC/MS purity: 99%, m/z 525 [M–H]⁻, m/z 527 [M–H]⁺ Rt. 3.19 min.

¹H NMR (300 MHz, DMSO-d6): 10.29 (s, 1H), 8.32 (d, 1H), 7.97 (m, 1H), 7.77 (d, 1H), 7.67 (m, 3H), 7.50 (s, 5H), 7.37 (s, 1H), 7.15 (s, 1H), 7.05 (s, 2H), 6.0 (d, 1H), 3.93 (s, 3H), 3.90 (s, 3H), 2.01 (s, 3H)

Melting point: 178-180° C. Yield: 55%

Example A76

N-[4-(6,7-Dimethoxy-quinolin-4-yloxy)-3-methyl-phenyl]-3-phenoxy-benzenesulfonamide

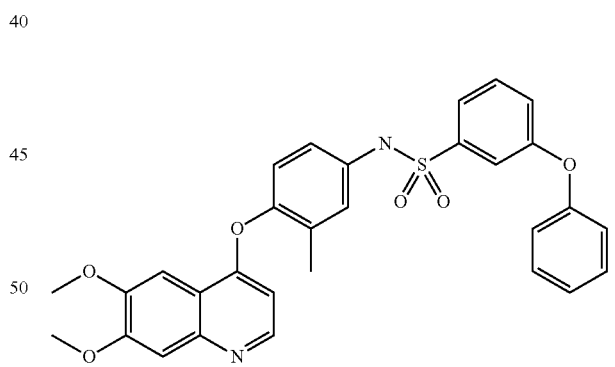

$C_{30}H_{26}N_2O_6S$ Mw. 542.62

LC/MS purity: 100%, m/z 541 [M–H]⁻, m/z 543 [M–H]⁺ Rt. 3.21 min.

¹H NMR (300 MHz, DMSO-d6): 10.28 (bs, 1H), 8.40 (d, 1H), 7.63-7.44 (m, 4H), 7.42-7.30 (m, 3H), 7.25-6.97 (m, 7H), 6.28 (d, 1H), 3.94 (s, 3H), 3.89 (s, 3H), 2.08 (s, 3H)

Melting point: 115-117° C. Yield: 65%

Example A77

Naphthalene-1-sulfonic acid [4-(6,7-dimethoxy-quinolin-4-yloxy)-3-methyl-phenyl]-amide

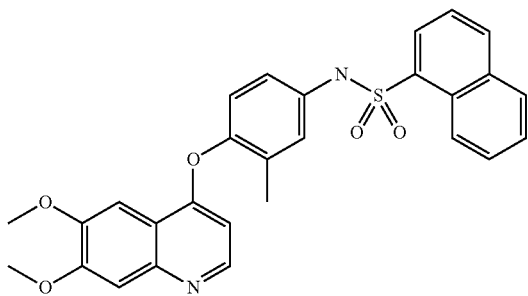 [SMILES: COc1cc2nccc(Oc3ccc(NS(=O)(=O)c4cccc5ccccc45)cc3C)c2cc1OC]

C$_{28}$H$_{24}$N$_2$O$_5$S Mw. 500.58

LC/MS purity: 95%, m/z 499 [M–H]$^-$, m/z 501 [M–H]$^+$ Rt. 2.87 min.

$^1$H NMR (300 MHz, DMSO-d6): 10.68 (s, 1H), 8.75 (d, 1H), 8.38 (d, 1H), 8.24 (m, 2H), 8.10 (d, 1H), 7.69 (m, 3H), 7.46 (s, 1H), 7.36 (s, 1H), 7.04 (s, 1H), 6.95 (m, 2H), 6.07 (d, 1H), 3.92 (s, 3H), 3.88 (s, 3H), 1.94 (s, 3H)

Melting point: 118-120° C. Yield: 43%

Example A78

Isoquinoline-5-sulfonic acid [4-(6,7-dimethoxy-quinolin-4-yloxy)-phenyl]-amide

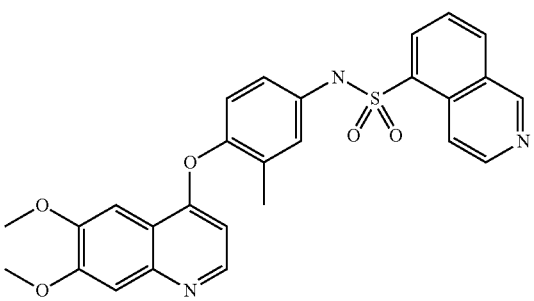 [SMILES: COc1cc2nccc(Oc3ccc(NS(=O)(=O)c4cccc5cnccc45)cc3C)c2cc1OC]

C$_{26}$H$_{21}$N$_3$O$_5$S Mw. 487.54

LC/MS purity: 100%, m/z 486 [M–H]$^-$, m/z 488 [M–H]$^+$ Rt. 2.51 min.

$^1$H NMR (300 MHz, DMSO-d6): 10.80 (s, 1H), 9.48 (s, 1H), 8.73 (d, 1H), 8.51 (d, 1H), 8.43 (m, 3H), 7.82 (t, 1H), 7.39 (s, 1H), 7.36 (s, 1H), 7.10 (dd, 4H), 6.26 (d, 1H), 3.92 (s, 3H), 3.87 (s, 3H)

Melting point: 229-231° C. Yield: 74%

Example A79

3,5-Dichloro-N-[4-(6,7-dimethoxy-quinolin-4-yloxy)-3-methyl-phenyl]-2-hydroxy-benzenesulfonamide

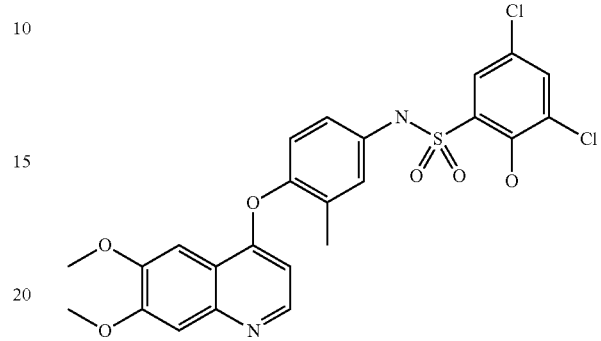

C$_{24}$H$_{20}$Cl$_2$N$_2$O$_6$S Mw. 535.41

LC/MS purity: 91%, m/z 533 [M–H]$^-$, m/z 535 [M–H]$^+$ Rt. 2.90 min.

$^1$H NMR (300 MHz, DMSO-d6): 10.2 (bs, 1H), 7.87 (d, 1H), 7.73 (s, 1H), 7.68 (d, 1H), 7.62 (s, 1H), 7.14 (m, 5H), 6.59 (d, 1H), 4.01 (s, 6H), 2.05 (s, 3H)

Melting point: 113-117° C. Yield: 25%

Example A80

2-Methyl-3H-imidazole-4-sulfonic acid [4-(6,7-dimethoxy-quinolin-4-yloxy)-phenyl]-amide

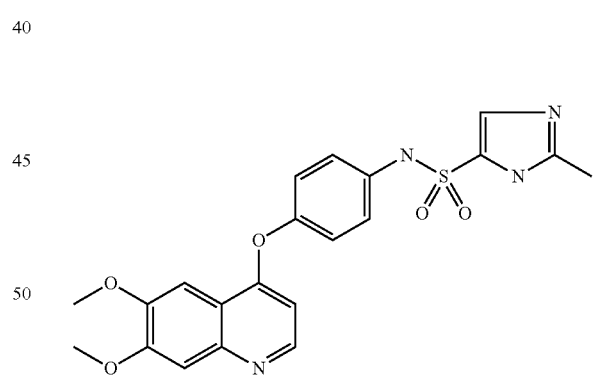

C$_{21}$H$_{20}$N$_4$O$_5$S Mw. 440.48

LC/MS purity: 99%, m/z 439 [M–H]$^-$, m/z 441 [M–H]$^+$ Rt. 2.02 min.

$^1$H NMR (300 MHz, DMSO-d6): 12.4 (s, 1H), 8.58 (dd, 1H), 8.45 (d, 1H), 7.78 (t, 1H), 7.65 (d, 1H), 7.47 (s, 1H), 7.26 (d, 2H), 7.13 (d, 1H), 6.39 (d, 1H), 3.94 (s, 3H), 3.91 (s, 3H), 2.28 (s, 3H)

Melting point: 268-269° C. Yield: 54%

Example A81

Biphenyl-4-sulfonic acid [4-(6,7-dimethoxy-quinolin-4-yloxy)-phenyl]-amide

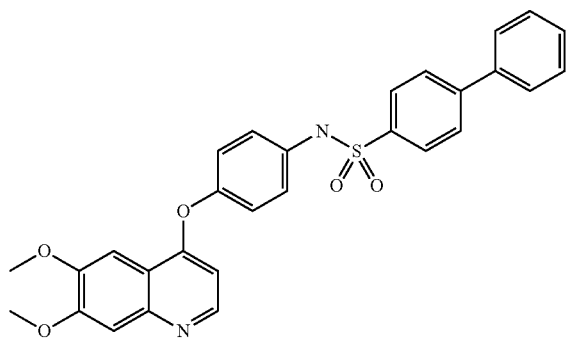 [SMILES: COc1cc2nccc(Oc3ccc(NS(=O)(=O)c4ccc(-c5ccccc5)cc4)cc3)c2cc1OC]

C$_{29}$H$_{24}$N$_2$O$_5$S Mw. 512.59
LC/MS purity: 96%, m/z 511 [M–H]$^-$, m/z 513 [M–H]$^+$ Rt. 3.12 min.
$^1$H NMR (300 MHz, DMSO-d6): 10.42 (bs, 1H), 8.42 (d, 1H), 7.87 (m, 4H), 7.73 (d, 2H), 7.49 (m, 3H), 7.43 (s, 1H), 7.37 (s, 1H), 7.25 (d, 2H), 7.17 (d, 2H), 6.36 (d, 1H), 3.93 (s, 3H), 3.88 (s, 3H)
Melting point: 191-194° C. Yield: 52%

Example A82

N-[4-(6,7-Dimethoxy-quinolin-4-yloxy)-phenyl]-3-pyrimidin-2-yl-benzenesulfonamide

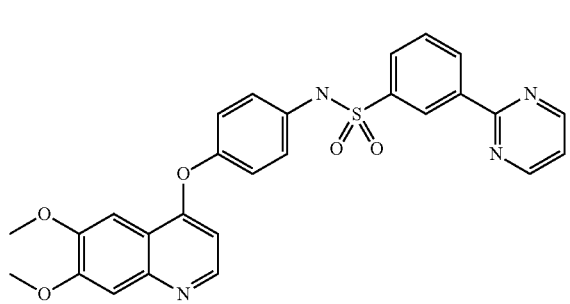 [SMILES: COc1cc2nccc(Oc3ccc(NS(=O)(=O)c4cccc(-c5ncccn5)c4)cc3)c2cc1OC]

C$_{27}$H$_{22}$N$_4$O$_5$S Mw. 514.56
LC/MS purity: 99%, m/z 513 [M–H]$^-$, m/z 515 [M–H]$^+$ Rt. 2.67 min.
$^1$H NMR (300 MHz, DMSO-d6): 10.2 (bs, 1H), 8.96 (d, 2H), 8.82 (s, 1H), 8.62 (d, 1H), 8.36 (d, 1H), 7.90 (d, 1H), 7.75 (t, 1H), 7.54 (t, 1H), 7.42 (s, 1H), 7.36 (s, 1H), 7.22 (d, 2H), 7.15 (d, 2H), 6.28 (d, 1H), 3.92 (s, 3H), 3.87 (s, 3H)
Melting point: 194-195° C. Yield: 61%

Example A83

Benzo[b]thiophene-2-sulfonic acid [4-(6,7-dimethoxy-quinolin-4-yloxy)-phenyl]-amide

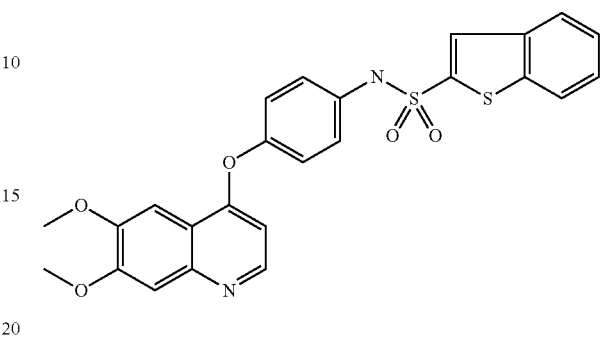

C$_{25}$H$_{20}$N$_2$O$_5$S$_2$ Mw. 492.58
LC/MS purity: 99%, m/z 491 [M–H]$^-$, m/z 493 [M–H]$^+$ Rt. 2.90 min.
$^1$H NMR (300 MHz, DMSO-d6): 10.72 (s, 1H), 8.44 (d, 1H), 8.08 (d, 1H), 8.02 (d, 1H), 7.51 (m, 3H), 7.44 (s, 1H), 7.37 (s, 1H), 7.29 (d, 2H), 7.19 (d, 2H), 6.36 (d, 1H), 3.93 (s, 3H), 3.88 (s, 3H)
Melting point: 222-225° C. Yield: 64%

Example A84

Benzo[b]thiophene-3-sulfonic acid [4-(6,7-dimethoxy-quinolin-4-yloxy)-phenyl]-amide

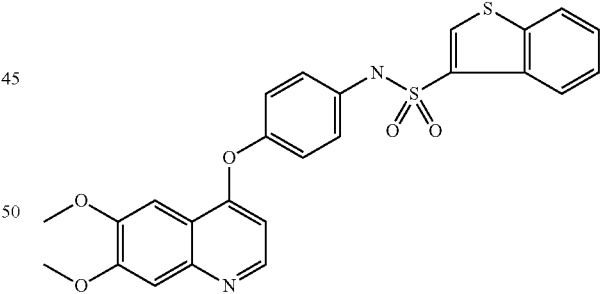

C$_{25}$H$_{20}$N$_2$O$_5$S$_2$ Mw. 492.58
LC/MS purity: 100%, m/z 491 [M–H]$^-$, m/z 493 [M–H]$^+$ Rt. 2.84 min.
$^1$H NMR (300 MHz, DMSO-d6): 10.25 (s, 1H), 8.39 (d, 1H), 8.28 (d, 1H), 8.25 (s, 1H), 8.01 (d, 1H), 7.42 (m, 3H), 7.35 (s, 1H), 7.04 (d, 2H), 6.93 (d, 2H), 6.31 (d, 1H), 3.92 (s, 3H), 3.88 (s, 3H)
Melting point: 267-270° C. Yield: 53%

Example A85

1-Methyl-2-oxo-2,3-dihydro-1H-indole-5-sulfonic acid [4-(6,7-dimethoxy-quinolin-4-yloxy)-phenyl]-amide

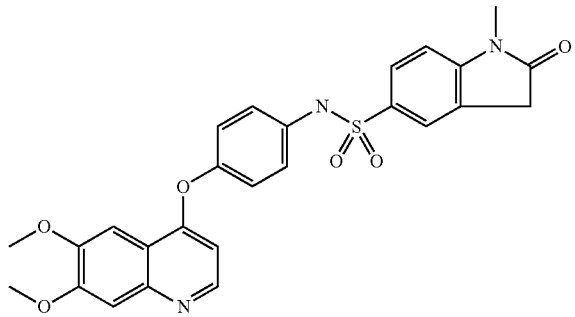 [SMILES: COc1cc2nccc(Oc3ccc(NS(=O)(=O)c4ccc5c(c4)CC(=O)N5C)cc3)c2cc1OC]

$C_{26}H_{23}N_3O_6S$ Mw. 505.55

LC/MS purity: 100%, m/z 504 [M–H]⁻, m/z 506 [M–H]⁺ Rt. 2.37 min.

¹H NMR (300 MHz, DMSO-d6): 10.1 (bs, 1H), 8.44 (m, 1H), 7.71 (d, 1H), 7.64 (s, 1H), 7.41 (d, 2H), 7.37 (d, 1H), 7.15 (m, 4H), 6.36 (m, 1H), 3.92 (s, 3H), 3.88 (s, 3H), 3.64 (s, 2H), 3.13 (s, 3H)

Melting point: 119-122° C. Yield: 54%

Example A86

Biphenyl-3-sulfonic acid [4-(6,7-dimethoxy-quinolin-4-yloxy)-phenyl]-amide

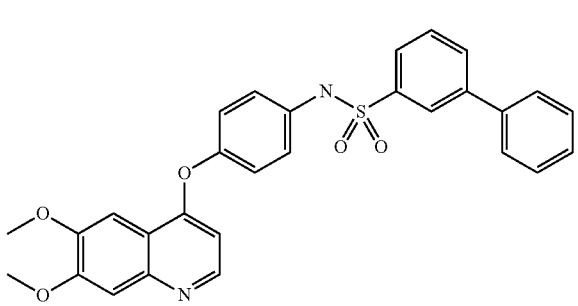 [SMILES: COc1cc2nccc(Oc3ccc(NS(=O)(=O)c4cccc(-c5ccccc5)c4)cc3)c2cc1OC]

$C_{29}H_{24}N_2O_5S$ Mw. 512.59

LC/MS purity: 97%, m/z 511 [M–H]⁻, m/z 513 [M–H]⁺ Rt. 3.09 min.

¹H NMR (300 MHz, DMSO-d6): 10.3 (bs, 1H), 8.36 (d, 1H), 7.98 (s, 1H), 7.95 (d, 1H), 7.76 (d, 1H), 7.66 (m, 3H), 7.51 (m, 3H), 7.43 (s, 1H), 7.37 (s, 1H), 7.24 (d, 2H), 7.17 (d, 2H), 6.29 (d, 1H), 3.93 (s, 3H), 3.88 (s, 3H)

Melting point: 197-200° C. Yield: 53%

Example A87

N-[4-(6,7-Dimethoxy-quinolin-4-yloxy)-phenyl]-4-(3,5-dimethyl-isoxazol-4-ylmethoxy)-benzenesulfonamide

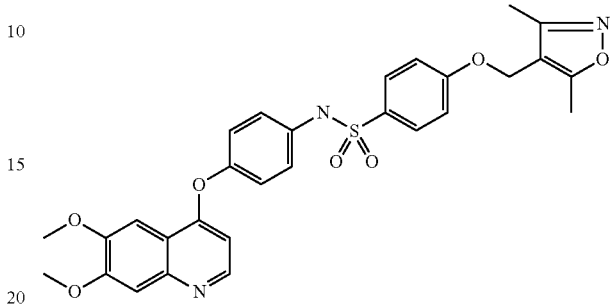

$C_{29}H_{27}N_3O_7S$ Mw. 561.62

LC/MS purity: 97%, m/z 560 [M–H]⁻, m/z 562 [M–H]⁺ Rt. 2.78 min.

¹H NMR (300 MHz, DMSO-d6): 10.2 (bs, 1H), 8.45 (d, 1H), 7.72 (d, 2H), 7.44 (s, 1H), 7.38 (s, 1H), 7.16 (m, 6H), 6.37 (d, 1H), 4.99 (s, 2H), 3.93 (s, 3H), 3.90 (s, 3H), 2.39 (s, 3H), 2.19 (s, 3H)

Melting point: 188-190° C. Yield: 11%

Example A88

N-[4-(6,7-Dimethoxy-quinolin-4-yloxy)-2-fluoro-phenyl]-3-fluoro-4-methoxy-benzenesulfonamide

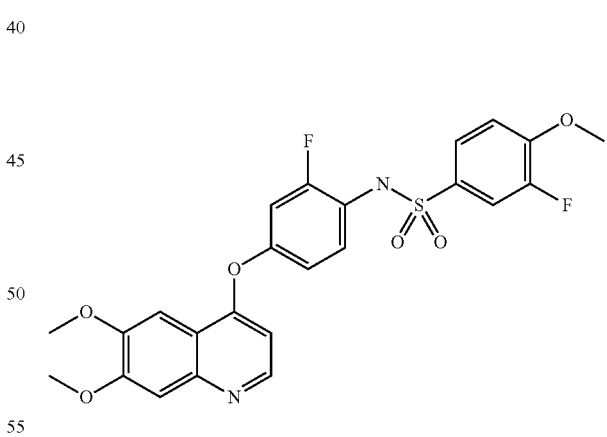

$C_{24}H_{20}F_2N_2O_6S$ Mw. 502.50

LC/MS purity: 100%, m/z 501 [M–H]⁻, m/z 503 [M–H]⁺ Rt. 2.62 min.

¹H NMR (300 MHz, DMSO-d6): 10.15 (bs, 1H), 8.50 (d, 1H), 7.51 (m, 3H), 7.41-7.21 (m, 4H), 7.04 (dd, 1H), 6.95 (d, 1H), 3.94 (s, 3H), 3.93 (s, 3H), 3.89 (s, 3H)

Melting point: 230-232° C. Yield: 23%

Example A89

Biphenyl-3-sulfonic acid [4-(6,7-dimethoxy-quinolin-4-yloxy)-2-methyl-phenyl]-amide

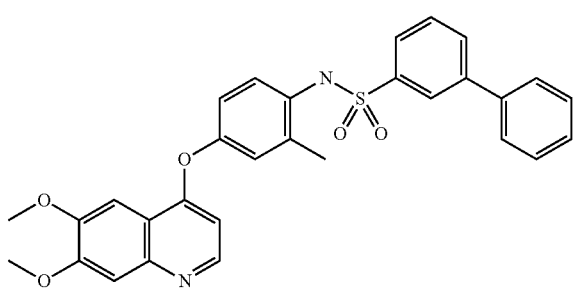

$C_{30}H_{26}N_2O_5S$ Mw. 526.62

LC/MS purity: 100%, m/z 525 [M−H]⁻, m/z 527 [M−H]⁺ Rt. 3.18 min.

¹H NMR (300 MHz, DMSO-d6): 9.69 (s, 1H), 8.40 (d, 1H), 7.97 (t, 1H), 7.87 (s, 1H), 7.66 (m, 4H), 7.48 (m, 4H), 7.38 (s, 1H), 7.06 (m, 3H), 6.39 (d, 1H), 3.94 (s, 3H), 3.90 (s, 3H), 2.00 (s, 3H)

Melting point: 220-222° C. Yield: 77%

Example A90

N-[4-(6,7-Dimethoxy-quinolin-4-yloxy)-2-methyl-phenyl]-3-phenoxy-benzenesulfonamide

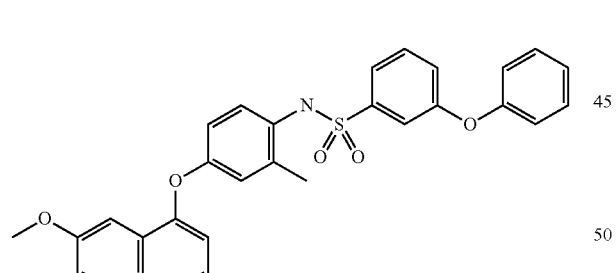

$C_{30}H_{26}N_2O_6S$ Mw. 542.62

LC/MS purity: 100%, m/z 541 [M−H]⁻, m/z 543 [M−H]⁺ Rt. 3.22 min.

¹H NMR (300 MHz, DMSO-d6): 9.71 (s, 1H), 8.46 (d, 1H), 7.61 (t, 1H), 7.43 (m, 5H), 7.18 (t, 1H), 7.08 (m, 7H), 6.44 (d, 1H), 3.94 (s, 3H), 3.91 (s, 3H), 1.98 (s, 3H)

Melting point: 169-170° C. Yield: 70%

Example A91

Naphthalene-1-sulfonic acid [4-(6,7-dimethoxy-quinolin-4-yloxy)-2-methyl-phenyl]-amide

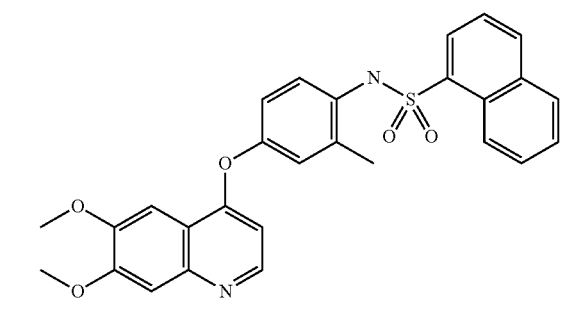 [SMILES: COc1cc2nccc(Oc3ccc(NS(=O)(=O)c4cccc5ccccc45)c(C)c3)c2cc1OC]

$C_{28}H_{24}N_2O_5S$ Mw. 500.58

LC/MS purity: 98%, m/z 499 [M−H]⁻, m/z 451 [M−H]⁺ Rt. 3.01 min.

¹H NMR (300 MHz, DMSO-d6): 9.93 (s, 1H), 8.71 (d, 1H), 8.47 (d, 1H), 8.25 (d, 1H), 8.08 (m, 2H), 7.70 (m, 2H), 7.61 (t, 1H), 7.41 (s, 1H), 7.37 (s, 1H), 7.03 (d, 1H), 6.94 (m, 2H), 6.37 (d, 1H), 3.93 (s, 3H), 3.89 (s, 3H), 1.85 (s, 3H)

Melting point: 233-235° C. Yield: 72%

Example A92

Biphenyl-4-sulfonic acid [4-(6,7-dimethoxy-quinolin-4-yloxy)-2-methyl-phenyl]-amide

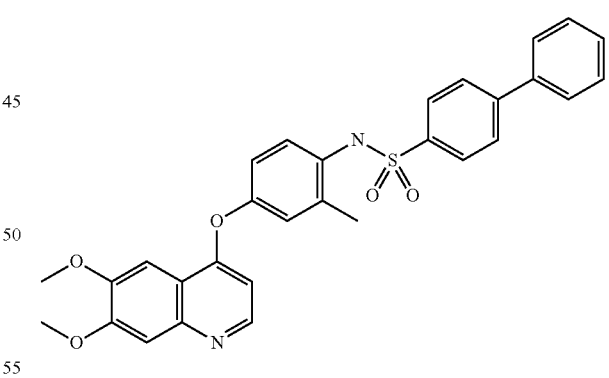

$C_{30}H_{26}N_2O_5S$ Mw. 526.62

LC/MS purity: 96%, m/z 525 [M−H]⁻, m/z 527 [M−H]⁺ Rt. 3.21 min.

¹H NMR (300 MHz, DMSO-d6): 9.71 (s, 1H), 8.48 (s, 1H), 7.90 (d, 2H), 7.51 (m, 4H), 7.46 (m, 3H), 7.44 (s, 1H), 7.38 (s, 1H), 7.08 (m, 3H), 6.47 (d, 1H), 3.93 (s, 3H), 3.89 (s, 3H), 2.04 (s, 3H)

Melting point: 228-230° C. Yield: 58%

Example A93

N-[4-(6,7-Dimethoxy-quinolin-4-yloxy)-2-methyl-phenyl]-3-pyrimidin-2-yl-benzenesulfonamide

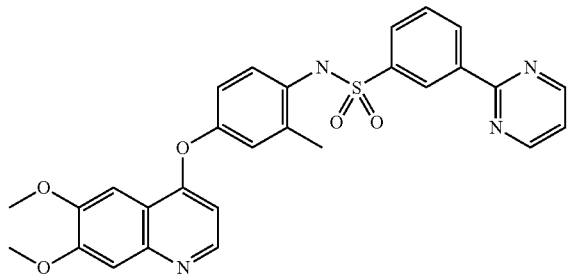 [SMILES: COc1cc2nccc(Oc3ccc(NS(=O)(=O)c4cccc(-c5ncccn5)c4)c(C)c3)c2cc1OC]

$C_{28}H_{24}N_4O_5S$ Mw. 528.59

LC/MS purity: 100%, m/z 527 [M−H]$^-$, m/z 529 [M−H]$^+$ Rt. 2.81 min.

$^1$H NMR (300 MHz, DMSO-d6): 9.79 (bs, 1H), 8.97 (d, 2H), 8.75 (d, 1H), 8.66 (d, 1H), 8.40 (d, 1H), 7.83 (dd, 1H), 7.75 (t, 1H), 7.54 (t, 1H), 7.43 (s, 1H), 7.37 (s, 1H), 7.06 (s, 1H), 7.02 (m, 2H), 6.39 (d, 1H), 3.93 (s, 3H), 3.89 (s, 3H), 2.01 (s, 3H)

Melting point: 103-105° C. Yield: 65%

Example A94

Benzo[b]thiophene-2-sulfonic acid [4-(6,7-dimethoxy-quinolin-4-yloxy)-2-methyl-phenyl]-amide

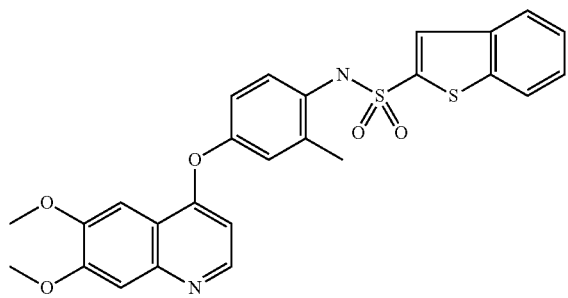 [SMILES: COc1cc2nccc(Oc3ccc(NS(=O)(=O)c4cc5ccccc5s4)c(C)c3)c2cc1OC]

$C_{26}H_{22}N_2O_5S_2$ Mw. 506.60

LC/MS purity: 98%, m/z 505 [M−H]$^-$, m/z 507 [M−H]$^+$ Rt. 3.05 min.

$^1$H NMR (300 MHz, DMSO-d6): 10.11 (s, 1H), 8.49 (d, 1H), 8.10 (d, 1H), 8.02 (d, 1H), 7.81 (s, 1H), 7.52 (m, 2H), 7.45 (s, 1H), 7.39 (s, 1H), 7.19 (d, 1H), 7.11 (d, 1H), 7.06 (dd, 1H), 6.48 (d, 1H), 3.94 (s, 3H), 3.91 (s, 3H), 2.07 (s, 3H)

Melting point: 255-257° C. Yield: 34%

Example A95

1-Methyl-2-oxo-2,3-dihydro-1H-indole-5-sulfonic acid [4-(6,7-dimethoxy-quinolin-4-yloxy)-2-methyl-phenyl]-amide

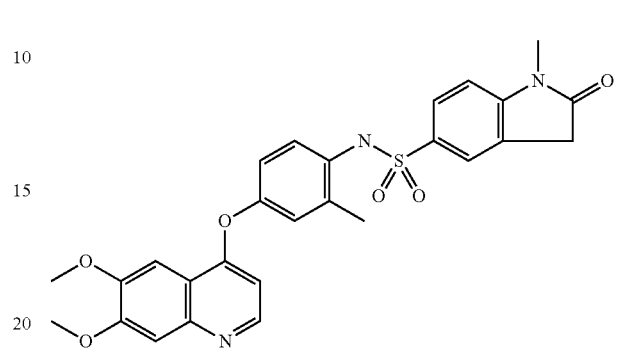

$C_{27}H_{25}N_3O_6S$ Mw. 519.58

LC/MS purity: 100%, m/z 518 [M−H]$^-$, m/z 520 [M−H]$^+$ Rt. 2.36 min.

$^1$H NMR (300 MHz, DMSO-d6): 9.5 (bs, 1H), 8.61 (m, 3H), 7.44 (s, 1H), 7.38 (s, 1H), 7.02 (m, 4H), 6.45 (d, 1H), 3.91 (s, 3H), 3.87 (s, 3H), 3.64 (s, 2H), 3.14 (s, 3H), 2.50 (s, 3H)

Melting point: 115-116° C. Yield: 71%

Example A96

N-[4-(6,7-Dimethoxy-quinolin-4-yloxy)-3-fluoro-phenyl]-2-trifluoromethyl-benzenesulfonamide

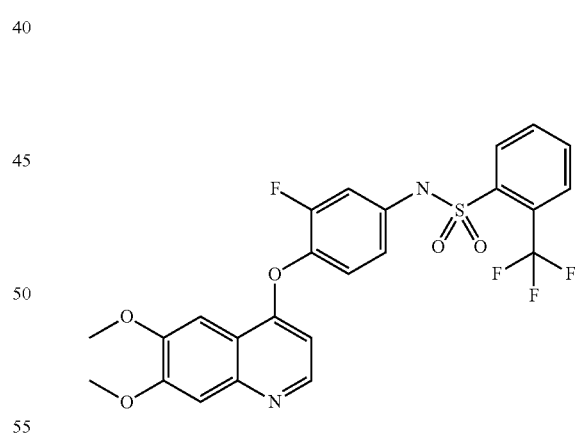

$C_{24}H_{18}F_4N_2O_5S$ Mw. 522.48

LC/MS purity: 99%, m/z 521 [M−H]$^-$, m/z 523 [M−H]$^+$ Rt. 2.99 min.

$^1$H NMR (300 MHz, DMSO-d6): 11.03 (bs, 1H), 8.45 (d, 1H), 8.16 (d, 1H), 8.04 (d, 1H), 7.90 (m, 3H), 7.47 (s, 1H), 7.40 (s, 1H), 7.38 (t, 1H), 7.16 (d, 1H), 7.03 (d, 1H), 3.94 (s, 3H), 3.91 (s, 3H)

Melting point: 80-83° C. Yield: 51%

Example A97

Biphenyl-3-sulfonic acid [4-(6,7-dimethoxy-quinolin-4-yloxy)-3-fluoro-phenyl]-amide

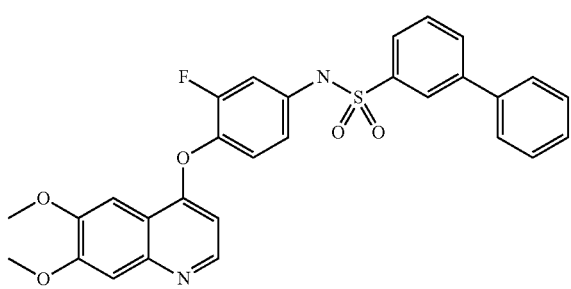 [SMILES: COc1cc2nccc(Oc3ccc(NS(=O)(=O)c4cccc(-c5ccccc5)c4)cc3F)c2cc1OC]

C$_{29}$H$_{23}$FN$_2$O$_5$S Mw. 530.58

LC/MS purity: 98%, m/z 529 [M−H]$^-$, m/z 531 [M−H]$^+$ Rt. 3.27 min.

$^1$H NMR (300 MHz, DMSO-d6): 10.5 (bs, 1H), 8.37 (d, 1H), 8.04 (s, 1H), 7.98 (d, 1H), 7.80 (d, 1H), 7.69 (m, 3H), 7.55-7.33 (m, 6H), 7.20 (dd, 1H), 7.06 (d, 1H), 6.28 (d, 1H), 3.97 (s, 3H), 3.90 (s, 3H)

Melting point: 109-111° C. Yield: 67%

Example A98

N-[4-(6,7-Dimethoxy-quinolin-4-yloxy)-3-fluoro-phenyl]-3-phenoxy-benzenesulfonamide

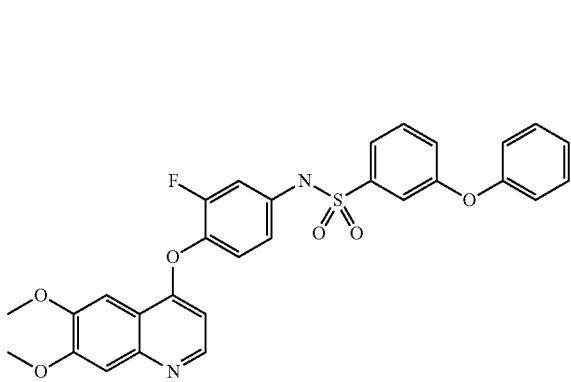 [SMILES: COc1cc2nccc(Oc3ccc(NS(=O)(=O)c4cccc(Oc5ccccc5)c4)cc3F)c2cc1OC]

C$_{29}$H$_{23}$FN$_2$O$_6$S Mw. 546.58

LC/MS purity: 99%, m/z 545 [M−H]$^-$, m/z 547 [M−H]$^+$ Rt. 3.28 min.

$^1$H NMR (300 MHz, DMSO-d6): 10.62 (bs, 1H), 8.45 (d, 1H), 7.62-7.52 (m, 8H), 7.24 (m, 2H), 7.14-7.00 (m, 4H), 6.36 (d, 1H), 3.95 (s, 3H), 3.93 (s, 3H)

Melting point: 197-199° C. Yield: 65%

Example A99

N-[4-(6,7-Dimethoxy-quinolin-4-yloxy)-3-fluoro-phenyl]-2,5-difluoro-benzenesulfonamide

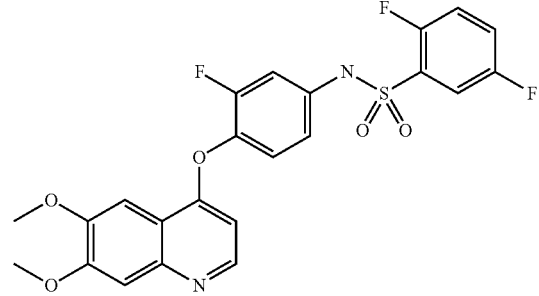

C$_{23}$H$_{17}$F$_3$N$_2$O$_5$S Mw. 490.46

LC/MS purity: 99%, m/z 489 [M−H]$^-$, m/z 491 [M−H]$^+$ Rt. 2.87 min.

$^1$H NMR (300 MHz, DMSO-d6): 11.12 (bs, 1H), 8.45 (d, 1H), 7.73-7.55 (m, 3H), 7.48 (s, 1H), 7.41 (s, 1H), 7.39 (t, 1H), 7.19 (dd, 1H), 7.05 (d, 1H), 6.36 (d, 1H), 3.94 (s, 3H), 3.92 (s, 3H)

Melting point: 232-234° C. Yield: 51%

Example A100

Naphthalene-1-sulfonic acid [4-(6,7-dimethoxy-quinolin-4-yloxy)-3-fluoro-phenyl]-amide

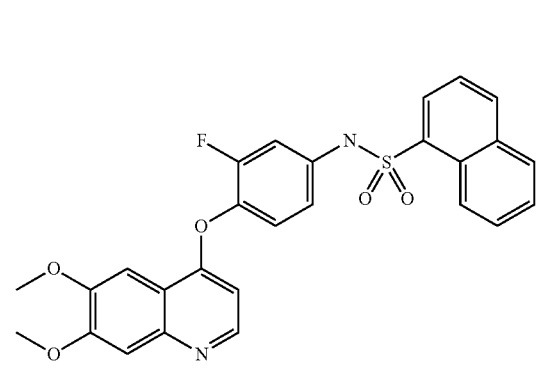 [SMILES: COc1cc2nccc(Oc3ccc(NS(=O)(=O)c4cccc5ccccc45)cc3F)c2cc1OC]

C$_{27}$H$_{21}$FN$_2$O$_5$S Mw. 504.54

LC/MS purity: 100%, m/z 503 [M−H]$^-$, m/z 505 [M−H]$^+$ Rt. 3.04 min.

$^1$H NMR (300 MHz, DMSO-d6): 11.04 (bs, 1H), 8.73 (d, 1H), 8.41 (d, 1H), 8.28 (m, 2H), 8.12 (d, 1H), 7.71 (m, 3H), 7.42 (s, 1H), 7.37 (s, 1H), 7.26 (t, 1H), 7.08 (dd, 1H), 6.93 (d, 1H), 6.26 (d, 1H), 3.92 (s, 3H), 3.88 (s, 3H)

Melting point: 118-120° C. Yield: 61%

Example A101

N-[4-(6,7-Dimethoxy-quinolin-4-yloxy)-3-fluoro-phenyl]-3-pyrimidin-2-yl-benzenesulfonamide

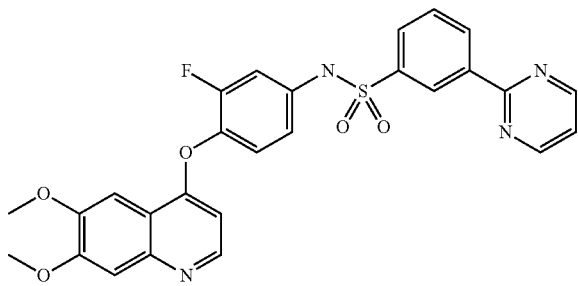

C$_{27}$H$_{21}$FN$_4$O$_5$S Mw. 532.55

LC/MS purity: 100%, m/z 531 [M−H]$^-$, m/z 533 [M−H]$^+$ Rt. 2.86 min.

$^1$H NMR (300 MHz, DMSO-d6): 10.75 (bs, 1H), 8.97 (d, 2H), 8.85 (s, 1H), 8.65 (d, 1H), 8.37 (d, 1H), 7.96 (d, 1H), 7.78 (t, 1H), 7.55 (t, 1H), 7.45 (s, 1H), 7.37 (s, 1H), 7.34 (d, 1H), 7.19 (dd, 1H), 7.02 (dd, 1H), 6.28 (d, 1H), 3.93 (s, 3H), 3.89 (s, 3H)

Melting point: 105-107° C. Yield: 39%

Example A102

N-[4-(6,7-Dimethoxy-quinolin-4-yloxy)-2-fluoro-phenyl]-3-pyrimidin-2-yl-benzenesulfonamide

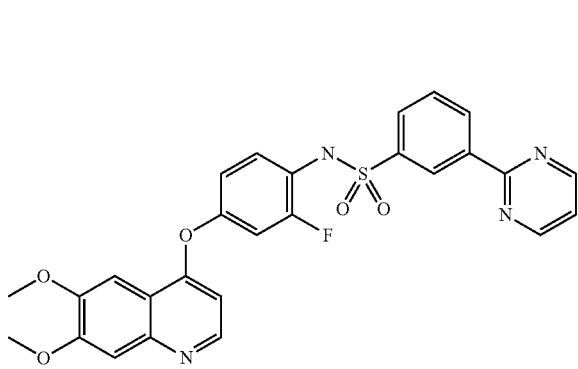 [SMILES: COc1cc2nccc(Oc3ccc(NS(=O)(=O)c4cccc(-c5ncccn5)c4)c(F)c3)c2cc1OC]

C$_{27}$H$_{21}$FN$_4$O$_5$S Mw. 532.55

LC/MS purity: 100%, m/z 531 [M−H]$^-$, m/z 533 [M−H]$^+$ Rt. 2.79 min.

$^1$H NMR (300 MHz, DMSO-d6): 10.33 (bs, 1H), 8.97 (d, 2H), 8.79 (s, 1H), 8.65 (d, 1H), 8.43 (d, 1H), 7.88 (d, 1H), 7.75 (t, 1H), 7.54 (t, 1H), 7.37 (m, 3H), 7.21 (dd, 1H), 7.06 (d, 1H), 6.47 (d, 1H), 3.93 (s, 3H), 3.89 (s, 3H)

Melting point: 137-140° C. Yield: 42%

Example A103

N-[4-(6,7-Dimethoxy-quinolin-4-yloxy)-phenyl]-2-trifluoromethyl-benzenesulfonamide

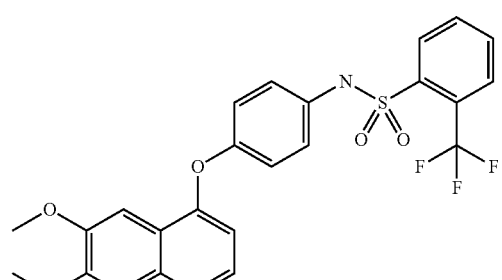

C$_{24}$H$_{19}$F$_3$N$_2$O$_5$S Mw. 504.49

LC/MS purity: 99%, m/z 503 [M−H]$^-$, m/z 505 [M−H]$^+$ Rt. 2.88 min.

$^1$H NMR (300 MHz, DMSO-d6): 10.71 (bs, 1H), 8.45 (d, 1H), 8.11 (dd, 1H), 8.02 (dd, 1H), 7.88 (m, 2H), 7.44 (s, 1H), 7.38 (s, 1H), 7.18 (dd, 4H), 6.37 (d, 1H), 3.93 (s, 3H), 3.81 (s, 3H)

Melting point: 224-227° C. Yield: 59%

Example A104

Naphthalene-1-sulfonic acid [4-(6,7-dimethoxy-quinolin-4-yloxy)-phenyl]-amide

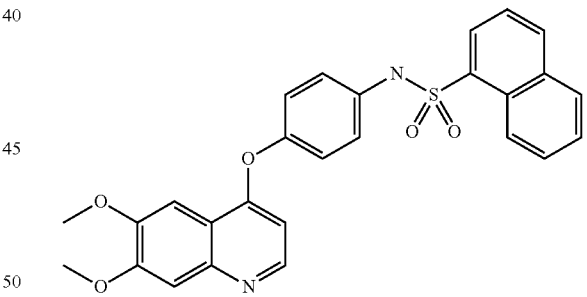

C$_{27}$H$_{22}$N$_2$O$_5$S Mw. 486.55

LC/MS purity: 100%, m/z 485 [M−H]$^-$, m/z 487 [M−H]$^+$ Rt. 2.96 min.

$^1$H NMR (300 MHz, DMSO-d6): 10.72 (bs, 1H), 8.75 (d, 1H), 8.41 (d, 1H), 8.22 (t, 2H), 8.09 (d, 1H), 7.71 (m, 3H), 7.39 (s, 1H), 7.35 (s, 1H), 7.09 (dd, 4H), 6.27 (d, 1H), 3.92 (s, 3H), 3.86 (s, 3H)

Melting point: 250-253° C. Yield: 61%

Example A105

3,5-Dichloro-N-[4-(6,7-dimethoxy-quinolin-4-yloxy)-2-methyl-phenyl]-4-hydroxy-benzenesulfonamide

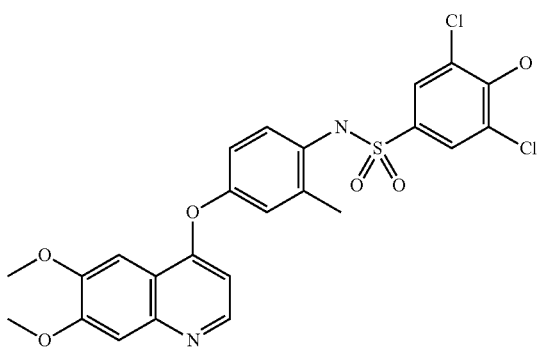 [SMILES: COc1cc2nccc(Oc3ccc(NS(=O)(=O)c4cc(Cl)c(O)c(Cl)c4)c(C)c3)c2cc1OC]

C₂₄H₂₀Cl₂N₂O₆S Mw. 535.41

LC/MS purity: 93%, m/z 533 [M–H]⁻, m/z 535 [M–H]⁺ Rt. 2.69 min.

¹H NMR (300 MHz, DMSO-d6): 9.71 (s, 1H), 8.55 (d, 1H), 7.56 (s, 3H), 7.52 (s, 1H), 7.43 (s, 1H), 7.16 (s, 2H), 7.06 (m, 2H), 6.53 (d, 1H), 3.96 (s, 3H), 3.93 (s, 3H), 2.09 (s, 3H)

Melting point: 255-259° C. Yield: 25%

Example A106

3,5-Dichloro-N-[4-(6,7-dimethoxy-quinolin-4-yloxy)-3-fluoro-phenyl]-2-methoxy-benzenesulfonamide

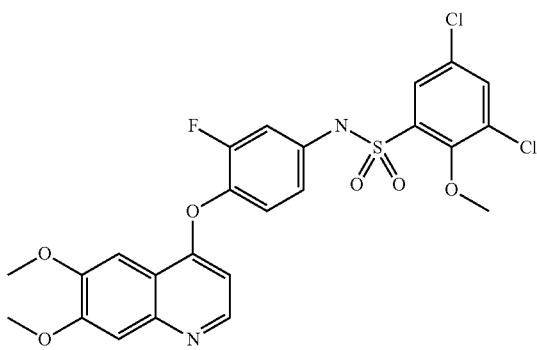 [SMILES: COc1cc2nccc(Oc3ccc(NS(=O)(=O)c4cc(Cl)cc(Cl)c4OC)cc3F)c2cc1OC]

C₂₄H₁₉Cl₂FN₂O₆S Mw. 553.40

LC/MS purity: 98%, m/z 551 [M–H]⁻, m/z 553 [M–H]⁺ Rt. 3.31 min.

¹H NMR (300 MHz, DMSO-d6): 10.86 (bs, 1H), 8.46 (d, 1H), 8.06 (d, 1H), 7.81 (d, 1H), 7.48 (s, 1H), 7.38 (m, 2H), 7.17 (dd, 1H), 7.04 (d, 1H), 6.36 (d, 1H), 3.96 (s, 3H), 3.94 (s, 3H), 3.91 (s, 3H)

Melting point: 155-158° C. Yield: 59%

Example A107

Biphenyl-4-sulfonic acid [4-(6,7-dimethoxy-quinolin-4-yloxy)-3-fluoro-phenyl]-amide

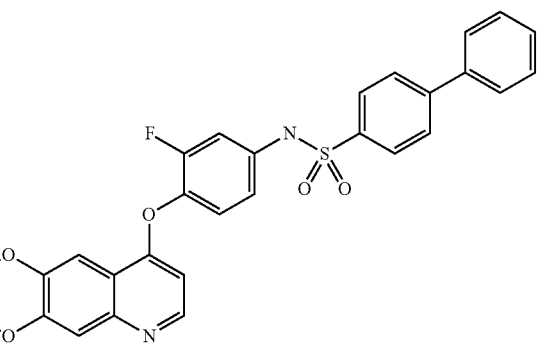

C₂₉H₂₃FN₂O₅S Mw. 530.58

LC/MS purity: 98%, m/z 529 [M–H]⁻, m/z 531 [M–H]⁺ Rt. 3.28 min.

¹H NMR (300 MHz, DMSO-d6): 10.72 (bs, 1H), 8.43 (d, 1H), 7.90 (s, 3H), 7.74 (d, 2H), 7.53-7.44 (m, 7H), 7.20 (d, 1H), 7.06 (d, 1H), 6.36 (d, 1H), 3.93 (s, 3H), 3.90 (s, 3H)

Melting point: 167-171° C. Yield: 40%

Example A108

Benzo[b]thiophene-3-sulfonic acid [4-(6,7-dimethoxy-quinolin-4-yloxy)-3-fluoro-phenyl]-amide

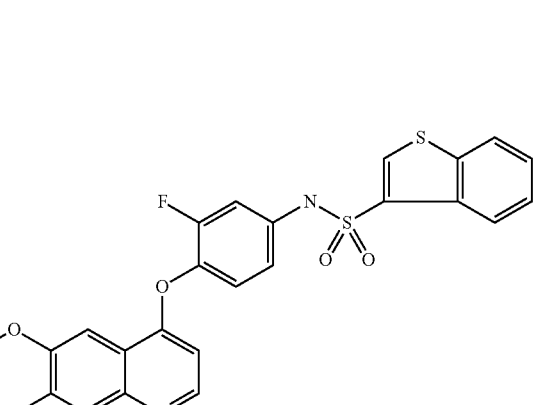

C₂₅H₁₉FN₂O₅S₂ Mw. 510.57

LC/MS purity: 99%, m/z 509 [M–H]⁻, m/z 511 [M–H]⁺ Rt. 3.03 min.

¹H NMR (300 MHz, DMSO-d6): 10.96 (bs, 1H), 8.72 (s, 1H), 8.43 (d, 1H), 8.23 (d, 1H), 8.14 (d, 1H), 7.55 (m, 2H), 7.45 (s, 1H), 7.38 (s, 1H), 7.31 (t, 1H), 7.16 (dd, 1H), 7.09 (d, 1H), 6.30 (d, 1H), 3.93 (s, 3H), 3.90 (s, 3H)

Melting point: 191-193° C. Yield: 63%

Example A109

N-[4-(6,7-Dimethoxy-quinolin-4-yloxy)-3-fluoro-phenyl]-4-fluoro-3-methoxy-benzenesulfonamide

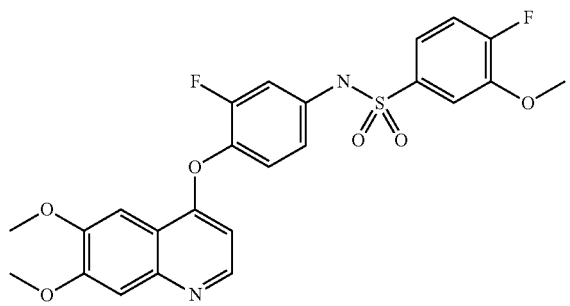

$C_{24}H_{20}F_2N_2O_6S$ Mw. 502.50

LC/MS purity: 97%, m/z 501 [M–H]$^-$, m/z 503 [M–H]$^+$ Rt. 2.92 min.

$^1$H NMR (300 MHz, DMSO-d6): 10.60 (bs, 1H), 8.46 (d, 1H), 7.54-7.34 (m, 6H), 7.19 (dd, 1H), 7.03 (d, 1H), 6.35 (d, 1H), 3.94 (s, 3H), 3.92 (s, 3H), 3.90 (s, 3H)

Melting point: 202-204° C. Yield: 61%

Example A110

4-Chloro-N-[4-(6,7-dimethoxy-quinolin-4-yloxy)-3-fluoro-phenyl]-2-fluoro-benzenesulfonamide

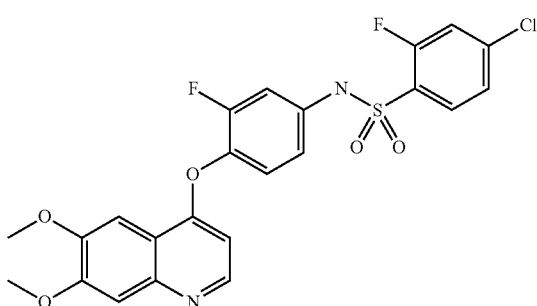 [SMILES: COc1cc2nccc(Oc3ccc(NS(=O)(=O)c4ccc(Cl)cc4F)cc3F)c2cc1OC]

$C_{23}H_{17}ClF_2N_2O_5S$ Mw. 506.92

LC/MS purity: 96%, m/z 505 [M–H]$^-$, m/z 507 [M–H]$^+$ Rt. 3.01 min.

$^1$H NMR (300 MHz, DMSO-d6): 11.08 (bs, 1H), 8.45 (d, 1H), 7.92 (m, 2H), 7.77 (dd, 1H), 7.52 (dd, 1H), 7.48 (s, 1H), 7.19 (s, 1H), 7.18 (t, 1H), 7.16 (dd, 1H), 7.03 (dd, 1H), 6.36 (d, 1H), 3.94 (s, 3H), 3.92 (s, 3H)

Melting point: 99-101° C. Yield: 54%

Example A111

3,5-Dichloro-N-[4-(6,7-dimethoxy-quinolin-4-yloxy)-2-methyl-phenyl]-2-methoxy-benzenesulfonamide

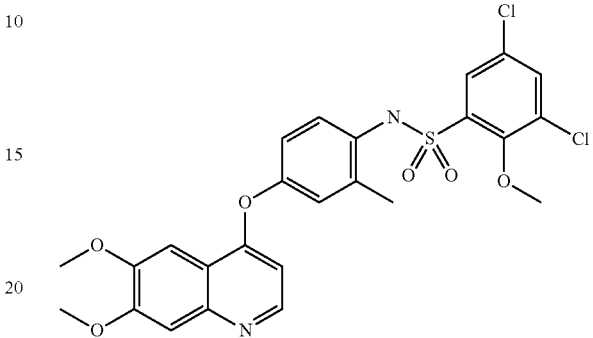

$C_{25}H_{22}Cl_2N_2O_6S$ Mw. 549.43

LC/MS purity: 97%, m/z 547 [M–H]$^-$, m/z 549 [M–H]$^+$ Rt. 3.27 min.

$^1$H NMR (300 MHz, DMSO-d6): 9.90 (bs, 1H), 8.48 (d, 1H), 8.05 (d, 1H), 7.56 (d, 1H), 7.44 (s, 1H), 7.39 (s, 1H), 7.07 (m, 3H), 6.45 (d, 1H), 3.94 (s, 6H), 3.90 (s, 3H), 2.07 (s, 3H), 2.08 (s, 3H)

Melting point: 159-162° C. Yield: 69%

Example A112

N-[4-(6,7-Dimethoxy-quinolin-4-yloxy)-2-methyl-phenyl]-2-trifluoromethoxy-benzenesulfonamide

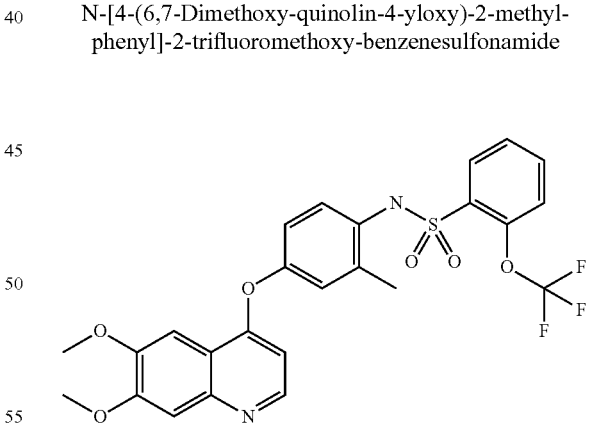

$C_{25}H_{21}F_3N_2O_6S$ Mw. 534.52

LC/MS purity: 98%, m/z 533 [M–H]$^-$, m/z 535 [M–H]$^+$ Rt. 2.91 min.

$^1$H NMR (300 MHz, DMSO-d6): 9.92 (bs, 1H), 8.48 (d, 1H), 7.86 (d, 1H), 7.79 (t, 1H), 7.69 (d, 1H), 7.53 (d, 1H), 7.44 (s, 1H), 7.39 (s, 1H), 7.09 (d, 1H), 7.07 (s, 1H), 7.01 (dd, 1H), 6.43 (d, 1H), 3.94 (s, 3H), 3.91 (s, 3H), 2.01 (s, 3H), 2.10 (s, 3H)

Melting point: 230-232° C. Yield: 64%

Example A113

N-[4-(6,7-Dimethoxy-quinolin-4-yloxy)-2-methyl-phenyl]-2-trifluoromethyl-benzenesulfonamide

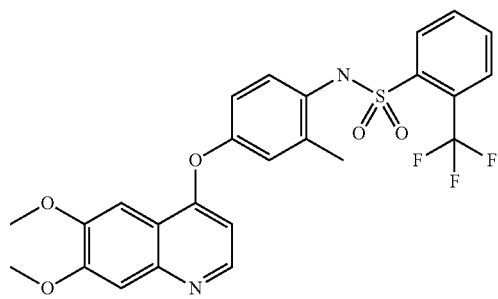 [SMILES: COc1cc2nccc(Oc3ccc(NS(=O)(=O)c4ccccc4C(F)(F)F)c(C)c3)c2cc1OC]

$C_{25}H_{21}F_3N_2O_5S$ Mw. 518.52

LC/MS purity: 96%, m/z 517 [M–H]⁻, m/z 519 [M–H]⁺ Rt. 2.96 min.

$^1$H NMR (300 MHz, DMSO-d6): 9.88 (bs, 1H), 8.48 (d, 1H), 8.02 (dd, 1H), 7.95 (dd, 1H), 7.86 (m, 2H), 7.44 (s, 1H), 7.39 (s, 1H), 7.05 (s, 1H), 6.44 (d, 1H), 3.94 (s, 3H), 3.91 (s, 3H), 2.01 (s, 3H), 2.11 (s, 3H)

Melting point: 254-257° C. Yield: 32%

Example A114

N-[4-(6,7-Dimethoxy-quinolin-4-yloxy)-phenyl]-2-trifluoromethoxy-benzenesulfonamide $C_{24}H_{19}F_3N_2O_6S$ Mw. 520.49

LC/MS purity: 100%, m/z 519 [M–H]⁻, m/z 521 [M–H]⁺ Rt. 2.96 min.

$^1$H NMR (300 MHz, DMSO-d6): 10.61 (bs, 1H), 8.45 (d, 1H), 7.98 (d, 1H), 7.79 (t, 1H), 7.56 (m, 2H), 7.44 (s, 1H), 7.38 (s, 1H), 7.18 (dd, 4H), 6.34 (d, 1H), 3.93 (s, 3H), 3.89 (s, 3H),

Melting point: 222-223° C. Yield: 63%

Example A115

N-[4-(6,7-Dimethoxy-quinolin-4-yloxy)-phenyl]-3-phenoxy-benzenesulfonamide

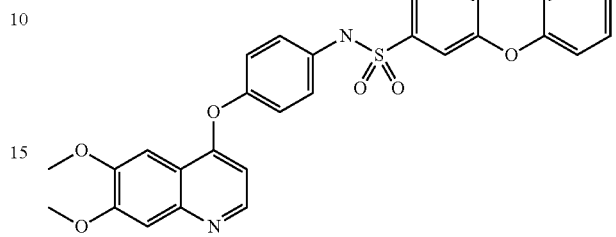

$C_{29}H_{24}N_2O_6S$ Mw. 528.59

LC/MS purity: 100%, m/z 527 [M–H]⁻, m/z 529 [M–H]⁺ Rt. 3.15 min.

$^1$H NMR (300 MHz, DMSO-d6): 10.32 (bs, 1H), 8.44 (d, 1H), 7.60 (t, 1H), 7.45 (m, 6H), 7.30 (d, 1H), 7.18 (m, 5H), 7.01 (d, 2H), 6.36 (d, 1H), 3.94 (s, 3H), 3.90 (s, 3H)

Melting point: 172-174° C. Yield: 57%

Example A116

N-[4-(6,7-Dimethoxy-quinolin-4-yloxy)-phenyl]-4-fluoro-3-methoxy-benzenesulfonamide

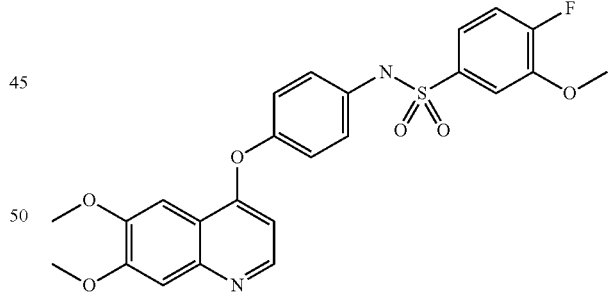

$C_{24}H_{21}FN_2O_6S$ Mw. 484.51

LC/MS purity: 100%, m/z 483 [M–H]⁻, m/z 485 [M–H]⁺ Rt. 2.81 min.

$^1$H NMR (300 MHz, DMSO-d6): 10.29 (bs, 1H), 8.45 (d, 1H), 7.38 (m, 5H), 7.19 (m, 4H), 6.36 (d, 1H), 3.93 (s, 3H), 3.89 (s, 3H), 3.87 (s, 3H)

Melting point: 222-224° C. Yield: 69%

Example A117

4-Bromo-3-chloro-N-[4-(6,7-dimethoxy-quinolin-4-yloxy)-phenyl]-benzenesulfonamide

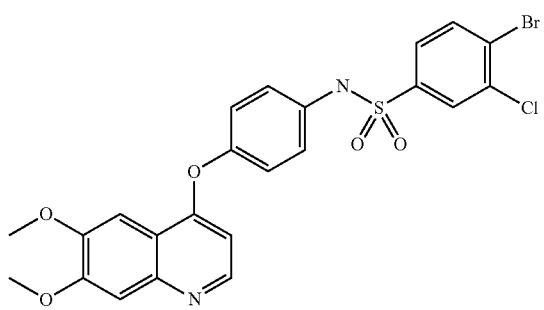 [SMILES: COc1cc2nccc(Oc3ccc(NS(=O)(=O)c4ccc(Br)c(Cl)c4)cc3)c2cc1OC]

C$_{23}$H$_{18}$BrClN$_2$O$_5$S Mw. 549.83

LC/MS purity: 99%, m/z 547 [M−H]$^-$, m/z 549 [M−H]$^+$ Rt. 3.11 min.

$^1$H NMR (300 MHz, DMSO-d6): 10.48 (bs, 1H), 8.46 (d, 1H), 8.02 (d, 1H), 7.88 (s, 1H), 7.59 (d, 1H), 7.45 (s, 1H), 7.38 (s, 1H), 7.20 (dd, 4H), 6.38 (d, 1H), 3.94 (s, 3H), 3.90 (s, 3H)

Melting point: 232-234° C. Yield: 73%

Example A118

N-[4-(6,7-Dimethoxy-quinolin-4-yloxy)-phenyl]-2,5-difluoro-benzenesulfonamide

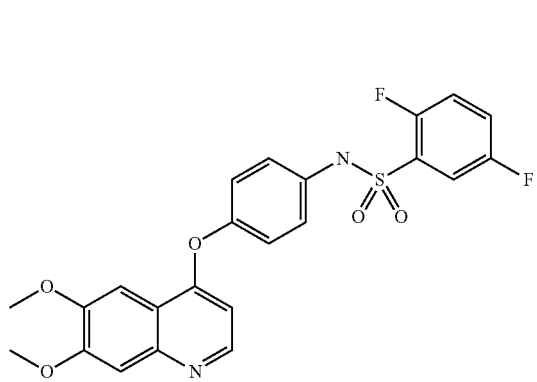 [SMILES: COc1cc2nccc(Oc3ccc(NS(=O)(=O)c4cc(F)ccc4F)cc3)c2cc1OC]

C$_{23}$H$_{18}$F$_2$N$_2$O$_5$S Mw. 472.47

LC/MS purity: 99%, m/z 471 [M−H]$^-$, m/z 473 [M−H]$^+$ Rt. 2.77 min.

$^1$H NMR (300 MHz, DMSO-d6): 10.80 (bs, 1H), 8.45 (d, 1H), 7.65-7.50 (m, 3H), 7.44 (s, 1H), 7.38 (s, 1H), 7.21 (dd, 4H), 6.36 (d, 1H), 3.93 (s, 3H), 3.89 (s, 3H)

Melting point: 260-263° C. Yield: 39%

Example A119

N-[4-(6,7-Dimethoxy-quinolin-4-yloxy)-3-methoxy-phenyl]-2-trifluoromethoxy-benzenesulfonamide

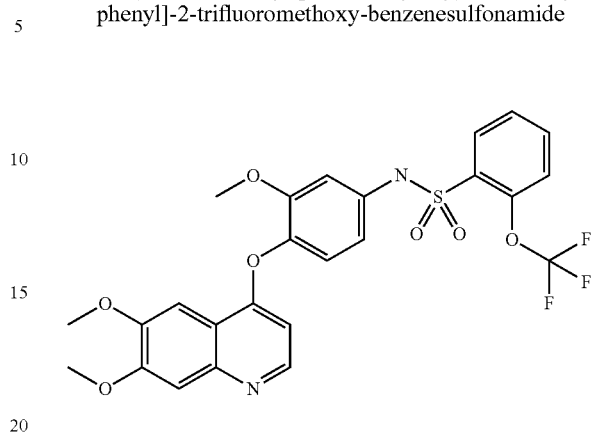

C$_{25}$H$_{21}$F$_3$N$_2$O$_7$S Mw. 550.51

LC/MS purity: 100%, m/z 549 [M−H]$^-$, m/z 551 [M−H]$^+$ Rt. 2.96 min.

$^1$H NMR (300 MHz, DMSO-d6): 10.62 (bs, 1H), 8.39 (d, 1H), 8.03 (dd, 1H), 7.80 (td, 1H), 7.59 (m, 2H), 7.46 (s, 1H), 7.36 (s, 1H), 7.13 (d, 1H), 6.97 (d, 1H), 6.72 (dd, 1H), 6.14 (d, 1H), 3.93 (s, 3H), 3.91 (s, 3H), 3.61 (s, 3H)

Melting point: 211-212° C. Yield: 59%

Example A120

N-[4-(6,7-Dimethoxy-quinolin-4-yloxy)-3-methoxy-phenyl]-3-phenoxy-benzenesulfonamide

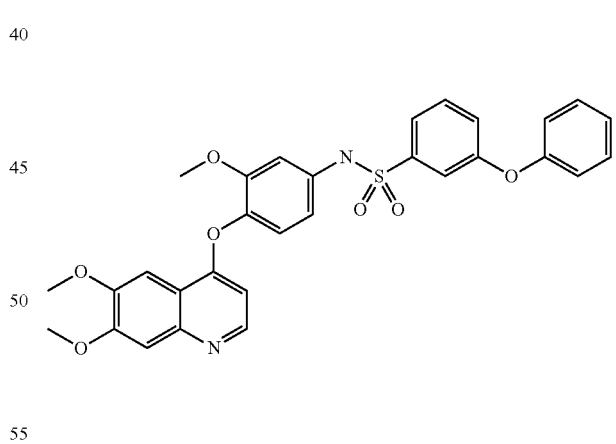

C$_{30}$H$_{26}$N$_2$O$_7$S Mw. 558.61

LC/MS purity: 99%, m/z 557 [M−H]$^-$, m/z 559 [M−H]$^+$ Rt. 3.19 min.

$^1$H NMR (300 MHz, DMSO-d6): 10.35 (bs, 1H), 8.38 (d, 1H), 7.59 (t, 1H), 7.47 (dd, 1H), 7.45 (m, 3H), 7.37 (s, 1H), 7.32 (d, 1H), 7.24 (m, 2H), 7.16 (d, 1H), 7.01 (d, 2H), 6.93 (d, 1H), 6.70 (dd, 1H), 6.16 (d, 1H), 3.94 (s, 3H), 3.92 (s, 3H), 3.61 (s, 3H)

Melting point: 106-107° C. Yield: 55%

Example A121

N-[4-(6,7-Dimethoxy-quinolin-4-yloxy)-3-methoxy-phenyl]-4-fluoro-3-methoxy-benzenesulfonamide

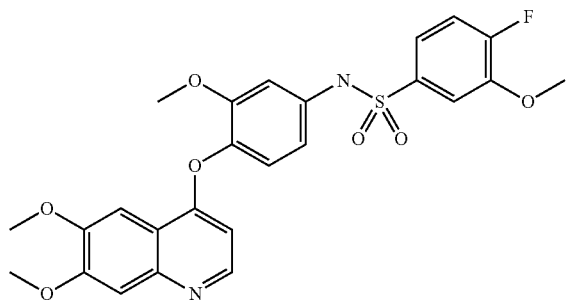

C$_{25}$H$_{23}$FN$_2$O$_7$S Mw. 514.53

LC/MS purity: 99%, m/z 513 [M–H]$^-$, m/z 515 [M–H]$^+$ Rt. 2.71 min.

$^1$H NMR (300 MHz, DMSO-d6): 10.3 (bs, 1H), 8.39 (d, 1H), 7.52 (dd, 1H), 7.45 (s, 1H), 7.39 (m, 2H), 7.36 (s, 1H), 7.14 (d, 1H), 6.97 (d, 1H), 6.15 (d, 1H), 3.93 (s, 3H), 3.91 (s, 3H), 3.89 (s, 3H), 3.64 (s, 3H)

Melting point: 109-110° C. Yield: 66%

Example A122

4-Bromo-3-chloro-N-[4-(6,7-dimethoxy-quinolin-4-yloxy)-3-methoxy-phenyl]-benzenesulfonamide

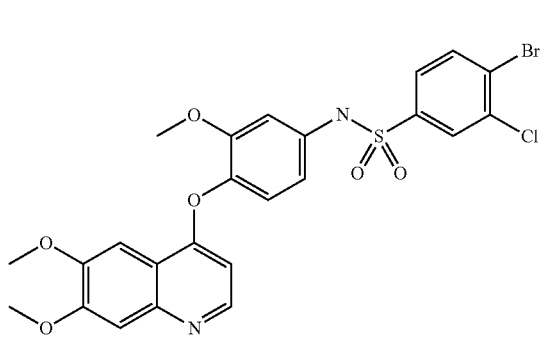 [SMILES: COc1cc2nccc(Oc3ccc(NS(=O)(=O)c4ccc(Br)c(Cl)c4)cc3OC)c2cc1OC]

C$_{24}$H$_{20}$BrClN$_2$O$_6$S Mw. 579.86

LC/MS purity: 99%, m/z 577 [M–H]$^-$, m/z 579 [M–H]$^+$ Rt. 3.12 min.

$^1$H NMR (300 MHz, DMSO-d6): 10.4 (bs, 1H), 8.40 (d, 1H), 8.30 (d, 1H), 7.92 (d, 1H), 7.63 (dd, 1H), 7.47 (s, 1H), 7.36 (s, 1H), 7.17 (d, 1H), 6.96 (d, 1H), 6.74 (d, 1H), 6.17 (d, 1H), 3.93 (s, 3H), 3.91 (s, 3H), 3.64 (s, 3H)

Melting point: 110-113° C. Yield: 75%

Example A123

N-[4-(6,7-Dimethoxy-quinolin-4-yloxy)-3-methoxy-phenyl]-2-trifluoromethyl-benzenesulfonamide

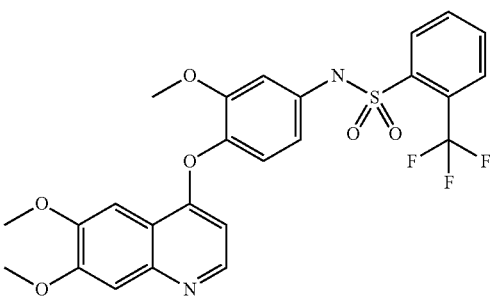 [SMILES: COc1cc2nccc(Oc3ccc(NS(=O)(=O)c4ccccc4C(F)(F)F)cc3OC)c2cc1OC]

C$_{25}$H$_{21}$F$_3$N$_2$O$_6$S Mw. 534.52

LC/MS purity: 100%, m/z 533 [M–H]$^-$, m/z 535 [M–H]$^+$ Rt. 2.91 min.

$^1$H NMR (300 MHz, DMSO-d6): 10.74 (bs, 1H), 8.39 (d, 1H), 8.15 (d, 1H), 7.89 (m, 2H), 7.45 (s, 1H), 7.36 (s, 1H), 7.14 (d, 1H), 6.98 (d, 2H), 6.73 (dd, 1H), 6.16 (d, 1H), 3.93 (s, 3H), 3.90 (s, 3H), 3.62 (s, 3H)

Melting point: 198-199° C. Yield: 49%

Example A124

4-Bromo-3-chloro-N-[4-(6,7-dimethoxy-quinolin-4-yloxy)-3-fluoro-phenyl]-benzenesulfonamide

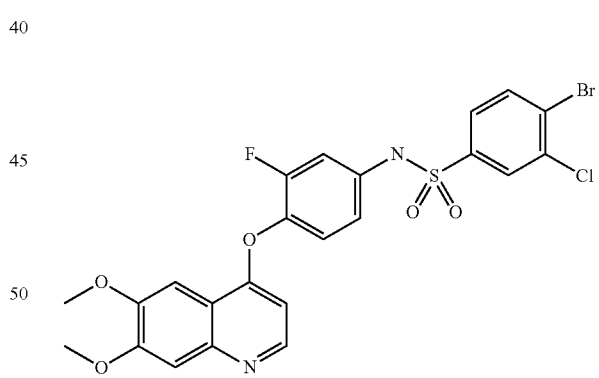

C$_{23}$H$_{17}$BrClFN$_2$O$_5$S Mw. 567.82

LC/MS purity: 99%, m/z 565 [M–H]$^-$, m/z 567 [M–H]$^+$ Rt. 3.22 min.

$^1$H NMR (300 MHz, DMSO-d6): 11 (bs, 1H), 8.46 (d, 1H), 8.01 (d, 1H), 7.93 (s, 1H), 7.63 (dd, 1H), 7.48 (s, 1H), 7.36 (s, 1H), 7.34 (t, 1H), 7.15 (dd, 1H), 6.98 (d, 1H), 6.37 (d, 1H), 3.94 (s, 3H), 3.92 (s, 3H)

Melting point: 144-147° C. Yield: 43%

Example A125

1-Methyl-2-oxo-2,3-dihydro-1H-indole-5-sulfonic acid [4-(6,7-dimethoxy-quinolin-4-yloxy)-3-fluoro-phenyl]-amide

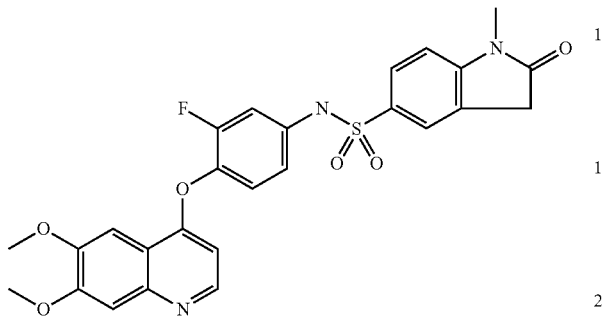

$C_{26}H_{22}FN_3O_6S$ Mw. 523.54

LC/MS purity: 99%, m/z 533 [M−H]⁻, m/z 535 [M−H]⁺ Rt. 2.60 min.

¹H NMR (300 MHz, DMSO-d6): 10.7 (bs, 1H), 8.45 (m, 1H), 7.76 (d, 1H), 7.67 (s, 1H), 7.46 (s, 1H), 7.39 (s, 1H), 7.33 (t, 1H), 7.15 (m, 2H), 7.00 (d, 1H), 6.36 (d, 1H), 3.94 (s, 3H), 3.91 (s, 3H), 3.65 (s, 2H), 3.14 (s, 3H)

Melting point: 163-165° C. Yield: 59%

Example A126

N-[4-(6,7-Dimethoxy-quinolin-4-yloxy)-3-fluoro-phenyl]-2-trifluoromethoxy-benzenesulfonamide

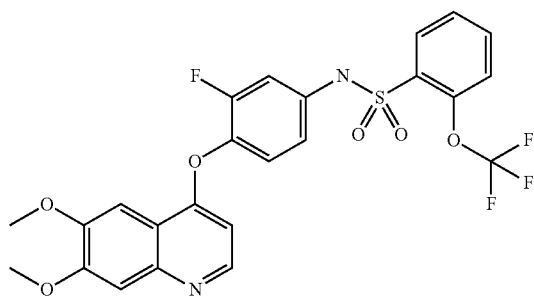

$C_{24}H_{18}F_4N_2O_6S$ Mw. 538.48

LC/MS purity: 100%, m/z 537 [M−H]⁻, m/z 539 [M−H]⁺ Rt. 3.05 min.

¹H NMR (300 MHz, DMSO-d6): 10.93 (bs, 1H), 8.45 (d, 1H), 8.04 (dd, 1H), 7.79 (dt, 1H), 7.58 (m, 3H), 7.47 (s, 1H), 7.39 (s, 1H), 7.35 (t, 1H), 7.15 (dd, 1H), 6.98 (d, 1H), 3.94 (s, 3H), 3.92 (s, 3H)

Melting point: 203-204° C. Yield: 42%

Example A127

3,5-Dichloro-N-[4-(6,7-dimethoxy-quinolin-4-yloxy)-3-methyl-phenyl]-2-methoxy-benzene-sulfonamide

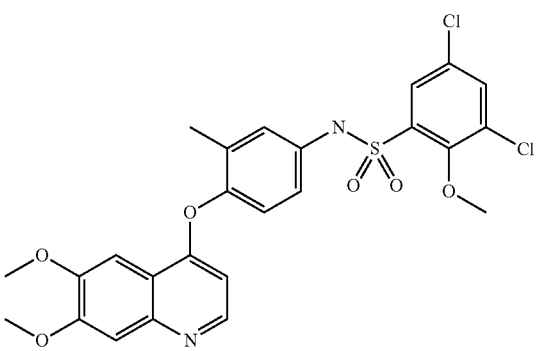

$C_{25}H_{22}Cl_2N_2O_6S$ Mw. 549.43

LC/MS purity: 98%, m/z 547 [M−H]⁻, m/z 549 [M−H]⁺ Rt. 3.27 min.

¹H NMR (300 MHz, DMSO-d6): 10.50 (bs, 1H), 8.41 (d, 1H), 7.74 (d, 1H), 7.51 (s, 1H), 7.44 (s, 1H), 7.38 (s, 1H), 7.07 (m, 3H), 6.17 (d, 1H), 3.96 (s, 3H), 3.94 (s, 3H), 3.91 (s, 3H), 2.03 (s, 3H)

Melting point: 206-208° C. Yield: 78%

Example A128

N-[4-(6,7-Dimethoxy-quinolin-4-yloxy)-3-methyl-phenyl]-2-trifluoromethyl-benzenesulfonamide

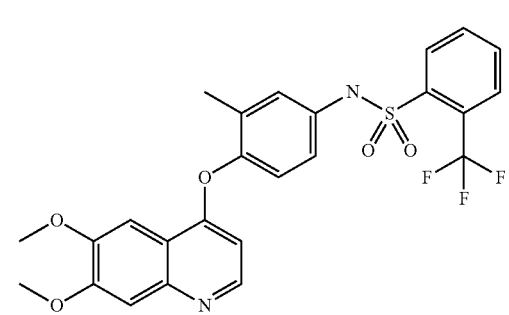

$C_{25}H_{21}F_3N_2O_5S$ Mw. 518.52

LC/MS purity: 100%, m/z 517 [M−H]⁻, m/z 519 [M−H]⁺ Rt. 2.98 min.

¹H NMR (300 MHz, DMSO-d6): 10.66 (bs, 1H), 8.42 (d, 1H), 8.12 (d, 1H), 8.02 (d, 1H), 7.88 (m, 2H), 7.50 (s, 1H), 7.38 (s, 1H), 7.08 (m, 3H), 6.18 (d, 1H), 3.93 (s, 3H), 3.91 (s, 3H), 2.03 (s, 3H)

Melting point: 209-211° C. Yield: 59%

Example A129

N-[4-(6,7-Dimethoxy-quinolin-4-yloxy)-3-methyl-phenyl]-2-trifluoromethoxy-benzenesulfonamide

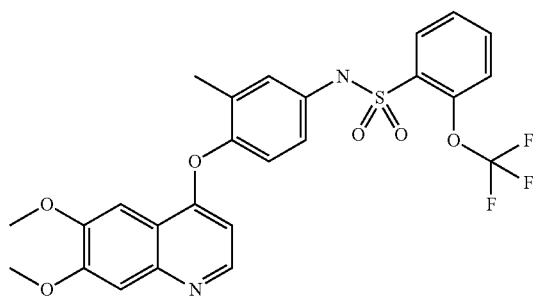 [SMILES: COc1cc2nccc(Oc3ccc(NS(=O)(=O)c4ccccc4OC(F)(F)F)cc3C)c2cc1OC]

$C_{25}H_{21}F_3N_2O_6S$ Mw. 534.52

LC/MS purity: 100%, m/z 533 [M−H]⁻, m/z 535 [M−H]⁺ Rt. 3.04 min.

¹H NMR (300 MHz, DMSO-d6): 10.55 (s, 1H), 8.41 (d, 1H), 7.99 (d, 1H), 7.79 (t, 1H), 7.55 (m, 2H), 7.51 (s, 1H), 7.38 (s, 1H), 7.12 (d, 1H), 7.08 (d, 1H), 7.01 (d, 1H), 6.15 (d, 1H), 3.94 (s, 3H), 3.92 (s, 3H), 2.02 (s, 3H)

Melting point: 207-209° C. Yield: 71%

Example A130

4-Methoxy-naphthalene-1-sulfonic acid [4-(6,7-dimethoxy-quinolin-4-yloxy)-3-methyl-phenyl]-amide

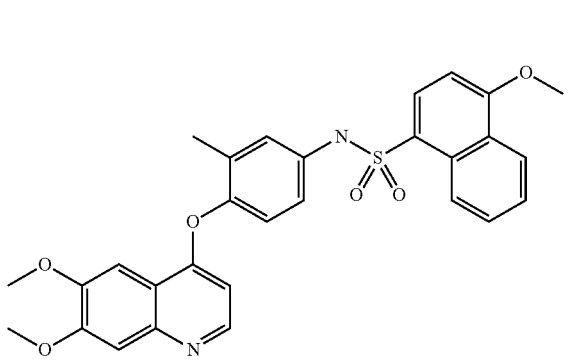

$C_{29}H_{26}N_2O_6S$ Mw. 530.60

LC/MS purity: 96%, m/z 529 [M−H]⁻, m/z 531 [M−H]⁺ Rt. 2.97 min.

¹H NMR (300 MHz, DMSO-d6): 10.54 (s, 1H), 8.70 (d, 1H), 8.37 (d, 1H), 8.25 (d, 1H), 8.22 (d, 1H), 7.58 (m, 2H), 7.45 (s, 1H), 7.36 (s, 1H), 6.99 (m, 4H), 6.09 (d, 1H), 4.05 (s, 3H), 3.92 (s, 3H), 3.88 (s, 3H), 1.95 (s, 3H)

Melting point: 233-235° C. Yield: 34%

Example A131

N-[4-(6,7-Dimethoxy-quinolin-4-yloxy)-3-methyl-phenyl]-2,5-difluoro-benzenesulfonamide

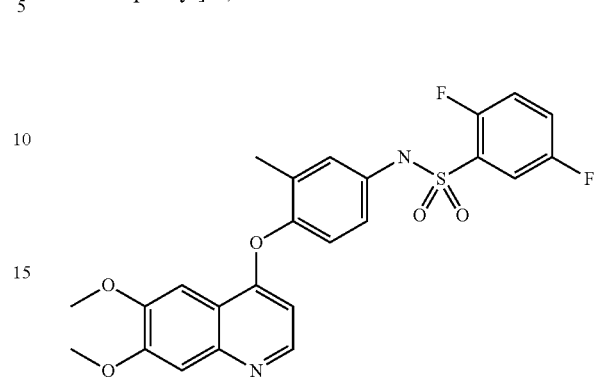

$C_{24}H_{20}F_2N_2O_5S$ Mw. 486.50

LC/MS purity: 100%, m/z 485 [M−H]⁻, m/z 487 [M−H]⁺ Rt. 2.72 min.

¹H NMR (300 MHz, DMSO-d6): 10.76 (s, 1H), 8.41 (d, 1H), 7.58 (m, 3H), 7.51 (s, 1H), 7.38 (s, 1H), 7.09 (m, 3H), 6.17 (d, 1H), 3.94 (s, 3H), 3.91 (s, 3H), 2.04 (s, 3H)

Melting point: 239-240° C. Yield: 74%

Example A132

N-[4-(6,7-Dimethoxy-quinolin-4-yloxy)-3-methyl-phenyl]-3-pyrimidin-2-yl-benzenesulfonamide

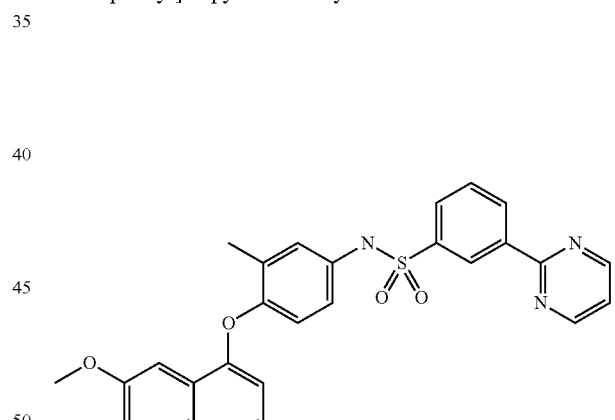

$C_{28}H_{24}N_4O_5S$ Mw. 528.59

LC/MS purity: 99%, m/z 527 [M−H]⁻, m/z 529 [M−H]⁺ Rt. 2.85 min.

¹H NMR (300 MHz, DMSO-d6): 11.38 (bs, 1H), 8.97 (d, 2H), 8.83 (s, 1H), 8.62 (d, 1H), 8.31 (d, 1H), 7.92 (d, 1H), 7.75 (t, 1H), 7.54 (t, 1H), 7.48 (s, 1H), 7.36 (s, 1H), 7.14 (s, 1H), 7.05 (dd, 2H), 6.10 (d, 1H), 3.93 (s, 3H), 3.90 (s, 3H), 2.00 (s, 3H)

Melting point: 188-190° C. Yield: 16%

Example A133

4-Methoxy-naphthalene-1-sulfonic acid [4-(6,7-dimethoxy-quinolin-4-yloxy)-phenyl]-amide

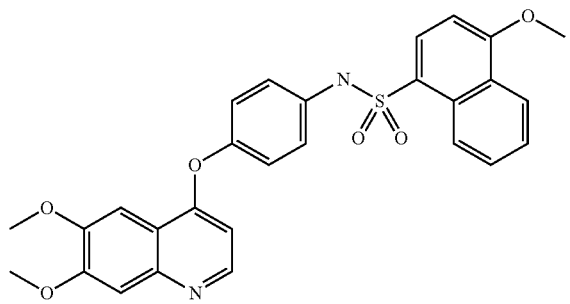

$C_{28}H_{24}N_2O_6S$ Mw. 516.58

LC/MS purity: 96%, m/z 515 [M–H]⁻, m/z 517 [M–H]⁺ Rt. 2.91 min.

¹H NMR (300 MHz, DMSO-d6): 10.60 (bs, 1H), 8.70 (d, 1H), 8.40 (d, 1H), 8.19 (d, 1H), 7.75 (t, 1H), 7.65 (t, 1H), 7.39 (s, 1H), 7.35 (s, 1H), 7.07 (m, 6H), 6.27 (d, 1H), 4.04 (s, 3H), 3.92 (s, 3H), 3.86 (s, 3H)

Melting point: 240-242° C. Yield: 14%

Example A134

4-Chloro-N-[4-(6,7-dimethoxy-quinolin-4-yloxy)-phenyl]-2-fluoro-benzenesulfonamide

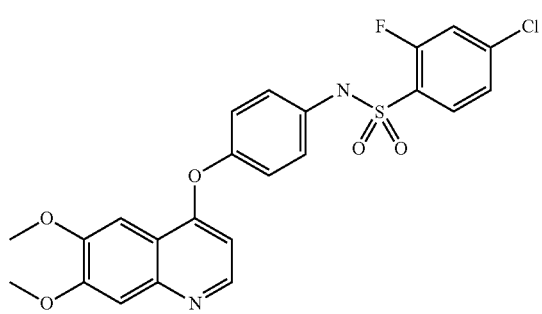 [SMILES: COc1cc2nccc(Oc3ccc(NS(=O)(=O)c4ccc(Cl)cc4F)cc3)c2cc1OC]

$C_{23}H_{18}ClFN_2O_6S$ Mw. 488.93

LC/MS purity: 100%, m/z 487 [M–H]⁻, m/z 489 [M–H]⁺ Rt. 2.92 min.

¹H NMR (300 MHz, DMSO-d6): 10.76 (bs, 1H), 8.45 (d, 1H), 7.83 (t, 1H), 7.75 (d, 1H), 7.49 (d, 1H), 7.44 (s, 1H), 7.38 (s, 1H), 7.18 (dd, 4H), 6.36 (d, 1H), 3.93 (s, 3H), 3.89 (s, 3H)

Melting point: 218-220° C. Yield: 69%

Example A135

4-Methoxy-naphthalene-1-sulfonic acid [4-(6,7-dimethoxy-quinolin-4-yloxy)-3-fluoro-phenyl]-amide

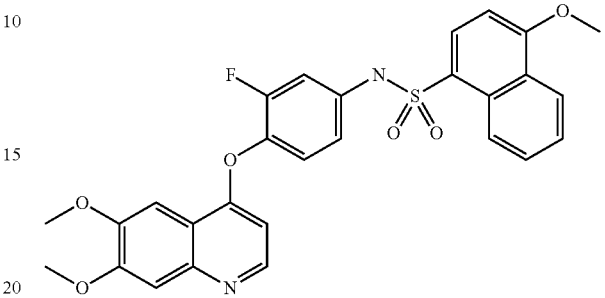

$C_{28}H_{23}FN_2O_6S$ Mw. 534.57

LC/MS purity: 96%, m/z 533 [M–H]⁻, m/z 535 [M–H]⁺ Rt. 3.14 min.

¹H NMR (300 MHz, DMSO-d6): 10.91 (bs, 1H), 8.69 (d, 1H), 8.40 (d, 1H), 8.27 (m, 2H), 7.77 (t, 1H), 7.65 (t, 1H), 7.42 (s, 1H), 7.37 (s, 1H), 7.25 (m, 1H), 7.08 (m, 2H), 6.91 (dd, 1H), 6.27 (d, 1H), 4.07 (s, 3H), 3.98 (s, 3H), 3.89 (s, 3H)

Melting point: 145-147° C. Yield: 31%

Example A136

Biphenyl-4-sulfonic acid [4-(6,7-dimethoxy-quinolin-4-yloxy)-2-fluoro-phenyl]-amide

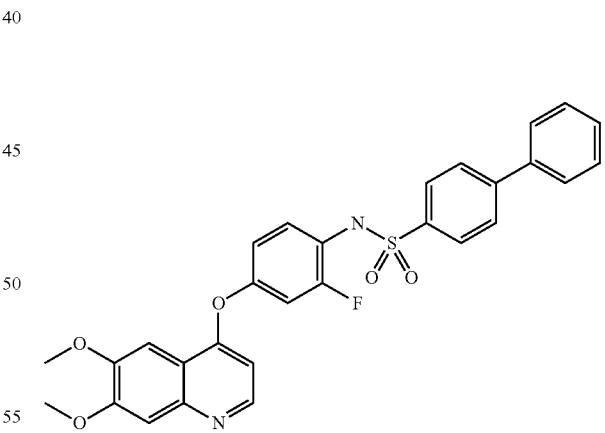

$C_{29}H_{23}FN_2O_5S$ Mw. 530.58

LC/MS purity: 99%, m/z 529 [M–H]⁻, m/z 531 [M–H]⁺ Rt. 3.20 min.

¹H NMR (300 MHz, DMSO-d6): 10.29 (bs, 1H), 8.49 (d, 1H), 7.89 (d, 2H), 7.82 (d, 2H), 7.74 (d, 2H), 7.44 (m, 6H), 7.23 (dd, 1H), 7.04 (d, 1H), 6.55 (d, 1H), 3.93 (s, 3H), 3.89 (s, 3H)

Melting point: 199-201° C. Yield: 38%

Example A137

1-Methyl-2-oxo-2,3-dihydro-1H-indole-5-sulfonic acid [4-(6,7-dimethoxy-quinolin-4-yloxy)-2-fluoro-phenyl]-amide

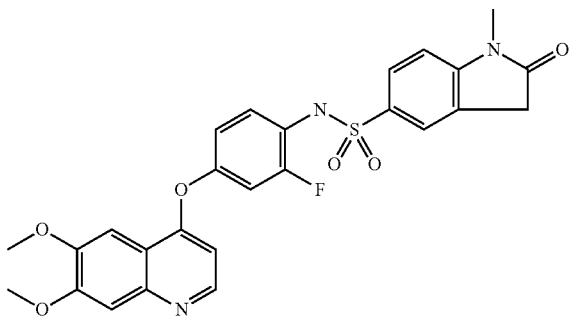 [SMILES: COc1cc2nccc(Oc3ccc(NS(=O)(=O)c4ccc5c(c4)CC(=O)N5C)c(F)c3)c2cc1OC]

$C_{26}H_{22}FN_3O_6S$ Mw. 523.54

LC/MS purity: 100%, m/z 522 [M–H]$^-$, m/z 524 [M–H]$^+$ Rt. 2.53 min.

$^1$H NMR (300 MHz, DMSO-d6): 10 (bs, 1H), 8.49 dm, 1H), 7.65 (m, 2H), 7.42-7.28 (m, 4H), 7.20 (dd, 1H), 7.01 (dd, 1H), 6.53 (d, 1H), 3.94 (s, 3H), 3.89 (s, 3H), 3.63 (s, 2H), 3.14 (s, 3H)

Melting point: 195-197° C. Yield: 54%

Example A138

Biphenyl-3-sulfonic acid [4-(6,7-dimethoxy-quinolin-4-yloxy)-3-methoxy-phenyl]-amide

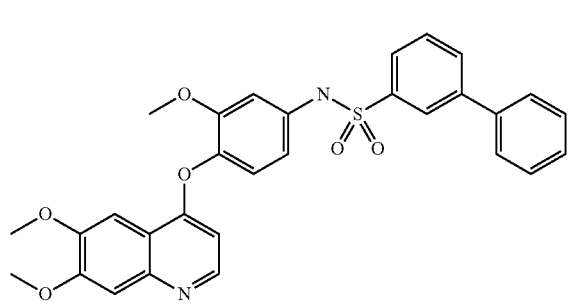

$C_{30}H_{26}N_2O_6S$ Mw. 542.62

LC/MS purity: 99%, m/z 541 [M–H]$^-$, m/z 543 [M–H]$^+$ Rt. 3.15 min.

$^1$H NMR (300 MHz, DMSO-d6): 0.37 (bs, 1H), 8.29 (d, 1H), 8.03 (s, 1H), 7.97 (d, 1H), 7.79 (d, 1H), 7.68 (m, 3H), 7.49 (m, 4H), 7.35 (s, 1H), 7.14 (d, 1H), 6.98 (d, 1H), 6.78 (dd, 1H), 6.08 (d, 1H), 3.92 (s, 3H), 3.89 (s, 3H), 3.60 (s, 3H)

Melting point: 108-110° C. Yield: 47%

Example A139

N-[4-(6,7-Dimethoxy-quinolin-4-yloxy)-3-methoxy-phenyl]-2,5-difluoro-benzenesulfonamide

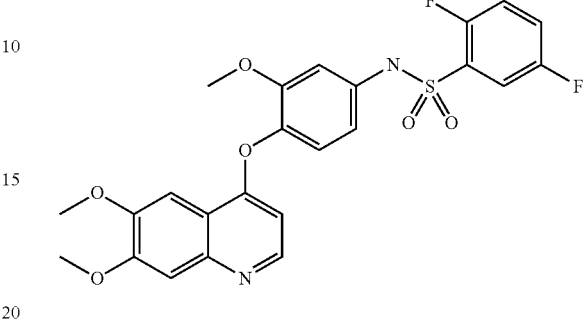

$C_{24}H_{20}F_2N_2O_6S$ Mw. 502.50

LC/MS purity: 99%, m/z 501 [M–H]$^-$, m/z 503 [M–H]$^+$ Rt. 2.82 min.

$^1$H NMR (300 MHz, DMSO-d6): 10.85 (bs, 1H), 8.39 (d, 1H), 7.70-7.54 (m, 3H), 7.46 (s, 1H), 7.36 (s, 1H), 7.16 (d, 1H), 6.98 (d, 1H), 6.77 (dd, 1H), 6.14 (d, 1H), 3.93 (s, 3H), 3.91 (s, 3H), 3.64 (s, 3H)

Melting point: 222-224° C. Yield: 43%

Example A140

Naphthalene-1-sulfonic acid [4-(6,7-dimethoxy-quinolin-4-yloxy)-3-methoxy-phenyl]-amide

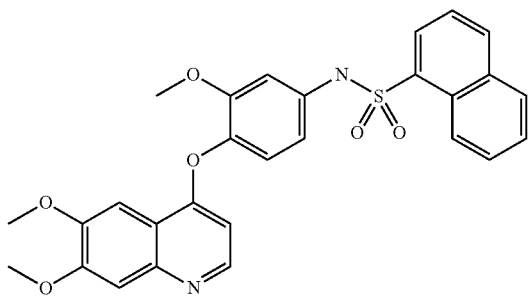 [SMILES: COc1cc2nccc(Oc3ccc(NS(=O)(=O)c4cccc5ccccc45)cc3OC)c2cc1OC]

$C_{28}H_{24}N_2O_6S$ Mw. 516.58

LC/MS purity: 98%, m/z 515 [M–H]$^-$, m/z 517 [M–H]$^+$ Rt. 2.98 min.

$^1$H NMR (300 MHz, DMSO-d6): 10.75 (bs, 1H), 8.79 (d, 1H), 8.35 (d, 1H), 8.25 (m, 2H), 8.09 (d, 1H), 7.70 (m, 3H), 7.41 (s, 1H), 7.33 (s, 1H), 6.99 (d, 1H), 6.84 (s, 1H), 6.62 (d, 1H), 6.04 (d, 1H), 3.91 (s, 3H), 3.88 (s, 3H), 3.52 (s, 3H)

Melting point: 136-138° C. Yield: 34%

Example A141

4-Chloro-N-[4-(6,7-dimethoxy-quinolin-4-yloxy)-3-methoxy-phenyl]-2-fluoro-benzenesulfonamide

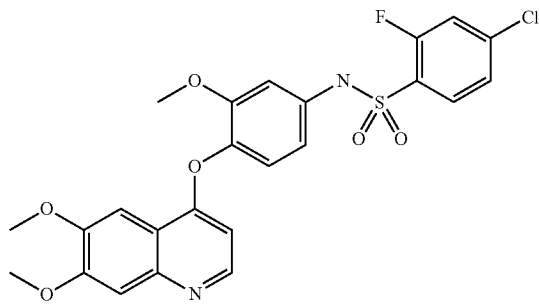 [SMILES: COc1cc2nccc(Oc3ccc(NS(=O)(=O)c4ccc(Cl)cc4F)cc3OC)c2cc1OC]

$C_{24}H_{20}ClFN_2O_6S$ Mw. 518.95

LC/MS purity: 100%, m/z 517 [M–H]$^-$, m/z 519 [M–H]$^+$ Rt. 2.84 min.

$^1$H NMR (300 MHz, DMSO-d6): 10.80 (bs, 1H), 8.38 (d, 1H), 7.87 (t, 1H), 7.76 (dd, 1H), 7.51 (d, 1H), 7.46 (s, 3H), 7.36 (s, 1H), 7.16 (d, 1H), 6.97 (d, 1H), 6.75 (dd, 1H), 6.15 (d, 1H), 3.93 (s, 3H), 3.91 (s, 3H), 3.66 (s, 3H)

Melting point: 124–126° C. Yield: 43%

Example A142

Biphenyl-4-sulfonic acid [4-(6,7-dimethoxy-quinolin-4-yloxy)-3-methoxy-phenyl]-amide

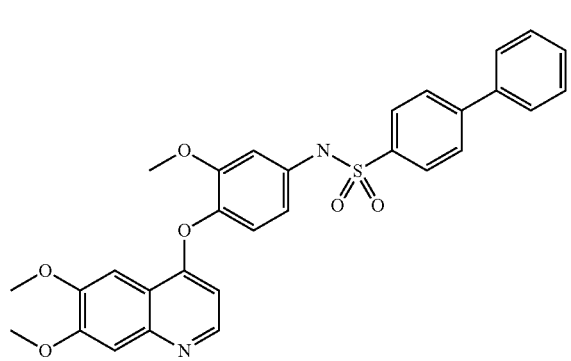 [SMILES: COc1cc2nccc(Oc3ccc(NS(=O)(=O)c4ccc(-c5ccccc5)cc4)cc3OC)c2cc1OC]

$C_{30}H_{26}N_2O_6S$ Mw. 542.62

LC/MS purity: 98%, m/z 541 [M–H]$^-$, m/z 543 [M–H]$^+$ Rt. 3.18 min.

$^1$H NMR (300 MHz, DMSO-d6): 10.4 (bs, 1H), 8.35 (d, 1H), 7.89 (dd, 4H), 7.73 (d, 1H), 7.50 (m, 4H), 7.44 (s, 1H), 7.35 (s, 1H), 7.15 (d, 1H), 7.00 (d, 1H), 6.78 (dd, 1H), 6.16 (d, 1H), 3.95 (s, 3H), 3.92 (s, 3H), 3.66 (s, 3H)

Melting point: 128–131° C. Yield: 39%

Example A143

N-[4-(6,7-Dimethoxy-quinolin-4-yloxy)-3-methoxy-phenyl]-3-pyrimidin-2-yl-benzenesulfonamide

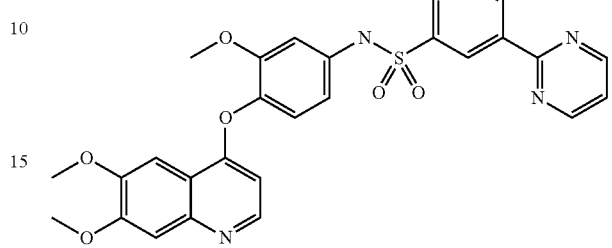

$C_{28}H_{24}N_4O_6S$ Mw. 544.59

LC/MS purity: 100%, m/z 543 [M–H]$^-$, m/z 545 [M–H]$^+$ Rt. 2.80 min.

$^1$H NMR (300 MHz, DMSO-d6): 10.48 (bs, 1H), 8.97 (d, 2H), 8.86 (s, 1H), 8.64 (d, 1H), 8.27 (d, 1H), 7.95 (d, 1H), 7.77 (t, 1H), 7.54 (t, 1H), 7.43 (d, 1H), 7.34 (s, 1H), 7.12 (d, 1H), 7.08 (d, 1H), 6.74 (dd, 1H), 6.07 (d, 1H), 3.92 (s, 3H), 3.89 (s, 3H), 3.63 (s, 3H)

Melting point: 135–137° C. Yield: 38%

Example A144

Benzo[b]thiophene-3-sulfonic acid [4-(6,7-dimethoxy-quinolin-4-yloxy)-3-methoxy-phenyl]-amide

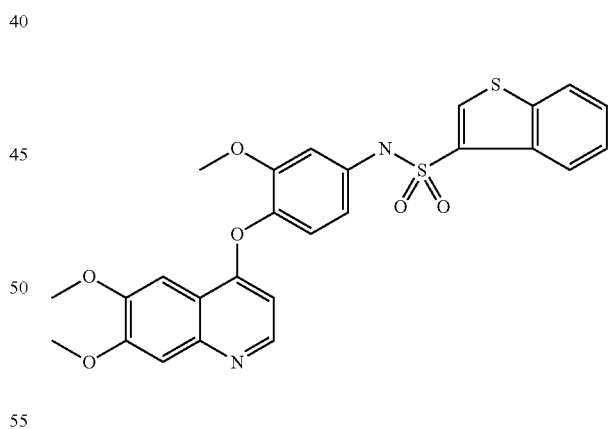

$C_{26}H_{22}N_2O_6S_2$ Mw. 522.60

LC/MS purity: 100%, m/z 521 [M–H]$^-$, m/z 523 [M–H]$^+$ Rt. 2.95 min.

$^1$H NMR (300 MHz, DMSO-d6): 10.68 (s, 1H), 8.67 (s, 1H), 8.37 (d, 1H), 8.24 (d, 1H), 8.13 (d, 1H), 7.54 (m, 2H), 7.43 (s, 1H), 7.35 (s, 1H), 7.18 (d, 1H), 6.93 (d, 1H), 6.70 (dd, 1H), 6.08 (d, 1H), 3.92 (s, 3H), 3.89 (s, 3H), 3.58 (s, 3H),

Melting point: 144–146° C. Yield: 61%

Example A145

1-Methyl-2-oxo-2,3-dihydro-1H-indole-5-sulfonic acid [4-(6,7-dimethoxy-quinolin-4-yloxy)-3-methoxy-phenyl]-amide

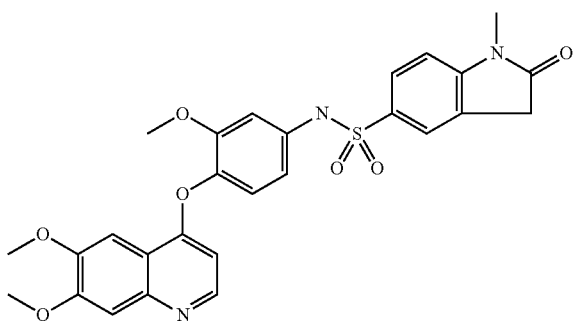 [SMILES: COc1cc2nccc(Oc3ccc(NS(=O)(=O)c4ccc5c(c4)CC(=O)N5C)cc3OC)c2cc1OC]

$C_{27}H_{25}N_3O_7S$ Mw. 535.58

LC/MS purity: 100%, m/z 534 [M−H]⁻, m/z 536 [M−H]⁺ Rt. 2.43 min.

¹H NMR (300 MHz, DMSO-d6): 10.5 (bs, 1H), 8.38 (d, 1H), 7.76 (d, 1H), 7.67 (s, 1H), 7.45 (s, 1H), 7.35 (s, 1H), 7.10 (t, 2H), 6.96 (d, 1H), 6.72 (d, 1H), 6.18 (d, 1H), 3.93 (s, 3H), 3.90 (s, 3H), 3.64 (s, 2H), 3.63 (s, 3H), 3.13 (s, 3H)

Melting point: 150-152° C. Yield: 18%

Example A146

4-Bromo-N-[4-(6,7-dimethoxy-quinolin-4-yloxy)-3-fluoro-phenyl]-2-trifluoromethoxy-benzenesulfonamide

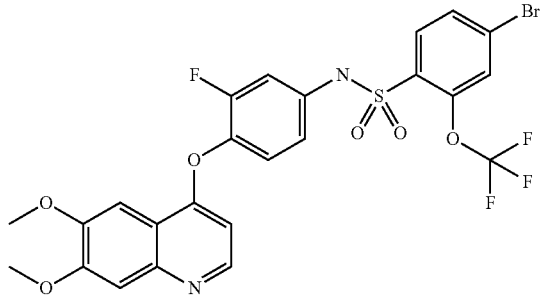 [SMILES: COc1cc2nccc(Oc3ccc(NS(=O)(=O)c4ccc(Br)cc4OC(F)(F)F)cc3F)c2cc1OC]

$C_{24}H_{17}BrN_4N_2O_6S$ Mw. 617.37

LC/MS purity: 99%, m/z 615 [M−H]⁻, m/z 617 [M−H]⁺ Rt. 3.30 min.

¹H NMR (300 MHz, DMSO-d6): 11 (bs, 1H), 8.46 (d, 1H), 7.96 (d, 1H), 7.84 (d, 1H), 7.82 (s, 1H), 7.48 (s, 1H), 7.39 (s, 1H), 7.35 (d, 1H), 7.16 (dd, 1H), 6.99 (d, 1H), 6.35 (d, 1H), 3.94 (s, 3H), 3.92 (s, 3H)

Melting point: 226-228° C. Yield: 34%

Example A147

4-Bromo-N-[4-(6,7-dimethoxy-quinolin-4-yloxy)-2-fluoro-phenyl]-2-trifluoromethoxy-benzenesulfonamide

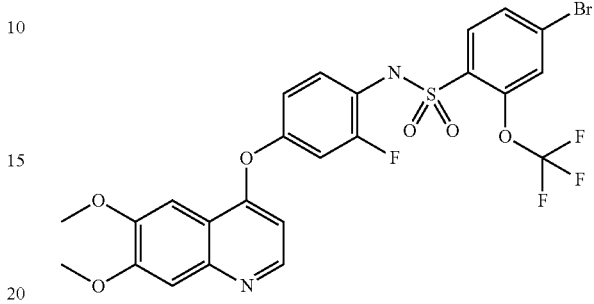

$C_{24}H_{17}BrN_4N_2O_6S$ Mw. 617.37

LC/MS purity: 100%, m/z 615 [M−H]⁻, m/z 617 [M−H]⁺ Rt. 3.27 min.

¹H NMR (300 MHz, DMSO-d6): 10.4 (bs, 1H), 8.51 (d, 1H), 7.80 (m, 3H), 7.41 (s, 1H), 7.40 (s, 1H), 7.34 (t, 1H), 7.24 (dd, 1H), 7.04 (d, 1H), 6.53 (d, 1H), 3.94 (s, 3H), 3.90 (s, 3H)

Melting point: 227-229° C. Yield: 36%

Example A148

4-Bromo-N-[4-(6,7-dimethoxy-quinolin-4-yloxy)-3-methoxy-phenyl]-2-trifluoromethoxy-benzenesulfonamide

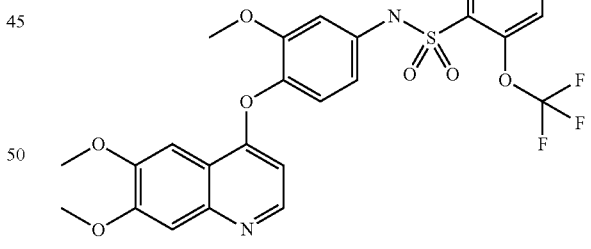

$C_{25}H_{20}BrF_3N_2O_7S$ Mw. 629.41

LC/MS purity: 99%, m/z 627 [M−H]⁻, m/z 629 [M−H]⁺ Rt. 3.21 min.

¹H NMR (300 MHz, DMSO-d6): 10.8 (bs, 1H), 8.39 (d, 1H), 7.94 (d, 1H), 7.83 (d, 1H), 7.81 (s, 1H), 7.47 (s, 1H), 7.36 (s, 1H), 7.13 (d, 1H), 6.95 (d, 1H), 6.70 (d, 1H), 6.15 (d, 1H), 3.93 (s, 3H), 3.91 (s, 3H), 3.63 (s, 3H)

Melting point: 176-177° C. Yield: 31%

Example A149

4-Bromo-N-[4-(6,7-dimethoxy-quinolin-4-yloxy)-phenyl]-2-trifluoromethoxy-benzenesulfonamide

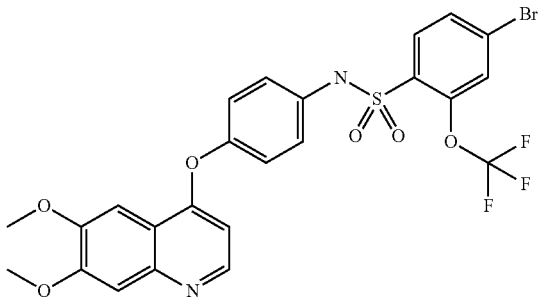 [SMILES: COc1cc2nccc(Oc3ccc(NS(=O)(=O)c4ccc(Br)cc4OC(F)(F)F)cc3)c2cc1OC]

$C_{24}H_{18}BrF_3N_2O_6S$ Mw. 599.38
LC/MS purity: 99%, m/z 597 [M−H]⁻, m/z 599 [M−H]⁺
Rt. 3.20 min.
¹H NMR (300 MHz, DMSO-d6): 10.8 (bs, 1H), 8.45 (d, 1H), 7.89 (d, 1H), 7.82 (d, 1H), 7.80 (s, 1H), 7.45 (s, 1H), 7.38 (s, 1H), 7.17 (dd, 4H), 6.35 (d, 1H), 3.93 (s, 3H), 3.90 (s, 3H)
Melting point: 237-239° C. Yield: 30%

Example A150

4-Methoxy-naphthalene-1-sulfonic acid [4-(6,7-dimethoxy-quinolin-4-yloxy)-2-methyl-phenyl]-amide

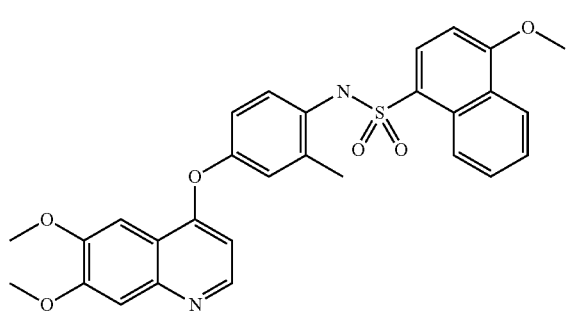

$C_{29}H_{26}N_2O_6S$ Mw. 530.60
LC/MS purity: 99%, m/z 529 [M−H]⁻, m/z 531 [M−H]⁺
Rt. 3.10 min.
¹H NMR (300 MHz, DMSO-d6): 10 (bs, 1H), 8.71 (d, 1H), 8.46 (d, 1H), 8.28 (d, 1H), 8.01 (d, 1H), 7.67 (m, 2H), 7.41 (s, 1H), 7.37 (s, 1H), 7.05 (d, 2H), 6.92 (s, 1H), 6.91 (d, 1H), 6.36 (d, 1H), 4.07 (s, 3H), 3.93 (s, 3H), 3.88 (s, 3H), 2.09 (s, 3H)
Melting point: 216-217° C. Yield: 34%

Example A151

N-[4-(6,7-Dimethoxy-quinolin-4-yloxy)-2-methyl-phenyl]-2,5-difluoro-benzenesulfonamide

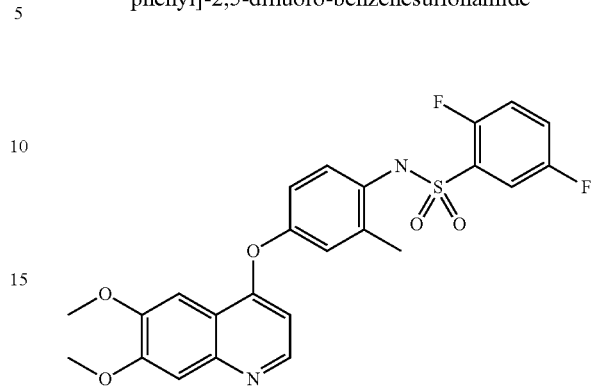

$C_{24}H_{20}F_2N_2O_5S$ Mw. 486.50
LC/MS purity: 98%, m/z 485 [M−H]⁻, m/z 487 [M−H]⁺
Rt. 2.82 min.
¹H NMR (300 MHz, DMSO-d6): 10.19 (bs, 1H), 8.48 (d, 1H), 7.59 (m, 2H), 7.48 (m, 1H), 7.44 (s, 1H), 7.39 (s, 1H), 7.04 (m, 3H), 6.46 (d, 1H), 3.94 (s, 3H), 3.90 (s, 3H), 2.13 (s, 3H)
Melting point: 259-260° C. Yield: 37%

Example A152

4-Bromo-3-chloro-N-[4-(6,7-dimethoxy-quinolin-4-yloxy)-2-methyl-phenyl]-benzenesulfonamide

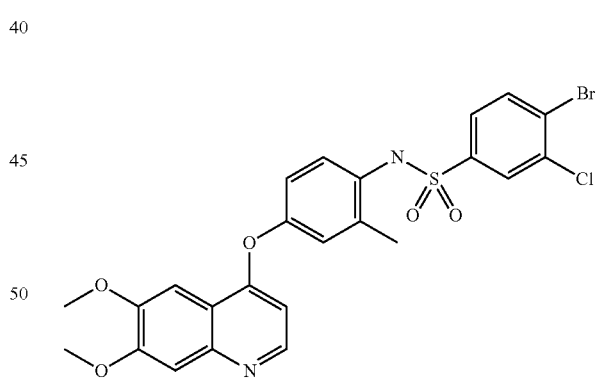

$C_{24}H_{20}BrClN_2O_5S$ Mw. 563.86
LC/MS purity: 100%, m/z 561 [M−H]⁻, m/z 563 [M−H]⁺
Rt. 3.17 min.
¹H NMR (300 MHz, DMSO-d6): 9.91 (bs, 1H), 8.48 (d, 1H), 8.03 (d, 1H), 7.79 (d, 1H), 7.54 (dd, 1H), 7.45 (s, 1H), 7.39 (s, 1H), 7.12 (s, 1H), 7.03 (dd, 2H), 6.47 (d, 1H), 3.94 (s, 3H), 3.91 (s, 3H), 2.06 (s, 3H)
Melting point: 212-213° C. Yield: 58%

Example A153

4-Chloro-N-[4-(6,7-dimethoxy-quinolin-4-yloxy)-2-methyl-phenyl]-2-fluoro-benzenesulfonamide

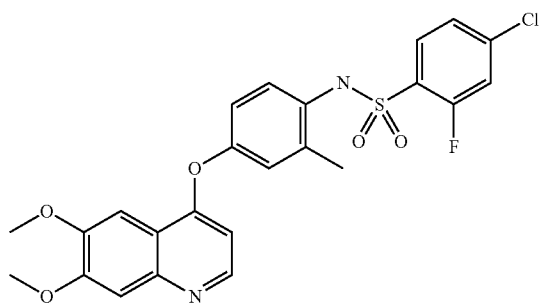 [SMILES: COc1cc2nccc(Oc3ccc(NS(=O)(=O)c4ccc(Cl)cc4F)c(C)c3)c2cc1OC]

$C_{24}H_{20}ClFN_2O_5S$ Mw. 502.95
LC/MS purity: 99%, m/z 501 [M−H]⁻, m/z 503 [M−H]⁺ Rt. 2.98 min.
¹H NMR (300 MHz, DMSO-d6): 10.13 (bs, 1H), 8.48 (d, 1H), 7.73 (m, 2H), 7.46 (d, 1H), 7.44 (s, 1H), 7.39 (s, 1H), 7.03 (m, 2H), 7.01 (dd, 1H), 6.45 (d, 1H), 3.94 (s, 3H), 3.90 (s, 3H), 2.13 (s, 3H)
Melting point: 248-250° C. Yield: 43%

Example A154

N-[4-(6,7-Dimethoxy-quinolin-4-yloxy)-2-methyl-phenyl]-4-fluoro-3-methoxy-benzenesulfonamide

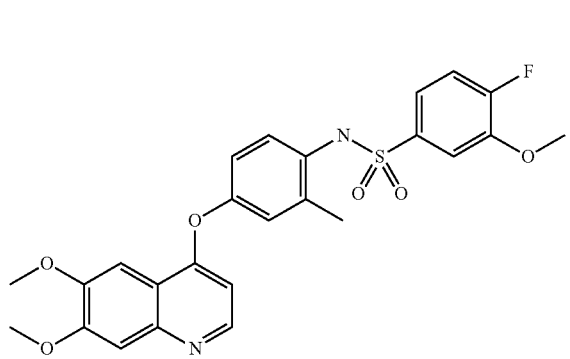

$C_{25}H_{23}FN_2O_6S$ Mw. 498.53
LC/MS purity: 98%, m/z 497 [M−H]⁻, m/z 499 [M−H]⁺ Rt. 2.87 min.
¹H NMR (300 MHz, DMSO-d6): 9.67 (bs, 1H), 8.47 (d, 1H), 7.40 (m, 4H), 7.28 (m, 1H), 7.10 (s, 1H), 7.03 (dd, 2H), 6.46 (d, 1H), 3.94 (s, 3H), 3.91 (s, 3H), 3.85 (s, 3H), 2.05 (s, 3H)
Melting point: 228-229° C. Yield: 38%

Example A155

3,5-Dichloro-N-[4-(6,7-dimethoxy-quinolin-4-yloxy)-phenyl]-4-hydroxy-benzenesulfonamide

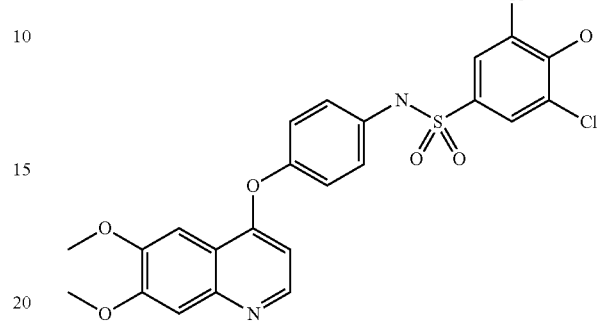

$C_{23}H_{18}Cl_2N_2O_6S$ Mw. 521.38
LC/MS purity: 92%, m/z 519 [M−H]⁻, m/z 521 [M−H]⁺ Rt. 2.79 min.
¹H NMR (300 MHz, DMSO-d6): 9.7 (bs, 1H), 8.42 (d, 1H), 7.49 (s, 1H), 7.37 (s, 1H), 7.27 (s, 2H), 7.10 (m, 4H), 6.35 (d, 1H), 3.94 (s, 3H), 3.91 (s, 3H) Melting point: >260° C. Yield: 45%

Example A156

3,5-Dichloro-N-[4-(6,7-dimethoxy-quinolin-4-yloxy)-3-methoxy-phenyl]-2-hydroxy-benzenesulfonamide

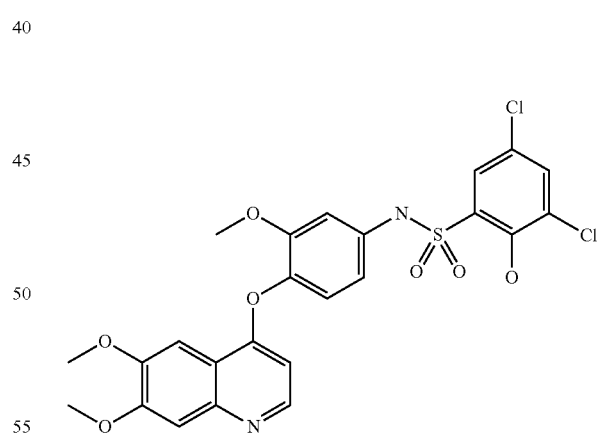

$C_{24}H_{20}Cl_2N_2O_7S$ Mw. 551.41
LC/MS purity: 99%, m/z 549 [M−H]⁻, m/z 551 [M−H]⁺ Rt. 3.00 min.
¹H NMR (300 MHz, DMSO-d6): 9.6 (bs, 1H), 8.38 (d, 1H), 7.49 (s, 1H), 7.47 (s, 1H), 7.09 (d, 1H), 6.94 (d, 1H), 6.75 (d, 1H), 3.93 (s, 3H), 3.90 (s, 3H), 3.59 (s, 3H)
Melting point: >240° C. Yield: 26%

Example B1

Thiophene-2-sulfonic acid [2-fluoro-4-(6-fluoro-2-methyl-quinolin-4-yloxy)-phenyl]-amide

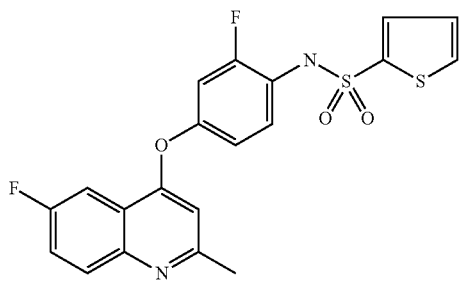 [SMILES: Cc1cc(Oc2ccc(NS(=O)(=O)c3cccs3)c(F)c2)c2cc(F)ccc2n1]

$C_{20}H_{14}F_2N_2O_3S_2$ Mw. 432.47

LC/MS purity: 96%, m/z 431 [M−H]⁻ Rt. 3.00 min.

¹H NMR (300 MHz, DMSO-d6): 10.37 (s, 1H), 7.97 (m, 2H), 7.83 (d, 1H), 7.68 (m, 1H), 7.53 (dd, 1H), 7.31 (m, 2H), 7.19 (m, 1H), 7.11 (d, 1H), 6.65 (s, 1H), 2.54 (s, 3H)

Melting point: 166-167° C. Yield: 60%

Example B2

3-Cyano-N-[2-fluoro-4-(6-fluoro-2-methyl-quinolin-4-yloxy)-phenyl]-benzenesulfonamide

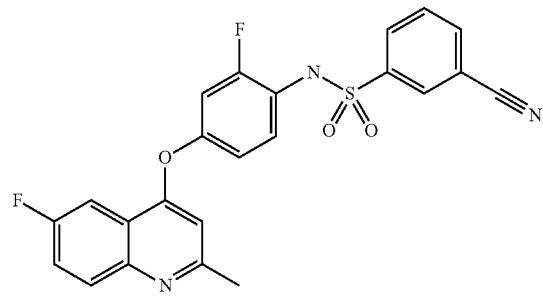 [SMILES: Cc1cc(Oc2ccc(NS(=O)(=O)c3cccc(C#N)c3)c(F)c2)c2cc(F)ccc2n1]

$C_{23}H_{15}F_2N_3O_3S$ Mw. 451.46

LC/MS purity: 97%, m/z 450 [M−H]⁻ Rt. 3.03 min.

¹H NMR (300 MHz, DMSO-d6): 10.46 (s, 1H), 8.14 (m, 2H), 8.00 (m, 2H), 7.81 (m, 2H), 7.68 (m, 1H), 7.33 (t, 1H), 7.26 (dd, 1H), 7.08 (d, 1H), 6.65 (s, 1H), 2.54 (s, 3H)

Melting point: 190-191° C. Yield: 37%

Example B3

N-[2-Fluoro-4-(6-fluoro-2-methyl-quinolin-4-yloxy)-phenyl]-3-methoxy-benzenesulfonamide

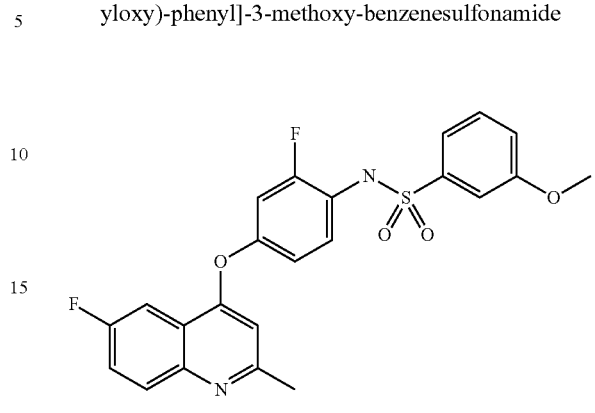

$C_{23}H_{18}F_2N_2O_4S$ Mw. 456.47

LC/MS purity: 98%, m/z 455 [M−H]⁻ Rt. 3.16 min.

¹H NMR (300 MHz, DMSO-d6): 10.22 (s, 1H), 8.00 (m, 1H), 7.82 (m, 1H), 7.67 (m, 1H), 7.49 (t, 1H), 7.37-7.21 (m, 6H), 7.07 (d, 1H), 6.62 (s, 1H), 3.80 (s, 3H), 2.53 (s, 3H)

Melting point: 150-151° C. Yield: 58%

Example B4

Cyclopropanesulfonic acid [2-fluoro-4-(6-fluoro-2-methyl-quinolin-4-yloxy)-phenyl]-amide

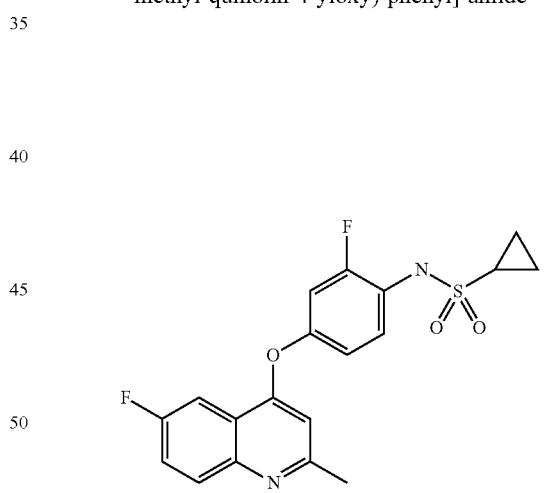

$C_{19}H_{16}F_2N_2O_3S$ Mw. 390.41

LC/MS purity: 96%, m/z 391 [M+H]⁺ Rt. 2.54 min.

¹H NMR (300 MHz, DMSO-d6): 9.67 (s, 1H), 8.01 (m, 1H), 7.85 (m, 1H), 7.70 (m, 1H), 7.52 (t, 1H), 7.37 (dd, 1H), 7.13 (d, 1H), 6.71 (s, 1H), 2.69 (s, 1H), 2.55 (s, 3H), 0.95 (m, 4H)

Melting point: 189-190° C. Yield: 42%

Example B5

3-Chloro-4-fluoro-N-[2-fluoro-4-(6-fluoro-2-methyl-quinolin-4-yloxy)-phenyl]-benzenesulfonamide

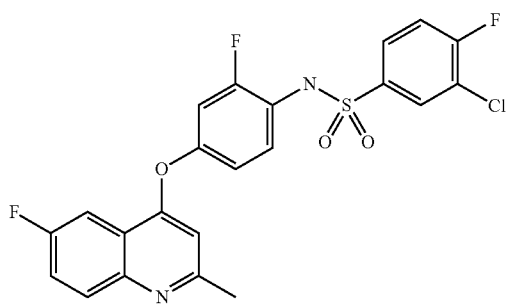 [SMILES: Cc1cc(Oc2ccc(NS(=O)(=O)c3ccc(F)c(Cl)c3)c(F)c2)c2cc(F)ccc2n1]

$C_{22}H_{14}ClF_3N_2O_3S$ Mw. 478.88

LC/MS purity: 94%, m/z 477 [M−H]⁻ Rt. 3.45 min.

¹H NMR (300 MHz, DMSO-d6): 10.38 (s, 1H), 8.00 (m, 1H), 7.91 (m, 1H), 7.84-7.66 (m, 4H), 7.31 (m, 2H), 7.11 (dd, 1H), 6.67 (s, 1H), 2.54 (s, 3H)

Melting point: 205-207° C. Yield: 62%

Example B6

2,6-Difluoro-N-[2-fluoro-4-(6-fluoro-2-methyl-quinolin-4-yloxy)-phenyl]-benzenesulfonamide

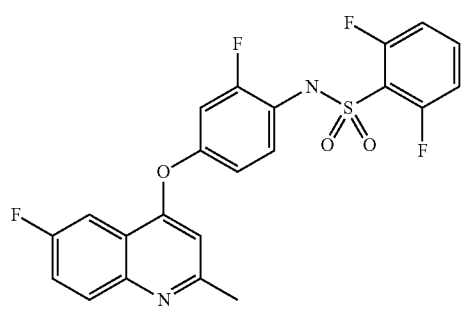 [SMILES: Cc1cc(Oc2ccc(NS(=O)(=O)c3c(F)cccc3F)c(F)c2)c2cc(F)ccc2n1]

$C_{22}H_{14}F_4N_2O_3S$ Mw. 462.43

LC/MS purity: 98%, m/z 461 [M−H]⁻ Rt. 3.06 min.

¹H NMR (300 MHz, DMSO-d6): 10.81 (s, 1H), 8.00 (m, 1H), 7.82 (dd, 1H), 7.68 (m, 2H), 7.38 (t, 1H), 7.27 (m, 3H), 7.08 (d, 1H), 6.62 (s, 1H), 2.54 (s, 3H)

Melting point: 188-190° C. Yield: 53%

Example B7

5-Methyl-thiophene-2-sulfonic acid [2-fluoro-4-(6-fluoro-2-methyl-quinolin-4-yloxy)-phenyl]-amide

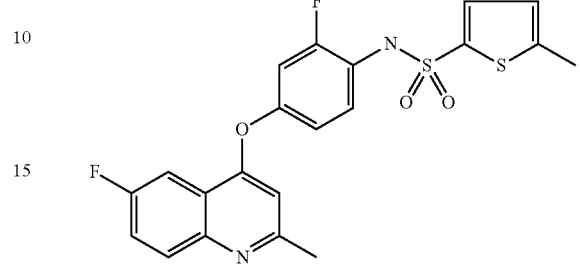

$C_{21}H_{16}F_2N_2O_3S_2$ Mw. 446.50

LC/MS purity: 97%, m/z 445 [M−H]⁻ Rt. 3.18 min.

¹H NMR (300 MHz, DMSO-d6): 10.30 (s, 1H), 8.00 (dd, 1H), 7.83 (dd, 1H), 7.69 (m, 1H), 7.32 (m, 3H), 7.10 (d, 1H), 6.87 (dd, 1H), 6.64 (s, 1H), 2.54 (s, 3H)

Melting point: 151-153° C. Yield: 62%

Example B8

N-[2-Fluoro-4-(6-fluoro-2-methyl-quinolin-4-yloxy)-phenyl]-3-trifluoromethyl-benzenesulfonamide

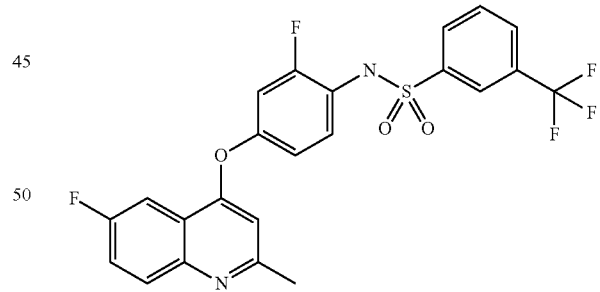

$C_{23}H_{15}F_5N_2O_3S$ Mw. 494.44

LC/MS purity: 95%, m/z 493 [M−H]⁻ Rt. 3.51 min.

¹H NMR (300 MHz, DMSO-d6): 10.45 (s, 1H), 8.00 (m, 4H), 7.83 (m, 2H), 7.68 (m, 1H), 7.34 (t, 1H), 7.26 (d, 1H), 7.09 (d, 1H), 6.63 (s, 1H), 2.53 (s, 3H)

Melting point: 150-152° C. Yield: 47%

Example B9

N-[4-(6-Fluoro-2-methyl-quinolin-4-yloxy)-phenyl]-benzenesulfonamide

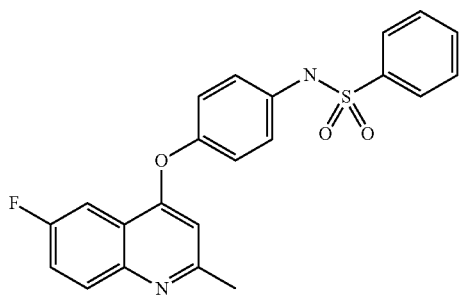 [SMILES: Cc1cc(Oc2ccc(NS(=O)(=O)c3ccccc3)cc2)c2cc(F)ccc2n1]

$C_{22}H_{17}FN_2O_3S$ Mw. 408.45

LC/MS purity: 95%, m/z 407 [M–H]⁻ Rt. 2.90 min.

¹H NMR (300 MHz, DMSO-d6): 10.37 (s, 1H), 7.97 (m, 1H), 7.81 (m, 3H), 7.70-7.55 (m, 4H), 7.19 (dd, 4H), 6.40 (s, 1H), 2.54 (s, 3H)

Melting point: 207-208° C. Yield: 65%

Example B10

3,5-Dichloro-N-[4-(6-fluoro-2-methyl-quinolin-4-yloxy)-phenyl]-benzenesulfonamide

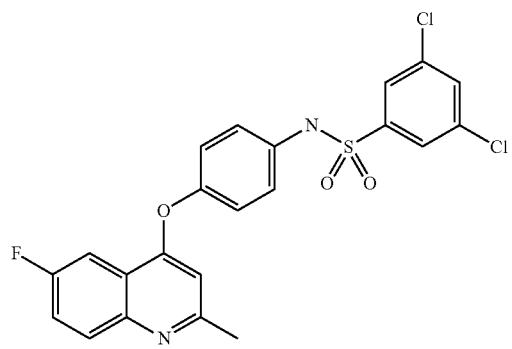 [SMILES: Cc1cc(Oc2ccc(NS(=O)(=O)c3cc(Cl)cc(Cl)c3)cc2)c2cc(F)ccc2n1]

$C_{22}H_{15}Cl_2FN_2O_3S$ Mw. 477.34

LC/MS purity: 97%, m/z 475 [M–H]⁻ Rt. 3.52 min.

¹H NMR (300 MHz, DMSO-d6): 10.52 (s, 1H), 7.98 (m, 2H), 7.85 (dd, 1H), 7.66 (m, 3H), 7.23 (dd, 4H), 6.45 (s, 1H), 2.54 (s, 3H)

Melting point: 238-240° C. Yield: 73%

Example B11

3,5-Dichloro-N-[4-(6-fluoro-2-methyl-quinolin-4-yloxy)-phenyl]-2-methoxy-benzenesulfonamide

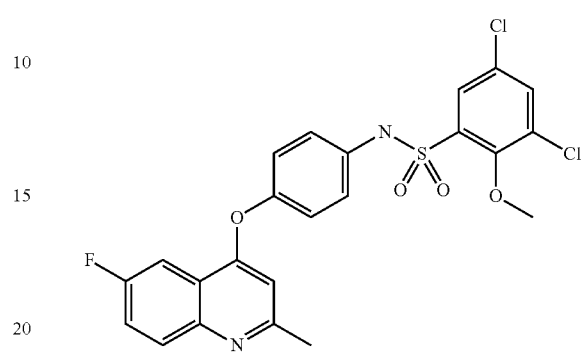

$C_{23}H_{17}Cl_2FN_2O_4S$ Mw. 507.37

LC/MS purity: 96%, m/z 505 [M–H]⁻ Rt. 3.60 min.

¹H NMR (300 MHz, DMSO-d6): 10.59 (s, 1H), 8.00 (m, 2H), 7.84 (dd, 1H), 7.73 (dd, 1H), 7.67 (m, 1H), 7.21 (dd, 4H), 6.42 (s, 1H), 3.96 (s, 3H), 2.54 (s, 3H)

Melting point: 192-193° C. Yield: 78%

Example B12

2,4-Difluoro-N-[4-(6-fluoro-2-methyl-quinolin-4-yloxy)-phenyl]-benzenesulfonamide

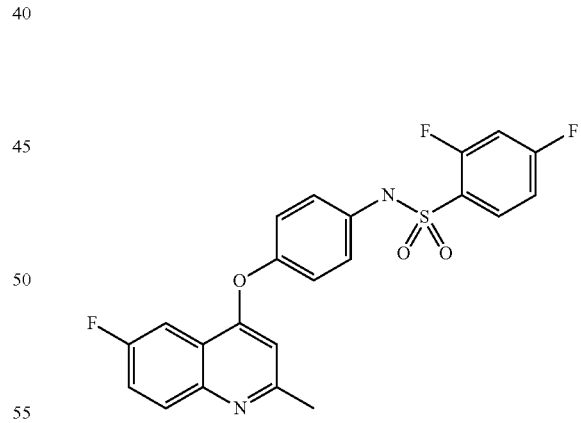

$C_{22}H_{15}F_3N_2O_3S$ Mw. 444.44

LC/MS purity: 95%, m/z 443 [M–H]⁻ Rt. 3.02 min.

¹H NMR (300 MHz, DMSO-d6): 10.75 (s, 1H), 8.00-7.81 (m, 3H), 7.69 (m, 1H), 7.55 (m, 1H), 7.31-7.17 (m, 5H), 6.40 (s, 1H), 2.54 (s, 3H)

Melting point: 179-180° C. Yield: 62%

Example B13

3,5-Difluoro-N-[4-(6-fluoro-2-methyl-quinolin-4-yloxy)-phenyl]-benzenesulfonamid

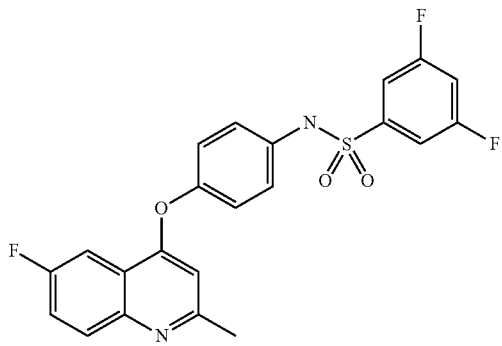 [SMILES: Cc1cc(Oc2ccc(NS(=O)(=O)c3cc(F)cc(F)c3)cc2)c2cc(F)ccc2n1]

C$_{22}$H$_{15}$F$_3$N$_2$O$_3$S Mw. 444.44

LC/MS purity: 95%, m/z 443 [M−H]$^-$ Rt. 3.17 min.

$^1$H NMR (300 MHz, DMSO-d6): 10.54 (s, 1H), 7.99 (m, 1H), 7.85 (m, 1H), 7.67 (m, 2H), 7.44 (m, 2H), 7.23 (dd, 4H), 6.43 (s, 1H), 2.54 (s, 3H)

Melting point: 194-195° C. Yield: 54%

Example B14

3-Bromo-N-[4-(6-fluoro-2-methyl-quinolin-4-yloxy)-phenyl]-benzenesulfonamide

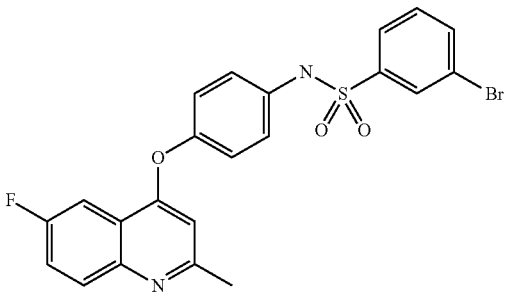 [SMILES: Cc1cc(Oc2ccc(NS(=O)(=O)c3cccc(Br)c3)cc2)c2cc(F)ccc2n1]

C$_{22}$H$_{16}$BrFN$_2$O$_3$S Mw. 487.35

LC/MS purity: 96%, m/z 485 [M−H]$^-$ Rt. 3.25 min.

$^1$H NMR (300 MHz, DMSO-d6): 10.45 (s, 1H), 7.98 (dd, 1H), 7.85 (m, 3H), 7.76 (d, 1H), 7.67 (m, 1H), 7.55 (t, 1H), 7.21 (dd, 4H), 6.43 (s, 1H), 2.54 (s, 3H)

Melting point: 183-184° C. Yield: 73%

Example B15

4-Bromo-N-[4-(6-fluoro-2-methyl-quinolin-4-yloxy)-phenyl]-2-trifluoromethyl-benzenesulfonamide

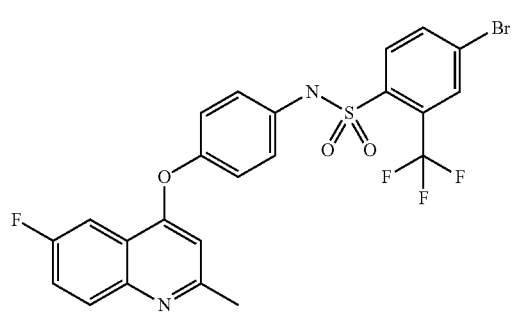 [SMILES: Cc1cc(Oc2ccc(NS(=O)(=O)c3ccc(Br)cc3C(F)(F)F)cc2)c2cc(F)ccc2n1]

C$_{23}$H$_{15}$BrF$_4$N$_2$O$_3$S Mw. 555.35

LC/MS purity: 96%, m/z 553 [M−H]$^-$ Rt. 3.52 min.

$^1$H NMR (300 MHz, DMSO-d6): 10.32 (s, 1H), 8.18 (dd, 1H), 8.00 (m, 1H), 7.85 (m, 2H), 7.70 (m, 5H), 6.44 (s, 1H), 2.54 (s, 3H)

Melting point: 191-193° C. Yield: 63%

Example B16

Thiophene-3-sulfonic acid [4-(6-fluoro-2-methyl-quinolin-4-yloxy)-phenyl]-amide

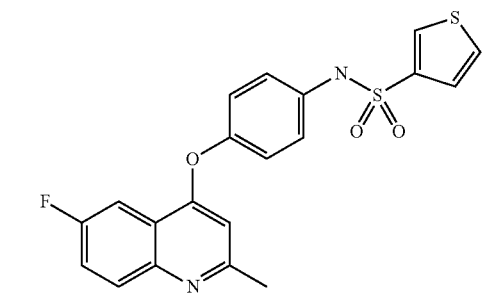 [SMILES: Cc1cc(Oc2ccc(NS(=O)(=O)c3ccsc3)cc2)c2cc(F)ccc2n1]

C$_{20}$H$_{15}$FN$_2$O$_3$S$_2$ Mw. 414.48

LC/MS purity: 97%, m/z 413 [M−H]$^-$ Rt. 2.81 min.

$^1$H NMR (300 MHz, DMSO-d6): 10.31 (s, 1H), 8.18 (dd, 1H), 7.99 (dd, 1H), 7.85 (dd, 1H), 7.73 (m, 1H), 7.67 (m, 1H), 7.30-7.18 (m, 5H), 6.44 (s, 1H), 2.54 (s, 3H)

Melting point: 195-196° C. Yield: 66%

Example B17

3-[4-(6-Fluoro-2-methyl-quinolin-4-yloxy)-phenyl-sulfamoyl]-thiophene-2-carboxylic acid methyl ester

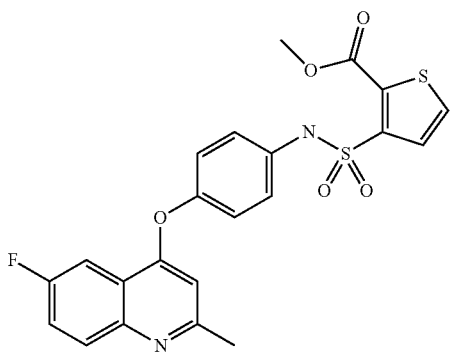 [SMILES: COC(=O)c1sccc1S(=O)(=O)Nc1ccc(Oc2cc(C)nc3ccc(F)cc23)cc1]

$C_{22}H_{17}FN_2O_5S_2$ Mw. 472.52

LC/MS purity: 96%, m/z 471 [M−H]⁻ Rt. 3.02 min.

¹H NMR (300 MHz, DMSO-d6): 10.20 (s, 1H), 7.99 (m, 2H), 7.84 (dd, 1H), 7.67 (m, 1H), 7.47 (d, 1H), 7.23 (d, 2H), 7.19 (d, 2H), 6.43 (s, 1H), 3.90 (s, 3H), 2.54 (s, 3H)

Melting point: 160-161° C. Yield: 72%

Example B18

5-Chloro-thiophene-2-sulfonic acid [4-(6-fluoro-2-methyl-quinolin-4-yloxy)-phenyl]-amide

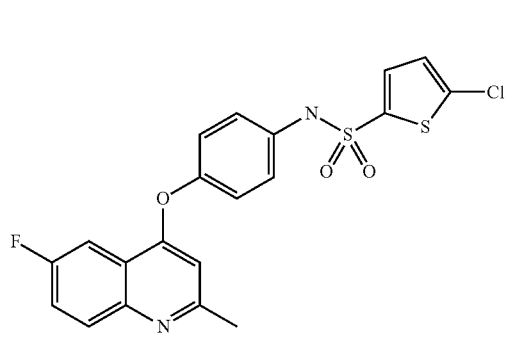 [SMILES: Cc1cc(Oc2ccc(NS(=O)(=O)c3ccc(Cl)s3)cc2)c2cc(F)ccc2n1]

$C_{20}H_{14}ClFN_2O_3S_2$ Mw. 448.93

LC/MS purity: 97%, m/z 447 [M−H]⁻ Rt. 3.23 min.

¹H NMR (300 MHz, DMSO-d6): 10.64 (s, 1H), 7.99 (m, 1H), 7.85 (m, 1H), 7.67 (m, 1H), 7.46 (dd, 1H), 7.25 (m, 5H), 6.47 (s, 1H), 2.54 (s, 3H)

Melting point: 170-172° C. Yield: 44%

Example B19

5-Oxazol-5-yl-thiophene-2-sulfonic acid [4-(6-fluoro-2-methyl-quinolin-4-yloxy)-phenyl]-amide

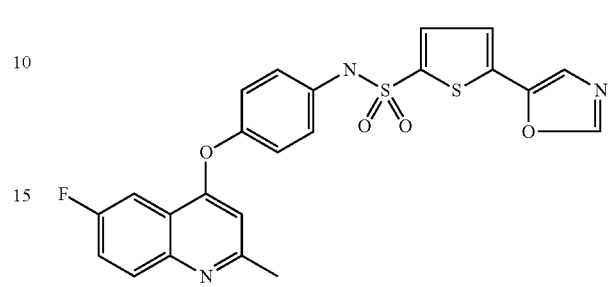

$C_{23}H_{16}FN_3O_4S_2$ Mw. 481.53

LC/MS purity: 95%, m/z 480 [M−H]⁻ Rt. 3.07 min.

¹H NMR (300 MHz, DMSO-d6): 10.73 (s, 1H), 8.72 (d, 1H), 7.98 (dd, 1H), 7.85 (dd, 1H) 7.73-7.64 (m, 3H), 7.27 (m, 4H), 7.10 (d, 1H), 6.45 (s, 1H), 2.54 (s, 3H)

Melting point: 164-166° C. Yield: 35%

Example B20

Naphthalene-1-sulfonic acid [4-(6-fluoro-2-methyl-quinolin-4-yloxy)-phenyl]-amide

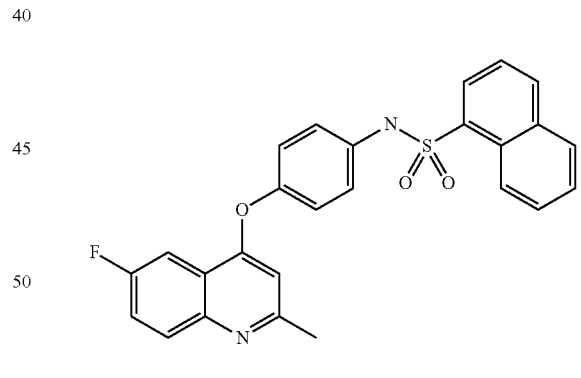

$C_{26}H_{19}FN_2O_3S$ Mw. 458.52

LC/MS purity: 95%, m/z 457 [M−H]⁻ Rt. 3.25 min.

¹H NMR (300 MHz, DMSO-d6): 10.8 (bs, 1H), 8.78 (d, 1H), 8.22 (d, 2H), 8.08 (d, 1H), 7.95 (dd, 1H), 7.81-7.60 (m, 5H), 7.12 (d, 2H), 7.05 (d, 2H), 6.33 (s, 1H), 2.55 (s, 3H)

Melting point: 223-225° C. Yield: 75%

Example B21

1-Ethyl-1H-pyrazole-4-sulfonic acid [4-(6-fluoro-2-methyl-quinolin-4-yloxy)-phenyl]-amide

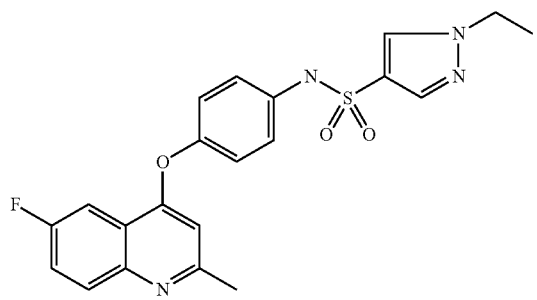 [SMILES: CCn1cc(S(=O)(=O)Nc2ccc(Oc3cc(C)nc4ccc(F)cc34)cc2)cn1]

$C_{21}H_{19}FN_4O_3S$ Mw. 426.47

LC/MS purity: 95%, m/z 425 [M–H]⁻ Rt. 2.59 min.

¹H NMR (300 MHz, DMSO-d6): 10.17 (s, 1H), 8.28 (s, 1H), 7.99 (dd, 1H), 7.86 (dd, 1H), 7.71 (s, 1H), 7.66 (dd, 1H), 7.25 (d, 4H), 6.47 (s, 1H), 4.16 (q, 2H), 2.48 (s, 3H), 1.33 (s, 3H)

Melting point: 165-167° C. Yield: 42%

Example B22

3,5-Dichloro-N-[4-(6-fluoro-2-methyl-quinolin-4-yloxy)-phenyl]-2-hydroxy-benzenesulfonamide

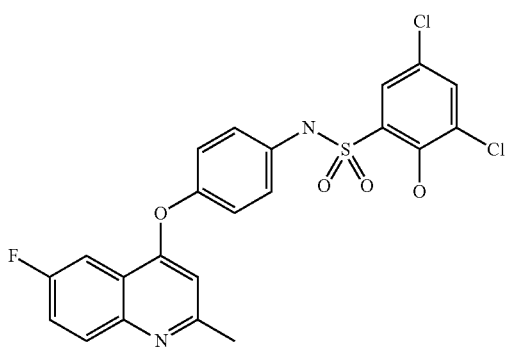 [SMILES: Cc1cc(Oc2ccc(NS(=O)(=O)c3cc(Cl)cc(Cl)c3O)cc2)c2cc(F)ccc2n1]

$C_{22}H_{15}Cl_2FN_2O_4S$ Mw. 493.34

LC/MS purity: 94%, m/z 493 [M+H]⁺ Rt. 3.24 min.

¹H NMR (300 MHz, DMSO-d6): 10.6 (bs, 2H), 7.99 (dd, 1H), 7.86 (m, 2H), 7.66 (m, 2H), 7.25 (d, 2H), 7.19 (d, 2H), 6.44 (s, 1H), 2.52 (s, 3H)

Melting point: 203-205° C. Yield: 56%

Example C1

3,5-Dichloro-N-[2-fluoro-4-(2-methyl-8-trifluoromethyl-quinolin-4-yloxy)-phenyl]-benzenesulfonamide

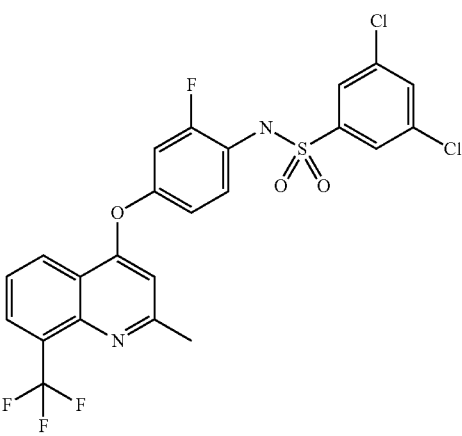 [SMILES: Cc1cc(Oc2ccc(NS(=O)(=O)c3cc(Cl)cc(Cl)c3)c(F)c2)c2cccc(C(F)(F)F)c2n1]

$C_{23}H_{14}Cl_2F_4N_2O_3S$ Mw. 545.34

LC/MS purity: 95%, m/z 543 [M–H]⁻, m/z 545 [M–H]⁺ Rt. 5.39 min.

¹H NMR (300 MHz, DMSO-d6): 10.52 (s, 1H), 8.47 (d, 1H), 8.19 (d, 1H), 8.01 (s, 1H), 7.70 (m, 3H), 7.37 (m, 2H), 7.15 (dd, 1H), 6.76 (s, 1H), 2.59 (s, 3H)

Melting point: 181-183° C. Yield: 44%

Example C2

Biphenyl-3-sulfonic acid [2-fluoro-4-(2-methyl-8-trifluoromethyl-quinolin-4-yloxy)-phenyl]-amide

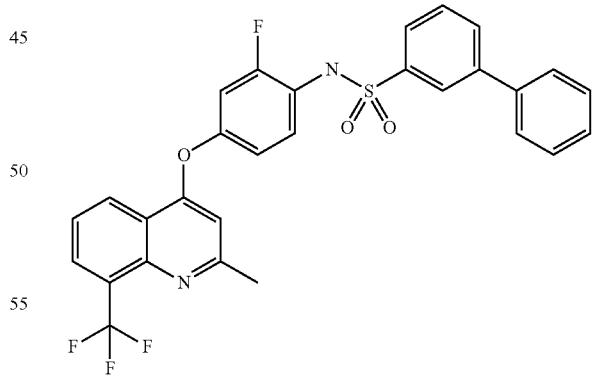

$C_{29}H_{20}F_4N_2O_3S$ Mw. 552.55

LC/MS purity: 98%, m/z 551 [M–H]⁻, m/z 553 [M–H]⁺ Rt. 5.34 min.

¹H NMR (300 MHz, DMSO-d6): 10.30 (s, 1H), 8.45 (d, 1H), 8.18 (d, 1H), 8.02 (s, 1H), 7.97 (d, 1H), 7.69 (m, 5H), 7.54-7.29 (m, 5H), 7.14 (dd, 1H), 6.70 (s, 1H), 2.53 (s, 3H)

Melting point: 187-188° C. Yield: 57%

Example C3

N-[2-Fluoro-4-(2-methyl-8-trifluoromethyl-quinolin-4-yloxy)-phenyl]-3-phenoxy-benzenesulfonamide

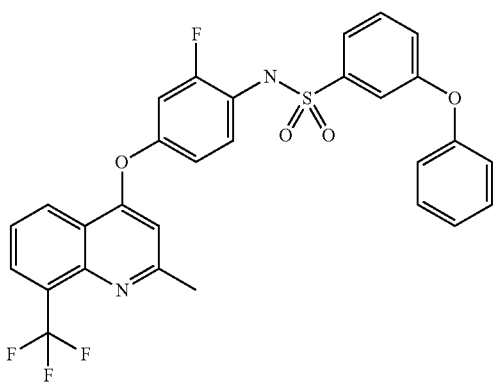 [SMILES: Cc1cc(Oc2ccc(NS(=O)(=O)c3cccc(Oc4ccccc4)c3)c(F)c2)c2cccc(C(F)(F)F)c2n1]

C$_{29}$H$_{20}$F$_4$N$_2$O$_4$S Mw. 568.55

LC/MS purity: 94%, m/z 567 [M−H]$^-$ Rt. 5.34 min.

$^1$H NMR (300 MHz, DMSO-d6): 10.27 (s, 1H), 8.48 (d, 1H), 8.19 (d, 1H), 7.74-7.01 (m, 13H), 6.72 (s, 1H), 2.57 (s, 3H)

Melting point: 167-168° C. Yield: 63%

Example C4

Naphthalene-1-sulfonic acid [2-fluoro-4-(2-methyl-8-trifluoromethyl-quinolin-4-yloxy)-phenyl]-amide

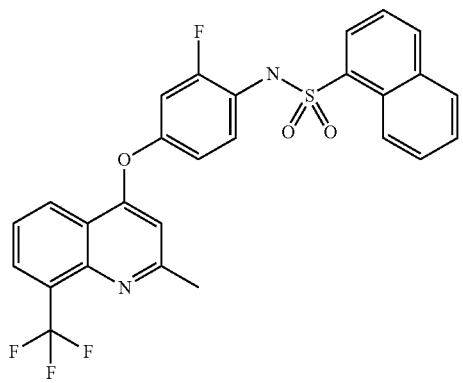 [SMILES: Cc1cc(Oc2ccc(NS(=O)(=O)c3cccc4ccccc34)c(F)c2)c2cccc(C(F)(F)F)c2n1]

C$_{27}$H$_{18}$F$_4$N$_2$O$_3$S Mw. 526.51

LC/MS purity: 95%, m/z 525 [M−H]$^-$, m/z 527 [M−H]$^+$ Rt. 5.15 min.

$^1$H NMR (300 MHz, DMSO-d6): 10.53 (s, 1H), 8.72 (d, 1H), 8.43 (d, 1H), 8.26 (d, 1H), 8.14 (m, 3H), 7.67 (m, 4H), 7.31 (t, 1H), 7.19 (dd, 1H), 7.07 (dd, 1H), 6.94 (s, 1H), 2.57 (s, 3H)

Melting point: 232-234° C. Yield: 42%

Example C5

2,5-Dichloro-N-[2-fluoro-4-(2-methyl-8-trifluoromethyl-quinolin-4-yloxy)-phenyl]-benzenesulfonamid

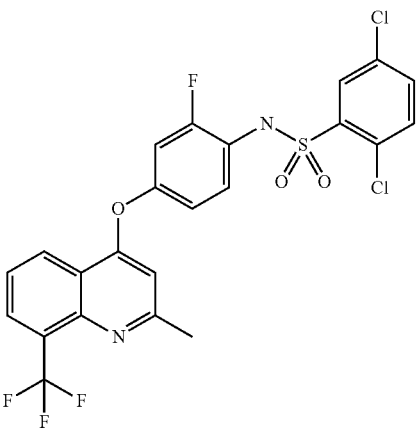 [SMILES: Cc1cc(Oc2ccc(NS(=O)(=O)c3cc(Cl)ccc3Cl)c(F)c2)c2cccc(C(F)(F)F)c2n1]

C$_{23}$H$_{14}$Cl$_2$F$_4$N$_2$O$_3$S Mw. 545.34

LC/MS purity: 95%, m/z 543 [M−H]$^-$, m/z 545 [M−H]$^+$ Rt. 5.24 min.

$^1$H NMR (300 MHz, DMSO-d6): 10.67 (s, 1H), 8.47 (d, 1H), 8.19 (d, 1H), 7.88 (s, 1H), 7.76 (s, 2H), 7.69 (m, 1H), 7.35 (m, 2H), 7.14 (dd, 1H), 6.72 (s, 1H), 2.59 (s, 3H)

Melting point: 207-209° C. Yield: 73%

Example C6

2,6-Dichloro-N-[2-fluoro-4-(2-methyl-8-trifluoromethyl-quinolin-4-yloxy)-phenyl]-benzenesulfonamide

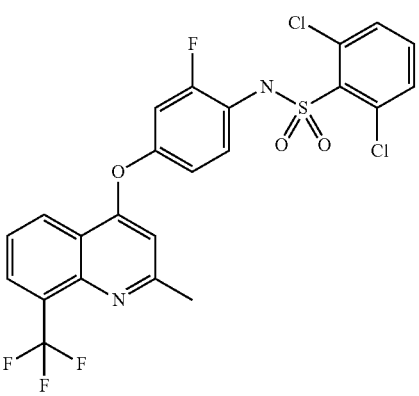 [SMILES: Cc1cc(Oc2ccc(NS(=O)(=O)c3c(Cl)cccc3Cl)c(F)c2)c2cccc(C(F)(F)F)c2n1]

C$_{23}$H$_{14}$Cl$_2$F$_4$N$_2$O$_3$S Mw. 545.34

LC/MS purity: 95%, m/z 543 [M−H]$^-$, m/z 545 [M−H]$^+$ Rt. 5.09 min.

$^1$H NMR (300 MHz, DMSO-d6): 10.66 (s, 1H), 8.47 (d, 1H), 8.19 (d, 1H), 7.65 (m, 4H), 7.35 (m, 2H), 7.13 (dd, 1H), 6.68 (s, 1H), 2.57 (s, 3H)

Melting point: 171-173° C. Yield: 54%

Example C7

N-[2-Fluoro-4-(2-methyl-8-trifluoromethyl-quinolin-4-yloxy)-phenyl]-2-trifluoromethyl-benzenesulfonamid

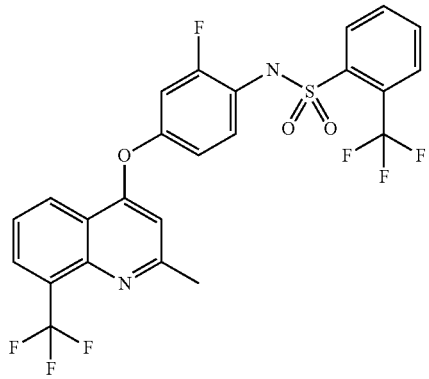 [SMILES: Cc1cc(Oc2ccc(NS(=O)(=O)c3ccccc3C(F)(F)F)c(F)c2)c2cccc(C(F)(F)F)c2n1]

$C_{24}H_{15}F_7N_2O_3S$ Mw. 544.45

LC/MS purity: 95%, m/z 543 [M−H]⁻ Rt. 5.05 min.

¹H NMR (300 MHz, DMSO-d6): 10.43 (s, 1H), 8.47 (d, 1H), 8.19 (d, 1H), 8.05 (m, 2H), 7.88 (m, 2H), 7.72 (t, 1H), 7.33 (m, 2H), 7.12 (dd, 1H), 6.69 (s, 1H), 2.58 (s, 3H)

Melting point: 183-185° C. Yield: 56%

Example C8

4-Methoxy-naphthalene-1-sulfonic acid [3-fluoro-4-(2-methyl-8-trifluoromethyl-quinolin-4-yloxy)-phenyl]-amide

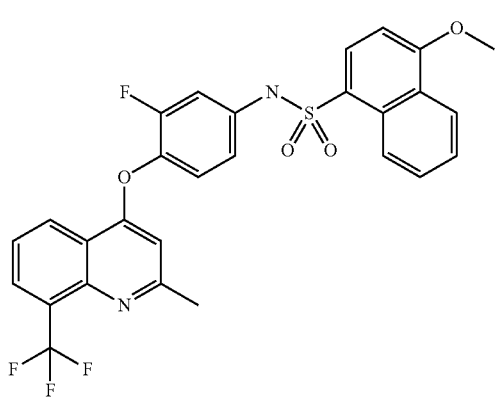 [SMILES: COc1ccc(S(=O)(=O)Nc2ccc(Oc3cc(C)nc4c(C(F)(F)F)cccc34)c(F)c2)c2ccccc12]

$C_{28}H_{20}F_4N_2O_4S$ Mw. 556.54

LC/MS purity: 94%, m/z 555 [M−H]⁻, m/z 557 [M−H]⁺ Rt. 5.25 min.

¹H NMR (300 MHz, DMSO-d6): 10.97 (s, 1H), 8.68 (d, 1H), 8.47 (d, 1H), 8.30 (d, 2H), 8.17 (d, 1H), 7.79 (t, 1H), 7.67 (m, 2H), 7.31 (t, 1H), 7.11 (m, 2H), 6.95 (d, 1H), 6.51 (s, 2H), 4.06 (s, 3H), 2.56 (s, 3H)

Melting point: 242-244° C. Yield: 74%

Example C9

3-Fluoro-N-[3-fluoro-4-(2-methyl-8-trifluoromethyl-quinolin-4-yloxy)-phenyl]-4-methoxy-benzenesulfonamide

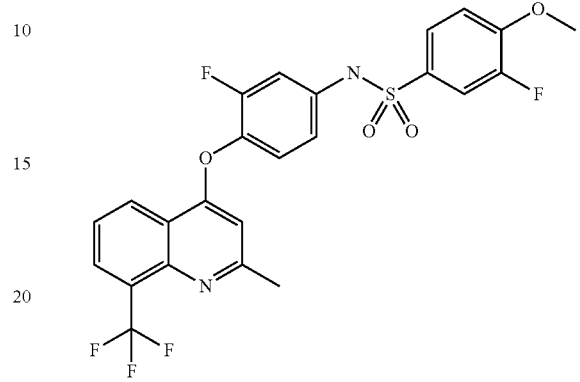

$C_{24}H_{17}F_5N_2O_4S$ Mw. 524.47

LC/MS purity: 98%, m/z 523 [M−H]⁻ Rt. 4.96 min.

¹H NMR (300 MHz, DMSO-d6): 10.63 (bs, 1H), 8.53 (d, 1H), 8.20 (d, 1H), 7.65 (m, 3H), 7.40 (m, 2H), 7.19 (dd, 1H), 7.05 (dd, 1H), 6.58 (s, 1H), 3.92 (s, 3H), 2.55 (s, 3H)

Melting point: 128-130° C. Yield: 70%

Example C10

N-[3-Fluoro-4-(2-methyl-8-trifluoromethyl-quinolin-4-yloxy)-phenyl]-2-methoxy-4,5-dimethyl-benzenesulfonamide

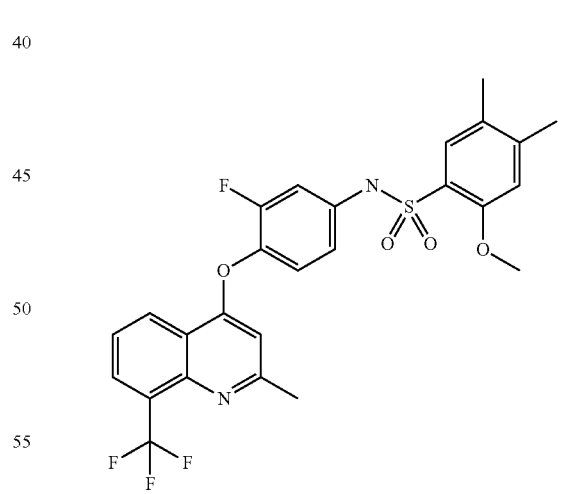

$C_{26}H_{22}F_4N_2O_4S$ Mw. 534.53

LC/MS purity: 95%, m/z 533 [M−H]⁻, m/z 535 [M−H]⁺ Rt. 5.19 min.

¹H NMR (300 MHz, DMSO-d6): 10.34 (s, 1H), 8.49 (d, 1H), 8.19 (d, 1H), 7.70 (t, 1H), 7.59 (s, 1H), 7.15 (dd, 1H), 7.03 (m, 2H), 6.54 (s, 1H), 3.86 (s, 3H), 2.58 (s, 3H), 2.26 (s, 3H), 2.19 (s, 3H)

Melting point: 230-232° C. Yield: 62%

Example C11

2,5-Difluoro-N-[2-fluoro-4-(2-methyl-8-trifluoromethyl-quinolin-4-yloxy)-phenyl]-benzenesulfonamide

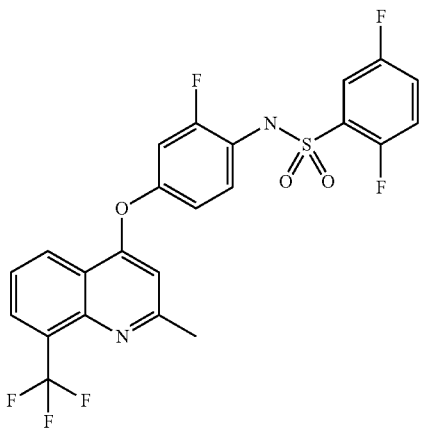 [SMILES: Cc1cc(Oc2ccc(NS(=O)(=O)c3cc(F)ccc3F)c(F)c2)c2cccc(C(F)(F)F)c2n1]

$C_{23}H_{14}F_6N_2O_3S$ Mw. 512.43

LC/MS purity: 100%, m/z 511 [M–H]⁻ Rt. 4.92 min.

¹H NMR (300 MHz, DMSO-d6): 10.70 (bs, 1H), 8.47 (d, 2H), 8.18 (d, 1H), 7.69 (t, 1H), 7.53 (m, 3H), 7.37 (t, 1H), 7.27 (d, 1H), 7.07 (d, 1H), 6.71 (s, 1H), 2.58 (s, 3H)

Melting point: 179-181° C. Yield: 52%

Example C12

3-Chloro-4-fluoro-N-[2-fluoro-4-(2-methyl-8-trifluoromethyl-quinolin-4-yloxy)-phenyl]-benzenesulfonamide

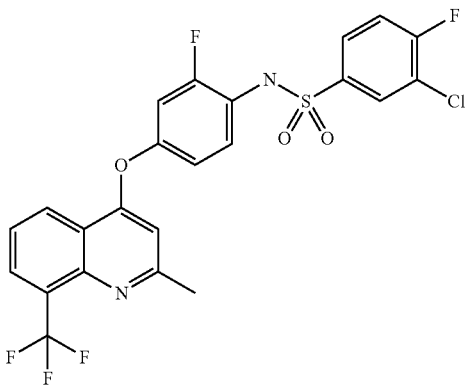 [SMILES: Cc1cc(Oc2ccc(NS(=O)(=O)c3ccc(F)c(Cl)c3)c(F)c2)c2cccc(C(F)(F)F)c2n1]

$C_{23}H_{14}ClF_5N_2O_3S$ Mw. 528.89

LC/MS purity: 98%, m/z 527 [M–H]⁻ Rt. 5.24 min.

¹H NMR (300 MHz, DMSO-d6): 10.41 (bs, 1H), 8.47 (d, 1H), 8.19 (d, 1H), 7.91 (dd, 1H), 7.71 (m, 3H), 7.33 (m, 2H), 7.12 (d, 1H), 6.75 (s, 1H), 2.58 (s, 3H)

Melting point: 202-203° C. Yield: 57%

Example C13

2-Methyl-3H-imidazole-4-sulfonic acid [3-fluoro-4-(2-methyl-8-trifluoromethyl-quinolin-4-yloxy)-phenyl]-amide

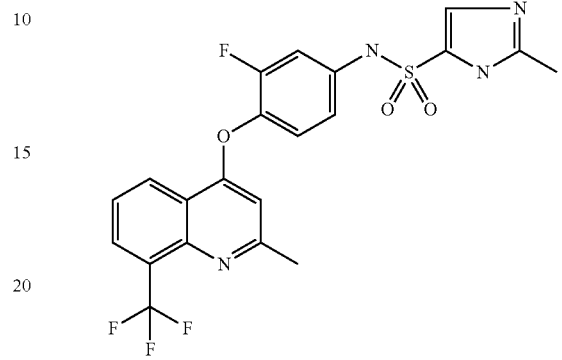

$C_{21}H_{16}F_4N_4O_3S$ Mw. 480.44

LC/MS purity: 98%, m/z 479 [M–H]⁻ Rt. 4.07 min.

¹H NMR (300 MHz, DMSO-d6): 12.5 (s, 1H), 10.6 (bs, 1H), 8.54 (d, 1H), 8.19 (d, 1H), 7.79 (s, 1H), 7.71 (t, 1H), 7.38 (t, 1H), 7.24 (d, 1H), 7.08 (d, 1H), 6.60 (s, 1H), 2.56 (s, 3H), 2.29 (s, 3H)

Melting point: 258-259° C. Yield: 57%

Example C14

4-(3,5-Dimethyl-isoxazol-4-ylmethoxy)-N-[3-fluoro-4-(2-methyl-8-trifluoromethyl-quinolin-4-yloxy)-phenyl]-benzenesulfonamide

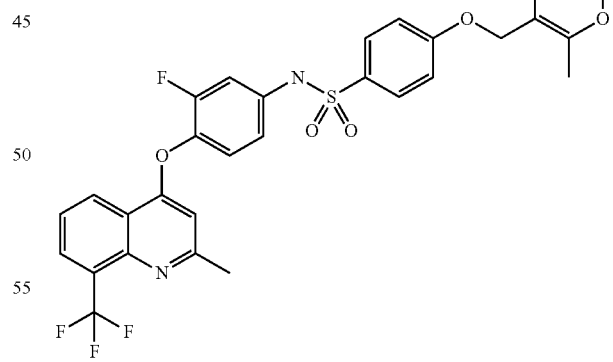

$C_{29}H_{23}F_4N_3O_5S$ Mw. 601.58

LC/MS purity: 95%, m/z 600 [M–H]⁻ Rt. 4.96 min.

¹H NMR (300 MHz, DMSO-d6): 12.20 (bs, 1H), 8.52 (d, 1H), 8.19 (d, 1H), 7.80 (d, 2H), 7.71 (t, 1H), 7.40 (t, 1H), 7.18 (m, 3H), 7.04 (dd, 1H), 6.58 (s, 1H), 5.00 (s, 2H), 2.55 (s, 3H), 2.40 (s, 3H), 2.20 (s, 3H)

Melting point: 193-195° C. Yield: 35%

Example C15

Biphenyl-4-sulfonic acid [2-fluoro-4-(2-methyl-8-trifluoromethyl-quinolin-4-yloxy)-phenyl-amide

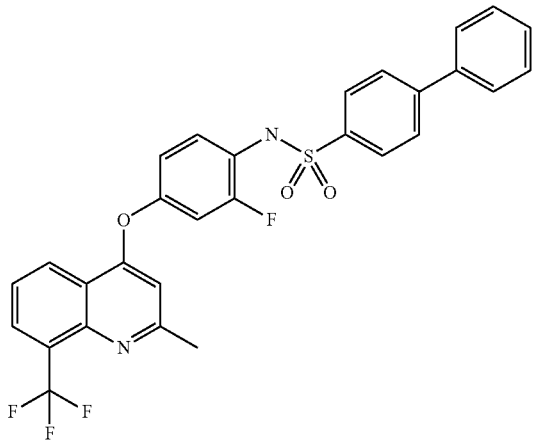 [SMILES: Cc1cc(Oc2ccc(NS(=O)(=O)c3ccc(-c4ccccc4)cc3)c(F)c2)c2cccc(C(F)(F)F)c2n1]

$C_{29}H_{20}F_4N_2O_3S$ Mw. 552.55

LC/MS purity: 96%, m/z 551 [M–H]$^-$, m/z 553 [M–H]$^+$ Rt. 5.34 min.

$^1$H NMR (300 MHz, DMSO-d6): 10.32 (bs, 1H), 8.46 (d, 1H), 8.18 (d, 1H), 7.87 (dd, 4H), 7.72 (m, 3H), 7.53-7.36 (m, 4H), 7.29 (dd, 1H), 7.10 (d, 1H), 6.73 (s, 1H), 2.56 (s, 3H); Melting point: 215-217° C.; Yield: 63%

Example C16

N-[2-Fluoro-4-(2-methyl-8-trifluoromethyl-quinolin-4-yloxy)-phenyl]-3-pyrimidin-2-yl-benzenesulfonamide

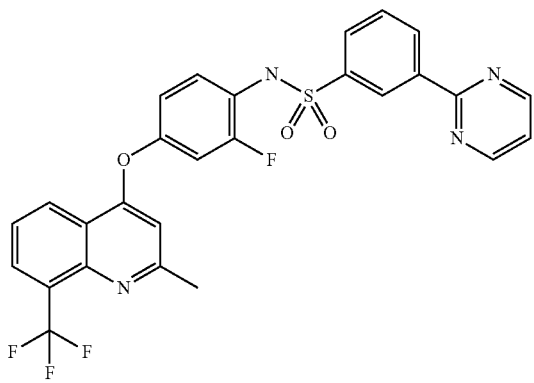 [SMILES: Cc1cc(Oc2ccc(NS(=O)(=O)c3cccc(-c4ncccn4)c3)c(F)c2)c2cccc(C(F)(F)F)c2n1]

$C_{27}H_{18}F_4N_4O_3S$ Mw. 554.53

LC/MS purity: 97%, m/z 553 [M–H]$^-$, m/z 555 [M–H]$^+$ Rt. 4.92 min.

$^1$H NMR (300 MHz, DMSO-d6): 10.39 (bs, 1H), 8.97 (s, 1H), 8.96 (s, 1H), 8.84 (t, 1H), 8.63 (d, 1H), 8.45 (d, 1H), 8.18 (d, 1H), 7.89 (d, 1H), 7.70 (m, 2H), 7.53 (t, 1H), 7.35 (t, 1H), 7.25 (dd, 1H), 7.07 (d, 1H), 6.68 (s, 1H), 2.58 (s, 3H); Melting point: 219-220° C.; Yield: 54%

Example C17

Benzo[b]thiophene-2-sulfonic acid [2-fluoro-4-(2-methyl-8-trifluoromethyl-quinolin-4-yloxy)-phenyl]-amide

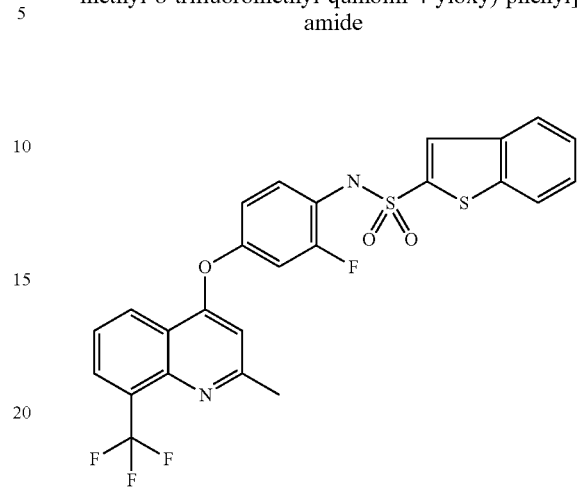

$C_{25}H_{16}F_4N_2O_3S_2$ Mw. 532.54

LC/MS purity: 96%, m/z 531 [M–H]$^-$, m/z 533 [M–H]$^+$ Rt. 5.16 min.

$^1$H NMR (300 MHz, DMSO-d6): 10.65 (s, 1H), 8.47 (d, 1H), 8.19 (d, 1H), 8.10 (d, 1H), 8.03 (d, 1H), 7.95 (s, 1H), 7.69 (t, 1H), 7.50 (m, 3H), 7.33 (dd, 1H), 7.15 (d, 1H), 6.75 (s, 1H), 2.58 (s, 3H)

Melting point: 182-184° C.; Yield: 51%

Example C18

Benzo[b]thiophene-3-sulfonic acid [2-fluoro-4-(2-methyl-8-trifluoromethyl-quinolin-4-yloxy)phenyl]-amide

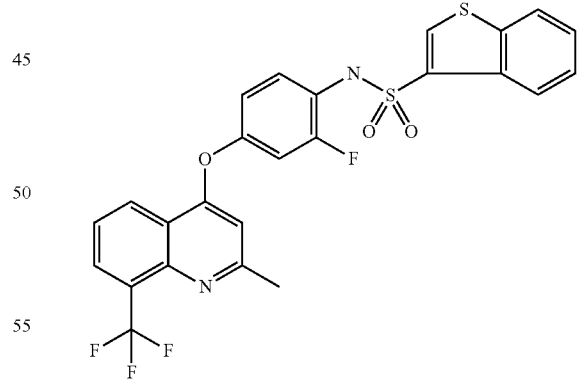

$C_{25}H_{16}F_4N_2O_3S_2$ Mw. 532.54

LC/MS purity: 96%, m/z 531 [M–H]$^-$, m/z 533 [M–H]$^+$ Rt. 5.11 min.

$^1$H NMR (300 MHz, DMSO-d6): 10.46 (s, 1H), 8.49 (s, 1H), 8.45 (d, 1H), 8.14 (m, 3H), 7.69 (t, 1H), 7.52 (m, 2H), 7.37 (t, 1H), 7.23 (dd, 1H), 7.09 (d, 1H), 6.68 (s, 1H), 2.58 (s, 3H)

Melting point: 242-244° C.; Yield: 75%

Example C19

1-Methyl-2-oxo-2,3-dihydro-1H-indole-5-sulfonic acid [2-fluoro-4-(2-methyl-8-trifluoro-methyl-quinolin-4-yloxy)-phenyl]-amide

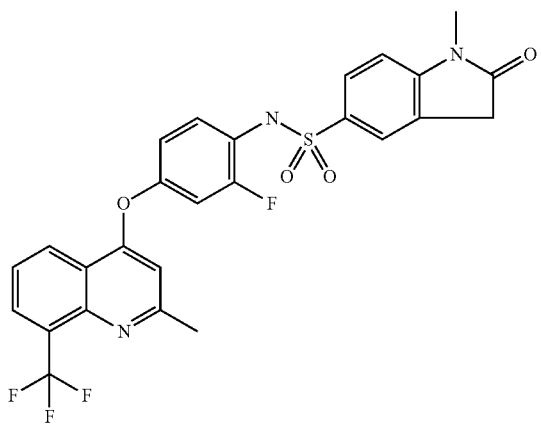 [SMILES: Cc1cc(Oc2ccc(NS(=O)(=O)c3ccc4c(c3)CC(=O)N4C)c(F)c2)c2cccc(C(F)(F)F)c2n1]

$C_{26}H_{19}F_4N_3O_4S$ Mw. 545.52

LC/MS purity: 90%, m/z 544 [M−H]⁻, m/z 546 [M−H]⁺ Rt. 4.45 min.

¹H NMR (300 MHz, DMSO-d6): 11.00 (bs, 1H), 8.47 (d, 1H), 8.18 (d, 1H), 7.69 (m, 2H), 7.63 (s, 1H), 7.34 (t, 1H), 7.25 (dd, 1H), 7.11 (d, 1H), 7.05 (d, 1H), 6.71 (s, 1H), 3.64 (s, 2H), 3.14 (s, 3H), 2.57 (s, 3H)

Melting point: 225-226° C.; Yield: 35%

Example D1

Biphenyl-3-sulfonic acid [4-(7-benzyloxy-6-methoxy-quinolin-4-yloxy)-2-fluoro-phenyl]-amide

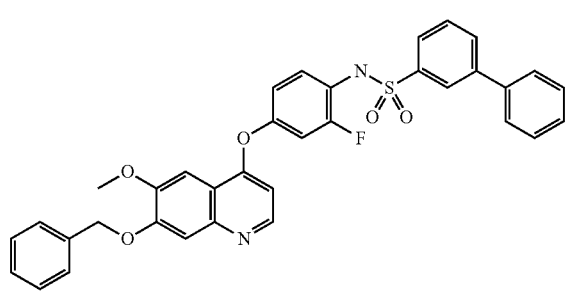 [SMILES: COc1cc2c(Oc3ccc(NS(=O)(=O)c4cccc(-c5ccccc5)c4)c(F)c3)ccnc2cc1OCc1ccccc1]

$C_{35}H_{27}FN_2O_5S$ Mw. 606.68

LC/MS purity: 100%, m/z 605 [M−H]⁻, m/z 607 [M−H]⁺ Rt. 3.71 min.

¹H NMR (300 MHz, DMSO-d6): 10.2 (bs, 1H), 8.43 (d, 1H), 7.96 (d, 2H), 7.72 (m, 4H), 7.68-7.25 (m, 11H), 7.18 (d, 1H), 7.23 (dd, 1H), 6.48 (d, 1H), 5.30 (s, 2H), 3.89 (s, 3H)

Melting point: 228-229° C.; Yield: 72%

Example D2

Naphthalene-1-sulfonic acid {4-[7-(3-amino-propoxy)-6-methoxy-quinolin-4-yloxy]-3-fluoro-phenyl}-amide hydrochloride

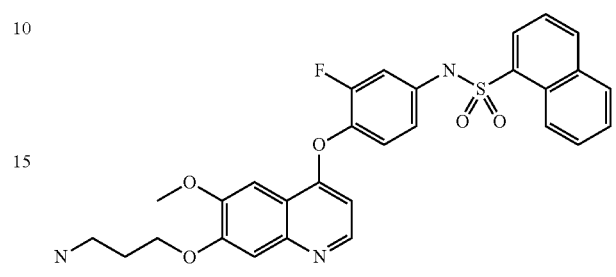

$C_{29}H_{26}FN_3O_5S \cdot HCl$ Mw (base). 547.61

LC/MS purity: 100%, m/z 546 [M−H]⁻, m/z 548 [M−H]⁺ Rt. 2.41 min.

¹H NMR (300 MHz, DMSO-d6): 11.28 (s, 1H), 8.72 (m, 2H), 8.30 (t, 2H), 8.12 (m, 3H), 7.77 (m, 5H), 7.38 (m, 1H), 7.16 (dd, 1H), 7.03 (d, 1H), 0.55 (s, 1H), 4.28 (t, 2H), 3.98 (s, 3H), 2.97 (t, 2H), 2.15 (t, 2H) Melting point: ° C. Yield: 85%

Example D3

Biphenyl-3-sulfonic acid {4-[7-(3-amino-propoxy)-6-methoxy-quinolin-4-yloxy]-3-fluoro-phenyl}-amide hydrochloride

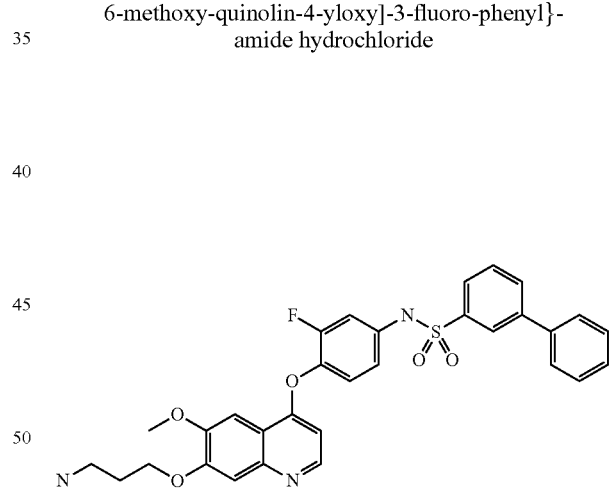

$C_{31}H_{28}FN_3O_5S \cdot HCl$ Mw (base). 573.65

LC/MS purity: 100%, m/z 572 [M−H]⁻, m/z 574 [M−H]⁺ Rt. 2.58 min.

¹H NMR (300 MHz, DMSO-d6): 10.96 (s, 1H), 8.72 (d, 1H), 8.05 (m, 5H), 7.83 (d, 1H), 7.69 (m, 5H), 7.50 (m, 4H), 7.31 (dd, 1H), 7.18 (dd, 1H), 6.81 (d, 1H), 4.33 (t, 2H), 4.00 (s, 3H), 3.00 (q, 2H), 2.18 (t, 2H)

Melting point: 198-202° C. Yield: 83%

Example D4

Biphenyl-3-sulfonic acid {3-fluoro-4-[6-methoxy-7-(2-morpholin-4-yl-ethoxy)-quinolin-4-yloxy]-phenyl}-amide

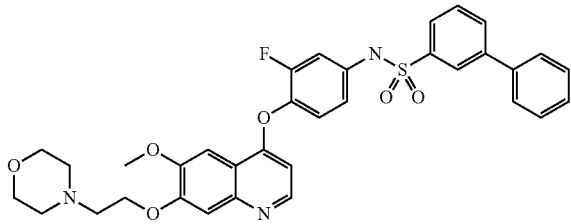 [SMILES: COc1cc2c(Oc3ccc(NS(=O)(=O)c4cccc(-c5ccccc5)c4)cc3F)ccnc2cc1OCCN1CCOCC1]

$C_{34}H_{32}FN_3O_6S$ Mw. 629.71

LC/MS purity: 99%, m/z 628 [M−H]⁻, m/z 630 [M−H]⁺ Rt. 2.68 min.

¹H NMR (300 MHz, DMSO-d6): 10.50 (bs, 1H), 8.37 (d, 1H), 8.03 (s, 1H), 7.96 (d, 1H), 7.79 (d, 1H), 7.66 (m, 3H), 7.48 (m, 5H), 7.34 (t, 1H), 7.02 (d, 1H), 6.28 (d, 1H), 4.26 (t, 2H), 3.90 (s, 3H), 3.39 (m, 4H), 2.78 (t, 2H), 2.60 (m, 4H)

Melting point: 103-104° C. Yield: 36%

Example D5

N-{3-Fluoro-4-[6-methoxy-7-(2-morpholin-4-yl-ethoxy)-quinolin-4-yloxy]-phenyl}-2-trifluoromethyl-benzenesulfonamide

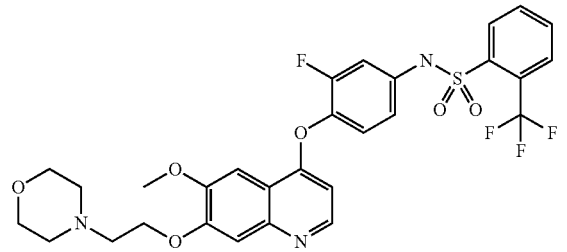 [SMILES: COc1cc2c(Oc3ccc(NS(=O)(=O)c4ccccc4C(F)(F)F)cc3F)ccnc2cc1OCCN1CCOCC1]

$C_{29}H_{27}F_4N_3O_6S$ Mw. 621.61

LC/MS purity: 100%, m/z 620 [M−H]⁻, m/z 622 [M−H]⁺ Rt. 2.26 min.

¹H NMR (300 MHz, DMSO-d6): 11.00 (bs, 1H), 8.45 (d, 1H), 8.16 (d, 1H), 8.02 (d, 1H), 7.90 (m, 2H), 7.47 (s, 1H), 7.42 (s, 1H), 7.38 (t, 1H), 7.16 (t, 1H), 7.02 (d, 1H), 6.36 (d, 1H), 4.27 (t, 2H), 3.91 (s, 3H), 3.59 (t, 4H), 2.79 (t, 2H), 2.53 (m, 4H)

Melting point: 178-180° C. Yield: 43%

Example D6

N-{3-Fluoro-4-[6-methoxy-7-(2-morpholin-4-yl-ethoxy)-quinolin-4-yloxy]-phenyl}-2-trifluoromethoxy-benzenesulfonamide

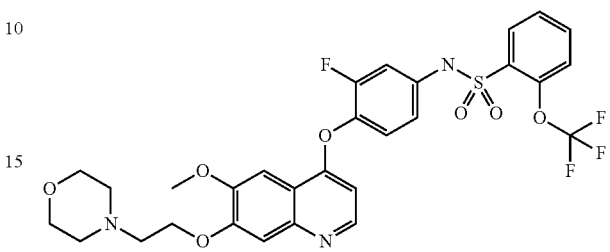

$C_{29}H_{27}F_4N_3O_7S$ Mw. 637.61

LC/MS purity: 100%, m/z 636 [M−H]⁻, m/z 638 [M−H]⁺ Rt. 2.45 min.

¹H NMR (300 MHz, DMSO-d6): 11.00 (bs, 1H), 8.45 (d, 1H), 8.04 (dd, 1H), 7.79 (t, 1H), 7.59 (m, 2H), 7.47 (s, 1H), 7.42 (s, 1H), 7.36 (t, 1H), 7.16 (dd, 1H), 7.00 (d, 1H), 6.33 (d, 1H), 4.27 (t, 2H), 3.91 (s, 3H), 3.59 (t, 4H), 2.79 (t, 2H), 2.53 (m, 4H)

Melting point: 185-187° C. Yield: 34%

Example D7

Biphenyl-3-sulfonic acid {4-[6-methoxy-7-(2-morpholin-4-yl-ethoxy)-quinolin-4-yloxy]-2-methyl-phenyl}-amide

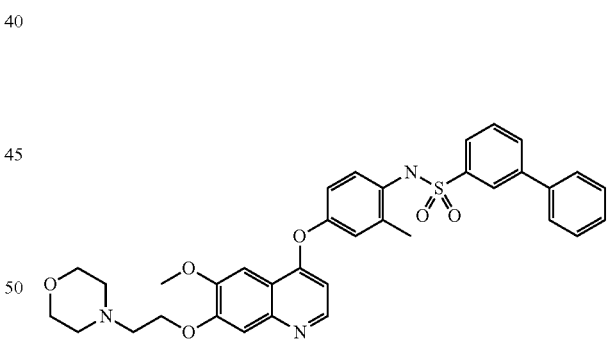

$C_{35}H_{35}N_3O_6S$ Mw. 625.75

LC/MS purity: 100%, m/z 624 [M−H]⁻, m/z 626 [M−H]⁺ Rt. 2.59 min.

¹H NMR (300 MHz, DMSO-d6): 9.82 (s, 1H), 8.40 (s, 1H), 8.01 (s, 1H), 7.86 (s, 1H), 7.67 (m, 4H), 7.48 (m, 3H), 7.46 (s, 1H), 7.44 (s, 1H), 7.07 (m, 3H), 6.37 (d, 1H), 4.26 (t, 2H), 3.90 (s, 3H), 3.59 (t, 4H), 2.78 (t, 2H), 2.53 (m, 4H), 199 (s, 3H)

Melting point: 105-107° C. Yield: 66%

Example D8

N-{4-[6-Methoxy-7-(2-morpholin-4-yl-ethoxy)-quinolin-4-yloxy]-2-methyl-phenyl}-2-trifluoromethoxy-benzenesulfonamide

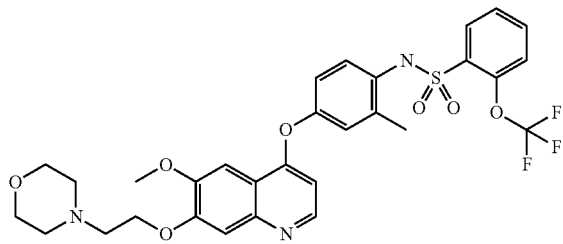 [SMILES: COc1cc2c(Oc3ccc(NS(=O)(=O)c4ccccc4OC(F)(F)F)c(C)c3)ccnc2cc1OCCN1CCOCC1]

$C_{30}H_{30}F_3N_3O_7S$ Mw. 633.65

LC/MS purity: 100%, m/z 632 [M−H]⁻, m/z 634 [M−H]⁺ Rt. 2.44 min.

¹H NMR (300 MHz, DMSO-d6): 9.25 (bs, 1H), 8.47 (d, 1H), 7.86 (d, 1H), 7.76 (t, 1H), 7.53 (m, 2H), 7.44 (s, 1H), 7.42 (s, 1H), 7.09 (d, 1H), 7.07 (s, 1H), 6.98 (d, 1H), 6.42 (d, 1H), 4.26 (t, 2H), 3.90 (s, 3H), 3.59 (t, 4H), 2.79 (t, 2H), 2.54 (t, 4H), 2.07 (m, 3H)

Melting point: 186-188° C. Yield: 46%

Example D9

2,5-Difluoro-N-{4-[6-methoxy-7-(2-morpholin-4-yl-ethoxy)-quinolin-4-yloxy]-2-methyl-phenyl}-benzenesulfonamide

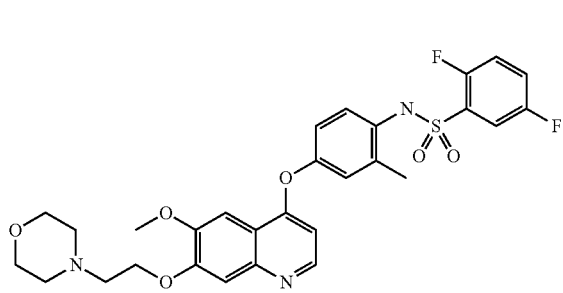 [SMILES: COc1cc2c(Oc3ccc(NS(=O)(=O)c4cc(F)ccc4F)c(C)c3)ccnc2cc1OCCN1CCOCC1]

$C_{29}H_{29}F_2N_3O_6S$ Mw. 585.63

LC/MS purity: 100%, m/z 584 [M−H]⁻, m/z 586 [M−H]⁺ Rt. 2.09 min.

¹H NMR (300 MHz, DMSO-d6): 10.18 (bs, 1H), 8.48 (d, 1H), 7.58 (m, 2H), 7.45 (m, 3H), 7.06 (m, 3H), 6.45 (d, 1H), 4.27 (t, 2H), 3.90 (s, 3H), 3.59 (t, 4H), 2.78 (t, 2H), 2.54 (t, 4H), 2.07 (m, 3H)

Melting point: 195-196° C. Yield: 41%

Example D10

2,5-Difluoro-N-{3-fluoro-4-[6-methoxy-7-(2-morpholin-4-yl-ethoxy)-quinolin-4-yloxy]-phenyl}-benzenesulfonamide

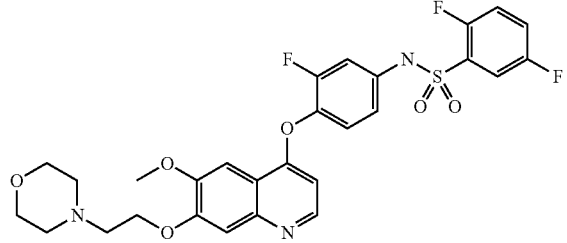 [SMILES: COc1cc2c(Oc3ccc(NS(=O)(=O)c4cc(F)ccc4F)cc3F)ccnc2cc1OCCN1CCOCC1]

$C_{28}H_{26}F_3N_3O_6S$ Mw. 589.60

LC/MS purity: 100%, m/z 588 [M−H]⁻, m/z 590 [M−H]⁺ Rt. 2.31 min.

¹H NMR (300 MHz, DMSO-d6): 10.6 (bs, 1H), 8.46 (s, 1H), 7.61 (m, 1H), 7.43 (m, 4H), 7.21 (t, 1H), 7.04 (d, 1H), 6.89 (d, 1H), 6.35 (d, 1H), 4.26 (t, 2H), 3.92 (s, 3H), 3.60 (t, 4H), 2.78 (t, 2H), 2.53 (m, 4H)

Melting point: 169-173° C. Yield: 26%

Example D11

N-{4-[6-Methoxy-7-(2-morpholin-4-yl-ethoxy)-quinolin-4-yloxy]-2-methyl-phenyl}-2-trifluoromethyl-benzenesulfonamide

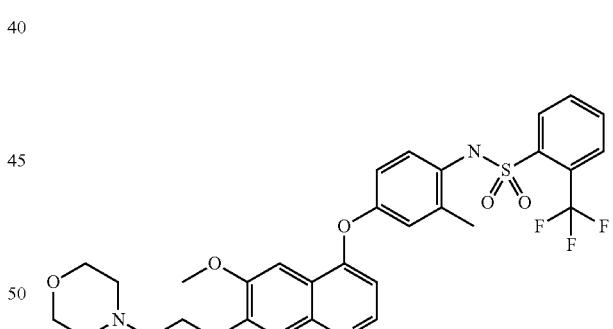

$C_{30}H_{30}F_3N_3O_6S$ Mw. 617.65

LC/MS purity: 100%, m/z 616 [M−H]⁻, m/z 618 [M−H]⁺ Rt. 2.41 min.

¹H NMR (300 MHz, DMSO-d6): 9.89 (bs, 1H), 8.48 (d, 1H), 8.01 (m, 1H), 7.95 (m, 1H), 7.86 (m, 2H), 7.42 (d, 2H), 7.03 (m, 3H), 6.43 (d, 1H), 4.27 (t, 2H), 3.90 (s, 3H), 3.59 (t, 4H), 2.78 (t, 2H), 2.53 (m, 4H), 2.10 (s, 3H)

Melting point: 127-130° C. Yield: 31%

Example D12

4-Chloro-2-fluoro-N-{3-fluoro-4-[6-methoxy-7-(2-morpholin-4-yl-ethoxy)-quinolin-4-yloxy]-phenyl}-benzenesulfonamide

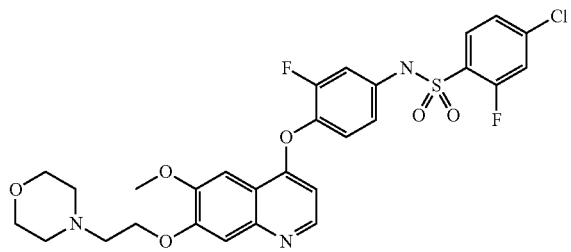 [SMILES: COc1cc2c(Oc3ccc(NS(=O)(=O)c4ccc(Cl)cc4F)cc3F)ccnc2cc1OCCN1CCOCC1]

$C_{28}H_{26}ClF_2N_3O_6S$ Mw. 606.05

LC/MS purity: 100%, m/z 604 [M–H]⁻, m/z 606 [M–H]⁺ Rt. 2.42 min.

¹H NMR (300 MHz, DMSO-d6): 11.2 (bs, 1H), 8.45 (d, 1H), 7.90 (t, 1H), 7.75 (d, 1H), 7.52-7.33 (m, 4H), 7.15 (d, 1H), 7.02 (d, 1H), 6.35 (d, 1H), 4.27 (t, 2H), 3.91 (s, 3H), 3.59 (t, 4H), 2.78 (t, 2H), 2.53 (m, 4H)

Melting point: 212-214° C. Yield: 42%

Example D13

4-Methoxy-naphthalene-1-sulfonic acid {3-fluoro-4-[6-methoxy-7-(2-morpholin-4-yl-ethoxy)-quinolin-4-yloxy]-phenyl}-amide

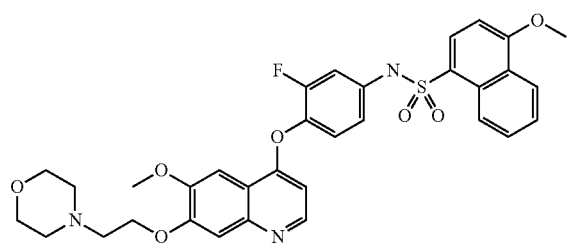 [SMILES: COc1cc2c(Oc3ccc(NS(=O)(=O)c4ccc(OC)c5ccccc45)cc3F)ccnc2cc1OCCN1CCOCC1]

$C_{33}H_{32}FN_3O_7S$ Mw. 633.70

LC/MS purity: 100%, m/z 632 [M–H]⁻, m/z 634 [M–H]⁺ Rt. 2.53 min.

¹H NMR (300 MHz, DMSO-d6): 11 (bs, 1H), 8.70 (d, 1H), 8.40 (d, 1H), 8.27 (t, 3H), 7.76 (t, 1H), 7.65 (t, 1H), 7.42 (s, 1H), 7.40 (s, 1H), 7.23 (t, 1H), 7.11 (d, 1H), 7.04 (d, 1H), 6.90 (d, 1H), 6.27 (d, 1H), 4.25 (t, 2H), 4.06 (s, 3H), 3.58 (t, 4H), 2.77 (t, 2H), 2.54 (m, 4H)

Melting point: 189-190° C. Yield: 35%

Example D14

N-{4-[7-(3-Amino-propoxy)-6-methoxy-quinolin-4-yloxy]-3-fluoro-phenyl}-2-trifluoromethyl-benzenesulfonamide hydrochloride

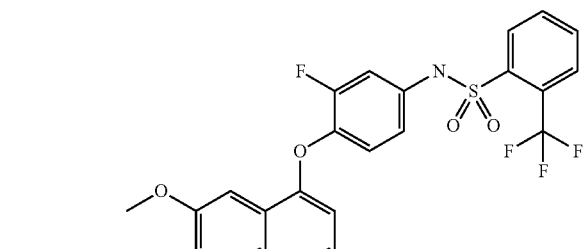

$C_{26}H_{23}F_4N_3O_5S \cdot HCl$ Mw (base). 565.55

LC/MS purity: 100%, m/z 564 [M–H]⁻, m/z 566 [M–H]⁺ Rt. 2.39 min.

¹H NMR (300 MHz, DMSO-d6): 11.28 (s, 1H), 8.75 (d, 1H), 8.20 (d, 1H), 8.04 (m, 4H), 7.90 (m, 2H), 7.70 (s, 1H), 7.68 (s, 1H), 7.51 (t, 1H), 7.25 (dd, 1H), 7.12 (d, 1H), 6.82 (d, 1H), 4.32 (t, 2H), 4.00 (s, 3H), 3.00 (m, 2H), 2.17 (t, 2H)

Melting point: 197-199° C. Yield: 86%

Example D15

N-{4-[7-(3-Amino-propoxy)-6-methoxy-quinolin-4-yloxy]-3-fluoro-phenyl}-2-trifluoromethoxy-benzenesulfonamide hydrochloride

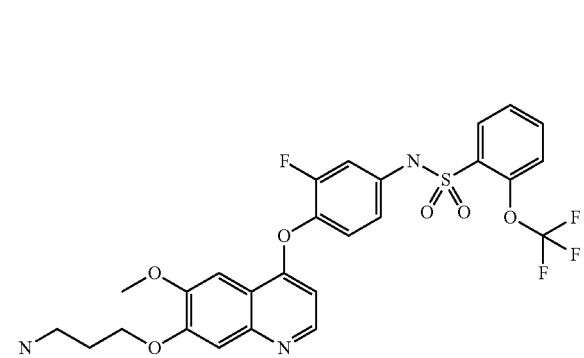 [SMILES: COc1cc2c(Oc3ccc(NS(=O)(=O)c4ccccc4OC(F)(F)F)cc3F)ccnc2cc1OCCCN]

$C_{26}H_{23}F_4N_3O_6S$ Mw. 581.55

LC/MS purity: 100%, m/z 580 [M–H]⁻, m/z 582 [M–H]⁺ Rt. 2.44 min.

¹H NMR (300 MHz, DMSO-d6): 11.16 (s, 1H), 8.76 (d, 1H), 8.07 (m, 6H), 7.82 (t, 1H), 7.69 (s, 2H), 7.50 (t, 1H), 7.23 (dd, 1H), 7.07 (d, 1H), 6.80 (d, 1H), 4.32 (t, 2H), 4.00 (s, 3H), 2.96 (m, 2H), 2.17 (t, 2H)

Melting point: 95-97° C. Yield: 90%

Example D16

(3-{4-[2-Fluoro-4-(2-trifluoromethoxy-benzene-sulfonylamino)-phenoxy]-6-methoxy-quinolin-7-yloxy}-propyl)-carbamic acid tert-butyl ester

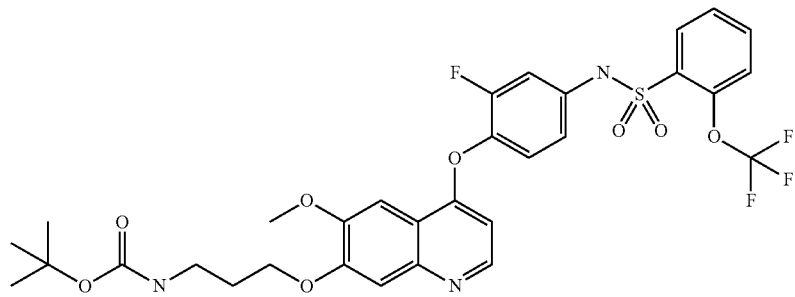 [SMILES: COc1cc2c(Oc3ccc(NS(=O)(=O)c4ccccc4OC(F)(F)F)cc3F)ccnc2cc1OCCCNC(=O)OC(C)(C)C]

$C_{31}H_{31}F_4N_3O_8S$ Mw. 681.67

LC/MS purity: 100%, m/z 680 [M−H]$^-$, m/z 682 [M−H]$^+$ Rt. 3.48 min.

$^1$H NMR (300 MHz, DMSO-d6): 10.94 (bs, 1H), 8.43 (d, 1H), 8.03 (d, 1H), 7.80 (t, 1H), 7.58 (m, 2H), 7.46 (s, 1H), 7.36 (dd, 2H), 7.14 (dd, 1H), 6.99 (d, 1H), 6.90 (t, 1H), 6.31 (d, 1H), 4.14 (t, 2H), 3.91 (s, 3H), 3.12 (m, 2H), 1.91 (t, 2H), 1.03 (s, 9H)

Melting point: 181-183° C. Yield: 76%

Example D17

N-(3-Fluoro-4-{6-methoxy-7-[3-(4-methyl-piperidin-1-yl)-propoxy]-quinolin-4-yloxy}-phenyl)-2-trifluoromethyl-benzenesulfonamide

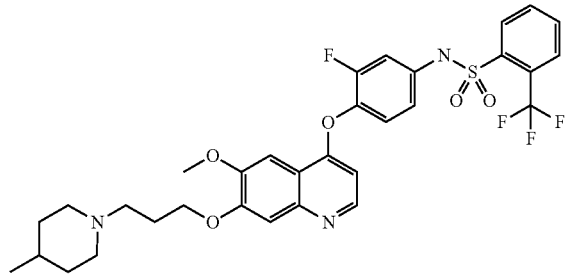 [SMILES: COc1cc2c(Oc3ccc(NS(=O)(=O)c4ccccc4C(F)(F)F)cc3F)ccnc2cc1OCCCN1CCC(C)CC1]

$C_{32}H_{33}F_4N_3O_5S$ Mw. 647.69

LC/MS purity: 98%, m/z 646 [M−H]$^-$, m/z 648 [M−H]$^+$ Rt. 2.78 min.

$^1$H NMR (300 MHz, DMSO-d6): 12 (bs, 1H), 8.40 (d, 1H), 8.08 (d, 1H), 7.76 (d, 1H), 7.64 (t, 1H), 7.55 (t, 1H), 7.46 (s, 1H), 7.33 (s, 1H), 6.96 (t, 1H), 6.75 (d, 1H), 6.63 (d, 1H), 6.32 (d, 1H), 4.15 (t, 2H), 3.90 (s, 3H), 2.84 (m, 2H), 2.55 (m, 2H), 2.42 (m, 1H), 1.92 (m, 2H), 1.56 (m, 2H), 1.29 (m, 2H), 1.14 (m, 2H), 0.87 (d, 3H)

Melting point: 110-112° C. Yield: 45%

Example D18

2-Bromo-N-(3-fluoro-4-{6-methoxy-7-[3-(4-methyl-piperidin-1-yl)-propoxy]-quinolin-4-yloxy}-phenyl)-benzenesulfonamide $C_{31}H_{33}BrFN_3O_5S$ Mw. 658.59

LC/MS purity: 99%, m/z 656 [M−H]$^-$, m/z 658 [M−H]$^+$ Rt. 2.76 min.

$^1$H NMR (300 MHz, DMSO-d6): 11.5 (bs, 1H), 8.39 (d, 1H), 7.97 (d, 1H), 7.58 (d, 1H), 7.46 (s, 1H), 7.35 (m, 2H), 7.23 (t, 1H), 6.91 (t, 1H), 6.73 (d, 1H), 6.61 (d, 1H), 6.33 (d, 1H), 4.15 (t, 2H), 3.90 (s, 3H), 2.82 (m, 2H), 2.40 (m, 1H), 1.90 (m, 4H), 1.55 (m, 2H), 1.30 (m, 2H), 1.10 (m, 2H), 0.87 (d, 3H)

Melting point: 184-186° C. Yield: 52%

Example D19

2,4-Difluoro-N-(3-fluoro-4-{6-methoxy-7-[3-(4-methyl-piperidin-1-yl)-propoxy]-quinolin-4-yloxy}-phenyl)-benzenesulfonamide

133

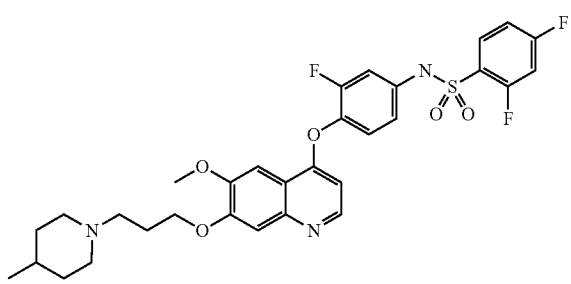 [SMILES: COc1cc2c(Oc3ccc(NS(=O)(=O)c4ccc(F)cc4F)cc3F)ccnc2cc1OCCCN1CCC(C)CC1]

C₃₁H₃₂F₃N₃O₅S Mw. 615.68

LC/MS purity: 100%, m/z 614 [M-H]⁻, m/z 616 [M-H]⁺ Rt. 2.73 min.

¹H NMR (300 MHz, DMSO-d6): 10.5 (bs, 1H), 8.42 (d, 1H), 7.87 (d, 1H), 7.47 (s, 1H), 7.35 (bs, 2H), 7.15 (bs, 2H), 6.96 (d, 1H), 6.80 (bs, 1H), 6.33 (d, 1H), 4.16 (t, 2H), 3.90 (s, 3H), 2.91 (m, 2H), 2.53 (m, 1H), 1.98 (m, 4H), 1.59 (m, 2H), 1.34 (m, 2H), 1.17 (m, 2H), 0.87 (d, 3H)

Melting point: 135-137° C. Yield: 46%

Example D20

2,6-Difluoro-N-(3-fluoro-4-{6-methoxy-7-[3-(4-methyl-piperidin-1-yl)-propoxy]-quinolin-4-yloxy}-phenyl)-benzenesulfonamide

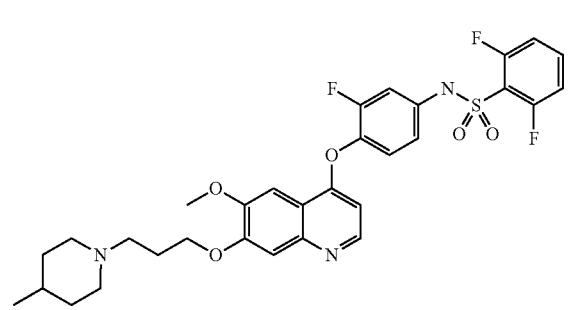 [SMILES: COc1cc2c(Oc3ccc(NS(=O)(=O)c4c(F)cccc4F)cc3F)ccnc2cc1OCCCN1CCC(C)CC1]

C₃₁H₃₂F₃N₃O₅S Mw. 615.68

LC/MS purity: 94%, m/z 614 [M-H]⁻, m/z 616 [M-H]⁺ Rt. 2.67 min.

¹H NMR (300 MHz, DMSO-d6): 10.5 (bs, 1H), 7.47 (bs, 2H), 7.35 (s, 1H), 7.08 (m, 3H), 6.94 (d, 1H), 6.76 (d, 1H), 6.33 (d, 1H), 4.16 (t, 2H), 3.90 (s, 3H), 2.92 (m, 2H), 2.54 (m, 1H), 1.98 (m, 5H), 1.59 (m, 2H), 1.35 (m, 2H), 1.18 (m, 2H), 0.88 (d, 3H)

Melting point: 200-203° C.; Yield: 37%

134

Example D21

Naphthalene-1-sulfonic acid (3-fluoro-4-{6-methoxy-7-[3-(4-methyl-piperidin-1-yl)-propoxy]-quinolin-4-yloxy}-phenyl)-amide

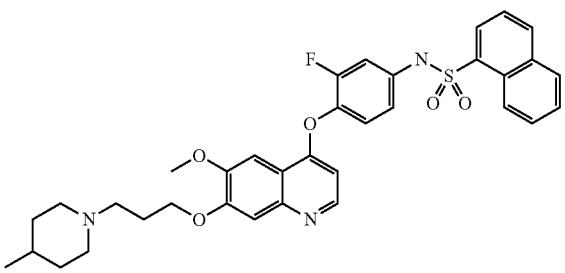 [SMILES: COc1cc2c(Oc3ccc(NS(=O)(=O)c4cccc5ccccc45)cc3F)ccnc2cc1OCCCN1CCC(C)CC1]

C₃₅H₃₆FN₃O₅S Mw. 629.76

LC/MS purity: 95%, m/z 628 [M-H]⁻, m/z 630 [M-H]⁺ Rt. 2.89 min.

¹H NMR (300 MHz, DMSO-d6): 10.7 (bs, 1H), 8.78 (d, 1H), 8.38 (d, 1H), 8.22 (m, 2H), 8.06 (d, 1H), 7.66 (m, 3H), 7.41 (s, 1H), 7.31 (s, 1H), 7.15 (t, 1H), 7.00 (d, 1H), 6.86 (d, 1H), 6.24 (d, 1H), 4.15 (t, 2H), 3.87 (s, 3H), 2.92 (m, 2H), 2.54 (m, 1H), 1.99 (m, 4H), 1.59 (m, 2H), 1.21 (m, 2H), 1.17 (m, 2H), 0.87 (d, 3H)

Melting point: 140-143° C. Yield: 35%

Example D22

Propane-1-sulfonic acid (3-fluoro-4-{6-methoxy-7-[3-(4-methyl-piperidin-1-yl)-propoxy]-quinolin-4-yloxy}-phenyl)-amide

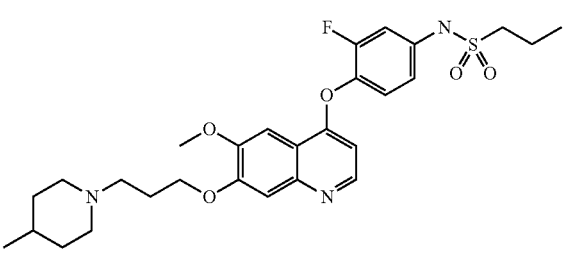 [SMILES: CCCS(=O)(=O)Nc1ccc(Oc2ccnc3cc(OCCCN4CCC(C)CC4)c(OC)cc23)c(F)c1]

C₂₈H₃₆FN₃O₅S Mw. 545.68

LC/MS purity: 99%, m/z 544 [M-H]⁻, m/z 546 [M-H]⁺ Rt. 2.50 min.

¹H NMR (300 MHz, DMSO-d6): 10.2 (bs, 1H), 8.45 (d, 1H), 7.49 (s, 1H), 7.36 (s, 1H), 7.34 (d, 1H), 7.16 (d, 1H), 7.03 (d, 1H), 6.44 (d, 1H), 4.26 (t, 1H), 3.93 (s, 3H), 3.07 (bs, 2H), 2.71 (m, 2H), 2.62 (m, 2H), 2.44 (m, 1H), 1.92 (m, 3H), 1.69 (m, 2H), 1.57 (m, 2H), 1.21 (m, 2H), 1.13 (m, 2H), 0.95 (t, 3H), 0.87 (d, 3H)

Melting point: 160-162° C.; Yield: 16%

Example D23

2-Cyano-N-(3-fluoro-4-{6-methoxy-7-[3-(4-methyl-piperidin-1-yl)-propoxy]-quinolin-4-yloxy}-phenyl)-benzenesulfonamide

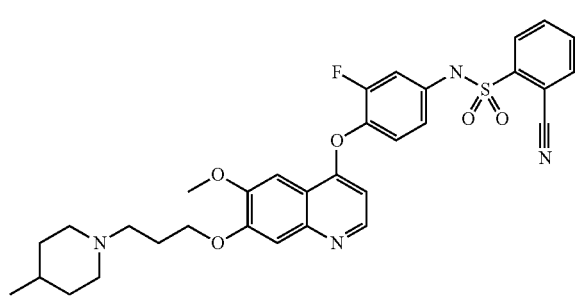 [SMILES: COc1cc2c(Oc3ccc(NS(=O)(=O)c4ccccc4C#N)cc3F)ccnc2cc1OCCCN1CCC(C)CC1]

$C_{32}H_{33}FN_4O_5S$ Mw. 604.71

LC/MS purity: 99%, m/z 603 [M−H]$^-$, m/z 605 [M−H]$^+$ Rt. 2.52 min.

$^1$H NMR (300 MHz, DMSO-d6): 10.5 (bs, 1H), 8.44 (d, 1H), 7.99 (d, 1H), 7.77 (t, 1H), 7.63 (t, 2H), 7.49 (s, 1H), 7.38 (s, 1H), 7.09 (t, 1H), 6.94 (d, 1H), 6.77 (d, 1H), 6.37 (d, 1H), 4.20 (t, 2H), 3.92 (s, 3H), 3.14 (m, 2H), 2.77 (m, 2H), 2.33 (m, 1H), 2.07 (m, 2H), 2.07 (m, 2H), 1.69 (m, 2H), 1.45 (m, 2H), 1.24 (m, 2H), 0.90 (d, 3H)

Melting point: 139-142° C.; Yield: 19%

Example D24

4-Chloro-2-fluoro-N-(3-fluoro-4-{6-methoxy-7-[3-(3-methyl-piperidin-1-yl)-propoxy]-quinolin-4-yloxy}-phenyl)-benzenesulfonamide

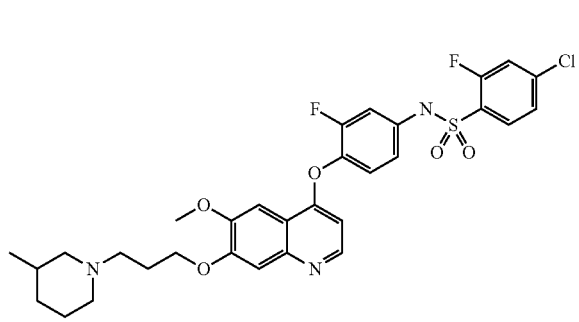 [SMILES: COc1cc2c(Oc3ccc(NS(=O)(=O)c4ccc(Cl)cc4F)cc3F)ccnc2cc1OCCCN1CCCC(C)C1]

$C_{31}H_{32}Cl\ F_2N_3O_5S$ Mw. 632.13

LC/MS purity: 99%, m/z 630 [M−H]$^-$, m/z 632 [M−H]$^+$ Rt. 2.58 min.

$^1$H NMR (300 MHz, DMSO-d6): 10.8 (bs, 1H), 8.44 (d, 1H), 7.86 (t, 1H), 7.62 (d, 1H), 7.49 (s, 1H), 7.45 (d, 1H), 7.39 (s, 1H), 7.26 (m, 2H), 7.06 (d, 1H), 6.92 (d, 1H), 6.36 (d, 1H), 4.21 (t, 1H), 3.92 (s, 3H), 3.05 (m, 2H), 2.75 (m, 2H), 2.51 (m, 1H), 2.00 (m, 4H), 1.61 (m, 4H), 0.87 (d, 3H)

Melting point: 136-138° C. Yield: 24%

Example D25

Butane-1-sulfonic acid (3-fluoro-4-{6-methoxy-7-[3-(3-methyl-piperidin-1-yl)-propoxy]-quinolin-4-yloxy}-phenyl)-amide

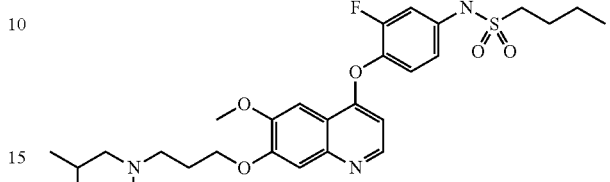

$C_{29}H_{38}FN_3O_5S$ Mw. 559.71

LC/MS purity: 96%, m/z 558 [M−H]$^-$, m/z 560 [M−H]$^+$ Rt. 2.68 min.

$^1$H NMR (300 MHz, DMSO-d6): 10.24 (bs, 1H), 8.47 (d, 1H), 7.51 (s, 1H), 7.43 (s, 1H), 7.41 (s, 1H), 7.26 (d, 1H), 7.14 (d, 1H), 6.46 (d, 1H), 4.21 (t, 2H), 3.94 (s, 3H), 3.18 (m, 6H), 3.00 (m, 2H), 2.51 (t, 1H), 3.94 (s, 3H), 3.18 (m, 6H), 3.00 (m, 2H), 2.51 (m, 1H), 2.16 (m, 2H), 1.65 (m, 6H), 1.37 (m, 2H), 0.85 (m, 6H)

Melting point: 104-106° C. Yield: 23%

Example D26

2-Bromo-N-{3-fluoro-4-[6-methoxy-7-(2-morpholin-4-yl-ethoxy)-quinolin-4-yloxy]-phenyl}-benzenesulfonamide

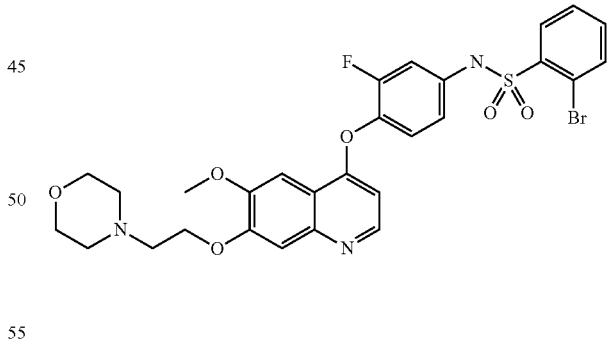

$C_{28}H_{27}BrFN_3O_6S$ Mw. 632.51

LC/MS purity: 99%, m/z 630 [M−H]$^-$, m/z 632 [M−H]$^+$ Rt. 2.53 min.

$^1$H NMR (300 MHz, DMSO-d6): 11 (bs, 1H), 8.44 (d, 1H), 8.13 (d, 1H), 7.85 (d, 1H), 7.56 (m, 2H), 7.46 (s, 1H), 7.42 (s, 1H), 7.32 (t, 1H), 7.10 (dd, 1H), 6.99 (d, 1H), 6.34 (d, 1H), 4.26 (t, 2H), 3.93 (s, 3H), 3.59 (t, 4H), 2.78 (t, 2H), 2.53 (m, 4H)

Melting point: 175-177° C. Yield: 18%

Example D27

2-Cyano-N-{3-fluoro-4-[6-methoxy-7-(2-morpholin-4-yl-ethoxy)-quinolin-4-yloxy]-phenyl}-benzenesulfonamide

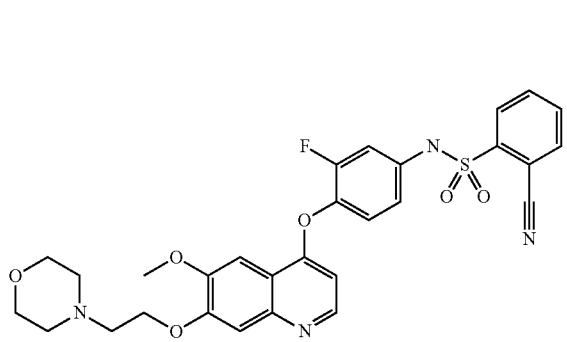 [SMILES: COc1cc2c(Oc3ccc(NS(=O)(=O)c4ccccc4C#N)cc3F)ccnc2cc1OCCN1CCOCC1]

$C_{29}H_{27}FN_4O_6S$ Mw. 578.62

LC/MS purity: 99%, m/z 577 [M−H]⁻, m/z 579 [M−H]⁺ Rt. 2.29 min.

¹H NMR (300 MHz, DMSO-d6): 11 (bs, 1H), 8.45 (d, 1H), 8.09 (m, 2H), 7.92 (t, 1H), 7.83 (t, 1H), 7.48 (s, 1H), 7.43 (s, 1H), 7.33 (t, 1H), 7.15 (d, 1H), 6.96 (d, 1H), 6.40 (d, 1H), 4.27 (t, 2H), 3.92 (s, 3H), 3.60 (m, 4H), 2.80 (t, 2H), 2.53 (m, 4H)

Melting point: 193-196° C. Yield: 23%

Example D28

2,4-Difluoro-N-{3-fluoro-4-[6-methoxy-7-(2-morpholin-4-yl-ethoxy)-quinolin-4-yloxy]-phenyl}-benzenesulfonamide

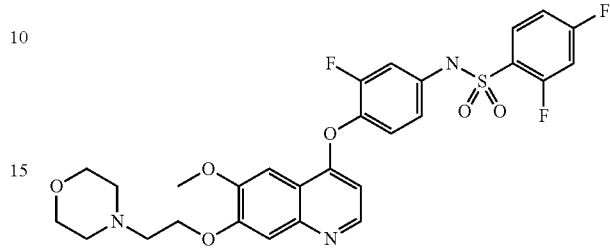

$C_{28}H_{26}F_3N_3O_6S$ Mw. 589.60

LC/MS purity: 99%, m/z 588 [M−H]⁻, m/z 590 [M−H]⁺ Rt. 2.42 min.

¹H NMR (300 MHz, DMSO-d6): 11 (bs, 1H), 8.45 (d, 1H), 7.97 (q, 1H), 7.59-7.27 (m, 5H), 7.15 (dd, 1H), 7.02 (d, 1H), 6.35 (t, 1H), 3.91 (s, 3H), 3.59 (m, 4H), 2.78 (m, 4H), 2.53 (m, 4H)

Melting point: 189-191° C. Yield: 19%

Example D29

Biphenyl-3-sulfonic acid (3-fluoro-4-{6-methoxy-7-[3-(4-methyl-piperidin-1-yl)-propoxy]-quinolin-4-yloxy}-phenyl)-amide

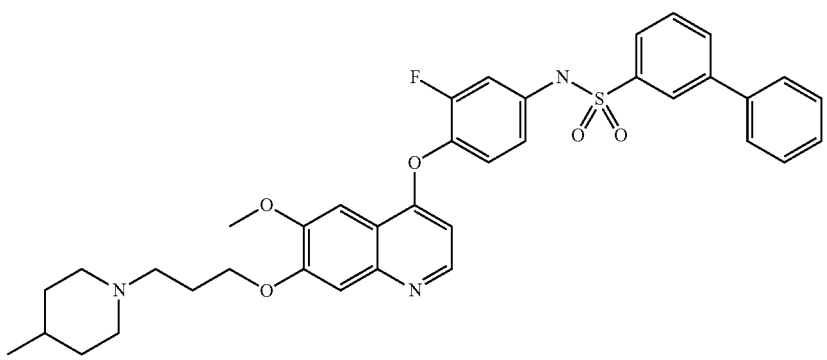 [SMILES: COc1cc2c(Oc3ccc(NS(=O)(=O)c4cccc(-c5ccccc5)c4)cc3F)ccnc2cc1OCCCN1CCC(C)CC1]

$C_{37}H_{38}FN_3O_5S$ Mw. 655.79

LC/MS purity: 100%, m/z 654 [M−H]⁻, m/z 656 [M−H]⁺ Rt. 2.93 min.

¹H NMR (300 MHz, DMSO-d6): 11 (bs, 1H), 8.36 (d, 1H), 8.02 (s, 1H), 7.94 (d, 1H), 7.79 (d, 1H), 7.70 (m, 3H), 7.52 (m, 4H), 7.36 (s, 1H), 7.30 (t, 1H), 7.14 (d, 1H), 7.00 (d, 1H), 6.28 (d, 1H), 4.17 (t, 2H), 3.90 (s, 3H), 2.88 (m, 2H), 2.50 (m, 1H), 1.98 (m, 4H), 1.58 (m, 2H), 1.34 (m, 2H), 1.15 (m, 2H), 0.88 (d, 3H)

Melting point: 196-198° C. Yield: 16%

Example D30

2-Fluoro-N-(3-fluoro-4-{6-methoxy-7-[3-(3-methyl-piperidin-1-yl)-propoxy]-quinolin-4-yloxy}-phenyl)-benzenesulfonamide

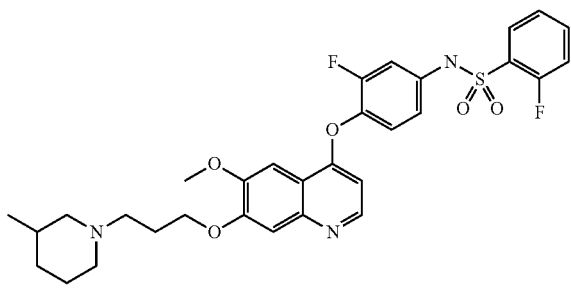 [SMILES: COc1cc2c(Oc3ccc(NS(=O)(=O)c4ccccc4F)cc3F)ccnc2cc1OCCCN1CCCC(C)C1]

$C_{31}H_{33}F_2N_3O_5S$ Mw. 597.69

LC/MS purity: 99%, m/z 596 [M−H]⁻, m/z 598 [M−H]⁺ Rt. 2.55 min.

¹H NMR (300 MHz, DMSO-d6): 10.5 (bs, 1H), 8.43 (d, 1H), 7.87 (t, 1H), 7.66 (q, 1H), 7.47 (s, 1H), 7.35 (m, 3H), 7.26 (t, 1H), 7.08 (dd, 1H), 6.94 (d, 1H), 6.33 (d, 1H), 4.18 (t, 2H), 3.92 (s, 3H), 2.86 (m, 2H), 2.54 (m, 3H), 1.99 (m, 3H), 1.60 (m, 5H), 0.84 (d, 3H)

Melting point: 102-106° C. Yield: 25%

Example D31

2-Cyano-N-(3-fluoro-4-{6-methoxy-7-[3-(3-methyl-piperidin-1-yl)-propoxy]-quinolin-4-yloxy}-phenyl)-benzenesulfonamide

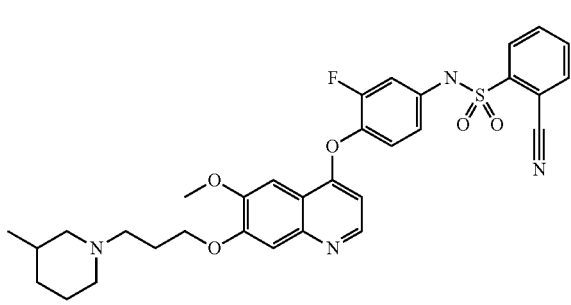 [SMILES: COc1cc2c(Oc3ccc(NS(=O)(=O)c4ccccc4C#N)cc3F)ccnc2cc1OCCCN1CCCC(C)C1]

$C_{32}H_{33}FN_4O_5S$ Mw. 604.71

LC/MS purity: 99%, m/z 603 [M−H]⁻, m/z 605 [M−H]⁺ Rt. 2.50 min.

¹H NMR (300 MHz, DMSO-d6): 10.8 (bs, 1H), 8.42 (d, 1H), 8.38 (d, 1H), 7.88 (d, 1H), 7.74 (t, 1H), 7.60 (t, 1H), 7.49 (s, 1H), 7.37 (s, 1H), 7.06 (t, 1H), 6.90 (dd, 1H), 6.74 (d, 1H), 6.37 (d, 1H), 4.19 (t, 2H), 3.92 (s, 3H), 3.07 (m, 2H), 2.63 (m, 2H), 2.50 (m, 1H), 2.03 (m, 3H), 1.66 (m, 5H), 0.87 (d, 3H)

Melting point: 131-132° C. Yield: 34%

Example D32

2,6-Difluoro-N-(3-fluoro-4-{6-methoxy-7-[3-(3-methyl-piperidin-1-yl)-propoxy]-quinolin-4-yloxy}-phenyl)-benzenesulfonamide

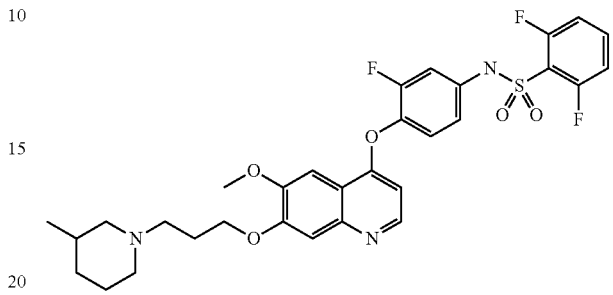

$C_{31}H_{32}F_3N_3O_5S$ Mw. 615.68

LC/MS purity: 100%, m/z 614 [M−H]⁻, m/z 616 [M−H]⁺ Rt. 2.71 min.

¹H NMR (300 MHz, DMSO-d6): 125 (bs, 1H), 8.44 (d, 1H), 7.59 (t, 1H), 7.49 (s, 1H), 7.33 (s, 1H), 7.20 (m, 3H), 7.04 (d, 1H), 6.88 (d, 1H), 6.35 (d, 1H), 4.20 (t, 2H), 3.92 (s, 3H), 2.98 (s, 2H), 2.67 (m, 2H), 2.04 (m, 3H), 1.86 (m, 1H), 1.60 (m, 5H), 0.86 (d, 3H)

Melting point: 117-119° C. Yield: 29%

Example D33

N-(3-Fluoro-4-{6-methoxy-7-[3-(4-methyl-piperidin-1-yl)-propoxy]-quinolin-4-yloxy}-phenyl)-2-trifluoromethoxy-benzenesulfonamide

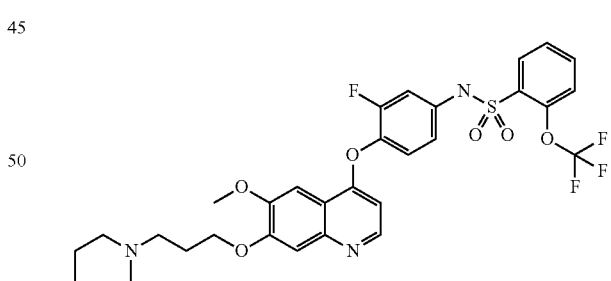

$C_{32}H_{33}F_4N_3O_6S$ Mw. 663.69

LC/MS purity: 99%, m/z 662 [M−H]⁻, m/z 664 [M−H]⁺ Rt. 2.75 min.

¹H NMR (300 MHz, DMSO-d6): 11.5 (bs, 1H), 8.41 (d, 1H), 7.89 (d, 1H), 7.48 (s, 1H), 7.45 (d, 1H), 7.34 (m, 3H), 6.93 (t, 1H), 6.80 (d, 1H), 6.61 (d, 1H), 6.33 (d, 1H), 4.16 (t, 2H), 3.92 (s, 3H), 2.85 (m, 2H), 2.43 (m, 1H), 1.90 (m, 4H), 1.57 (m, 2H), 1.31 (m, 2H), 1.14 (m, 2H), 0.88 (d, 3H)

Melting point: 206-208° C. Yield: 32%

Example D34

2,5-Difluoro-N-(3-fluoro-4-{6-methoxy-7-[3-(4-methyl-piperidin-1-yl)-propoxy]-quinolin-4-yloxy}-phenyl)-benzenesulfonamide

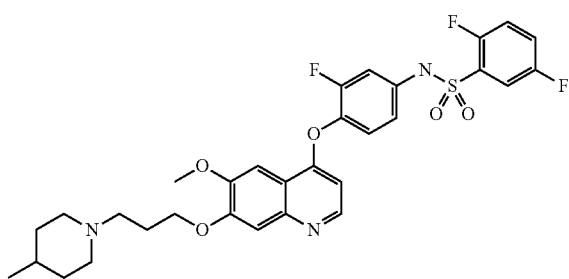 [SMILES: COc1cc2c(Oc3ccc(NS(=O)(=O)c4cc(F)ccc4F)cc3F)ccnc2cc1OCCCN1CCC(C)CC1]

$C_{31}H_{32}F_3N_3O_5S$ Mw. 615.68
LC/MS purity: 100%, m/z 614 [M–H]⁻, m/z 616 [M–H]⁺ Rt. 2.61 min.
¹H NMR (300 MHz, DMSO-d6): 10.2 (bs, 1H), 7.59 (m, 1H), 7.49 (s, 1H), 7.42 (s, 2H), 7.38 (s, 1H), 7.18 (t, 1H), 7.02 (dd, 1H), 6.86 (d, 1H), 6.36 (d, 1H), 4.20 (t, 1H), 3.93 (s, 3H), 3.08 (m, 2H), 2.73 (m, 2H), 2.63 (m, 1H), 2.27 (m, 2H), 2.04 (m, 2H), 1.66 (m, 2H), 1.44 (m, 1H), 1.21 (m, 2H), 0.90 (d, 3H)
Melting point: 223-225° C. Yield: 42%

Example D35

N-(3-Fluoro-4-{6-methoxy-7-[3-(3-methyl-piperidin-1-yl)-propoxy]-quinolin-4-yloxy}phenyl)-2-trifluoromethyl-benzenesulfonamide

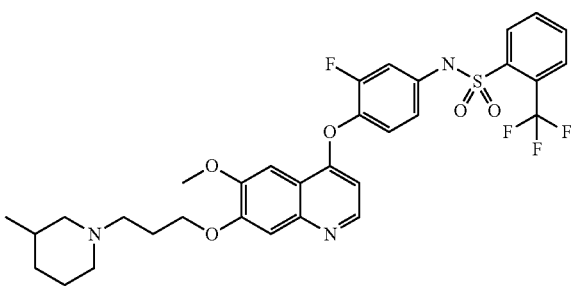 [SMILES: COc1cc2c(Oc3ccc(NS(=O)(=O)c4ccccc4C(F)(F)F)cc3F)ccnc2cc1OCCCN1CCCC(C)C1]

$C_{32}H_{33}F_4N_3O_5S$ Mw. 647.69
LC/MS purity: 94%, m/z 646 [M–H]⁻, m/z 648 [M–H]⁺ Rt. 2.86 min.
¹H NMR (300 MHz, DMSO-d6): 10.6 (bs, 1H), 8.44 (d, 1H), 8.15 (d, 1H), 7.97 (d, 1H), 7.84 (m, 2H), 7.48 (s, 1H), 7.39 (s, 1H), 7.28 (t, 1H), 7.07 (d, 1H), 6.94 (d, 1H), 6.36 (d, 1H), 4.21 (t, 2H), 3.92 (m, 3H), 2.89 (m, 2H), 2.76 (m, 2H), 2.26 (m, 1H), 1.99 (m, 3H), 1.68 (m, 4H), 1.02 (m, 1H), 0.86 (d, 3H)
Melting point: 118-121° C. Yield: 38%

Example D36

2,5-Difluoro-N-(3-fluoro-4-{6-methoxy-7-[3-(3-methyl-piperidin-1-yl)-propoxy]-quinolin-4-yloxy}-phenyl)-benzenesulfonamide $C_{31}H_{32}F_3N_3O_5S$ Mw. 615.68
LC/MS purity: 95%, m/z 614 [M–H]⁻, m/z 616 [M–H]⁺ Rt. 2.83 min.
¹H NMR (300 MHz, DMSO-d6): 10.3 (bs, 1H), 8.44 (d, 1H), 7.61 (bs, 1H), 7.44 (m, 4H), 7.22 (t, 1H), 7.05 (d, 1H), 6.90 (d, 1H), 6.36 (d, 1H), 4.21 (m, 2H), 3.93 (s, 3H), 3.07 (bs, 2H), 2.63 (bs, 2H), 2.39 (m, 1H), 2.25 (m, 3H), 1.69 (m, 5H), 0.87 (d, 3H)
Melting point: 103-107° C. Yield: 45%

Example D37

Biphenyl-3-sulfonic acid (3-fluoro-4-{6-methoxy-7-[3-(3-methyl-piperidin-1-yl)-propoxy]-quinolin-4-yloxy}-phenyl)-amide

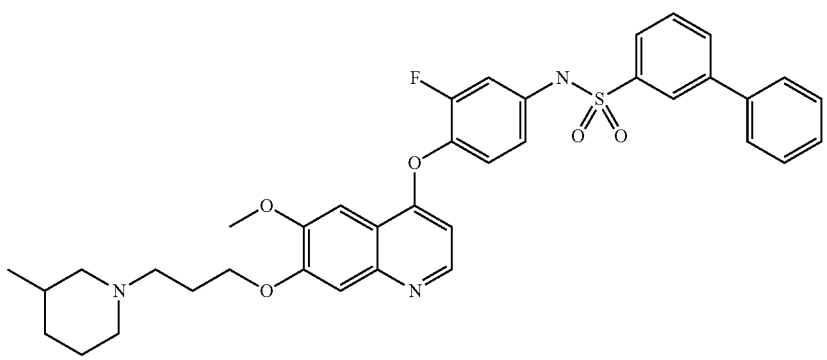 [SMILES: COc1cc2c(Oc3ccc(NS(=O)(=O)c4cccc(-c5ccccc5)c4)cc3F)ccnc2cc1OCCCN1CCCC(C)C1]

$C_{37}H_{38}FN_3O_5S$ Mw. 655.79
LC/MS purity: 97%, m/z 654 [M–H]⁻, m/z 656 [M–H]⁺ Rt. 3.06 min.
¹H NMR (300 MHz, DMSO-d6): 10.5 (bs, 1H), 8.36 (d, 1H), 8.02 (s, 1H), 7.94 (d, 1H), 7.79 (d, 1H), 7.67 (m, 3H), 7.49 (m, 4H), 7.36 (s, 1H), 7.29 (t, 1H), 7.14 (d, 1H), 6.99 (d, 1H), 6.28 (d, 1H), 4.16 (t, 2H), 3.90 (s, 3H), 2.81 (m, 2H), 2.46 (m, 3H), 1.95 (m, 3H), 1.60 (m, 5H), 0.83 (d, 3H)
Melting point: 190-192° C. Yield: 39%

Example D38

4-Fluoro-N-(3-fluoro-4-{6-methoxy-7-[3-(3-methyl-piperidin-1-yl)-propoxy]-quinolin-4-yloxy}-phenyl)-3-methoxy-benzenesulfonamide

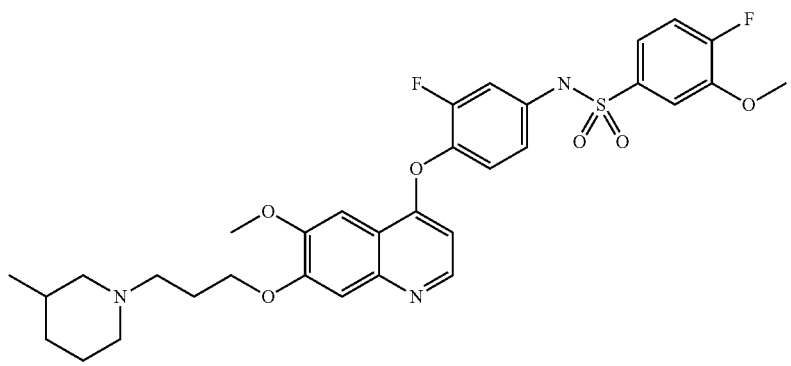

$C_{32}H_{35}F_2N_3O_6S$ Mw. 627.71
LC/MS purity: 97%, m/z 626 [M–H]⁻, m/z 628 [M–H]⁺ Rt. 2.88 min.
¹H NMR (300 MHz, DMSO-d6): 10.4 (bs, 1H), 8.45 (d, 1H), 7.55-7.31 (m, 6H), 7.17 (dd, 1H), 7.01 (d, 1H), 6.35 (d, 1H), 4.19 (t, 2H), 3.92 (s, 3H), 3.89 (s, 3H), 2.90 (m, 2H), 2.60 (m, 3H), 2.02 (m, 3H), 1.65 (m, 5H), 0.85 (d, 3H)
Melting point: 98-101° C. Yield: 34%

Example D39

N-{3-Fluoro-4-[6-methoxy-7-(3-morpholin-4-yl-propoxy)-quinolin-4-yloxy]-phenyl}-2-trifluoromethyl-benzenesulfonamide

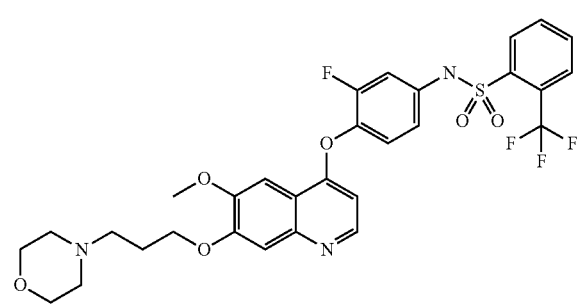 [SMILES: COc1cc2c(Oc3ccc(NS(=O)(=O)c4ccccc4C(F)(F)F)cc3F)ccnc2cc1OCCCN1CCOCC1]

$C_{30}H_{29}F_4N_3O_6S$ Mw. 635.64

LC/MS purity: 99%, m/z 634 [M–H]⁻, m/z 636 [M–H]⁺ Rt. 2.71 min.

¹H NMR (300 MHz, DMSO-d6): 11 (bs, 1H), 8.45 (d, 1H), 8.16 (d, 1H), 8.02 (d, 1H), 7.88 (m, 2H), 7.47 (s, 1H), 7.38 (s, 1H), 7.35 (t, 1H), 7.14 (d, 1H), 7.01 (d, 1H), 6.36 (d, 1H), 4.19 (t, 2H), 3.91 (s, 3H), 3.60 (t, 4H), 2.51 (m, 2H), 2.41 (m, 4H), 1.98 (t, 2H)

Melting point: 180-181° C. Yield: 29%

Example D40

N-{3-Fluoro-4-[6-methoxy-7-(3-morpholin-4-yl-propoxy)-quinolin-4-yloxy]-phenyl}-2-trifluoromethoxy-benzenesulfonamide

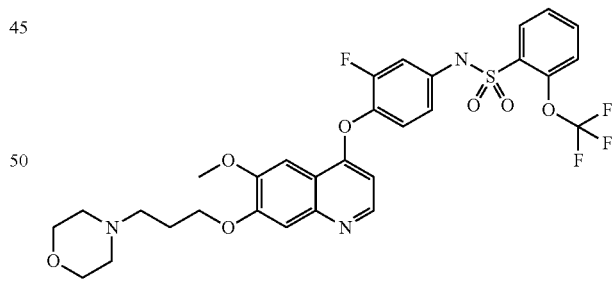

$C_{30}H_{29}F_4N_3O_7S$ Mw. 651.64
LC/MS purity: 98%, m/z 650 [M–H]⁻, m/z 652 [M–H]⁺ Rt. 2.79 min.
¹H NMR (300 MHz, DMSO-d6): 10.9 (bs, 1H), 8.44 (d, 1H), 8.03 (d, 1H), 7.77 (m, 1H), 7.57 (m, 2H), 7.47 (s, 1H), 7.38 (s, 1H), 7.33 (t, 1H), 7.14 (d, 1H), 6.98 (d, 1H), 4.19 (t, 2H), 3.92 (s, 3H), 3.58 (bs, 4H), 2.51 (m, 2H), 2.40 (m, 6H), 1.98 (t, 1H)
Melting point: 183-184° C. Yield: 40%

Example D41

2,5-Difluoro-N-{3-fluoro-4-[6-methoxy-7-(3-morpholin-4-yl-propoxy)-quinolin-4-yloxy]-phenyl}-benzenesulfonamide

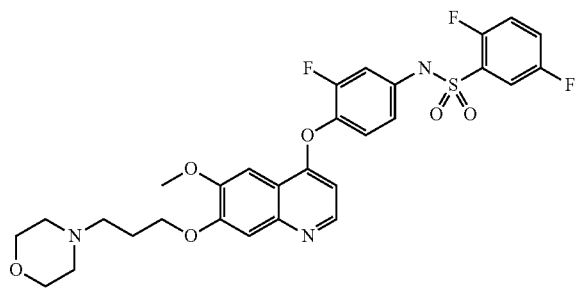 [SMILES: COc1cc2c(Oc3ccc(NS(=O)(=O)c4cc(F)ccc4F)cc3F)ccnc2cc1OCCCN1CCOCC1]

$C_{29}H_{28}F_3N_3O_6S$ Mw. 603.62
LC/MS purity: 97%, m/z 602 [M−H]⁻, m/z 604 [M−H]⁺
Rt. 2.59 min.
¹H NMR (300 MHz, DMSO-d6): 11 (bs, 1H), 8.44 (d, 1H), 7.70 (bs, 1H), 7.56 (m, 2H), 7.48 (s, 1H), 7.39 (s, 1H), 7.33 (d, 1H), 7.16 (dd, 1H), 7.04 (d, 1H), 6.35 (d, 1H), 4.19 (t, 2H), 3.92 (s, 3H), 3.60 (bs, 4H), 2.43 (m, 6H), 1.98 (t, 2H)
Melting point: 192-195° C. Yield: 43%

Example D42 Biphenyl-3-sulfonic acid {3-fluoro-4-[6-methoxy-7-(3-morpholin-4-yl-propoxy)-quinolin-4-yloxy]-phenyl}-amide

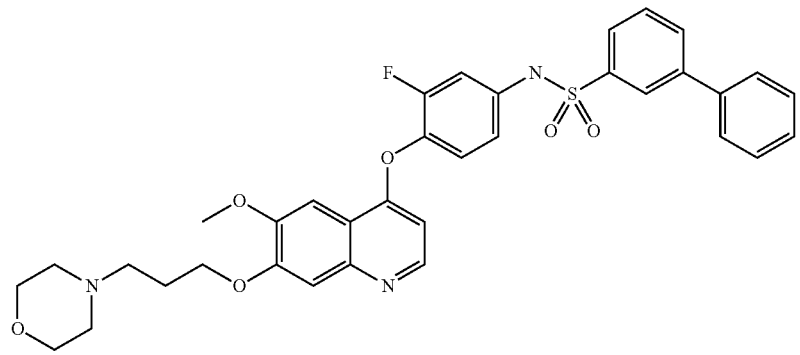 [SMILES: COc1cc2c(Oc3ccc(NS(=O)(=O)c4cccc(-c5ccccc5)c4)cc3F)ccnc2cc1OCCCN1CCOCC1]

$C_{35}H_{34}FN_3O_6S$ Mw. 643.74

LC/MS purity: 97%, m/z 642 [M−H]⁻, m/z 644 [M−H]⁺
Rt. 2.97 min.

¹H NMR (300 MHz, DMSO-d6): 10.7 (bs, 1H), 8.37 (d, 1H), 8.03 (s, 1H), 7.97 (d, 1H), 7.80 (d, 1H), 7.69 (m, 3H), 7.52 (m, 4H), 7.45 (s, 1H), 7.32 (s, 1H), 7.18 (d, 1H), 7.05 (d, 1H), 6.28 (d, 1H), 4.18 (t, 2H), 3.90 (s, 3H), 3.58 (m, 4H), 2.46 (t, 2H), 2.38 (m, 4H), 1.96 (t, 2H)

Melting point: 210-212° C. Yield: 39%

Example D43

4-Chloro-2-fluoro-N-{3-fluoro-4-[6-methoxy-7-(3-morpholin-4-yl-propoxy)-quinolin-4-yloxy]-phenyl}-benzenesulfonamide

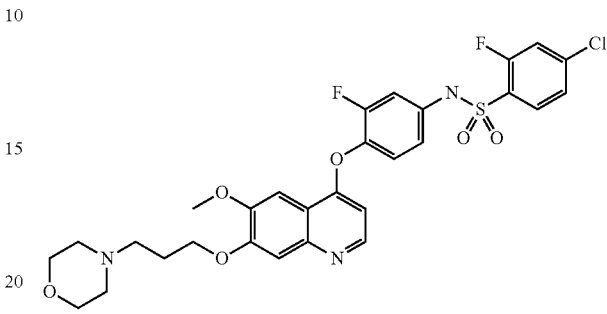

$C_{29}H_{28}ClF_2N_3O_6S$ Mw. 620.08
LC/MS purity: 95%, m/z 618 [M−H]⁻, m/z 620 [M−H]⁺
Rt. 2.73 min.
¹H NMR (300 MHz, DMSO-d6): 11 (bs, 1H), 8.45 (d, 1H), 7.89 (t, 1H), 7.74 (d, 1H), 7.49 (d, 1H), 7.47 (s, 1H), 7.38 (s, 1H), 7.33 (d, 1H), 7.14 (d, 1H), 7.00 (d, 1H), 6.35 (d, 1H), 4.19 (t, 2H), 3.92 (s, 3H), 3.59 (bs, 4H), 2.48 (bs, 2H), 2.42 (bs, 4H), 1.98 (t, 2H)
Melting point: 200-203° C. Yield: 35%

Example D44

4-Fluoro-N-{3-fluoro-4-[6-methoxy-7-(3-morpholin-4-yl-propoxy)-quinolin-4-yloxy]-phenyl}-3-methoxy-benzenesulfonamide

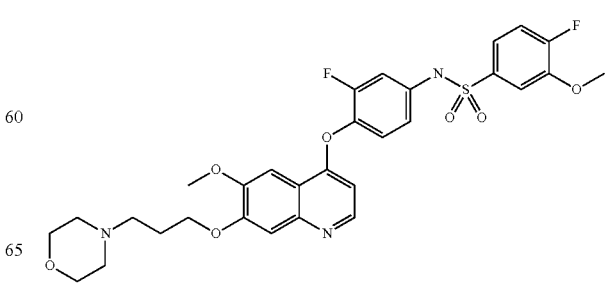

$C_{30}H_{31}F_2N_3O_7S$ Mw. 615.66

LC/MS purity: 96%, m/z 614 [M−H]⁻, m/z 616 [M−H]⁺ Rt. 2.63 min.

¹H NMR (300 MHz, DMSO-d6): 10.8 (bs, 1H), 8.44 (d, 1H), 7.54-7.32 (m, 6H), 7.17 (dd, 1H), 7.02 (d, 1H), 6.34 (d, 1H), 4.19 (t, 2H), 3.92 (s, 3H), 3.89 (s, 3H), 3.31 (m, 4H), 2.44 (t, 2H), 2.39 (m, 4H), 1.98 (t, 2H)

Melting point: 90-93° C. Yield: 58%

Example D45

2-Fluoro-N-{3-fluoro-4-[6-methoxy-7-(3-morpholin-4-yl-propoxy)-quinolin-4-yloxy]-phenyl}-benzenesulfonamide

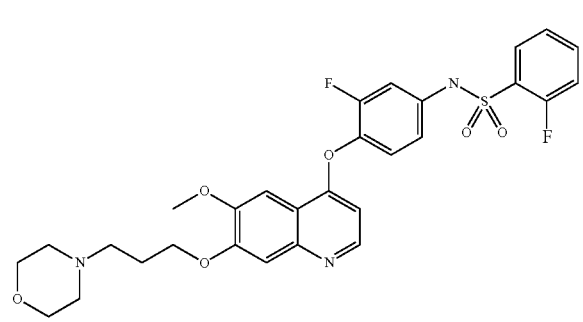

$C_{29}H_{29}F_2N_3O_6S$ Mw. 585.63

LC/MS purity: 99%, m/z 584 [M−H]⁻, m/z 586 [M−H]⁺ Rt. 2.49 min.

¹H NMR (300 MHz, DMSO-d6): 11 (bs, 1H), 8.44 (d, 1H), 7.90 (t, 1H), 7.73 (m, 1H), 7.46 (s, 1H), 7.40 (m, 3H), 7.38 (s, 1H), 7.15 (dd, 1H), 7.02 (d, 1H), 6.33 (d, 1H), 4.19 (t, 2H), 3.91 (s, 3H), 3.59 (m, 4H), 2.47 (t, 2H), 2.40 (m, 4H), 1.98 (t, 2H)

Melting point: 179-181° C. Yield: 59%

Example D46

N-{3-Fluoro-4-[6-methoxy-7-(3-morpholin-4-yl-propoxy)-quinolin-4-yloxy]-phenyl}-2-nitro-benzenesulfonamide

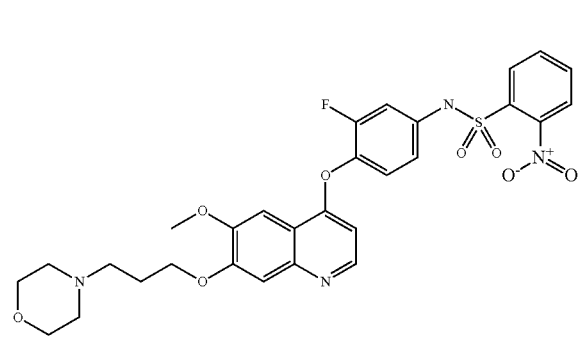 [SMILES: COc1cc2c(Oc3ccc(NS(=O)(=O)c4ccccc4[N+](=O)[O-])cc3F)ccnc2cc1OCCCN1CCOCC1]

$C_{29}H_{29}FN_4O_8S$ Mw. 612.64

LC/MS purity: 99%, m/z 611 [M−H]⁻, m/z 613 [M−H]⁺ Rt. 2.58 min.

¹H NMR (300 MHz, DMSO-d6): 11 (bs, 1H), 8.45 (d, 1H), 8.03 (m, 1H), 7.94 (m, 1H), 7.84 (m, 2H), 7.48 (s, 1H), 7.39 (s, 1H), 7.34 (t, 1H), 7.13 (d, 1H), 6.98 (d, 1H), 6.37 (d, 1H), 4.20 (t, 2H), 3.92 (s, 3H), 3.61 (bs, 4H), 2.56 (bs, 6H), 2.00 (m, 2H)

Melting point: 166-168° C. Yield: 29%

Example D47

2,6-Dichloro-N-{3-fluoro-4-[6-methoxy-7-(3-morpholin-4-yl-propoxy)-quinolin-4-yloxy]-phenyl}-benzenesulfonamide

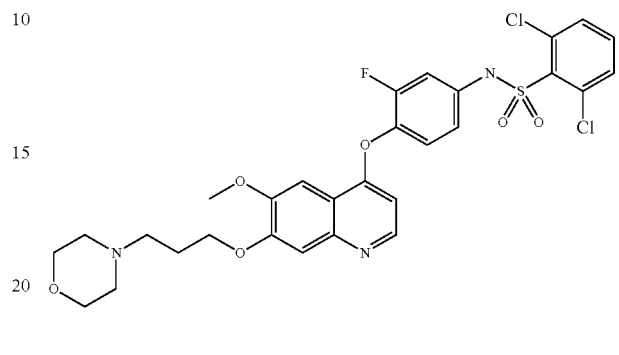

$C_{29}H_{28}Cl_2FN_3O_6S$ Mw. 636.53

LC/MS purity: 99%, m/z 634 [M−H]⁻, m/z 636 [M−H]⁺ Rt. 2.71 min.

¹H NMR (300 MHz, DMSO-d6): 11.1 (bs, 1H), 8.44 (d, 1H), 7.60 (m, 2H), 7.47 (s, 1H), 7.38 (s, 1H), 7.34 (m, 2H), 7.13 (d, 1H), 6.99 (d, 1H), 6.33 (d, 1H), 4.19 (bs, 2H), 3.91 (s, 3H), 3.59 (bs, 4H), 3.17 (bs, 2H), 2.43 (m, 4H), 1.99 (bs, 2H)

Melting point: 194-196° C.; Yield: 16%

Example D48

Naphthalene-1-sulfonic acid {3-fluoro-4-[6-methoxy-7-(3-morpholin-4-yl-propoxy)-quinolin-4-yloxy]-phenyl}-amide

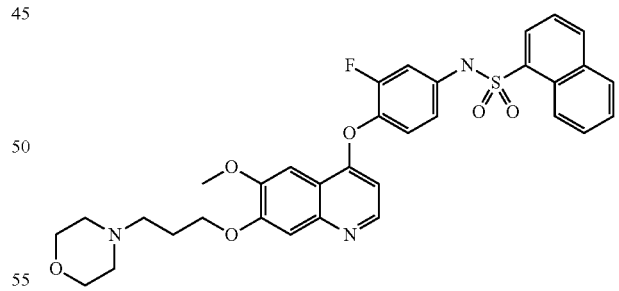

$C_{33}H_{32}FN_3O_6S$ Mw. 617.70

LC/MS purity: 96%, m/z 616 [M−H]⁻, m/z 618 [M−H]⁺ Rt. 2.62 min.

¹H NMR (300 MHz, DMSO-d6): 11.1 (bs, 1H), 8.75 (d, 1H), 8.40 (d, 1H), 8.28 (m, 2H), 8.11 (d, 1H), 7.71 (m, 3H), 7.42 (s, 1H), 7.36 (s, 1H), 7.24 (t, 1H), 7.05 (d, 1H), 6.91 (d, 1H), 6.31 (dd, 1H), 4.18 (t, 2H), 3.89 (s, 3H), 3.57 (bs, 4H), 2.46 (m, 2H), 2.38 (bs, 4H), 1.96 (m, 2H)

Melting point: 108-111° C. Yield: 26%

Example D49

2-Bromo-N-{3-fluoro-4-[6-methoxy-7-(3-morpholin-4-yl-propoxy)-quinolin-4-yloxy]-phenyl}-benzenesulfonamide

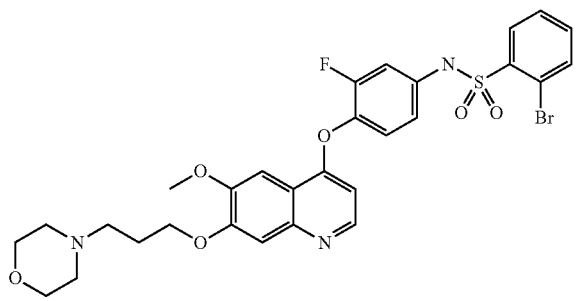 [SMILES: COc1cc2c(Oc3ccc(NS(=O)(=O)c4ccccc4Br)cc3F)ccnc2cc1OCCCN1CCOCC1]

$C_{29}H_{29}BrFN_3O_6S$ Mw. 646.54
LC/MS purity: 98%, m/z 644 [M−H]⁻, m/z 646 [M−H]⁺
Rt. 2.63 min.
¹H NMR (300 MHz, DMSO-d6): 11 (bs, 1H), 8.43 (d, 1H), 8.13 (d, 1H), 7.86 (d, 1H), 7.58 (m, 2H), 7.46 (s, 1H), 7.38 (s, 1H), 7.33 (t, 1H), 7.12 (dd, 1H), 7.00 (dd, 1H), 6.33 (d, 1H), 4.19 (t, 2H), 3.91 (s, 3H), 3.58 (bs, 4H), 2.45 (t, 2H), 2.39 (m, 4H), 1.97 (t, 2H)
Melting point: 185-188° C.; Yield: 35%

3) Inhibitory Activity of Compounds on Axl Phosphorylation in NIH-3T3-AXL Cellular Tyrosine Kinase Assay Establishment of Wild Type AXL (wtAXL) Receptor Tyrosine Kinase-Overexpressing Stable Cell Line NIH-3T3-AXL (Clone 22) WtAXL cDNA was cloned into vector pLX-SN(ESK) and transfected into Phoenix E packaging cells. The viral supernatant was collected and used to infect target cells NIH3T3 N7. Monoclonal NIH3T3-AXL cell lines stably expressing wtAXL were generated by selecting retrovirally infected cells in medium containing puromycin (2 μg/ml) and subsequent clonal separation. NIH-3T3-AXL (clone 22) cells were used for further experiment because AXL was highly expressed and constitutively phosphorylated in these cells. In addition, these cells demonstrated aggressive behaviors on matrigel matrix (Matrigel™ Matrix, BD Biosciences, Bedford, Mass., USA). Moreover, the inhibitory effects of compounds on AXL phosphorylation discovered by using NIH-3T3 AXL (clone 22) system have been confirmed in human breast cancer cells endogenously expressing AXL in our previous study (Zhang Y X, et al. AXL is a potential target for therapeutic intervention in breast cancer progression. Cancer Res. 2008; 68:1905-15).

Determination of the morphology of cells grown on matrigel was carried out as described previously, with some modifications (Thompson E W, et al. Association of increased basement membrane invasiveness with absence of estrogen receptor and expression of vimentin in human breast cancer cell lines. J Cell Physiol 1992; 150:534-44). Briefly, in a 96-well flat-bottomed plate, 10000 cells/100 μl cell suspension was plated on the surface of precoated matrigel (3 mg/ml). Colony outgrowth was visualized with a Zeiss Axiovert S100 microscope (Carl Zeiss UK, Welwyn Garden City, UK).

NIH-3T3-AXL Cellular Kinase Assay

NIH-3T3-AXL (Clone 22) cells were seeded onto 6-well plates (1.5×10⁵ cells/well) in 1.5 ml culture medium and cultured overnight, followed by serum depletion in 0.1% heat inactivated FCS/DMEM for 24 h. Serial dilutions of compounds were added, and the cells were further incubated or 2 h. Cells were washed wall PBS, and lysed on ice in 500 μl lysis buffer (50 mM HEPES (pH 7.5), 150 mM NaCl, 1 mM EGTA, 10% Glycerol, 1% Triton X-100, 100 mM NaF, 10 mM $Na_4P_2O_7 \cdot 10H_2O$, 1 mM $Na_3VO_4$, 1 mM phenylmethylsulfonyl fluoride, and 10 mg/ml aprotinin) for 15 min. The clarified cell lysate (10 min at 13000 rpm at 4° C.) were used for immunoprecipitation. Equal amounts of protein were mixed with 2 μg anti-AXL polyclonal antibody (homemade) and 20 μl Protein A sepharose beads, and rotated for 6 hr at 4° C. After immunoprecipitation, the beads were washed three times with 1×HNTG (50 mM HEPES (pH 7.5), 150 mM NaCl, 10% Glycerol, 0.2% Triton X-100). The final pellet was suspended in 20 μl 2× Laemmli buffer, and boiled for 5 min at 100° C. The immunoprecipitates were separated by 7.5% SDS-PAGE gel electrophoresis, and the proteins were transferred to nitrocellulose membrane. Unspecific binding was blocked by incubating the membrane for 1 hr in 0.25% gelatin in 1×NET buffer (50 mM Tris.HCl (ph7.5), 150 nM NaCl, 5 mM EDTA, 0.1% Triton X-100). The membrane was then incubated with anti-phosphotyrosine antibody (4G10) overnight at 4° C. followed by washing with 1×TBST buffer three times. After incubating membrane with HRP-conjugated anti-mouse secondary antibody for 1 hour at room temperature followed by washing with 1×TBST buffer three times, the proteins were visualized by ECL. Afterwards, the membrane was stripped and reprobed with anti-AXL, antibody (SC-1096, Santa Cruz Biotechnology, Santa Cruz, Calif.), The results of the assay are described in Table 2.

| | Cellular IC50 [μM] |
|---|---|
| A1-50 | |
| A1 | 4.5 |
| A2 | 3.01 |
| A3 | 3.4 |
| A4 | 6 |
| A5 | 0.5 |
| A6 | 4.3 |
| A7 | >10 |
| A8 | 10 |
| A9 | 3.7 |
| A10 | 2.6 |
| A11 | 2.26 |
| A12 | 1.26 |
| A13 | 2.9 |
| A14 | 1.4 |
| A15 | 2.265 |
| A16 | 1.805 |
| A17 | 0.89 |
| A18 | 2.1 |
| A19 | 4.5 |
| A20 | 5.05 |
| A21 | 4.7 |
| A22 | 9.6 |
| A23 | 6 |
| A24 | 2.4 |
| A25 | 2.38 |
| A26 | 4.73 |
| A27 | 2.54 |
| A28 | 3.9 |
| A29 | 2.3 |
| A30 | 0.63 |
| A31 | >10 |
| A32 | >10 |

| | Cellular IC50 [μM] |
|---|---|
| A33 | >10 |
| A34 | 0.43 |
| A35 | 3 |
| A36 | 2.8 |
| A37 | >10 |
| A38 | >10 |
| A39 | 6.4 |
| A40 | <1 |
| A41 | <1 |
| A42 | <1 |
| A43 | <1 |
| A44 | <1 |
| A45 | >10 |
| A46 | >10 |
| A47 | 10 |
| A48 | 1.5 |
| A49 | 3,00 |
| A50 | <1 |
| A51 | <3 |
| A52 | >3 |
| A53 | 3 |
| A54 | >1 |
| A55 | >1 |
| A56 | >1 |
| A57 | >3 |
| A58 | >1 |
| A59 | >1 |
| A60 | 0.8 |
| A61 | 0.7 |
| A62 | 0.47 |
| A63 | >1 |
| A64 | >1 |
| A65 | >10 |
| A66 | >10 |
| A67 | >10 |
| A68 | >10 |
| A69 | >10 |
| A70 | >10 |
| A71 | >3 |
| A72 | 0.58 |
| A73 | >3 |
| A74 | >1 |
| A75 | >3 |
| A76 | >10 |
| A77 | >10 |
| A78 | >3 |
| A79 | 0.48 |
| A80 | >10 |
| A81 | >10 |
| A82 | >1 |
| A83 | >3 |
| A84 | >3 |
| A85 | >3 |
| A86 | >1 |
| A87 | 3 |
| A88 | >1 |
| A89 | 0.45 |
| A90 | >10 |
| A91 | >10 |
| A92 | >10 |
| A93 | >3 |
| A94 | >10 |
| A95 | >10 |
| A96 | 0.077 |
| A97 | 0.54 |
| A98 | 0.74 |
| A99 | 0.18 |
| A100 | 0.74 |
| A101 | >1 |
| A102 | >1 |
| A103 | 0.35 |
| A104 | 3 |
| A105 | 10 |
| A106 | 0.75 |
| A107 | >10 |
| A108 | >1 |
| A109 | >1 |
| A110 | 1.18 |
| A111 | >3 |
| A112 | >3 |
| A113 | >3 |
| A114 | 0.47 |
| A115 | 1.26 |
| A116 | >3 |
| A117 | >10 |
| A118 | 0.54 |
| A119 | >3 |
| A120 | >10 |
| A121 | >10 |
| A122 | >10 |
| A123 | 1.96 |
| A124 | >3 |
| A125 | 10 |
| A126 | 0.13 |
| A127 | >3 |
| A128 | 2.25 |
| A129 | >3 |
| A130 | >10 |
| A131 | 1.68 |
| A132 | >10 |
| A133 | >10 |
| A134 | >1 |
| A135 | 0.82 |
| A136 | >10 |
| A137 | >10 |
| A138 | >10 |
| A139 | 2.2 |
| A140 | >10 |
| A141 | >10 |
| A142 | >10 |
| A143 | >10 |
| A144 | >10 |
| A145 | >10 |
| A146 | 0.89 |
| A147 | >3 |
| A148 | >10 |
| A149 | >3 |
| A150 | >10 |
| A151 | >10 |
| A152 | >10 |
| A153 | >10 |
| A154 | >10 |
| A155 | >3 |
| A156 | >1 |

B1-22

| | |
|---|---|
| B1 | >10 |
| B2 | >10 |
| B3 | 8,00 |
| B4 | >10 |
| B5 | >10 |
| B6 | >10 |
| B7 | >10 |
| B8 | >10 |
| B9 | >10 |
| B10 | >10 |
| B11 | <1 |
| B12 | >10 |
| B13 | <1 |
| B14 | <1 |
| B15 | >10 |
| B16 | >10 |
| B17 | >10 |
| B18 | >10 |
| B19 | 8,00 |
| B20 | >10 |
| B21 | >10 |
| B22 | 7,00 |

-continued

| | Cellular IC50 [μM] |
|---|---|
| C01 | >10 |
| C02 | >10 |
| C03 | >10 |
| C04 | >10 |
| C05 | >10 |
| C06 | >10 |
| C07 | >10 |
| C08 | >10 |
| C09 | >10 |
| C10 | >10 |
| C11 | >10 |
| C12 | >10 |
| C13 | >1 |
| C14 | >10 |
| C15 | >10 |
| C16 | >10 |
| C17 | >10 |
| C18 | >10 |
| C19 | >10 |
| D01 | >10 |
| D02 | 0.695 |
| D03 | 0.837 |
| D04 | 0.32 |
| D05 | 0.049 |
| D06 | 0.069 |
| D07 | 0.35 |
| D08 | 2.5 |
| D09 | 2.46 |
| D10 | 0.052 |
| D11 | >3 |
| D12 | 0.3 |
| D13 | 0.057 |
| D14 | 0.238 |
| D15 | 0.364 |
| D16 | 0.271 |
| D17 | 0.046 |
| D18 | 0.151 |
| D19 | 0.128 |
| D20 | 0.029 |
| D21 | 0.347 |
| D22 | 0.477 |
| D23 | 0.211 |
| D24 | 0.181 |
| D25 | 0.378 |
| D26 | 0.15 |
| D27 | 0.783 |
| D28 | >1 |
| D29 | 0.178 |
| D30 | 0.082 |
| D31 | 0.323 |
| D32 | 0.042 |
| D33 | 0.068 |
| D34 | 0.016 |

LIST OF REFERENCES

1. Weigelt B, Peterse J L, van 't Veer L J. Breast cancer metastasis: markers and models. Nat Rev Cancer 2005; 5:591-602.

2. Shawver L K, Slamon D, Ullrich A. Smart drugs: tyrosine kinase inhibitors in cancer therapy. Cancer Cell 2002; 1:117-123.

3. Sebolt-Leopold J S, English J M. Mechanisms of drug inhibition of signalling molecules. Nature 2006; 441:457-462.

4. Hanahan D, Weinberg R A. The hallmarks of cancer. Cell 2000; 100:57-70.

5. Blume-Jensen P, Hunter T. Oncogenic kinase signalling. Nature 2001; 411:355-365.

6. Slamon D J, Clark G M, Wong S G, et al. Human breast cancer: correlation of relapse and survival with amplification of the HER-2/neu oncogene. Science 1987; 235:177-182.

7. Slamon D J, Leyland-Jones B, Shak S, et al. Use of chemotherapy plus a monoclonal antibody against HER2 for metastatic breast cancer that overexpresses HER2. N Engl J Med 2001; 344:783-792.

8. Cobleigh M A, Vogel C L, Tripathy D, et al. Multinational study of the efficacy and safety of humanized anti-HER2 monoclonal antibody in women who have HER2-overexpressing metastatic breast cancer that has progressed after chemotherapy for metastatic disease. J Clin Oncol 1999; 17:2639-2648.

9. Varnum B C, Young C, Elliott G, et al. Axl receptor tyrosine kinase stimulated by the vitamin K-dependent protein encoded by growth-arrest-specific gene 6. Nature 1995; 373:623-626.

10. Stitt T N, Conn G, Gore M, et al. The anticoagulation factor protein S and its relative, Gas6, are ligands for the Tyro 3/Axl family of receptor tyrosine kinases. Cell 1995; 80:661-670.

11. Nagata K, Ohashi K, Nakano T, et al. Identification of the product of growth arrest-specific gene 6 as a common ligand for Axl, Sky, and Mer receptor tyrosine kinases. J Biol Chem 1996; 271:30022-30027.

12. Hafizi S, Dahlback B. Signalling and functional diversity within the Axl subfamily of receptor tyrosine kinases. Cytokine Growth Factor Rev 2006; 17:295-304.

13. Janssen J W, Schulz A S, Steenvoorden A C, et al. A novel putative tyrosine kinase receptor with oncogenic potential. Oncogene 1991; 6:2113-2120.

14. O'Bryan J P, Frye R A, Cogswell P C, et al. axl, a transforming gene isolated from primary human myeloid leukemia cells, encodes a novel receptor tyrosine kinase. Mol Cell Biol 1991; 11:5016-5031.

15. Berclaz G, Altermatt H J, Rohrbach V, et al. Estrogen dependent expression of the receptor tyrosine kinase axl in normal and malignant human breast. Ann Oncol 2001; 12:819-824.

16. Craven R J, Xu L H, Weiner™, et al. Receptor tyrosine kinases expressed in metastatic colon cancer. Int J Cancer 1995; 60:791-797.

17. Shieh Y S, Lai C Y, Kao Y R, et al. Expression of axl in lung adenocarcinoma and correlation with tumor progression. Neoplasia 2005; 7:1058-1064.

18. Sun W, Fujimoto J, Tamaya T. Coexpression of Gas6/Axl in human ovarian cancers. Oncology 2004; 66:450-457.

19. Green J, Ikram M, Vyas J, et al. Overexpression of the Axl tyrosine kinase receptor in cutaneous SCC-derived cell lines and tumours. Br J Cancer 2006; 94:1446-1451.

20. Ito T, Ito M, Naito S, et al. Expression of the Axl receptor tyrosine kinase in human thyroid carcinoma. Thyroid 1999; 9:563-567.

21. Holland S J, Powell M J, Franci C, et al. Multiple roles for the receptor tyrosine kinase axl in tumor formation. Cancer Res 2005; 65:9294-9303.

22. Vajkoczy P, Knyazev P, Kunkel A, et al. Dominant-negative inhibition of the Axl receptor tyrosine kinase suppresses brain tumor cell growth and invasion and prolongs survival. Proc Natl Acad Sci USA 2006; 103:5799-5804.

The invention claimed is:

1. Compounds of the formula (I):

(I)

[Structure diagram of quinoline compound with substituents R1-R11, R15]

wherein
R¹ is hydrogen;
R² is fluorine, or methoxy;
R³ is hydrogen, benzyloxy, methoxy, 3-amino-propoxy, 2-morpholin-4-yl-ethoxy, 3-(4-methyl-piperidin-1-yl)-propoxy, 3-(3-methyl-piperidin-1-yl)-propoxy, or 3-morpholin-4-yl-propoxy;
R⁴ is hydrogen, or —CF3;
R⁵ is hydrogen, or —CH3;
R⁶ is hydrogen;
R⁷, R⁸, R⁹ and R¹⁰, which may be the same or different, represent a hydrogen atom, halogen, $C_{1-6}$ alkyl, and/or $C_{1-6}$ alkoxy,
R¹¹ represents
a saturated or unsaturated three- to twelve-membered carbocyclic or heterocyclic ring system which is optionally substituted,
R¹⁵ represents hydrogen; or
pharmaceutically acceptable salts thereof.

2. The compounds of claim 1, wherein R⁷ and R¹⁰ are hydrogen.

3. The compounds of claim 1, wherein at least one of R⁸ and R⁹ is different from hydrogen and halogen.

4. The compounds of claim 1 wherein the substituents of the carbocyclic or heterocyclic ring system in R¹¹ are selected from halogen, $C_{1-4}$ alkyl optionally halogenated, $C_{1-4}$ alkoxy optionally halogenated, hydroxyl, cyano, and optionally substituted amino.

5. The compounds of claim 4, wherein the carbocyclic or heterocyclic group in R¹¹ is optionally mono- or polysubstituted by at least one halogen, trifluoromethyl or a trifluoromethoxy substituent.

6. The compounds of claim 1 selected from
3-Cyano-N-[4-(6,7-dimethoxy-quinolin-4-yloxy)-2-fluoro-phenyl]-benzenesulfonamide,
N-[4-(6,7-Dimethoxy-quinolin-4-yloxy)-2-fluoro-phenyl]-3-fluoro-benzenesulfonamide,
N-[4-(6,7-Dimethoxy-quinolin-4-yloxy)-2-fluoro-phenyl]-3,4-difluoro-benzenesulfonamide,
Thiophene-2-sulfonic acid 4-(6,7-dimethoxy-quinolin-4-yloxy)-2-fluoro-phenyl]-amide,
3,5-Dichloro-N-[4-(6,7-Dimethoxy-quinolin-4-yloxy)-2-fluoro-phenyl]-2-hydroxy-benzenesulfonamide,
N-[4-(6,7-Dimethoxy-quinolin-4-yloxy)-2-fluoro-phenyl]-3-fluoro-4-methyl-benzenesulfonamide,
N-{5-[4-(6,7-Dimethoxy-quinolin-4-yloxy)-2-fluoro-phenylsulfamoyl]-4-methyl-thiophen-2-yl}-acetamide,
Quinoline-8-sulfonic acid [4-(6,7-dimethoxy-quinolin-4-yloxy)-2-fluoro-phenyl]amide,
3-[4-(6,7-Dimethoxy-quinolin-4-yloxy)-2-fluoro-phenyl-sulfamoyl]-thiophene-2-carboxylic acid methyl ester,
N-[4-(6,7-Dimethoxy-quinolin-4-yloxy)-2-fluoro-phenyl]-benzenesulfonamide,
4-Bromo-N-[4-(6,7-dimethoxy-quinolin-4-yloxy)-2-fluoro-phenyl]-3-fluoro-benzenesulfonamide,
3-Chloro-N-[4-(6,7-dimethoxy-quinolin-4-yloxy)-2-fluoro-phenyl]-4-fluoro-benzenesulfonamide,
4-Chloro-N-[4-(6,7-dimethoxy-quinolin-4-yloxy)-2-fluoro-phenyl]-2-fluoro-benzenesulfonamide,
N-[4-(6,7-Dimethoxy-quinolin-4-yloxy)-2-fluoro-phenyl]-2,6-difluoro-benzenesulfonamide,
3-Difluoromethoxy-N-[4-(6,7-dimethoxy-quinolin-4-yloxy)-2-fluoro-phenyl]-benzenesulfonamide,
Naphthalene-1-sulfonic acid [4-(6,7-dimethoxy-quinolin-4-yloxy)-2-fluoro-phenyl]-amide,
2,5-Dichloro-thiophene-3-sulfonic acid [4-(6,7-dimethoxy-quinolin-4-yloxy)-2-fluoro-phenyl]-amide,
4-Bromo-N-[4-(6,7-dimethoxy-quinolin-4-yloxy)-2-fluoro-phenyl]-3-methyl-benzenesulfonamide,
N-[4-(6,7-Dimethoxy-quinolin-4-yloxy)-2-fluoro-phenyl]-2,3,4-trifluoro-benzenesulfonamide,
5-Methyl-thiophene-2-sulfonic acid [4-(6,7-dimethoxy-quinolin-4-yloxy)-2-fluoro-phenyl]-amide,
Furan-2-sulfonic acid [4-(6,7-dimethoxy-quinolin-4-yloxy)-2-fluoro-phenyl]-amide,
N-[4-(6,7-Dimethoxy-quinolin-4-yloxy)-2-fluoro-phenyl]-3-trifluoromethyl-benzenesulfonamide,
3-Bromo-N-[4-(6,7-dimethoxy-quinolin-4-yloxy)-2-fluoro-phenyl]-benzenesulfonamide,
3-Chloro-N-[4-(6,7-dimethoxy-quinolin-4-yloxy)-2-fluoro-phenyl]-benzenesulfonamide,
N-[4-(6,7-Dimethoxy-quinolin-4-yloxy)-2-fluoro-phenyl]-3-methyl-benzenesulfonamide,
N-[4-(6,7-Dimethoxy-quinolin-4-yloxy)-2-fluoro-phenyl]-3-methoxy-benzenesulfonamide,
5-Chloro-thiophene-2-sulfonic acid [4-(6,7-dimethoxy-quinolin-4-yloxy)-2-fluoro-phenyl]-amide,
5-Bromo-thiophene-2-sulfonic acid [4-(6,7-dimethoxy-quinolin-4-yloxy)-2-fluoro-phenyl]-amide,
N-[4-(6,7-Dimethoxy-quinolin-4-yloxy)-2-fluoro-phenyl]-3-phenoxy-benzenesulfonamide,
1-Ethyl-1H-pyrazole-4-sulfonic acid [4-(6,7-dimethoxy-quinolin-4-yloxy)-2-fluoro-phenyl]-amide,
1-Methyl-1H-imidazole-4-sulfonic acid [4-(6,7-dimethoxy-quinolin-4-yloxy)-2-fluoro-phenyl]-amide,
Cyclopropanesulfonic acid [4-(6,7-dimethoxy-quinolin-4-yloxy)-2-fluoro-phenyl]-amide,
Biphenyl-3-sulfonic acid [4-(6,7-dimethoxy-quinolin-4-yloxy)-2-fluoro-phenyl]-amide,
N-[4-(6,7-Dimethoxy-quinolin-4-yloxy)-2-fluoro-phenyl]-3-trifluoromethoxy-benzenesulfonamide,
5-Phenyl-thiophene-2-sulfonic acid [4-(6,7-dimethoxy-quinolin-4-yloxy)-2-fluoro-phenyl]-amide,
5-Oxazol-5-yl-thiophene-2-sulfonic acid [4-(6,7-dimethoxy-quinolin-4-yloxy)-2-fluoro-phenyl]-amide,
N-[4-(6,7-Dimethoxy-quinolin-4-yloxy)-2-fluoro-phenyl]-3,5-difluoro-benzenesulfonamide,
N-[4-(6,7-Dimethoxy-quinolin-4-yloxy)-2-fluoro-phenyl]-2,4-difluoro-benzenesulfonamide,
N-[4-(6,7-Dimethoxy-quinolin-4-yloxy)-2-fluoro-phenyl]-2,5-difluoro-benzenesulfonamide,
2,6-Dichloro-N-[4-(6,7-dimethoxy-quinolin-4-yloxy)-2-fluoro-phenyl]-benzenesulfonamide, 2,5-Dichloro-N-[4-(6,7-dimethoxy-quinolin-4-yloxy)-2-fluoro-phenyl]-benzenesulfonamide,
3,5-Dichloro-N-[4-(6,7-dimethoxy-quinolin-4-yloxy)-2-fluoro-phenyl]-benzenesulfonamide,
N-[4-(6,7-Dimethoxy-quinolin-4-yloxy)-2-fluoro-phenyl]-2-trifluoromethyl-benzenesulfonamide,
2-Bromo-N-[4-(6,7-dimethoxy-quinolin-4-yloxy)-2-fluoro-phenyl]-4-trifluoromethyl-benzenesulfonamide,
2-Bromo-N-[4-(6,7-dimethoxy-quinolin-4-yloxy)-2-fluoro-phenyl]-5-trifluoromethyl-benzenesulfonamide,
3-Bromo-N-[4-(6,7-dimethoxy-quinolin-4-yloxy)-2-fluoro-phenyl]-5-trifluoromethyl-benzenesulfonamide,
4-Bromo-N-[4-(6,7-dimethoxy-quinolin-4-yloxy)-2-fluoro-phenyl]-2-trifluoromethyl-benzenesulfonamide,
3,4-Dichloro-N-[4-(6,7-dimethoxy-quinolin-4-yloxy)-2-fluoro-phenyl]-benzenesulfonamide,
3,5-Dichloro-N-[4-(6,7-dimethoxy-quinolin-4-yloxy)-2-fluoro-phenyl]-2-methoxy-benzenesulfonamide,
N-[4-(6,7-Dimethoxy-quinolin-4-yloxy)-2-fluoro-phenyl]-2-methyl-benzenesulfonamide,
N-[4-(6,7-Dimethoxy-quinolin-4-yloxy)-2-fluoro-phenyl]-2-methoxy-benzenesulfonamide,
N-[4-(6,7-Dimethoxy-quinolin-4-yloxy)-2-fluoro-phenyl]-2-trifluoromethoxy-benzenesulfonamide,
2-Chloro-N-[4-(6,7-dimethoxy-quinolin-4-yloxy)-2-fluoro-phenyl]-benzenesulfonamide,
2-Bromo-N-[4-(6,7-dimethoxy-quinolin-4-yloxy)-2-fluoro-phenyl]-benzenesulfonamide,
N-[4-(6,7-Dimethoxy-quinolin-4-yloxy)-2-fluoro-phenyl]-4-ethyl-benzenesulfonamide,
N-[4-(6,7-Dimethoxy-quinolin-4-yloxy)-2-fluoro-phenyl]-4-phenoxy-benzenesulfonamide,
N-[4-(6,7-Dimethoxy-quinolin-4-yloxy)-2-fluoro-phenyl]-3-fluoro-2-methyl-benzenesulfonamide,
N-[4-(6,7-Dimethoxy-quinolin-4-yloxy)-2-fluoro-phenyl]-2-fluoro-benzenesulfonamide,
4-Bromo-3-chloro-N-[4-(6,7-dimethoxy-quinolin-4-yloxy)-2-fluoro-phenyl]-benzenesulfonamide,
N-[4-(6,7-Dimethoxy-quinolin-4-yloxy)-2-fluoro-phenyl]-4-fluoro-3-methoxy-benzenesulfonamide,
N-{2-[4-(6,7-Dimethoxy-quinolin-4-yloxy)-phenylsulfamoyl]-4-methyl-phenyl}-acetamide,
N-{4-[4-(6,7-Dimethoxy-quinolin-4-yloxy)-phenylsulfamoyl]-2,6-dimethyl-phenyl}-acetamide,
3-Chloro-N-[4-(6,7-dimethoxy-quinolin-4-yloxy)-phenyl]-4-methoxy-benzenesulfonamide,
5-Chloro-N-[4-(6,7-dimethoxy-quinolin-4-yloxy)-phenyl]-2-methoxy-benzenesulfonamide,
5-Chloro-N-[4-(6,7-dimethoxy-quinolin-4-yloxy)-phenyl]-2-methoxy-4-methyl-benzenesulfonamide,
3-tert-Butyl-N-[4-(6,7-dimethoxy-quinolin-4-yloxy)-phenyl]-4-methoxy-benzenesulfonamide,
N-[4-(6,7-Dimethoxy-quinolin-4-yloxy)-2-fluoro-phenyl]-4-ethoxy-3-methyl-benzenesulfonamide,
4-Methoxy-naphthalene-1-sulfonic acid [4-(6,7-dimethoxy-quinolin-4-yloxy)-2-fluoro-phenyl]-amide,
N-[4-(6,7-Dimethoxy-quinolin-4-yloxy)-2-fluoro-phenyl]-2-methoxy-4,5-dimethyl-benzenesulfonamide,
3-Bromo-N-[4-(6,7-dimethoxy-quinolin-4-yloxy)-phenyl]-4-methoxy-benzenesulfonamide,
Biphenyl-3-sulfonic acid [4-(6,7-dimethoxy-quinolin-4-yloxy)-3-methyl-phenyl]-amide,
N-[4-(6,7-Dimethoxy-quinolin-4-yloxy)-3-methyl-phenyl]-3-phenoxy-benzenesulfonamide,
Naphthalene-1-sulfonic acid [4-(6,7-dimethoxy-quinolin-4-yloxy)-3-methyl-phenyl]-amide,
Isoquinoline-5-sulfonic acid [4-(6,7-dimethoxy-quinolin-4-yloxy)-phenyl]-amide,
3,5-Dichloro-N-[4-(6,7-dimethoxy-quinolin-4-yloxy)-3-methyl-phenyl]-2-hydroxy-benzenesulfonamide,
2-Methyl-3H-imidazole-4-sulfonic acid [4-(6,7-dimethoxy-quinolin-4-yloxy)-phenyl]-amide,
Biphenyl-4-sulfonic acid [4-(6,7-dimethoxy-quinolin-4-yloxy)-phenyl]-amide,
N-[4-(6,7-Dimethoxy-quinolin-4-yloxy)-phenyl]-3-pyrimidin-2-yl-benzenesulfonamide,
Benzo[b]thiophene-2-sulfonic acid [4-(6,7-dimethoxy-quinolin-4-yloxy)-phenyl]-amide,
Benzo[b]thiophene-3-sulfonic acid [4-(6,7-dimethoxy-quinolin-4-yloxy)-phenyl]-amide,
1-Methyl-2-oxo-2,3-dihydro-1H-indole-5-sulfonic acid [4-(6,7-dimethoxy-quinolin-4-yloxy)-phenyl]-amide,
Biphenyl-3-sulfonic acid [4-(6,7-dimethoxy-quinolin-4-yloxy)-phenyl]-amide,
N-[4-(6,7-Dimethoxy-quinolin-4-yloxy)-phenyl]-4-(3,5-dimethyl-isoxazol-4-ylmethoxy)-benzenesulfonamide,
N-[4-(6,7-Dimethoxy-quinolin-4-yloxy)-2-fluoro-phenyl]-3-fluoro-4-methoxy-benzenesulfonamide,
Biphenyl-3-sulfonic acid [4-(6,7-dimethoxy-quinolin-4-yloxy)-2-methyl-phenyl]-amide,
N-[4-(6,7-Dimethoxy-quinolin-4-yloxy)-2-methyl-phenyl]-3-phenoxy-benzenesulfonamide,
Naphthalene-1-sulfonic acid [4-(6,7-dimethoxy-quinolin-4-yloxy)-2-methyl-phenyl]-amide,
Biphenyl-4-sulfonic acid [4-(6,7-dimethoxy-quinolin-4-yloxy)-2-methyl-phenyl]-amide,
N-[4-(6,7-Dimethoxy-quinolin-4-yloxy)-2-methyl-phenyl]-3-pyrimidin-2-yl-benzenesulfonamide,
Benzo[b]thiophene-2-sulfonic acid [4-(6,7-dimethoxy-quinolin-4-yloxy)-2-methyl-phenyl]-amide,
1-Methyl-2-oxo-2,3-dihydro-1H-indole-5-sulfonic acid [4-(6,7-dimethoxy-quinolin-4-yloxy)-2-methyl-phenyl]-amide,
N-[4-(6,7-Dimethoxy-quinolin-4-yloxy)-3-fluoro-phenyl]-2-trifluoromethyl-benzenesulfonamide,
Biphenyl-3-sulfonic acid [4-(6,7-dimethoxy-quinolin-4-yloxy)-3-fluoro-phenyl]-amide,
N-[4-(6,7-Dimethoxy-quinolin-4-yloxy)-3-fluoro-phenyl]-3-phenoxy-benzenesulfonamide,
N-[4-(6,7-Dimethoxy-quinolin-4-yloxy)-3-fluoro-phenyl]-2,5-difluoro-benzenesulfonamide,
Naphthalene-1-sulfonic acid [4-(6,7-dimethoxy-quinolin-4-yloxy)-3-fluoro-phenyl]-amide,
N-[4-(6,7-Dimethoxy-quinolin-4-yloxy)-3-fluoro-phenyl]-3-pyrimidin-2-yl-benzenesulfonamide,
N-[4-(6,7-Dimethoxy-quinolin-4-yloxy)-2-fluoro-phenyl]-3-pyrimidin-2-yl-benzenesulfonamide,
N-[4-(6,7-Dimethoxy-quinolin-4-yloxy)-phenyl]-2-trifluoromethyl-benzenesulfonamide,
Naphthalene-1-sulfonic acid [4-(6,7-dimethoxy-quinolin-4-yloxy)-phenyl]-amide,
3,5-Dichloro-N-[4-(6,7-dimethoxy-quinolin-4-yloxy)-2-methyl-phenyl]-4-hydroxy-benzenesulfonamide,
3,5-Dichloro-N-[4-(6,7-dimethoxy-quinolin-4-yloxy)-3-fluoro-phenyl]-2-methoxy-benzenesulfonamide,
Biphenyl-4-sulfonic acid [4-(6,7-dimethoxy-quinolin-4-yloxy)-3-fluoro-phenyl]-amide,
Benzo[b]thiophene-3-sulfonic acid [4-(6,7-dimethoxy-quinolin-4-yloxy)-3-fluoro-phenyl]-amide,
N-[4-(6,7-Dimethoxy-quinolin-4-yloxy)-3-fluoro-phenyl]-4-fluoro-3-methoxy-benzenesulfonamide,
4-Chloro-N-[4-(6,7-dimethoxy-quinolin-4-yloxy)-3-fluoro-phenyl]-2-fluoro-benzenesulfonamide, 3,5-Dichloro-N-[4-(6,7-dimethoxy-quinolin-4-yloxy)-2-methyl-phenyl]-2-methoxy-benzenesulfonamide,
N-[4-(6,7-Dimethoxy-quinolin-4-yloxy)-2-methyl-phenyl]-2-trifluoromethoxy-benzenesulfonamide,
N-[4-(6,7-Dimethoxy-quinolin-4-yloxy)-2-methyl-phenyl]-2-trifluoromethyl-benzenesulfonamide,
N-[4-(6,7-Dimethoxy-quinolin-4-yloxy)-phenyl]-2-trifluoromethoxy-benzenesulfonamide,
N-[4-(6,7-Dimethoxy-quinolin-4-yloxy)-phenyl]-3-phenoxy-benzenesulfonamide,
N-[4-(6,7-Dimethoxy-quinolin-4-yloxy)-phenyl]-4-fluoro-3-methoxy-benzenesulfonamide,
4-Bromo-3-chloro-N-[4-(6,7-dimethoxy-quinolin-4-yloxy)-phenyl]-benzenesulfonamide,
N-[4-(6,7-Dimethoxy-quinolin-4-yloxy)-phenyl]-2,5-difluoro-benzenesulfonamide,
N-[4-(6,7-Dimethoxy-quinolin-4-yloxy)-3-methoxy-phenyl]-2-trifluoromethoxy-benzenesulfonamide,
N-[4-(6,7-Dimethoxy-quinolin-4-yloxy)-3-methoxy-phenyl]-3-phenoxy-benzenesulfonamide,
N-[4-(6,7-Dimethoxy-quinolin-4-yloxy)-3-methoxy-phenyl]-4-fluoro-3-methoxy-benzenesulfonamide,
4-Bromo-3-chloro-N-[4-(6,7-dimethoxy-quinolin-4-yloxy)-3-methoxy-phenyl]-benzenesulfonamide,
N-[4-(6,7-Dimethoxy-quinolin-4-yloxy)-3-methoxy-phenyl]-2-trifluoromethyl-benzenesulfonamide,
4-Bromo-3-chloro-N-[4-(6,7-dimethoxy-quinolin-4-yloxy)-3-fluoro-phenyl]-benzenesulfonamide,
1-Methyl-2-oxo-2,3-dihydro-1H-indole-5-sulfonic acid [4-(6,7-dimethoxy-quinolin-4-yloxy)-3-fluoro-phenyl]-amide,
N-[4-(6,7-Dimethoxy-quinolin-4-yloxy)-3-fluoro-phenyl]-2-trifluoromethoxy-benzenesulfonamide,
3,5-Dichloro-N-[4-(6,7-dimethoxy-quinolin-4-yloxy)-3-methyl-phenyl]-2-methoxy-benzenesulfonamide,
N-[4-(6,7-Dimethoxy-quinolin-4-yloxy)-3-methyl-phenyl]-2-trifluoromethyl-benzenesulfonamide,
N-[4-(6,7-Dimethoxy-quinolin-4-yloxy)-3-methyl-phenyl]-2-trifluoromethoxy-benzenesulfonamide,
4-Methoxy-naphthalene-1-sulfonic acid [4-(6,7-dimethoxy-quinolin-4-yloxy)-3-methyl-phenyl]-amide,
N-[4-(6,7-Dimethoxy-quinolin-4-yloxy)-3-methyl-phenyl]-2,5-difluoro-benzenesulfonamide,
N-[4-(6,7-Dimethoxy-quinolin-4-yloxy)-3-methyl-phenyl]-3-pyrimidin-2-yl-benzenesulfonamide,
4-Methoxy-naphthalene-1-sulfonic acid [4-(6,7-dimethoxy-quinolin-4-yloxy)-phenyl]-amide,
4-Chloro-N-[4-(6,7-dimethoxy-quinolin-4-yloxy)-phenyl]-2-fluoro-benzenesulfonamide,
4-Methoxy-naphthalene-1-sulfonic acid [4-(6,7-dimethoxy-quinolin-4-yloxy)-3-fluoro-phenyl]-amide,
Biphenyl-4-sulfonic acid [4-(6,7-dimethoxy-quinolin-4-yloxy)-2-fluoro-phenyl]-amide,
1-Methyl-2-oxo-2,3-dihydro-1H-indole-5-sulfonic acid [4-(6,7-dimethoxy-quinolin-4-yloxy)-2-fluoro-phenyl]-amide,
Biphenyl-3-sulfonic acid [4-(6,7-dimethoxy-quinolin-4-yloxy)-3-methoxy-phenyl]-amide,
N-[4-(6,7-Dimethoxy-quinolin-4-yloxy)-3-methoxy-phenyl]-2,5-difluoro-benzenesulfonamide,
Naphthalene-1-sulfonic acid [4-(6,7-dimethoxy-quinolin-4-yloxy)-3-methoxy-phenyl]-amide,
4-Chloro-N-[4-(6,7-dimethoxy-quinolin-4-yloxy)-3-methoxy-phenyl]-2-fluoro-benzenesulfonamide,
Biphenyl-4-sulfonic acid [4-(6,7-dimethoxy-quinolin-4-yloxy)-3-methoxy-phenyl]-amide,
N-[4-(6,7-Dimethoxy-quinolin-4-yloxy)-3-methoxy-phenyl]-3-pyrimidin-2-yl-benzenesulfonamide,
Benzo[b]thiophene-3-sulfonic acid [4-(6,7-dimethoxy-quinolin-4-yloxy)-3-methoxy-phenyl]-amide,
1-Methyl-2-oxo-2,3-dihydro-1H-indole-5-sulfonic acid [4-(6,7-dimethoxy-quinolin-4-yloxy)-3-methoxy-phenyl]-amide,
4-Bromo-N-[4-(6,7-dimethoxy-quinolin-4-yloxy)-3-fluoro-phenyl]-2-trifluoromethoxy-benzenesulfonamide,
4-Bromo-N-[4-(6,7-dimethoxy-quinolin-4-yloxy)-2-fluoro-phenyl]-2-trifluoromethoxy-benzenesulfonamide,
4-Bromo-N-[4-(6,7-dimethoxy-quinolin-4-yloxy)-3-methoxy-phenyl]-2-trifluoromethoxy-benzenesulfonamide,
4-Bromo-N-[4-(6,7-dimethoxy-quinolin-4-yloxy)-phenyl]-2-trifluoromethoxy-benzenesulfonamide,
4-Methoxy-naphthalene-1-sulfonic acid [4-(6,7-dimethoxy-quinolin-4-yloxy)-2-methyl-phenyl]-amide,
N-[4-(6,7-Dimethoxy-quinolin-4-yloxy)-2-methyl-phenyl]-2,5-difluoro-benzenesulfonamide,
4-Bromo-3-chloro-N-[4-(6,7-dimethoxy-quinolin-4-yloxy)-2-methyl-phenyl]-benzenesulfonamide,
4-Chloro-N-[4-(6,7-dimethoxy-quinolin-4-yloxy)-2-methyl-phenyl]-2-fluoro-benzenesulfonamide,
N-[4-(6,7-Dimethoxy-quinolin-4-yloxy)-2-methyl-phenyl]-4-fluoro-3-methoxy-benzenesulfonamide,
3,5-Dichloro-N-[4-(6,7-dimethoxy-quinolin-4-yloxy)-phenyl]-4-hydroxy-benzenesulfonamide,
3,5-Dichloro-N-[4-(6,7-dimethoxy-quinolin-4-yloxy)-3-methoxy-phenyl]-2-hydroxy-benzenesulfonamide,
Thiophene-2-sulfonic acid [2-fluoro-4-(6-fluoro-2-methyl-quinolin-4-yloxy)-phenyl]-amide,
3-Cyano-N-[2-fluoro-4-(6-fluoro-2-methyl-quinolin-4-yloxy)-phenyl]-benzenesulfonamide,
N-[2-Fluoro-4-(6-fluoro-2-methyl-quinolin-4-yloxy)-phenyl]-3-methoxy-benzenesulfonamide,
Cyclopropanesulfonic acid [2-fluoro-4-(6-fluoro-2-methyl-quinolin-4-yloxy)-phenyl]-amide,
3-Chloro-4-fluoro-N-[2-fluoro-4-(6-fluoro-2-methyl-quinolin-4-yloxy)-phenyl]-benzenesulfonamide,
2,6-Difluoro-N-[2-fluoro-4-(6-fluoro-2-methyl-quinolin-4-yloxy)-phenyl]-benzenesulfonamide,
5-Methyl-thiophene-2-sulfonic acid [2-fluoro-4-(6-fluoro-2-methyl-quinolin-4-yloxy)-phenyl]-amide,
N-[2-Fluoro-4-(6-fluoro-2-methyl-quinolin-4-yloxy)-phenyl]-3-trifluoromethyl-benzenesulfonamide,
N-[4-(6-Fluoro-2-methyl-quinolin-4-yloxy)-phenyl]-benzenesulfonamide,
3,5-Dichloro-N-[4-(6-fluoro-2-methyl-quinolin-4-yloxy)-phenyl]-benzenesulfonamide,
3,5-Dichloro-N-[4-(6-fluoro-2-methyl-quinolin-4-yloxy)-phenyl]-2-methoxy-benzenesulfonamide,
2,4-Difluoro-N-[4-(6-fluoro-2-methyl-quinolin-4-yloxy)-phenyl]-benzenesulfonamide,
3,5-Difluoro-N-[4-(6-fluoro-2-methyl-quinolin-4-yloxy)-phenyl]-benzenesulfonamide,
3-Bromo-N-[4-(6-fluoro-2-methyl-quinolin-4-yloxy)-phenyl]-benzenesulfonamide,
4-Bromo-N-[4-(6-fluoro-2-methyl-quinolin-4-yloxy)-phenyl]-2-trifluoromethyl-benzenesulfonamide,
Thiophene-3-sulfonic acid [4-(6-fluoro-2-methyl-quinolin-4-yloxy)-phenyl]-amide,
3-[4-(6-Fluoro-2-methyl-quinolin-4-yloxy)-phenylsulfamoyl]-thiophene-2-carboxylic acid methyl ester, 5-Chloro-thiophene-2-sulfonic acid [4-(6-fluoro-2-methyl-quinolin-4-yloxy)-phenyl]-amide,
5-Oxazol-5-yl-thiophene-2-sulfonic acid [4-(6-fluoro-2-methyl-quinolin-4-yloxy)-phenyl]-amide,
Naphthalene-1-sulfonic acid [4-(6-fluoro-2-methyl-quinolin-4-yloxy)-phenyl]-amide,
1-Ethyl-1H-pyrazole-4-sulfonic acid [4-(6-fluoro-2-methyl-quinolin-4-yloxy)-phenyl]-amide,
3,5-Dichloro-N-[4-(6-fluoro-2-methyl-quinolin-4-yloxy)-phenyl]-2-hydroxy-benzenesulfonamide,
Biphenyl-3-sulfonic acid [4-(7-benzyloxy-6-methoxy-quinolin-4-yloxy)-2-fluoro-phenyl]-amide,
Naphthalene-1-sulfonic acid {4-[7-(3-amino-propoxy)-6-methoxy-quinolin-4-yloxy]-3-fluoro-phenyl}-amide,
Biphenyl-3-sulfonic acid {4-[7-(3-amino-propoxy)-6-methoxy-quinolin-4-yloxy]-3-fluoro-phenyl}-amide,
Biphenyl-3-sulfonic acid {3-fluoro-4-[6-methoxy-7-(2-morpholin-4-yl-ethoxy)-quinolin-4-yloxy]-phenyl}-amide,
N-{3-Fluoro-4-[6-methoxy-7-(2-morpholin-4-yl-ethoxy)-quinolin-4-yloxy]-phenyl}-2-trifluoromethyl-benzenesulfonamide,
N-{3-Fluoro-4-[6-methoxy-7-(2-morpholin-4-yl-ethoxy)-quinolin-4-yloxy]-phenyl}-2-trifluoromethoxy-benzenesulfonamide,
Biphenyl-3-sulfonic acid {4-[6-methoxy-7-(2-morpholin-4-yl-ethoxy)-quinolin-4-yloxy]-2-methyl-phenyl}-amide,
N-{4-[6-Methoxy-7-(2-morpholin-4-yl-ethoxy)-quinolin-4-yloxy]-2-methyl-phenyl}-2-trifluoromethoxy-benzenesulfonamide,
2,5-Difluoro-N-{4-[6-methoxy-7-(2-morpholin-4-yl-ethoxy)-quinolin-4-yloxy]-2-methyl-phenyl}-benzene sulfonamide,
2,5-Difluoro-N-{3-fluoro-4-[6-methoxy-7-(2-morpholin-4-yl-ethoxy)-quinolin-4-yloxy]-phenyl}-benzene sulfonamide,
N-{4-[6-Methoxy-7-(2-morpholin-4-yl-ethoxy)-quinolin-4-yloxy]-2-methyl-phenyl}-2-trifluoromethyl-benzenesulfonamide,
4-Chloro-2-fluoro-N-{3-fluoro-4-[6-methoxy-7-(2-morpholin-4-yl-ethoxy)-quinolin-4-yloxy]-phenyl}-benzene sulfonamide,
4-Methoxy-naphthalene-1-sulfonic acid {3-fluoro-4-[6-methoxy-7-(2-morpholin-4-yl-ethoxy)-quinolin-4-yloxy]-phenyl}-amide,
N-{4-[7-(3-Amino-propoxy)-6-methoxy-quinolin-4-yloxy]-3-fluoro-phenyl}-2-trifluoromethyl-benzenesulfonamide,
N-{4-[7-(3-Amino-propoxy)-6-methoxy-quinolin-4-yloxy]-3-fluoro-phenyl}-2-trifluoromethoxy-benzenesulfonamide,
N-(3-Fluoro-4-{6-methoxy-7-[3-(4-methyl-piperidin-1-yl)-propoxy]-quinolin-4-yloxy}-phenyl)-2-trifluoromethyl-benzenesulfonamide,
2-Bromo-N-(3-fluoro-4-{6-methoxy-7-[3-(4-methyl-piperidin-1-yl)-propoxy]-quinolin-4-yloxy}-phenyl)-benzene sulfonamide,
2,4-Difluoro-N-(3-fluoro-4-{6-methoxy-7-[3-(4-methyl-piperidin-1-yl)-propoxy]-quinolin-4-yloxy}-phenyl)-benzenesulfonamide,
2,6-Difluoro-N-(3-fluoro-4-{6-methoxy-7-[3-(4-methyl-piperidin-1-yl)-propoxy]-quinolin-4-yloxy}-phenyl)-benzenesulfonamide,
Naphthalene-1-sulfonic acid (3-fluoro-4-{6-methoxy-7-[3-(4-methyl-piperidin-1-yl)-propoxy]-quinolin-4-yloxy}-phenyl)-amide,
2-Cyano-N-(3-fluoro-4-{6-methoxy-7-[3-(4-methyl-piperidin-1-yl)-propoxy]-quinolin-4-yloxy}-phenyl)-benzenesulfonamide,
4-Chloro-2-fluoro-N-(3-fluoro-4-{6-methoxy-7-[3-(3-methyl-piperidin-1-yl)-propoxy]-quinolin-4-yloxy}-phenyl)-benzenesulfonamide,
2-Bromo-N-{3-fluoro-4-[6-methoxy-7-(2-morpholin-4-yl-ethoxy)-quinolin-4-yloxy]-phenyl}-benzene sulfonamide,
2-Cyano-N-{3-fluoro-4-[6-methoxy-7-(2-morpholin-4-yl-ethoxy)-quinolin-4-yloxy]-phenyl}-benzene sulfonamide,
2,4-Difluoro-N-{3-fluoro-4-[6-methoxy-7-(2-morpholin-4-yl-ethoxy)-quinolin-4-yloxy]-phenyl}-benzene sulfonamide,
Biphenyl-3-sulfonic acid (3-fluoro-4-{6-methoxy-7-[3-(4-methyl-piperidin-1-yl)-propoxy]-quinolin-4-yloxy}-phenyl)-amide,
2-Fluoro-N-(3-fluoro-4-{6-methoxy-7-[3-(3-methyl-piperidin-1-yl)-propoxy]-quinolin-4-yloxy}-phenyl)-benzene sulfonamide,
2-Cyano-N-(3-fluoro-4-{6-methoxy-7-[3-(3-methyl-piperidin-1-yl)-propoxy]-quinolin-4-yloxy}-phenyl)-benzene sulfonamide,
2,6-Difluoro-N-(3-fluoro-4-{6-methoxy-7-[3-(3-methyl-piperidin-1-yl)-propoxy]-quinolin-4-yloxy}-phenyl)-benzenesulfonamide,
N-(3-Fluoro-4-{6-methoxy-7-[3-(4-methyl-piperidin-1-yl)-propoxy]-quinolin-4-yloxy}-phenyl)-2-trifluoromethoxy-benzenesulfonamide,
2,5-Difluoro-N-(3-fluoro-4-{6-methoxy-7-[3-(4-methyl-piperidin-1-yl)-propoxy]-quinolin-4-yloxy}-phenyl)-benzenesulfonamide,
N-(3-Fluoro-4-{6-methoxy-7-[3-(3-methyl-piperidin-1-yl)-propoxy]-quinolin-4-yloxy}phenyl)-2-trifluoromethyl-benzenesulfonamide,
2,5-Difluoro-N-(3-fluoro-4-{6-methoxy-7-[3-(3-methyl-piperidin-1-yl)-propoxy]-quinolin-4-yloxy}-phenyl)-benzenesulfonamide,
Biphenyl-3-sulfonic acid (3-fluoro-4-{6-methoxy-7-[3-(3-methyl-piperidin-1-yl)-propoxy]-quinolin-4-yloxy}-phenyl)-amide,
4-Fluoro-N-(3-fluoro-4-{6-methoxy-7-[3-(3-methyl-piperidin-1-yl)-propoxy]-quinolin-4-yloxy}-phenyl)-3-methoxy-benzenesulfonamide,
N-{3-Fluoro-4-[6-methoxy-7-(3-morpholin-4-yl-propoxy)-quinolin-4-yloxy]-phenyl}-2-trifluoromethyl-benzenesulfonamide,
N-{3-Fluoro-4-[6-methoxy-7-(3-morpholin-4-yl-propoxy)-quinolin-4-yloxy]-phenyl}-2-trifluoromethoxy-benzenesulfonamide,
2,5-Difluoro-N-{3-fluoro-4-[6-methoxy-7-(3-morpholin-4-yl-propoxy)-quinolin-4-yloxy]-phenyl}-benzene sulfonamide,
Biphenyl-3-sulfonic acid {3-fluoro-4-[6-methoxy-7-(3-morpholin-4-yl-propoxy)-quinolin-4-yloxy]-phenyl}-amide,
4-Chloro-2-fluoro-N-{3-fluoro-4-[6-methoxy-7-(3-morpholin-4-yl-propoxy)-quinolin-4-yloxy]-phenyl}-benzene sulfonamide,
4-Fluoro-N-{3-fluoro-4-[6-methoxy-7-(3-morpholin-4-yl-propoxy)-quinolin-4-yloxy]-phenyl}-3-methoxy-benzene sulfonamide,
2-Fluoro-N-{3-fluoro-4-[6-methoxy-7-(3-morpholin-4-yl-propoxy)-quinolin-4-yloxy]-phenyl}-benzene sulfonamide, N-{3-Fluoro-4-[6-methoxy-7-(3-morpholin-4-yl-propoxy)-quinolin-4-yloxy]-phenyl}-2-nitro-benzenesulfonamide, 2,6-Dichloro-N-{3-fluoro-4-[6-methoxy-7-(3-morpholin-4-yl-propoxy)-quinolin-4-yloxy]-phenyl}-benzene sulfonamide, Naphthalene-1-sulfonic acid {3-fluoro-4-[6-methoxy-7-(3-morpholin-4-yl-propoxy)-quinolin-4-yloxy]-phenyl}-amide, and 2-Bromo-N-{3-fluoro-4-[6-methoxy-7-(3-morpholin-4-yl-propoxy)-quinolin-4-yloxy]-phenyl}-benzene sulfonamide.

7. A pharmaceutical composition comprising at least one compound according to claim 1.

8. The pharmaceutical composition according to claim 7, further comprising pharmaceutically acceptable carriers, diluents and/or adjuvants.

9. The pharmaceutical composition of claim 7, wherein the composition is administrable parenterally, topically, rectally, nasally, buccally, vaginally, transdermally, by inhalation, by injection or infusion, by spray or via implanted reservoir.

* * * * *